United States Patent
Elpek et al.

(10) Patent No.: US 11,058,725 B2
(45) Date of Patent: Jul. 13, 2021

(54) CA2 COMPOSITIONS AND METHODS FOR TUNABLE REGULATION

(71) Applicant: Obsidian Therapeutics, Inc., Cambridge, MA (US)

(72) Inventors: Kutlu Goksu Elpek, Arlington, MA (US); Dhruv Kam Sethi, Westwood, MA (US); Meghan C. Langley, Stoughton, MA (US); Tucker Read Ezell, Acton, MA (US); Dexue Sun, Cambridge, MA (US); Jennifer Leah Gori, Jamaica Plain, MA (US); Geetha Hanna Mylvaganam, Boston, MA (US); Michelle Ols, Northborough, MA (US); Michelle Fleury, Cambridge, MA (US); Celeste Richardson, Brookline, MA (US); James A. Storer, Medford, MA (US); Vipin Suri, Belmont, MA (US); Shyamsundar Subramanian, Downingtown, PA (US); Colleen Foley, Cambridge, MA (US); Molly Reed Perkins, Milton, MA (US); Jeremy Hatem Tchaicha, Belmont, MA (US); Scott Francis Heller, Stoughton, MA (US)

(73) Assignee: Obsidian Therapeutics, Inc., Cambridge, MA (US)

( * ) Notice: Subject to any disclaimer, the term of this patent is extended or adjusted under 35 U.S.C. 154(b) by 0 days.

(21) Appl. No.: 17/017,670

(22) Filed: Sep. 10, 2020

(65) Prior Publication Data
US 2021/0069248 A1 Mar. 11, 2021

Related U.S. Application Data

(60) Provisional application No. 62/898,520, filed on Sep. 10, 2019.

(51) Int. Cl.
| | |
|---|---|
| *A61K 35/17* | (2015.01) |
| *C12N 15/86* | (2006.01) |
| *C07K 14/54* | (2006.01) |
| *A61K 31/433* | (2006.01) |
| *C12N 9/88* | (2006.01) |
| *C12N 15/867* | (2006.01) |
| *C12N 15/864* | (2006.01) |
| *C12N 15/869* | (2006.01) |
| *C12N 15/861* | (2006.01) |

(52) U.S. Cl.
CPC ............ *A61K 35/17* (2013.01); *A61K 31/433* (2013.01); *C07K 14/5443* (2013.01); *C12N 9/88* (2013.01); *C12N 15/86* (2013.01); *C12N 15/861* (2013.01); *C12N 15/867* (2013.01); *C12N 15/869* (2013.01); *C12N 15/8645* (2013.01); *C07K 2319/00* (2013.01); *C07K 2319/02* (2013.01); *C07K 2319/03* (2013.01); *C12N 2740/15043* (2013.01); *C12Y 402/01001* (2013.01)

(58) Field of Classification Search
CPC ...... A61K 35/17; C12N 15/86; C12N 15/861; C12N 15/8645; C12N 15/867; C12N 15/869; C07K 2319/00; C07K 2319/02; C07K 2319/03; C12Y 402/01001
See application file for complete search history.

(56) References Cited

U.S. PATENT DOCUMENTS

| | | |
|---|---|---|
| 5,532,123 A | 7/1996 | Schlessinger |
| 5,540,926 A | 7/1996 | Aruffo et al. |
| 6,083,477 A | 7/2000 | Goldenberg |
| 6,475,784 B1 | 11/2002 | Papkoff |
| 6,548,249 B1 | 4/2003 | Anderson et al. |
| 6,548,632 B1 | 4/2003 | Anderson et al. |
| 6,562,617 B1 | 5/2003 | Anderson et al. |
| 6,797,263 B2 | 9/2004 | Strom et al. |
| 7,323,450 B2 | 1/2008 | Chu et al. |
| 7,347,995 B2 | 3/2008 | Strom et al. |
| 7,569,670 B2 | 8/2009 | Novak et al. |
| 7,579,439 B2 | 8/2009 | Strom et al. |
| 7,605,139 B2 | 10/2009 | Yu et al. |
| 8,013,114 B2 | 9/2011 | Kundra |
| 8,173,792 B2 | 5/2012 | Wandless et al. |
| 8,278,066 B2 | 10/2012 | Kundra |
| 8,450,470 B2 | 5/2013 | Bookbinder et al. |
| 8,530,636 B2 | 9/2013 | Wandless et al. |
| 8,722,618 B2 | 5/2014 | Jacobs et al. |
| 8,871,191 B2 | 10/2014 | Pavlakis et al. |
| 9,006,400 B2 | 4/2015 | Boettcher et al. |
| 9,290,746 B2 | 3/2016 | Ciani et al. |
| 9,458,214 B2 | 10/2016 | Boettcher et al. |

(Continued)

FOREIGN PATENT DOCUMENTS

| | | |
|---|---|---|
| CA | 3055202 A1 | 9/2018 |
| EP | 0932417 B1 | 3/2003 |

(Continued)

OTHER PUBLICATIONS

Hernandez et al, Clin. Cancer Res. 9:1906-1916, 2003.*

(Continued)

*Primary Examiner* — Kevin K Hill
(74) *Attorney, Agent, or Firm* — Honigman LLP; Fernando Alberdi; Jonathan P. O'Brien

(57) ABSTRACT

The present disclosure provides drug responsive domains derived from human carbonic anhydrase 2 that can modulate protein stability for human interleukin 15 (IL15) payloads, as well as compositions and methods of use thereof.

21 Claims, 12 Drawing Sheets
Specification includes a Sequence Listing.

(56) References Cited

U.S. PATENT DOCUMENTS

| | | |
|---|---|---|
| 9,475,862 B2 | 10/2016 | Connors et al. |
| 9,487,787 B2 | 11/2016 | Wandless et al. |
| 9,487,800 B2 | 11/2016 | Schonfeld et al. |
| 9,586,996 B2 | 3/2017 | Allla et al. |
| 9,631,218 B2 | 4/2017 | Tsourkas et al. |
| 9,677,061 B2 | 6/2017 | Bookbinder et al. |
| 9,725,492 B2 | 8/2017 | Felber et al. |
| 9,944,910 B2 | 4/2018 | Ciani et al. |
| 9,963,495 B2 | 5/2018 | Liu et al. |
| 10,040,835 B2 | 8/2018 | Luo |
| 10,125,193 B2 | 11/2018 | Cooper et al. |
| 10,137,180 B2 | 11/2018 | Wandless et al. |
| 10,202,433 B2 | 2/2019 | Jacques et al. |
| 10,351,612 B2 | 7/2019 | Schonfeid et al. |
| 10,415,017 B2 | 9/2019 | O'Neill |
| 10,428,305 B2 | 10/2019 | Campana et al. |
| 10,472,637 B2 | 11/2019 | Wang et al. |
| 10,570,186 B2 | 2/2020 | Cooper et al. |
| 10,675,305 B2 | 6/2020 | Wang et al. |
| 10,688,132 B2 | 6/2020 | Wang et al. |
| 10,774,311 B2 | 9/2020 | Campana et al. |
| 2002/0100068 A1 | 7/2002 | Chambon et al. |
| 2004/0038373 A1 | 2/2004 | Platz et al. |
| 2004/0063912 A1 | 4/2004 | Blumberg et al. |
| 2004/0102370 A1 | 5/2004 | Saffell |
| 2005/0048573 A1 | 3/2005 | Artis et al. |
| 2005/0175582 A1 | 8/2005 | Goldenberg |
| 2006/0160104 A1 | 7/2006 | Johnson et al. |
| 2006/0257361 A1 | 11/2006 | Watanabe et al. |
| 2007/0009483 A1 | 1/2007 | Yoon et al. |
| 2007/0048845 A1 | 3/2007 | Novak et al. |
| 2007/0098683 A1 | 5/2007 | Novak et al. |
| 2008/0280830 A1 | 11/2008 | Choi et al. |
| 2009/0087871 A1 | 4/2009 | Kanacher et al. |
| 2009/0105455 A1 | 4/2009 | Herrmann |
| 2009/0117618 A1 | 5/2009 | Herrmann et al. |
| 2009/0215169 A1 | 8/2009 | Wandless et al. |
| 2010/0021997 A1 | 1/2010 | Koochekpour et al. |
| 2010/0034777 A1 | 2/2010 | Wandless et al. |
| 2010/0196370 A1 | 8/2010 | Yu et al. |
| 2010/0292089 A1 | 11/2010 | Bachmann et al. |
| 2010/0297063 A1 | 11/2010 | Novak et al. |
| 2011/0150861 A1 | 6/2011 | Carson et al. |
| 2011/0312872 A1 | 12/2011 | Tamm et al. |
| 2012/0076732 A1 | 3/2012 | Feng et al. |
| 2012/0178168 A1 | 7/2012 | Wandless et al. |
| 2012/0276142 A1 | 11/2012 | Weiner et al. |
| 2013/0266551 A1 | 10/2013 | Campana et al. |
| 2013/0302276 A1 | 11/2013 | Cantor et al. |
| 2014/0010791 A1* | 1/2014 | Wandless ............ A61K 31/445 424/93.21 |
| 2014/0206599 A1 | 7/2014 | Baumann et al. |
| 2014/0255361 A1 | 9/2014 | Wandless et al. |
| 2014/0255363 A1 | 9/2014 | Metelitsa et al. |
| 2014/0271635 A1 | 9/2014 | Brogdon et al. |
| 2015/0191711 A1 | 7/2015 | Carlsson et al. |
| 2015/0307564 A1 | 10/2015 | Young et al. |
| 2016/0017012 A1 | 1/2016 | Ildefonso et al. |
| 2016/0017017 A1 | 1/2016 | Zhao et al. |
| 2016/0108105 A1 | 4/2016 | Yang et al. |
| 2016/0145337 A1 | 5/2016 | Galetto et al. |
| 2016/0152686 A1 | 6/2016 | Camphausen et al. |
| 2017/0002060 A1 | 1/2017 | Bolen et al. |
| 2017/0088597 A1 | 3/2017 | Wong et al. |
| 2017/0119874 A1 | 5/2017 | Lanzavecchia et al. |
| 2017/0157176 A1 | 6/2017 | Wang et al. |
| 2017/0216275 A1 | 8/2017 | Feng et al. |
| 2017/0224732 A1 | 8/2017 | Cantor et al. |
| 2017/0224798 A1 | 8/2017 | Cooper et al. |
| 2018/0134761 A1 | 5/2018 | Lindhout et al. |
| 2018/0155439 A1 | 6/2018 | Galipeau et al. |
| 2018/0200299 A1 | 7/2018 | Cooper et al. |
| 2018/0256644 A1 | 9/2018 | Swanson et al. |
| 2018/0282386 A1 | 10/2018 | Vallera et al. |
| 2018/0327725 A1 | 11/2018 | Ciani et al. |
| 2018/0353544 A1 | 12/2018 | Rezvani et al. |
| 2018/0355013 A1 | 12/2018 | Dranoff et al. |
| 2018/0369334 A1 | 12/2018 | Cochran et al. |
| 2019/0060440 A1 | 2/2019 | Zhu et al. |
| 2019/0070264 A1 | 3/2019 | Qu et al. |
| 2019/0106472 A1 | 4/2019 | Jacques et al. |
| 2019/0119343 A1 | 4/2019 | Chung et al. |
| 2019/0151359 A1 | 5/2019 | Sullivan et al. |
| 2019/0192691 A1 | 6/2019 | Barrett et al. |
| 2019/0256818 A1 | 8/2019 | Swee et al. |
| 2019/0281797 A1 | 9/2019 | Lee et al. |
| 2019/0321403 A1 | 10/2019 | Levitsky |
| 2019/0330277 A1 | 10/2019 | Chen et al. |
| 2019/0345222 A1 | 11/2019 | Hirano et al. |
| 2019/0359655 A1 | 11/2019 | Zhu et al. |
| 2019/0375854 A1 | 12/2019 | Sabzevari et al. |
| 2020/0085872 A1 | 3/2020 | Rezvani et al. |
| 2020/0085929 A1 | 3/2020 | Cooper et al. |
| 2020/0101142 A1 | 4/2020 | Suri et al. |
| 2020/0102366 A1 | 4/2020 | Cooper et al. |
| 2020/0123514 A1 | 4/2020 | Wandless et al. |
| 2020/0131244 A1 | 4/2020 | Leong et al. |
| 2020/0179447 A1 | 6/2020 | Gaensler |
| 2020/0216826 A1 | 7/2020 | Cooper et al. |
| 2020/0283778 A1 | 9/2020 | Shah et al. |

FOREIGN PATENT DOCUMENTS

| | | |
|---|---|---|
| EP | 1550457 B1 | 12/2008 |
| EP | 1809321 B1 | 3/2012 |
| EP | 2388266 B1 | 4/2014 |
| EP | 1638987 B1 | 11/2014 |
| EP | 2177620 B1 | 11/2014 |
| EP | 2776463 B1 | 9/2017 |
| EP | 3013356 B1 | 10/2018 |
| EP | 2755487 B1 | 12/2018 |
| EP | 3110837 B1 | 6/2019 |
| EP | 2614151 B1 | 7/2019 |
| EP | 2968613 B1 | 9/2019 |
| EP | 3105335 B1 | 10/2019 |
| EP | 3215534 B1 | 4/2020 |
| EP | 3235830 B1 | 9/2020 |
| WO | 2000023091 A2 | 4/2000 |
| WO | 2001036460 A2 | 5/2001 |
| WO | 2003030946 A1 | 4/2003 |
| WO | 2004101751 A2 | 11/2004 |
| WO | 2005012493 A2 | 2/2005 |
| WO | 2007142929 A2 | 12/2007 |
| WO | 2009002562 A2 | 12/2008 |
| WO | 2011064758 A2 | 6/2011 |
| WO | 2012079000 A1 | 6/2012 |
| WO | 2012175222 A1 | 12/2012 |
| WO | 2013041487 A1 | 3/2013 |
| WO | 2013059593 A1 | 4/2013 |
| WO | 2014028311 A2 | 2/2014 |
| WO | 2014066527 A2 | 5/2014 |
| WO | 2014134165 A1 | 9/2014 |
| WO | 2015018528 A1 | 2/2015 |
| WO | 2015142675 A2 | 9/2015 |
| WO | 2015150771 A1 | 10/2015 |
| WO | WO 15/174928 * | 11/2015 |
| WO | 2016012623 A1 | 1/2016 |
| WO | 2016018920 A1 | 2/2016 |
| WO | WO 16/040395 * | 3/2016 |
| WO | 2016113203 A1 | 7/2016 |
| WO | 2016134284 A1 | 8/2016 |
| WO | 2016210293 A1 | 12/2016 |
| WO | 2017024318 A1 | 2/2017 |
| WO | 2017062953 A1 | 4/2017 |
| WO | 2017106937 A1 | 6/2017 |
| WO | 2017178562 A1 | 10/2017 |
| WO | 2017180587 A2 | 10/2017 |
| WO | 2017205810 A1 | 11/2017 |
| WO | 2017210617 A2 | 12/2017 |
| WO | 2018005617 A2 | 1/2018 |
| WO | 2018023025 A1 | 2/2018 |
| WO | 2018102795 A2 | 6/2018 |
| WO | 2018140733 A1 | 8/2018 |
| WO | 2018160993 A1 | 9/2018 |

(56) References Cited

FOREIGN PATENT DOCUMENTS

| | | | |
|---|---|---|---|
| WO | 2018161000 A1 | 9/2018 | |
| WO | 2018161017 A1 | 9/2018 | |
| WO | 2018161026 A1 | 9/2018 | |
| WO | 2018161038 A1 | 9/2018 | |
| WO | WO 18/161026 | * | 9/2018 |
| WO | WO 18/161038 | * | 9/2018 |
| WO | 2018183385 A1 | 10/2018 | |
| WO | 2016212770 A1 | 11/2018 | |
| WO | 2018213328 A1 | 11/2018 | |
| WO | 2018213731 A1 | 11/2018 | |
| WO | 2018213747 A1 | 11/2018 | |
| WO | 2018231759 A1 | 12/2018 | |
| WO | 2018237323 A1 | 12/2018 | |
| WO | 2019111194 A1 | 6/2019 | |
| WO | 2019135879 A1 | 7/2019 | |
| WO | 2019154986 A1 | 8/2019 | |
| WO | 2019155286 A2 | 8/2019 | |
| WO | 2019155288 A1 | 8/2019 | |
| WO | 2019157130 A1 | 8/2019 | |
| WO | 2019162521 A1 | 8/2019 | |
| WO | 2019166617 A1 | 9/2019 | |
| WO | 2019180279 A1 | 9/2019 | |
| WO | 2019185828 A1 | 10/2019 | |
| WO | 2019202035 A1 | 10/2019 | |
| WO | 2019213517 A1 | 11/2019 | |
| WO | 2019241315 A1 | 12/2019 | |
| WO | 2020014366 A1 | 1/2020 | |
| WO | 2020056045 A1 | 3/2020 | |
| WO | 2020072546 A2 | 4/2020 | |
| WO | 2020086742 A1 | 4/2020 | |
| WO | 2020123716 A1 | 6/2020 | |
| WO | 2020180882 A1 | 9/2020 | |
| WO | 2020185628 A1 | 9/2020 | |
| WO | 2020185632 A1 | 9/2020 | |
| WO | 2020185698 A1 | 9/2020 | |
| WO | 2020190902 A1 | 9/2020 | |
| WO | 2020252404 A1 | 12/2020 | |
| WO | 2020252405 A1 | 12/2020 | |

OTHER PUBLICATIONS

Ahlskog et al, Bioorg. & Medicinal Chem. Lett. 19: 4851-4856, 2009.*
Hoyos et al, Leukemia 24: 1160-1170, 2010.*
Chen et al, Mol. Therapy 21(1): 167-174, 2013.*
Iwamoto, M. et al., "A General Chemical Method to Regulate Protein Stability in the Mammalian Central Nervous System," Chemistry and Biology, Sep. 1, 2010, vol. 17, No. 9, pp. 981-988.
Juillerat, A. et al., "Design of chimeric antigen receptors with integrated controllable transient functions," Scientific Reports, Jan. 11, 2016, vol. 6, p. 18950.
Kassum, T. "Company Overview", Oral presentation presented at: Boston Cancer Summit. Apr. 16, 2019; Boston, MA, 16 pages.
Kaufman, H. et al., "Brief Report: Local delivery of vaccinia virus expressing multiple costimulatory molecules for the treatment of established tumors," Human Gene Therapy, 2006, vol. 17, No. 2, pp. 239-244.
Kermer, V. et al., "An Antibody Fusion Protein for Cancer Immunotherapy Mimicking IL-15 trans-Presentation at the Tumor Site," Mol Cancer Ther., Jun. 11, 2012, vol. 11, No. 6, pp. 279-1288.
Khawam, K. et al., "Human Renal Cancer Cells Express a Novel Membrane-Bound Interleukin-15 that Induces, in Response to the Soluble Interleukin-15 Receptor A Chain, Epithelial-to-Mesenchymal Transition," Cancer Res., Feb. 15, 2009, vol. 69, No. 4, pp. 1561-1569. Epub Feb. 3, 2009.
Kochenderfer, J. N. et al., "Lymphoma Remissions Caused by Anti-CD19 Chimeric Antigen Receptor T Cells Are Associated With High Serum Interleukin-15 Levels," J Clin Oncol., Jun. 1, 2017, vol. 35, No. 16, pp. 1803-1813.
Lusty, E. et al., "IL-18/IL-15/IL-12 synergy induces elevated and prolonged IFN- production by ex vivo expanded NK cells which is not due to enhanced STAT4 activation," Molecular Immunology, 2017, vol. 88, pp. 138-147.

Machado Diaz, A. C. et al., "Proinflammatory Soluble Interleukin-15 Receptor Alpha Is Increased in Rheumatoid Arthritis" Arthritis, Epub Jul. 25, 2012. vol. 2012, Article ID 943156, 7 pages.
Malhotra, S., "Deducing the Essentiality of a Putative Apicoplast Deubiquitinating Protease: the OTU-like cysteine protease PF10_0308 in Plasmodium falciparum," Research Thesis, Feb. 2012, 33 pages.
Mesén-Ramirez, P. et al., "Stable Translocalion Intermediates Jam Global Protein Export I Plasmodium falciparum Parasites and Link the PTEX Component EXP2 with Translocation Activity," PLoS Pathogens, May 11, 2016, vol. 2, No. 5, pp. 1-28.
Miyazaki, Y. et al., "Destabilizing Domains Derived From the Human Estrogen Receptor," Journal of the American Chemical Society, Mar. 7, 2012, vol. 134, No. 8, pp. 1-9. Epub Feb. 22, 2012.
Mortier, E. et al., "Soluble Interleukin-15 Receptor (IL-15R)-sushi as a Selective and Potent Agonist of IL-15 Action through IL-15R beta/gamma. Hyperagonist IL-15/IL-15R alpha fusion proteins," J Biol Chem., Jan. 20, 2006, vol. 281, No. 3, pp. 1612-1619.
Musso, T. et al., "Naturally occurring isoform: Human Monocytes Constitutively Express Membrane-Bound, Biologically Active, and Interferon-g—Upregulated Interleukin-15," Blood, May 15, 1999, vol. 93, No. 10, pp. 3531-3539. Erratum in: Blood, Sep. 2012; vol. 20, No. 10, pp. 3531-3539.
Neely, G. G. et al., "Monocyte Surface-Bound IL-15 Can Function as an Activating Receptor and Participate in Reverse Signaling," Apr. 1, 2004, vol. 172, No. 7, pp. 4225-4234.
Nishimura, H. et al., "A novel autoregulatory mechanism for transcriptional activation of the IL-15 gene by a nonsecretable isoform of IL-15 generated by alternative splicing," FASEB J., Jan. 2005, vol. 19, No. 1, pp. 19-28.
Non-final Office Action for U.S. Appl. No. 12/069,235, dated Jul. 6, 2011, 13 pages.
Non-final Office Action for U.S. Appl. No. 12/069,235, dated Jun. 3, 2010, 17 pages.
Non-final Office Action for U.S. Appl. No. 12/437,279, dated May 10, 2012, 13 pages.
Non-final Office Action for U.S. Appl. No. 12/437,279, dated Oct. 7, 2010, 14 pages.
Ochoa, M. C. et al., "Antitumor Immunotherapeutic and toxic Properties of an HDL-Conjugated Chimeric IL-15 Fusion Protein," Cancer Res., Jan. 1, 2013, vol. 73, No. 1; pp. 139-149.
Olinger, G., "365. Pharmacological Control of In Vivo Tumor Regression by T Cells Engineered with CD19-Car Regulated with PDE5 Derived Destabilizing Domains", Molecular Therapy, Apr. 2019, vol. 27, No. 4S1, p. 173.
Olinger, G., "Fine tuning of CD19 CAR T cell activity using drug responsive domains", Oral presentation presented at: American Society of Gene & Cell therapy (ASGCT) 22nd Annual Meeting. Apr. 29-May 2, 2019; Washington, D.C., 14 pages.
Ols, M. "Enhancing Adoptive Immunotherapy with Pharmacologic Operating Systems", Oral presentation presented at: Medical University of South Carolina. Oct. 15, 2018; Charleston, SC, 25 pages.
Ols, M., et al., "Enhancing Adoptive Cell Therapies Through Regulation of IL12", Poster presented at: Keystone Symposium: Cancer Immunotherapy: Mechanistic Insights to Improve Clinical Benefit; Mar. 10-14, 2019; Whistler BC CA, 1 page.
Ols, M., et al., "Abstract LB-013: CAR-Ts armored with small molecule-regulated IL12 or CD40L cassettes for enhanced activity against solid tumors", Cancer Research Jul. 1, 2019, vol. 79, 13 Supplement, LB-013; 4 pages.
Ols, M., et al., "Abstract LB-013: CAR-Ts Armored With Small Molecule-Regulated IL12 or CD40L Cassettes for Enhanced Activity Against Solid Tumors", Poster presented at: Proceedings of the American Association for Cancer Research Annual Meeting 2019; Mar. 29-Apr. 3 2019, Atlanta, GA, 1 page.
Pacheco, Y. et al., "Despite an impaired response to IL-7, CD4R+ EM T cells from HIV-positive patients proliferate normally in response to IL-15 and its superagonist, RLI," AIDS, Sep. 10, 2011, vol. 25, No. 14, pp. 1701-1710.
Qian, L. et al., "Construction of a plasmid for co-expression of mouse membrane-bound form of IL-15 and RAE-1e and its biological activity," Plasmid, May 2011, vol. 65, No. 3, pp. 239-245. Epub Mar. 4, 2011.

(56) References Cited

OTHER PUBLICATIONS

Reardon, C. et al., "Dose-Dependent Exogenous Regulation of Membrane Bound Interleukin 15-Interleukin 15 Receptor Alpha Fusion Protein for Adoptive T-Cell Therapy", Poster Presented at: ASGCT 21st Annual Meeting 2018; May 16-19, 2018; Chicago, IL, 1 page.

Reardon, C., et al., "442. Kinetics of Lentiviral Integration and Transgene Expression, in Cell Lines and Primary Human T-Cells, Transduced with VSV-G Pseudotyped 3rd Generation Lentivirus", Molecular Therapy, Apr. 2019, vol. 27, No. 4S1, p. 211.

Reardon, C., et al., "Kinetics of lentiviral copy numbers and transgene expression in primary human T cells transduced with VSV-G pseudotyped 3rd generation lentivirus", Poster presented at: American Society of Gene & Cell therapy (ASGCT) 22nd Annual Meeting. Apr. 29-May 2, 2019; Washington, D.C., 1 page.

Richardson, C., et al., "Abstract 3580: Enhancing adoptive cell therapies through exogenous regulation", Cancer Research Jul. 1, 2018, vol. 78,13 Supplement, 3580; 4 pages.

Schebesta, M. "Enhancing Adoptive Cell Therapies Through Regulation of CD40 Ligand", Oral presentation presented at: Keystone Symposium: Cancer Immunotherapy Mechanistic Insights to Improve Clinical Benefit. Mar. 10-14, 2019; Whistler, BC, 11 pages.

Schebesta, M. et al., "Enhancing Adoptive Cell Therapies Through Regulation of CD40 Ligand", Poster presented at: Keystone Symposium: Cancer Immunotherapy Mechanistic Insights to Improve Clinical Benefit. Mar. 10-14, 2019; Whistler, BC, 1 page.

Shamah, S. "Development of a novel system for exogenous regulation of adoptive cell therapy", Oral presentation presented at: CAR-TCR Summit. Sep. 5-8, 2017; Boston, MA, 22 pages.

Shamah, S. "Enhancing Adoptive Cell Therapies through Exogenous Regulation", Oral presentation presented at: Summit for Cancer Immunotherapy. Oct. 27-30, 2018; Banff, AB, 25 pages.

Shamah, S. "Enhancing CAR-T Therapies with Regulated Immunomodulatory Factors", Oral presentation presented at: CAR-TCR Summit. Sep. 10-13, 2019; Boston, MA, 18 pages.

Shamah, S., et al., "P271 Titratable and reversible regulation of IL12 or IL15 with FDA-approved drugs enhances CAR-T therapy", Journal for ImmunoTherapy of Cancer Nov. 6, 2018, vol. 6, Suppl. 1: 114, p. 139.

Stone, J. D. et ai., "Design and characterization of a protein superagonist of IL-15 fused with IL-15R and a high-affinity T cell receptor," Biotechnol Prog., Nov. 2012, vol. 28, No. 6, pp. 1588-1597.

Sun, D. et al., "Exogenous In Vitro and In Vivo Regulation of Interleukin-12 Secretion From T Cells Using Destabilizing Domain Technology", Poster Presented at: ASGCT 21st Annual Meeting 2018; May 16-19, 2018; Chicago, IL, 1 page.

Suri, V. "Small Molecule Regulated Cytokine Expression Enables Potent and Durable Responses to Engineered T-Cell Therapy: Blood: American Society of Hematology," Blood, Nov. 29, 2018, vol. 132, Supplement 1:2045, 6 pages.

Suri, V., "Titratable therapeutic protein expression using FDA approved drugs", Oral presentation presented at: American Society of Gene & Cell therapy (ASGCT) 22nd Annual Meeting. Apr. 29-May 2, 2019; Washington, D.C.; 22 pages.

Suri, V., et al., "75. Titratable and Reversible Regulation of Therapeutic Proteins in Cell and Gene Therapies Using FDA Approved Drugs and a Modular Protein Stabilization Platform", Molecular Therapy, Apr. 2019, vol. 27, No. 4S1, pp. 40-41.

Suri, V., et al., "Small molecule regulated cytokine expression enables potent and durable responses to engineered T-cell therapy", Poster presented at: 60th American Society of Hematology Annual Meeting and Exposition; Dec. 1-4, 2018; San Diego, CA, 1 page.

Tagaya, Y. et al., "Generation of secretable and nonsecretable interleukin 15 isoforms through alternate usage of signal peptides," Cell Biology, Proc. Natl. Acad. Sci. USA, Dec. 1997, vol. 94, pp. 14444-14449.

Tran, K. "Abstract A220: Destabilizing domain technology facilitates exogenous regulation of IL15 and IL12 for adaptive T-cell therapy," Fourth CRI-CIMT-EATI-AACR International Cancer Immunotherapy Conference: Translating Science into Survival; Sep. 30-Oct. 3, 2, Cancer Immunol Res, Feb. 1, 2019, vol. 7, 2 Suppl., 2 pages.

Tran, K. et al., "Destabilizing Domain Technology Facilitates Exogenous Regulation of IL12 and IL15 for Adoptive T-Cell Therapy", Poster presented at: Fourth CRI-CIMT-EATI-AACR International Cancer Immunotherapy Conference: Translating Science into Survival; Sep. 30-Oct. 3, 2017; New York, NY, 1 page.

Turko et al., Potential Roles of Conserved Amino Acids in the Catalytic Domain of the cGMP-binding cGMP-specific Phosphodiesterase (PDE5), J Biol Chem, Mar. 13, 1998, vol. 273, No. 11, pp. 6460-6466.

Vincent, M. et al., "Tumor targeting of the IL-15 superagonist RLI by an anti-GD2 antibody strongly enhances its antitumor potency," Int. J. Cancer, 2013, vol. 133, 757-766 .

Wang, et al., "Conformational Variations of Both Phosphodiesterase-5 and Inhibitors Provide—The Structural Basis for the Physiological Effects of Vardenafil and Sildenafil. Molecular Pharmacology," Oct. 5, 2010, vol. 73, No. 1, pp. 1-15.

Wang, L. et al., "Overcoming intrinsic inhibitory pathways to augment the antineoplastic activity of adoptively transferred T cells: Re-tuning your CAR before hitting a rocky road," Oncolmmunology, Nov. 3, 2013, vol. 2, No. 11, pp. e26492-1-e26492-3.

Weisman, E., et al., "568. Regulation of CD40L Transgene Expression in Human CAR-T Cells Using FDA Approved Ligands", Molecular Therapy, Apr. 2019, vol. 27, No. 451, p. 266.

Weisman, E., et al., "Regulation of CD40 Ligand Transgene Expression in Human CAR-T Cells Using FDA Approved Drugs", Poster presented at: American Society of Gene & Cell therapy (ASGCT) 22nd Annual Meeting. Apr. 29-May 2, 2019; Washington, D.C., 1 page.

Wittnebel, S. et al., "Membrane-Bound Interleukin (IL)-15 on Renal Tumor Cells Rescues Natural Killer Cells from IL-2 Starvation-Induced Apoptosis," Cancer Res., Jun. 15, 2007, vol. 67, No. 12, pp. 5594-5599.

Wu C. M. et al., "Genetic engineering in primary human B cells with CRISPR-Cas9 ribonucleoproteins," Journal of Immunological Methods, Elsevier Science Publishers B.V.,Amsterdam, NL, Mar. 31, 2018, vol. 457, pp. 33-40.

Yuan, H. et al. "Transmembrane-Bound IL-15—Promoted Epithelial-Mesenchymal Transition in Renal Cancer Cells Requires the Src-Dependent Akt/GSK-3 / -Catenin Pathway," Neoplasia, May 2015, vol. 17, No. 5, pp. 410-420.

Zhang, L. et al., "Improving Adoptive T Cell Therapy by Targeting and Controlling IL-12 Expression to the Tumor Environment," Molecular Therapy, Feb. 1, 2011, vol. 19, No. 4, pp. 751-759.

"33rd Annual Meeting & Pre-Conference Programs of the Society for Immunotherapy of Cancer (SITC 2018)," Journal for ImmunoTherapy of Cancer, Biomed Central Ltd, London, UK, Nov. 6, 2018, vol. 6, Suppl. 1:114, pp. 1-205.

"Company Overview", Oral presentation presented at: MaidStone Life Science/William Blair 9th Annual Cancer Immunotherapy Conference, Mar. 20-21, 2019; New York, NY, 17 pages.

"Corporate Presentation", Oral presentation presented Nov. 2019, 20 pages.

"Corporate Presentation", Oral presentation presented Sep. 11, 2019, 18 pages.

"Corporate Presentation", Oral presentation presented Sep. 23, 2020, 24 pages.

Anguille S. et al., "Interleukin-15 Dendritic Cells Harness NK Cell Cytotoxic Effector Function in a Contact- and IL-15-Dependent Manner," PLos One, May 7, 2015, Vo. 10, No. 5, e0123340, eCollection 2015.

Banaszynski, L. A. et al., "A Rapid, Reversible, and Tunable Method to Regulate Protein Function in Living Cells Using Synthetic Small Molecules," Cell, Elsevier, Amsterdam, NL, Sep. 8, 2006, vol. 126, No. 5, pp. 995-1004.

Bessard, A. et al., "High antitumor activity of RLI, an interleukin-15 (IL-15)-1L-15 receptor fusion protein, in metastatic melanoma and colorectal cancer," Mol Cancer Ther., Sep. 2009 vol. 8, No. 9, pp. 2736-2745.

(56) References Cited

OTHER PUBLICATIONS

Cheng, T. et al., "Membrane?tethered proteins for basic research, imaging, and therapy," Med. Res. Rev., Nov. 2008, vol. 28, No. 6, pp. 885-928.

Chmielewski, M. et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Research, Jul. 6, 2011, vol. 71, No. 17, pp. 5697-5706.

Chu, B. W. et al., "Recent progress with FKBP-derived destabilizing domains," Bioorganic & Medicinal Chemistry Letters, Pergamon, Amsterdam, NL, Sep. 12, 2008, vol. 18, No. 22, pp. 5941-5944.

Clackson, T. et al., "Redesigning an FKBP-ligand interface to generate chemical dimerizers with novel specificity," Proc. Natl. Acad. Sci, U.S.A., Sep. 1, 1998, vol. 95, No. 18, pp. 10437-10442.

Dai, S. et al., "Prediction of the Tissue-Specificity of Selective Estrogen Receptor Modulators by Using a Single Biochemical Method," Proceedings of the National Academy of Sciences of the U.S.A., May 20, 2008. vol. 105, No. 20, pp. 7171-7176.

Desbois, M. et al., "IL-15 Trans-Signaling with the Superagonist RLI Promotes Effector/Memory CD8 + T Cell Responses and Enhances Antitumor Activity of PD-1 Antagonists," J. Immunol., Jul. 1, 2016, vol. 197, No. 1, pp. 163-178.

Dolinski, B., et al., "Enhancing Adoptive Cell Therapies Through Exogenous Regulation", Poster presented at: Keystone Symposium: Emerging Cellular Therapies: T Cells and Beyond (joint meeting with Lymphocytes and their Roles in Cancer); Feb. 11-15, 2018; Keystone, CO, 1 page.

Dolinski, B., et al., "Enhancing Adoptive Cell Therapies Through Exogenous Regulation", Poster presented at: AACR Annual Meeting 2018; Apr. 14-18, 2018; Chicago, IL, 1 page.

Dolinski, B., et al., "Regulation of in vivo anti-tumor activity of adoptively transferred CAR-T cells using FDA approved small molecule drugs", Poster presented at: The Society for Immunotherapy of Cancer (SITC) 33rd Annual Meeting; Nov. 7-11, 2018; Washington, D.C., 1 page.

Dolinski, B., et al., "Titratable and reversible regulation of IL12 or IL15 with FDA-approved drugs for enhanced CAR-T therapy", Poster presented at: The Society for Immunotherapy of Cancer (SITC) 33rd Annual Meeting; Nov. 7-11, 2018; Washington, D.C., 1 page.

Doty, R.T. et al., "Two Regions in the CD80 Cytoplasmic Tail Regulate CD80 Redistribution and T Cell Costimulation," The Journal of Immunology, Sep. 15, 1998, vol. 161, No. 6, pp. 2700-2707.

Elpek, K. G., et al., "Mature natural killer cells with phenotypic and functional alterations accumulate upon sustained stimulation with IL-15/IL-15R? complexes," PNAS, Dec. 14, 2010, vol. 107, No. 50, pp. 21647-21652.

"Epardaud, M., et al.,""Interleukin-15/Interleukin-15RA Complexes Promote Destruction of Established Tumors by Reviving Tumor-Resident CD8+ T Cells,""Cancer Res., Apr. 15, 2008, vol. 68, No. 8, pp. 2972-2983."

Fanning, S. et al., "The SERM/SERD Bazedoxilene Disrupts ESR1 Helix 12 to Overcome Acquired Hormone Resistance in Breast Cancer Cells. Elife," Nov. 29, 2018, Epub Apr. 24, 2018, vol. 7, pp. 1-26.

Felices, M. et al., "Continuous treatment with IL-15 exhausts human NK cells via a metabolic defect," JCI Insight., Feb. 8, 2018, vol. 3, No. 3:e96219, pp. 1-14.

Final Office Action for U.S. Appl. No. 12/069,235, dated Nov. 4, 2011, 20 pages.

Final Office Action for U.S. Appl. No. 12/437,279, dated Apr. 1, 2011, 10 pages.

Final Office Action for U.S. Appl. No. 12/437,279, dated Jan. 22, 2013, 13 pages.

Fleury, M. "Regulation of CD40L Transgene Expression in Human CAR-T cells using FDA Approved Ligands", Oral presentation presented at: AACR Immune Cell Therapies for Cancer. Jul. 19-22, 2019; San Francisco, CA, 12 pages.

Foa, R. et al., "IL2 treatment for cancer: from biology to gene therapy," British J. Cancer, Dec. 1992, vol. 66, No. 6, pp. 992-998.

Giron-Michel, J. et al., "Membrane-bound and soluble IL-15/IL-15R complexes display differential signaling and functions on human hematopoietic progenitors" Blood, Oct. 1, 2005, vol. 106, No. 7, pp. 2302-2310, Epub Jun. 23, 2005.

Gori, J. "Enhancing Adoptive Cell Therapies through Exogenous Regulation," Oral presentation presented at: Genome Writers Guild Annual Conference. Jul. 19-21, 2018; Minneapolis, MN, 23 pages.

Gori, J., et al., "P238 Regulation of in vivo anti-tumor activity of adoptively transferred CAR-T cells using FDA approved small molecule drugs", Journal for ImmunoTherapy of Cancer Nov. 6, 2018, vol. 6, Suppl 1:114, p. 121.

Hurton, L. "Tethered IL-15 to Augment the Therapeutic Potential of T Cells Expressing Chimeric Antigen Receptor: Maintaining Memory Potential, Persistence, and Antitumor Activity," 2014, UT GSBS Dissertations and Theses (Open Access), Paper 421, 173 pages.

Hurton, L. V. et al., "Tethered IL-15 augments antitumor activity and promotes a stem-cell memory subset in tumor-specific T cells," Proc Natl Acad Sci USA, Nov. 29, 2016, vol. 113, No. 48, pp. E7788-E779.first published Nov. 14, 2016.

Imamura, M. et al., "Autonomous Growth and Increased Cytotoxicity of Natural Killer Cells Expressing Membrane-Bound Interleukin-15," Blood, Aug. 14, 2014, vol. 124, No. 7, pp. 1081-1088.

* cited by examiner

CA2 COMPOSITIONS AND METHODS FOR TUNABLE REGULATION

CROSS REFERENCE TO RELATED APPLICATIONS

This application claims benefit of priority to U.S. Provisional Application No. 62/898,520, filed Sep. 10, 2019. The entire contents of the aforementioned application are incorporated herein by reference in their entireties.

REFERENCE TO THE SEQUENCE LISTING

The instant application contains a Sequence Listing which has been submitted electronically in ASCII format and is hereby incorporated by reference in its entirety. Said ASCII copy, created on Sep. 10, 2020, is named 268052_473951_SL.txt and is 178,693 bytes in size.

FIELD

The present disclosure relates to drug responsive domains (DRDs) derived from human carbonic anhydrase 2 (CA2) which can modulate protein stability for at least one payload comprising human interleukin 15 (IL15), compositions and methods of use thereof. Provided in the present disclosure are polypeptides of CA2 biocircuit systems, CA2 effector modules, stimulus response elements (SREs), polynucleotides encoding the same, vectors and cells containing the polypeptides and/or polynucleotides for use in augmenting responses from immune cells.

BACKGROUND

Utilization of the DRD technology described herein with methods of regulating cytokine function and/or expression represent a significant improvement on existing immunotherapy strategies, and can expand the universe of protein therapeutics that can be safely and effectively incorporated into gene transfer and adoptive T cell transfer (ACT) therapies, including applications that have previously been considered unsuitable for therapeutic use. Improved Natural Killer cells (NK cells), Tumor Infiltrating Lymphocytes (TIL) and T cell-based immunotherapies are needed to enhance and improve the functionality of the treatments, for example, by improving the persistence and/or survival of engineered immune cells, for use in various immunotherapies upon administration to subjects. Provided are CA2 DRDs linked to human IL15, modified cells comprising such DRDs, compositions, and methods that meet such needs.

SUMMARY

The present disclosure provides novel protein domains derived from human carbonic anhydrase 2 (CA2) displaying small molecule-dependent stability. Such protein domains are called drug responsive domains (DRDs). In the absence of its binding (i.e., stabilizing) ligand, the DRD is destabilizing and causes degradation of a payload operably linked to the DRD (e.g., a protein of interest (POI)), while in the presence of its binding ligand, the DRD and its operably linked payload are stabilized. The stability of the DRD and its operably linked payload is dependent on the dose of the binding ligand.

In some embodiments, the present disclosure provides a stimulus response element (SRE), which may comprise a drug responsive domain (DRD) derived from human carbonic anhydrase 2 (CA2, having the amino acid sequence of SEQ ID NO: 1) in whole or in part. In one embodiment, the DRD may be derived from the full-length CA2 polypeptide (SEQ ID NO: 1). In some embodiments, the DRD may be derived from a portion or region of the human carbonic anhydrase. The portion or region of CA2 may be selected from amino acids 2-260 of CA2 (SEQ ID NO: 2).

In some embodiments, the SRE may include a DRD comprising one, two, three, four or more mutations in CA2 relative to SEQ ID NO:1 or SEQ ID NO: 2. In some embodiments, the SRE may include a DRD comprising one, two, three, four or more amino acid substitutions in CA2 relative to SEQ ID NO:1 or SEQ ID NO: 2.

In some embodiments, the SRE may include a DRD comprising one, two, three, four or more mutations in a portion of CA2. In some embodiments, the SRE may include a DRD comprising one, two, three, four or more mutations in CA2 or portion thereof, and may further comprise additional amino acids. In some embodiments, the SRE may include a DRD comprising one, two, three, four or more amino acid substitutions in a portion of CA2. In some embodiments, the SRE may include a DRD comprising one, two, three, four or more amino acid substitutions in CA2 or portion thereof, and may further comprise additional amino acids.

Also provided herein are isolated polypeptide variants comprising at least one mutation relative to SEQ ID NO: 1. Non-limiting examples of CA2 mutations relative to SEQ ID NO: 1 include M1del and L156H. In another aspect, a DRD is a polypeptide comprising or consisting of the amino acid sequence of SEQ ID NO:4, wherein the CA2 mutation comprises Mdel1 and L156H relative to SEQ ID NO: 1. In another aspect, the DRD is a polypeptide containing the amino acid deletion M1del and amino acid substitution L156H relative to SEQ ID NO: 1 and may further comprise additional amino acids. In another aspect, the DRD is a polypeptide consisting of the amino acid sequence of SEQ ID NO:4.

Also provided herein are biocircuit systems that include at least one effector module. The effector module of the biocircuit may include a stimulus response element (SRE), and the SRE may include a DRD derived from a human carbonic anhydrase 2 (CA2; SEQ ID NO: 1) or a mutant thereof comprising one, two, three, four or more mutations of CA2 relative to the amino acid sequence of SEQ ID NO: 1 or SEQ ID NO: 2. In some embodiments, the effector module of the biocircuit includes an SRE including a DRD comprising one, two, three, four or more amino acid substitutions in CA2 relative to SEQ ID NO:1 or SEQ ID NO: 2. The biocircuits may also include at least one payload, which may be attached, appended or associated with the SRE. The payload may include but is not limited to (i) a human IL15 comprising the amino acid sequence of SEQ ID NO: 8.

The SRE of the biocircuit system may include one, two, three or more mutations of CA2 (SEQ ID NO: 1 or SEQ ID NO: 2) such as, but not limited to, Mdel1 and L156H. The SRE of the biocircuit system may include one, two, three or more amino acid substitutions in CA2 (SEQ ID NO: 1 or SEQ ID NO: 2), such as, but not limited to L156H.

In some embodiments, the SRE in the CA2 biocircuit system may be CA2 having the mutations M1del and L156H, wherein the numbering is relative to the amino acid sequence of SEQ ID NO:1 (SEQ ID NO: 4). In some embodiments, the SRE is a polypeptide comprising or consisting of the amino acid sequence of SEQ ID NO:4. In some embodiments, the SRE is a polypeptide consisting of the amino acid sequence of SEQ ID NO:4.

The biocircuit system described herein may include SREs that are responsive to one or more stimuli.

In some embodiments, the stimulus may be a small molecule, wherein the small molecule is acetazolamide (ACZ).

In another aspect, the present disclosure provides an effector module comprising at least one payload. In some embodiments, the effector module comprises an SRE comprising a CA2 DRD operably linked to an IL15 payload. In some embodiments, the IL15 payload comprises the amino acid sequence of SEQ ID NO: 8. In some embodiments, the IL15 payload may be encoded in part by a nucleic acid sequence comprising the nucleotide sequence of SEQ ID NO: 9. In some embodiments, the IL15 payload is a membrane-bound form of IL15. In some embodiments, the IL15 payload is a membrane-bound form of IL15 comprising a functional IL15 component or domain, a transmembrane domain and an intracellular tail. In some embodiments, the IL15 payload is a membrane-bound form of IL15 comprising a functional IL15 component or domain, a transmembrane domain, an intracellular tail and a leader sequence. In some embodiments, the present disclosure provides an SRE comprising a CA2 DRD operably linked to a membrane-bound IL15 polypeptide. In some embodiments, the present disclosure provides an SRE comprising a CA2 DRD operably linked to a membrane-bound IL15 polypeptide, wherein the membrane-bound IL15 polypeptide comprises, from N-terminal to C-terminal, a leader sequence, an IL15 polypeptide comprising the amino acid sequence of SEQ ID NO: 8, a peptide linker, a transmembrane domain, and an intracellular tail.

In another aspect, the present disclosure provides a method of making a modified or genetically engineered cell comprising introducing a polynucleotide encoding an effector module into the cell. In some embodiments, the modified or engineered cell is an immune cell. In some embodiments, the immune cell is a T cell, a natural killer (NK) cell or a tumor infiltrating lymphocyte (TIL). In some embodiments, the polynucleotide encodes a CA2 DRD operably linked to an IL15 payload. In some embodiments, the polynucleotide encodes a CA2 DRD operably linked to a membrane-bound IL15 payload. In some embodiments, the polynucleotide is introduced into the cell by a non-viral vector delivery method. In some embodiments, the polynucleotide is introduced into the cell by viral transduction. In some embodiments, the polynucleotide in introduced into the cell by lentiviral transduction. In some embodiments, the polynucleotide is introduced into the cell by lentiviral transduction into a T cell, an NK cell or a TIL. In some embodiments, the present disclosure provides a method of making a modified or genetically engineered T cell, NK cell or TIL comprising introducing a polynucleotide encoding a CA2 DRD operably linked to a membrane-bound IL15 payload into the T cell, NK cell or TIL by a viral vector, such as a lentiviral vector.

In another aspect, the present disclosure provides a method of treatment, comprising (a) administering a modified cell comprising a recombinant construct comprising an SRE linked to a payload of the present disclosure or a composition comprising a plurality of such modified cells to a subject having a disease or condition, and (b) administering to the subject a therapeutically effective amount of a stimulus to which the SRE responds. In some embodiments of this aspect, the disease or condition is a cancer, a neoplasm or a tumor. In some embodiments, the SRE is a CA2 DRD. In some embodiments, the payload is IL15 or membrane-bound IL15. In some embodiments, the modified cells comprise a CA2 SRE operably linked to an IL15 payload. In some embodiments, the modified cells comprise a CA2 SRE operably linked to a membrane-bound IL15 payload. In some embodiments, the stimulus is acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the modified cells comprise a CA2 SRE operably linked to a membrane-bound IL15 payload and the stimulus is acetazolamide. In some related aspects, the modified cells are engineered or modified immune cells, for example, CA2-IL15 biocircuits and systems may be used with immune cells including T cells such as CD8+ T cells and CD4+ T cells, natural killer (NK) cells, NK T cells, cytotoxic T lymphocytes (CTLs), tumor infiltrating lymphocytes (TIL), lymphokine-activated killer (LAK) cells, memory T cells, regulatory T cells (Tregs), helper T cells, cytokine-induced killer (CIK) cells, and any combination thereof. In other embodiments, immune stimulatory cells for ACT may be generated from embryonic stem cell (ESC) and induced pluripotent stem cell (iPSC). In some embodiments, autologous or allogeneic immune cells are used for ACT. In some embodiments, the immune cells are T cells, TIL or NK cells. In some embodiments, the immune cells are NK cells derived from iPSCs, cord blood, or peripheral blood mononuclear cells, wherein the modified immune cells exhibit increased or longer expansion and/or persistence in the subject than in a subject administered the same or about the same dosage amount of a reference cell composition lacking the SRE linked to a payload.

In another aspect, the present disclosure provides a method of treating a malignant tumor in a subject, comprising (a) administering a modified T cell, modified NK cell or a modified TIL, wherein the T cell, NK cell or TIL comprises a recombinant construct comprising an SRE linked to a payload of the present disclosure or a composition comprising a plurality of such modified cells to the subject, and (b) administering to the subject a therapeutically effective amount of a stimulus to which the SRE responds. In some embodiments, the tumor expresses a tumor-associated antigen. In some embodiments, the modified T cell or modified NK cell further comprises a chimeric antigen receptor (CAR) or T cell receptor (TCR) that comprises an antigen-binding domain specific to the tumor-associated antigen. In some embodiments, the modified T cell or modified NK cell comprises a CAR comprising an antigen-binding domain specific to the tumor-associated antigen. In some embodiments, the modified T cell, modified NK cell or modified TIL comprise an SRE that is a CA2 DRD. In some embodiments, the modified T cell, modified NK cell or modified TIL comprise a payload that is IL15 or membrane-bound IL15. In some embodiments, the modified the modified T cell, modified NK cell or modified TIL comprise a CA2 SRE operably linked to an IL15 payload. In some embodiments, the modified the modified T cell, modified NK cell or modified TIL comprise a CA2 SRE operably linked to a membrane-bound IL15 payload. In some embodiments, the stimulus is acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the modified cells comprise a CA2 SRE operably linked to a membrane-bound IL15 payload and the stimulus is acetazolamide.

In another aspect, the present disclosure provides polynucleotides and vectors encoding the biocircuit system, and a pharmaceutical composition that includes the biocircuit system and a pharmaceutically acceptable excipient.

In another aspect, the present disclosure provides recombinant proteins encoded by the polynucleotides of the disclosure. In some embodiments, the recombinant proteins comprise an effector module comprising a CA2 DRD operably linked to an IL15 payload.

BRIEF DESCRIPTION OF THE DRAWINGS

The foregoing and other objects, features, and advantages will be apparent from the following description of particular embodiments of the present disclosure, as illustrated in the accompanying drawings. The drawings are not necessarily to scale; emphasis instead being placed upon illustrating the principles of various embodiments of the present disclosure.

FIG. 5A shows in vivo expansion of T cells expressing constitutive IL15 (IL15-292 and IL15-294) and regulated IL15 (IL15-293 and IL15-295) constructs. FIG. 5B shows in vivo expansion of bystander NK cells under the same conditions. T cell and NK cell frequencies in blood was determined by flow cytometry. FIG. 5C shows expression of IL15 on T cells on day 25, analyzed by flow cytometry. Empty vector (EV) transduced cells were used as controls.

FIG. 7A shows flow cytometry analyses for expression of mbIL15 and CAR in peripheral blood T cells. FIG. 7B shows tumor growth curves of individual mice implanted with CD19+ Nalm6-Luc tumors and infused with T cells that were transduced with lentiviral vectors expressing CD19 CAR with or without constitutive or regulated mbIL15. FIG. 7C shows tumor growth curves with group averages and standard error. FIG. 7D shows frequency of T cells in blood collected from animals on days 7, 14 and 21 post T cell infusion. FIG. 7E shows frequency of T cells in bone marrow harvested from animals on day 14 post T cell infusion.

FIG. 8 shows analyses of TILs from patient tumor samples after a culturing process and after transduction with mbIL15-expressing constructs.

DETAILED DESCRIPTION

Figure 1:
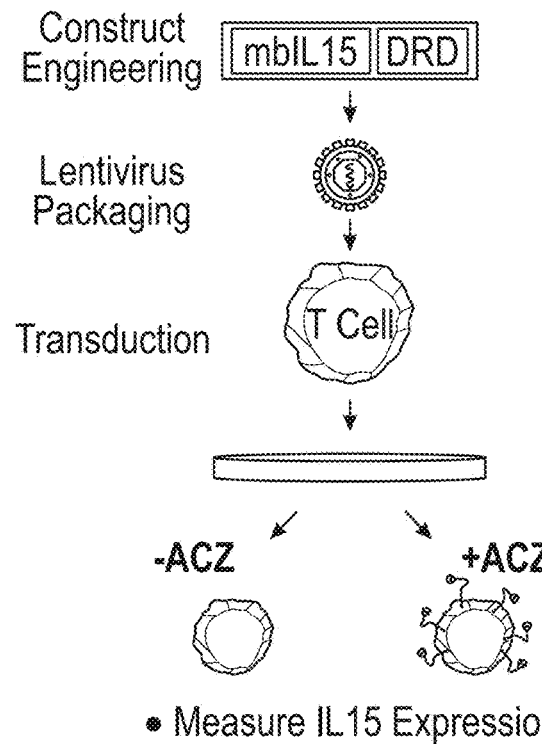
FIG. 1 depicts a representative procedure for in vitro characterization and/or validation of ACZ-regulated membrane-bound IL15 (mbIL15) expression in T cells.

The details of one or more embodiments of the present disclosure are set forth in the accompanying description below. Although any materials and methods similar or equivalent to those described herein can be used in the practice or testing of the present disclosure, the preferred materials and methods are now described. Other features, objects and advantages of the present disclosure will be apparent from the description. In the description, the singular forms also include the plural unless the context clearly dictates otherwise. Unless defined otherwise, all technical and scientific terms used herein have the same meaning as commonly understood by one of ordinary skill in the art to which the present disclosure belongs. In the case of conflict, the present description will control.

Cancer immunotherapy aims to induce or restore the reactivity of the immune system towards cancer. Significant advances in immunotherapy research have led to the development of various strategies which may broadly be classified into active immunotherapy and passive immunotherapy. In general, these strategies may be utilized to directly kill cancer cells or to counter the immunosuppressive tumor microenvironment. Active immunotherapy aims at induction of an endogenous, long-lasting tumor-antigen specific immune response. The response can further be enhanced by non-specific stimulation of immune response modifiers such as cytokines. In contrast, passive immunotherapy includes approaches where immune effector molecules such as tumor-antigen specific cytotoxic T cells or antibodies are administered to the host. This approach is short lived and requires multiple applications.

Efficient T cell activation requires three signals, T cell receptor (TCR) signaling (Signal 1), activation by co-stimulatory molecules (Signal 2), and immune-stimulatory cytokines (Signal 3). So far, the majority of the CAR-based immunotherapies designed and discussed possess Signal 1 and Signal 2; however, Signal 3, generally provided by homeostatic cytokines, is typically absent in conventional CAR T cells and is also less abundant in the tumor microenvironment.

Therefore, there exists a need to engineer T cells (including for example, CAR T cells) that are capable of supplying additional cytokine signaling to satisfy the need for Signal 3 for optimal T cell activation. The major cytokines involved in T cell activation, which encompass Signal 3 cytokines, belong to γc class like IL-2, IL-7, IL-15, IL-21, and IL-9. These cytokines control T cell survival and proliferation, which ultimately has significant roles in T cell persistence and efficacy. These cytokines are currently employed in ex vivo expansion of CAR T cells prior to therapy in combinations or alone.

Supporting T cell longevity via continuous exposure to IL15 however may have risk, because chronic high exposure to IL-15 may cause aberrant T cell proliferation or toxicities. In humans, dysregulated IL15 production, elevated serum levels, or abnormal IL15 signaling has been associated with autoimmune disease and may be involved in the pathogenesis of large granular lymphocytic leukemia and cutaneous T cell lymphoma.

Natural killer (NK) cells are members of the innate lymphoid cell family and characterized in humans by expression of the phenotypic marker CD56 (neural cell adhesion molecule) in the absence of CD3 (T cell co-receptor). NK cells are potent effector cells of the innate immune system which mediate cytotoxic attack without the requirement of prior antigen priming, forming the first line of defense against diseases including cancer malignancies and viral infection.

Several pre-clinical and clinical trials have demonstrated that adoptive transfer of NK cells is a promising treatment approach against cancers such as acute myeloid leukemia (Ruggeri et al., Science; 2002, 295: 2097-2100; and Geller et al., Immunotherapy, 2011, 3: 1445-1459). Adoptive transfer of NK cells expressing CAR such as DAP12-Based Activating CAR revealed improved eradication of tumor cells (Topfer et al., J Immunol. 2015; 194:3201-3212). NK cell engineered to express a CS-1 specific CAR also displayed enhanced cytolysis and interferon-γ (IFN-γ) production in multiple myeloma (Chu et al., Leukemia, 2014, 28(4): 917-927).

NK cell activation is characterized by an array of receptors with activating and inhibitory functions. The important activation receptors on NK cells include CD94/NKG2C and NKG2D (the C-type lectin-like receptors), and the natural cytotoxicity receptors (NCR) NKp30, NKp44 and NKp46, which recognize ligands on tumor cells or virally infected cells. NK cell inhibition is essentially mediated by interactions of the polymorphic inhibitory killer cell immunoglobulin-like receptors (KIRs) with their cognate human-leukocyte-antigen (HLA) ligands via the alpha-1 helix of the HLA molecule. The balance between signals that are generated from activating receptors and inhibitory receptors mainly determines the immediate cytotoxic activation.

NK cells may be isolated from peripheral blood mononuclear cells (PBMCs) and cord blood, or derived from human embryonic stem (ES) cells and induced pluripotent stem cells (iPSCs). NK cells may be further expanded for adoptive immunotherapy. Strategies and protocols useful for the expansion of NK cells may include interleukin 2 (IL2) stimulation and the use of autologous feeder cells, or the use of genetically modified allogeneic feeder cells. In some aspects, NK cells can be selectively expanded with a combination of stimulating ligands including IL15, IL21, IL2, 41BBL, IL12, IL18, MICA, 2B4, LFA-1, and BCM1/SLAMF2 (e.g., US patent publication NO. US20150190471).

NK cell-based immunotherapy is rapidly evolving due to the ability of NK cells to directly lyse tumor targets, the emergence of antibodies and molecules that mediate NK cell-driven antibody-dependent cell-mediated cytotoxicity (ADCC), and the ability of NK cells to induce inflammatory responses. NK cells are being exploited in clinical trials using autologous and allogeneic NK cell infusion strategies alone or with hematopoietic stem cell transplantation. In addition, other modalities of NK cell therapy, such as use of NK cell line products and NK cells transduced with chimeric antigen receptors (CARs) are on the horizon. Others have shown that in vivo persistence and expansion of NK cells correlate with antitumor efficacy in patients with advanced AML. Among the strategies being evaluated preclinically to address this issue, utilization of cytokines to induce NK cell persistence and expansion seems to dominate current clinical trials. IL15 has a known physiologic role on NK cell development and homeostasis without stimulating regulatory T cells but experimental findings indicate that continuous treatment with IL-15 results in a functional NK cell changes consistent with exhaustion. For example, continuously IL15-treated NK cells have been experimentally shown in at least one study to initially display better proliferation and expansion during a 9-day experimental continuous treatment with IL15 but were more susceptible to cell death. In addition, cell cycle gene expression data show that NK cells continuously dosed with IL15 are enriched for expression of cell cycle checkpoint and arrest genes, indicating that at day 9 of culture these cells transition to an arrested state due to cellular stress.

Tumor infiltrating lymphocytes (TIL) consist of all lymphocytic cell populations that have invaded the tumor tissue. The cellular constituents of tumors include TIL, NK cells, macrophages, dendritic cells, and myeloid lineage cells, suggesting a productive immune response. However, most of the immune cells residing in the tumor microenvironment are functionally impaired in some manner because many of the immune cell populations are converted to phenotypes that further impair immune system responses. Tumors are able to recruit Treg lymphocytes, TAMs, myeloid-derived suppressor cells (MDSCs), and cancer-associated fibroblasts (CAFs) to aid them in escape from immune recognition. Tregs and MDSCs have both been shown to immunosuppressing functions, limiting response by TIL and other cells. Depletion of CD4+ Tregs improves clinical responses in patients during immune reconstitution treated with autologous TIL during TIL therapy. In mouse models, even small numbers of Tregs can abrogate effective CD8+ T cell-mediated adoptive cell therapy.

TIL have been described in a number of solid tumors, including breast cancer and melanoma, and are emerging as an important biomarker in predicting the efficacy and outcome of treatment. In breast cancer, TIL are comprised primarily of cytotoxic (CD8+) and helper (CD4+) T cells, and a smaller proportion of B- and NK cells. Breast cancer patients who had advanced tumors with higher CD8+ T cell infiltrates or a high density of TIL have more favorable outcomes. In melanoma, TIL therapy is improved by including lymphodepleting preparative regimens prior to cell infusion. Investigations in humans and murine models of melanoma suggest that lymphodepletion depletes negative regulatory cells including regulatory T cells (Tregs) and peripheral myeloid-derived suppressor cells, which can suppress T cell proliferation in melanoma patients, both of which aid in the proliferation of adoptively transferred T lymphocytes.

Adoptive cell therapy (ACT) using TIL is a personalized cancer treatment based on the infusion of autologous CD4+ and CD8+T lymphocytes expanded from tumors in the presence of interleukin-2 (IL-2) alone or in combination with IL-7, IL-15, and/or IL-21. TIL are polyclonal populations enriched for lymphocytes recognizing tumor-specific antigens, including shared tumor-associated antigens as well as individual tumor neoantigens. Studies at the National Cancer Institute (NCI) initiated in 1980 demonstrated tumor regression in selected patients receiving adoptive transfer of lymphokine-activated killer cells in combination with recombinant IL-2. Subsequent methods for large-scale expansion of human TIL, simplified and shortened TIL production processes, and improved patient preconditioning and treatment protocols have resulted in enhanced response rates for patients. However, complete response rates for TIL therapy are still quite low and need improvement.

The present disclosure provides systems, compositions, immunotherapeutic agents and methods that avoid the issues of continuously dosed or expressed IL15 by providing tunable regulation of IL15 gene expression and function for cancer immunotherapy. The present invention also provides biocircuit systems, effector modules, stimulus response elements (SREs) and IL15 payloads, as well as polynucleotides encoding any of the foregoing. In one aspect, the systems, compositions, immunotherapeutic agents and other components of the invention can be controlled by a separately added stimulus, which provides a significant flexibility to regulate cancer immunotherapy.

The tunable nature of the systems and compositions of the invention has the potential to improve the potency and duration of the efficacy of immunotherapies. The ability to reversibly increase, decrease or silence the biological activity of adoptively transferred cells using compositions of the present invention allows maximizing the potential of cell therapy, which is not available using a "kill switch" that will terminate the therapy. Without being bound by any particular theory, it is believed that the long-term engraftment of T cells can be achieved through temporal, intermittent exposure of IL15 in NK cells, TIL and T cell groups used in various therapies, including cancer immunotherapies, without dysregulated proliferation or activation and no phenotypic, functional, or chromosomal anomalies.

The present invention provides methods for fine tuning of immunotherapy after administration to patients. This in turn improves the safety and efficacy of immunotherapy and increases the subject population that may benefit from immunotherapy. Effector module(s) as described and disclosed in the present disclosure are independently associated, or integral therewith, one or more stimulus response elements (SREs), which may be operably linked to an IL15, to form an effector module comprising mbIL15. The biocircuits, SRE, DRDs of the present disclosure can be employed with immune cells and may provide a desired signaling enabling adoptively transferred NK cells and T cells, including TIL, to prolong persistence, thereby providing durable immune surveillance and therapeutic potential.

As used herein, a "biocircuit" or "biocircuit system" is defined as a circuit within or useful in biologic systems comprising a stimulus and at least one effector module responsive to a stimulus, where the response to the stimulus produces at least one signal or outcome within, between, as an indicator of, or on a biologic system. Biologic systems are generally understood to be any cell, tissue, organ, organ system or organism, whether animal, plant, fungi, bacterial, or viral. It is also understood that biocircuits may be artificial circuits which employ the stimuli or effector modules taught by the present disclosure and effect signals or outcomes in acellular environments such as with diagnostic, reporter systems, devices, assays or kits.

The biocircuits of the present disclosure include at least one effector module. As used herein, an "effector module" is a single or multi-component construct or complex comprising at least (a) one or more stimulus response elements (SREs) and (b) one or more payloads (e.g., proteins of interest (POIs)). In some embodiments, the effector module comprises one SRE and one payload.

Effector modules may be designed to include one or more payloads, one or more SREs, one or more cleavage sites, one or more signal sequences and one or more additional features including the presence or absence of one or more linkers.

In one embodiment, the effector module comprises at least one immunotherapeutic agent, for example, IL15.

Effector modules, including their SREs and payloads, may be nucleic acid-based, protein-based or a combination thereof. They may be in the form of DNA, RNA, mRNA, proteins, fusion proteins, or any combination of the foregoing. In one embodiment, the effector module is a fusion protein. In one embodiment, the effector module is encoded by nucleic acid, such as DNA.

Effector modules, including their SREs and payloads may individually, collectively or independently comprise peptides, polypeptides or proteins. At the protein level, such payload may be any natural or artificial peptide or polypeptide or fragment thereof. Natural peptides or polypeptide components of the payload may be derived from any known protein of any species.

Effector modules may be designed to operate in groups of one, two, three, four or more modules. When more than one effector module is utilized in a biocircuit, it is known as an effector module system of that biocircuit.

As used herein a "stimulus response element" (SRE) is a component of an effector module which is joined, attached, linked to or associated with one or more payloads and in some instances, is responsible for the responsive nature of the effector module to one or more stimuli. As used herein, the "responsive" nature of an SRE to a stimulus may be characterized by a covalent or non-covalent interaction, a direct or indirect association or a structural or chemical reaction to the stimulus. Further, the response of any SRE to a stimulus may be a matter of degree or kind. The response may be a partial response. The response may be a reversible response. The response may ultimately lead to a regulated signal or output. Such output signal may be of a relative nature to the stimulus, e.g., producing a modulatory effect of between 1% and 100% or a factored increase or decrease such as 2-fold, 3-fold, 4-fold, 5-fold, 10-fold or more. In some embodiments, the SRE is a polypeptide operably linked to a polypeptide payload. In some embodiments, the SRE is a polypeptide fused to a polypeptide payload.

In some embodiments, the present disclosure provides methods for modulating protein expression, function or level. In some aspects, the modulation of protein expression, function or level refers to modulation of expression, function or level by at least about 20%, such as by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

Drug responsive domains (DRDs) are small protein domains that can be appended to a target protein of interest. In some embodiments, a DRD is operably linked to a target protein of interest. DRDs render the attached protein of interest unstable in the absence of a DRD-binding ligand. However, when a specific small molecule ligand binds its intended DRD as a ligand binding partner, the instability is reversed, and protein function is restored. The conditional nature of DRD stability allows a rapid and non-perturbing switch from stable protein to unstable substrate for degradation. Moreover, its dependency on the concentration of its ligand further provides tunable control of degradation rates. The term drug responsive domain (DRD) is interchangeable with the term destabilizing domain (DD).

In one embodiment, the SRE is a drug responsive domain (DRD). In some embodiments, the CA2 drug responsive domains described herein may be used as SREs in the biocircuit systems of the present disclosure in association with any of the IL15 payloads taught herein.

Regions or portions or domains of wild type proteins (e.g., CA2) may be utilized as SREs/DRDs in whole or in part. In one embodiment, the SRE is derived from parent protein CA2 or from a mutant CA2 protein. In various embodiments, the DRD comprises one, two, three, or four or more mutations compared to the parent CA2 protein, for example, a human CA2 SEQ ID NO: 1 having the amino acid sequence:

```
MSHHWGYGKH NGPEHWHKDF PIAKGERQSP VDIDTHTAKY
DPSLKPLSVS YDQATSLRIL NNGHAFNVEF DDSQDKAVLK
GGPLDGTYRL IQFHFHWGSL DGQGSEHTVD KKKYAAELHL
VHWNTKYGDF GKAVQQPDGL AVLGIFLKVG SAKPGLQKVV
DVLDSIKTKG KSADFTNFDP RGLLPESLDY WTYPGSLTTP
PLLECVTWIV LKEPISVSSE QVLKFRKLNF NGEGEPEELM
VDNWRPAQPL KNRQIKASFK
``` or SEQ ID NO: 2 having the amino acid sequence:

```
 SHHWGYGKH NGPEHWHKDF PIAKGERQSP VDIDTHTAKY
DPSLKPLSVS YDQATSLRIL NNGHAFNVEF DDSQDKAVLK
GGPLDGTYRL IQFHFHWGSL DGQGSEHTVD KKKYAAELHL
VHWNTKYGDF GKAVQQPDGL AVLGIFLKVG SAKPGLQKVV
DVLDSIKTKG KSADFTNFDP RGLLPESLDY WTYPGSLTTP
PLLECVTWIV LKEPISVSSE QVLKFRKLNF NGEGEPEELM
VDNWRPAQPL KNRQIKASFK.
```

Human CA2 having the amino acid sequence of SEQ ID NO: 1 is encoded by the polynucleotide having a nucleic acid sequence of SEQ ID NO: 3:

```
atgtcccatcactgggggtacggcaaacacaacggacctgagca
ctggcataaggacttccccattgccaagggagagcgccagtccc
ctgttgacatcgacactcatacagccaagtatgaccottccctg
```

-continued
```
aagcccctgtctgtttcctatgatcaagcaacttccctgaggat
cctcaacaatggtcatgctttcaacgtggagtttgatgactdca
ggacaaagcagtgctcaagggaggacccctggatggcacttaca
gattgattcagtttcactttcactggggttcacttgatggacaa
ggttcagagcatactgtggataaaaagaaatatgctgcagaact
tcacttggttcactggaacaccaaatatggggattttgggaaag
ctgtgcagcaacctgatggactggccgttctaggtattttttg
aaggttggcagcgctaaacgggccttcagaaagttgttgatgt
gctggattccattaaaacaaagggcaagagtgctgacttcacta
acttcgatcctcgtggcctccttcctgaatccctggattactgg
acctacccaggctcactgaccaccccctcctcttctggaatgtgt
gacctggattgtgctcaaggaacccatcagcgtcagcagcgagc
aggtgttgaaattccgtaaacttaacttcaatggggaggtgaa
cccgaagaactgatggtggacaactggcgcccagctcagccact
gaagaacaggcaaatcaaagcttccttcaaa
```

As used herein, the phrase "derived from" as it relates to effector modules, SREs or payloads means that the effector module, SRE or payload originates at least in part from the stated parent molecule or sequence. For example, in designing an SRE, such SRE may be derived from an epitope or region of a naturally occurring protein but then have been modified in any of the ways taught herein to optimize the SRE function.

In some embodiments, the DRDs of the present disclosure may be derived from CA2 (SEQ ID NO: 1; Uniprot ID: P00918) which may be stabilized by ligands such as small molecule inhibitors of CA2. As used herein, the term "CA2 WT", refers to the human wildtype CA2 protein sequence, which is defined as SEQ ID NO: 1, with the GenBank Access NO. P00918. In some aspects, the DRDs may be derived from CA2 of SEQ ID NO: 2.

In some embodiments, DRDs may be derived from CA2 having amino acids 2-260 of the parent CA2 sequence. This is referred to herein as an M1del mutation. The M1del mutation may also be referred herein as an amino acid deletion. In some embodiments, human DRD constructs disclosed herein may not comprise an N-terminal methionine corresponding to the N-terminal methionine of SEQ ID NO: 1. Regardless of the presence or absence of the N-terminal methionine in a disclosed CA2 DRD, the present disclosure identifies positions of the CA2 DRD relative to the wildtype human CA2 (Uniprot ID: P00918) of SEQ ID NO: 1, wherein reference position 1 is the N-terminal methionine of SEQ ID NO: 1. For example, a hypothetical CA2 DRD comprising a G12A mutation, refers herein to a CA2 DRD construct wherein glycine (G) is mutated to alanine (A) at a position in the CA2 DRD construct that corresponds to the twelfth amino acid of SEQ ID NO: 1, regardless of whether the CA2 DRD construct itself comprises an N-terminal methionine corresponding to the N-terminal methionine of SEQ ID NO: 1. In this hypothetical CA2 DRD comprising a G12A mutation example, the glycine (G) to alanine (A) change may also be referred to as an amino acid substitution.

In some embodiments, DRDs may be derived from human CA2 having amino acids 2-260 of the wild type human CA2 sequence of SEQ ID NO: 1. This may be referred to as an M1del mutation and has an amino acid sequence of SEQ ID NO: 2. In some embodiments, the DRD of the present disclosure has an amino acid sequence as set forth in SEQ ID NO: 4.

Table 1 provides a CA2 DRD. The position of the mutated amino acids listed in Table 1 is relative to the full length CA2 of SEQ ID NO: 1.

TABLE 1

CA2 DRD amino acid and nucleotide sequences.

| Description | AA SEQUENCE | Nucleic Acid Sequence | AA SEQ ID NO | NA SEQ ID NO |
|---|---|---|---|---|
| CA2 mutant (M1del, L156H) relative to SEQ ID NO: 1 | SHHWGYGKHN GPEHWHKDFP IAKGERQSVD IDTHTAKYDP SLKPLSVSYD QATSLRILNN GHAFNVEFDD SQDKAVLKGG PLDGTYRLIQ FHFHWGSLDG QGSEHTVDKK KYAAELHLVH WNTKYGDFGK AVQQPDGLAV LGIFLKVGSA KPGHQKVVDV LDSIKTKGKS ADFTNFDPRG LLPESLDYWT YPGSLTTPPL LECVTWIVLK EPISVSSEQV LKFRKLNFNG EGEPEELMVD NWRPAQPLKN RQIKASFK | TCCCATCACTG GGGGTACGGCA AACACAACGGA CCTGAGCACTG GCATAAGGACT TCCCCATTGCC AAGGGAGAGCG CCAGTCCCCTG TTGACATCGAC ACTCATACAGC CAAGTATGACC CTTCCCTGAAG CCCCTGTCTGT TTCCTATGATC AAGCAACTTCC CTGAGAATCCT CAACAATGGTC ATGCTTTCAAC GTGGAGTTTGA TGACTCTCAGG ACAAAGCAGTG CTCAAGGGAGG ACCCCTGGATG GCACTTACAGA TTGATTCAGTT TCACTTTCACT GGGGTTCACTT GATGGACAAGG TTCAGAGCATA CTGTGGATAAA AAGAAATATGC TGCAGAACTTC ACTTGGTTCAC TGGAACACCAA ATATGGGGATT TTGGGAAAGCT GTGCAGCAACC TGATGGACTGG CCGTTCTAGGT ATTTTTTTGAA GGTTGGCAGCG CTAAACCGGGC CATCAGAAAGT TGTTGATGTGC TGGATTCCATT AAAACAAAGGG CAAGAGTGCTG ACTTCACTAAC TTCGATCCTCG TGGCCTCCTTC CTGAATCCCTG GATTACTGGAC CTACCCAGGCT CACTGACCACC CCTCCTCTTCT GGAATGTGTGA CCTGGATTGTG CTCAAGGAACC CATCAGCGTCA GCAGCGAGCAG GTGTTGAAATT CCGTAAACTTA | 4 | 5 |

TABLE 1-continued

CA2 DRD amino acid and nucleotide sequences.

| Description | AA SEQUENCE | Nucleic Acid Sequence | AA SEQ ID NO | NA SEQ ID NO |
|---|---|---|---|---|
| | | ACTTCAATGGG GAGGGTGAACC CGAAGAACTGA TGGTGGACAAC TGGCGCCCAGC TCAGCCACTGA AGAACAGGCAA ATCAAAGCTTC CTTCAAA | | |

In some embodiments, an exemplary DRD derived from CA2 that regulates an operably linked IL15 payload comprises or consists of the amino acid sequence of SEQ ID NO: 4 or is encoded by the nucleotide sequence of SEQ ID NO: 5.

In some embodiments, the CA2 DRD useful for the regulated and tunable expression of IL15 as described herein may include one or more mutations that are relative to Uniprot ID: P00918 (SEQ ID NO: 1) and include but are not limited to (M1del, L156H) relative to the amino acid sequence of SEQ ID NO: 1. In some embodiments, the CA2 DRD useful for the regulated and tunable expression of IL15 as described herein may include one mutation relative to (SEQ ID NO: 2) (L156H). In some embodiments, the CA2 DRD useful for the regulated and tunable expression of IL15 as described herein may include one amino acid substitution relative to (SEQ ID NO: 2) (L156H). In some embodiments, the CA2 DRD comprises the amino acid sequence of SEQ ID NO: 4. In some embodiments, the CA2 DRD consists of the amino acid sequence of SEQ ID NO: 4.

The SRE described herein may include CA2 DRDs which include but are not limited to one or two mutations such as, but not limited to, M1del, and L156H relative to the CA2 WT of SEQ ID NO: 1. In some embodiments, the CA2 DRD comprises the L156H mutation relative to SEQ ID NO: 1 and further comprises one or more additional mutations. In some embodiments, the CA2 DRD comprises the M1del and L156H mutation relative to SEQ ID NO: 1 and further comprises one or more additional mutations. In some embodiments, the CA2 DRD comprises the M1del amino acid deletion and L156H amino acid substitution relative to SEQ ID NO: 1 and further comprises one or more additional amino acid substitutions.

Also provided herein are biocircuit systems that include at least one effector module. The effector module of the biocircuit may include a stimulus response element (SRE) derived from CA2 (SEQ ID NO: 1 or SEQ ID NO: 2). In one embodiment, the SRE comprises or consists of the amino acid sequence of SEQ ID NO: 4. The biocircuits may also include at least one payload, which may be attached, appended or associated with the SRE. The payload may include a human IL15, comprising the amino acid sequence of SEQ ID NO: 8; the payload may be encoded by a nucleic acid sequence comprising the nucleotide sequence of SEQ ID NO: 9.

TABLE 2

An 1L15 payload of the present disclosure.

| Description | AA SEQUENCE | Nucleic Acid Sequence | AA SEQ ID NO | NA SEQ ID NO |
|---|---|---|---|---|
| IL15 | NWVNVIS DLKKIED LIQSMHI DATLYTE SDVHPSC KVTAMKC FLLELQV ISLESGD ASIHDTV ENLIILA NNSLSSN GNVTESG CKECEEL EEKNIKE FLQSFVH IVQMFIN TS | AATTGGGTA AATGTTATC AGTGATCTC AAGAAGATA GAGGATCTC ATCCAGTCC ATGCATATT GATGCCACG CTGTACACA GAAAGCGAT GTGCATCCT AGCTGTAAG GTGACAGCG ATGAAGTGT TTTCTTTTG GAGCTGCAG GTAATTAGT CTTGAGTCC GGCGATGCC AGCATTCAT GATACCGTA GAAAACTTG ATTATCCTG GCCAACAAT TCTCTGTCC TCAAACGGA AACGTAACC GAGAGCGGT TGTAAAGAA TGTGAAGAA CTGGAAGAA AAGAACATC AAGGAGTTT CTGCAATCA TTCGTTCAC ATCGTACAA ATGTTCATA AATACGTCA | 8 | 9 |

In some embodiments, the present disclosure provides methods for modulating protein, expression, function or level by measuring the stabilization ratio and destabilization ratio. As used herein, the stabilization ratio may be defined as the ratio of expression, function or level of a protein of interest in response to the stimulus to the expression, function or level of the protein of interest in the absence of the stimulus specific to the SRE. As used herein, the destabilization ratio may be defined as the ratio of expression, function or level of a protein of interest in the absence of the stimulus specific to the effector module to the expression, function or level of the protein of interest, that is expressed constitutively and in the absence of the stimulus specific to the SRE. As used herein "constitutively" refers to the expression, function or level of a protein of interest that is not linked to an SRE and is therefore expressed both in the presence and absence of the stimulus.

As used herein a "payload" or "target payload" or "payload of interest (POI)" is defined as any protein whose function is to be altered. Payloads may include any protein or fragment thereof.

In some embodiments, payloads of the present disclosure include IL15. It is understood in the art that certain gene and/or protein nomenclature for the same gene or protein may be inclusive or exclusive of punctuation such as a dash "-" or symbolic such as Greek letters. Whether these are included or excluded herein, the meaning is not meant to be changed as would be understood by one of skill in the art. For example, IL15, IL 15 and IL-15 refer to the same interleukin. In some embodiments, payloads of the present disclosure may be an IL15 interleukin cytokine that stimulate certain immune responses.

Payloads of the present disclosure may comprise amino acid sequences similar to the amino acid sequence of human IL15, for example, UniProtKB—P40933 (IL15_HUMAN). In one embodiment, the IL15 payload comprises the amino acid sequence provided in Table 2 (SEQ ID NO. 8).

In some embodiments, payloads of the present disclosure may be utilized to improve expansion, survival, persistence, and potency of immune cells such as CD8+ TEM, natural killer (NK) cells and tumor infiltrating lymphocytes (TIL), and CAR T cells used for immunotherapy. In one aspect, the present disclosure provides biocircuits and compositions to minimize toxicity related to cytokine therapy.

In some embodiments, the effector module may be a CA2 DRD-IL15 fusion polypeptide. In some embodiments, the IL15-containing constructs of the disclosure may be placed under the transcriptional control of the human cytomegalovirus (CMV) promoter, an Elongation Factor 1α (EF1α) promoter, HIV LTR promoter, 3-phosphoglycerate kinase (PGK) promoter, Rous sarcoma virus long terminal repeat (RSV) promoter, spleen focus forming virus (SFFV) promoter, synthetic MND promoter, murine stem cell virus (MSCV) promoter, synthetic RPBSA promoter or a ubiquitin promoter.

A unique feature of IL15 mediated activation is the mechanism of trans-presentation in which IL15 is presented as a complex with the alpha subunit of IL15 receptor (IL15Ra) that binds to and activates membrane bound IL15 beta/gamma receptor, either on the same cell or a different cell. In various embodiments, the payload of the present disclosure is a membrane bound IL15, wherein the amino acid sequence of said membrane bound IL15 comprises the amino acid sequence of SEQ ID NO: 8.

Payloads of the present disclosure may comprise nucleic acid sequences as disclosed herein but the payload may comprise additional or fewer nucleotides than those listed. Such nucleic acid sequences may comprise about 1 more or fewer nucleotides, about 2 more or fewer nucleotides, about 3 more or fewer nucleotides, about 4 more or nucleotides acids, about 5 more or fewer nucleotides, about 6 more or fewer nucleotides, about 7 more or fewer nucleotides, about 8 more or fewer nucleotides, about 9 more or fewer nucleotides, about 10 more or fewer nucleotides or greater than 10 nucleotides.

Biocircuit components including effector modules, their SREs and payloads, may be nucleic acid-based. The term "nucleic acid," in its broadest sense, includes any compound and/or substance that comprise a polymer of nucleotides, e.g., linked nucleosides. These polymers are often referred to as polynucleotides. Exemplary nucleic acids or polynucleotides of the disclosure include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

In some embodiments, the nucleic acid molecule is DNA. In some embodiments, the nucleic acid molecule is a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo. Polynucleotides of the disclosure may be mRNA or any nucleic acid molecule and may or may not be chemically modified.

In some embodiments, polynucleotides of the present disclosure may harbor 5'UTR sequences which play a role in translation initiation. 5'UTR sequences may include features such as Kozak sequences which are commonly known to be involved in the process by which the ribosome initiates translation of genes, Kozak sequences have the consensus XCCR(A/G) CCAUG, where R is a purine (adenine or guanine) three bases upstream of the start codon (AUG) and X is any nucleotide. In one embodiment, the Kozak sequence is ACCGCC. By engineering the features that are typically found in abundantly expressed genes of target cells or tissues, the stability and protein production of the polynucleotides of the disclosure can be enhanced.

In one embodiment, polynucleotides of the present disclosure may encode variant polypeptides which have a certain identity with a reference polypeptide sequence. As used herein, a "reference polypeptide sequence" refers to a starting polypeptide sequence. Reference sequences may be wild type sequences or any sequence to which reference is made in the design of another sequence.

The term "identity" as known in the art, refers to a relationship between two or more sequences, as determined by comparing the sequences. In the art, identity also means the degree of sequence relatedness between sequences, as determined by the number of matches between strings of two or more residues (amino acid or nucleic acid). Identity measures the percent of identical matches between two or more sequences with gap alignments (if any) aDRDressed by a particular mathematical model or computer program (i.e., "algorithms"). Identity of related sequences can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the variant sequence may have the same or a similar activity as the reference sequence. Alternatively, the variant may have an altered activity (e.g., increased or decreased) relative to a reference sequence. Generally, variants of a particular polynucleotide or polypeptide of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, Thomas L. MaDRDen, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.)

The effector module of the present disclosure may further comprise a signal sequence which regulates the distribution of the payload of interest, a cleavage and/or processing feature which facilitate cleavage of the payload from the effector module construct, a targeting and/or penetrating signal which can regulate the cellular localization of the effector module, a tag, and/or one or more linker sequences which link different components of the effector module.

In addition to the SRE and payload region, effector modules of the disclosure may further comprise one or more additional features such as one or more signal sequences.

Signal sequences (sometimes referred to as signal peptides, targeting signals, target peptides, localization sequences, transit peptides, leader sequences or leader peptides) direct proteins (e.g., the effector module of the present disclosure) to their designated cellular and/or extracellular locations. Protein signal sequences play a central role in the targeting and translocation of nearly all secreted proteins and many integral membrane proteins.

A signal sequence is a short (5-30 amino acids long) peptide present at the N-terminus of the majority of newly synthesized proteins that are destined towards a particular location. Signal sequences can be recognized by signal recognition particles (SRPs) and cleaved using type I and type II signal peptide peptidases. Signal sequences derived from human proteins can be incorporated as a regulatory module of the effector module to direct the effector module to a particular cellular and/or extracellular location.

In some embodiments, a signal sequence may be, although not necessarily, located at the N-terminus or C-terminus of the effector module, and may be, although not necessarily, cleaved off the desired effector module to yield a "mature" payload.

In some embodiments, the signal sequence used herein may exclude the methionine at the position 1 of amino acid sequence of the signal sequence. This may be referred to as an M1del mutation.

In addition to signal sequences naturally occurring such as from a secreted protein, a signal sequence may be a variant modified from a known signal sequence of a protein.

In some instances, signal sequences directing the payload of interest to the surface membrane of the target cell may be used. Expression of the payload on the surface of the target cell may be useful to limit the diffusion of the payload to non-target in vivo environments, thereby potentially improving the safety profile of the payloads. Additionally, the membrane presentation of the payload may allow for physiologically and qualitative signaling as well as stabilization and recycling of the payload for a longer half-life. Membrane sequences may be the endogenous signal sequence of the N terminal component of the payload of interest. Optionally, it may be desirable to exchange this sequence for a different signal sequence. Signal sequences may be selected based on their compatibility with the secretory pathway of the cell type of interest so that the payload is presented on the surface of the T cell. In some embodiments, the signal sequence may be IgE signal sequence, CD8a signal sequence (also referred to as CD8α leader), or IL15Ra signal sequence (also referred to as IL15Ra leader) or M1del CD8a signal sequence (also referred to as M1del CD8 leader sequence).

In some embodiments, the effector module comprises a cleavage and/or processing feature. In some embodiments, the effector module of the present disclosure may include at least one protein cleavage signal/site. The protein cleavage signal/site may be located at the N-terminus, the C-terminus, at any space between the N- and the C-termini such as, but not limited to, half-way between the N- and C-termini, between the N-terminus and the half-way point, between the half-way point and the C-terminus, and combinations thereof.

In some embodiments, the effector module comprises a linker.

In some embodiments, the effector module of the disclosure may further comprise a linker sequence. The linker region serves primarily as a spacer between two or more polypeptides within the effector module. The "linker" or "spacer", as used herein, refers to a molecule or group of molecules that connects two molecules, or two parts of a molecule such as two domains of a recombinant protein.

In some embodiments, "Linker" (L) or "linker domain" or "linker region" or "linker module" or "peptide linker" as used herein refers to an oligo- or polypeptide region of from about 1 to 100 amino acids in length, which links together any of the domains/regions of the effector module (also called peptide linker).

In some embodiments, an artificially designed peptide linker may be composed of a polymer of flexible residues such as Glycine (G) and Serine (S) so that the adjacent protein domains are free to move relative to one another. Longer linkers may be used when it is desirable to ensure that two adjacent domains do not interfere with one another. The choice of a particular linker sequence may be of concern if it affects biological activity, stability, folding, targeting and/or pharmacokinetic features of the fusion construct.

A linker sequence may be a natural linker derived from a multi-domain protein. A natural linker is a short peptide sequence that separates two different domains or motifs within a protein.

In one embodiment, the linker may be a BamHI site. As a non-limiting example, the BamHI site has the amino acid sequence GS and/or the DNA sequence GGATCC.

Biocircuits of the present disclosure are triggered by one or more stimuli. In some embodiments, the stimulus is a small molecule. In some embodiments, the small molecules are cell permeable. In some embodiments, the small molecules are FDA-approved, safe and orally administered.

In some embodiments, the ligands bind to carbonic anhydrases. In some embodiments, the ligand binds to and inhibits carbonic anhydrase function and is herein referred to as carbonic anhydrase inhibitor.

In some embodiments, the ligand is a small molecule that binds to carbonic anhydrase 2. In one embodiment, the small molecule is CA2 inhibitor. In some embodiments, the ligand is a small molecule selected from acetazolamide, celecoxib, valdecoxib, rofecoxib, methazolamide, dorzolamide, brinzolamide, diclofenamide, ethoxzolamide, zonisamide, dansylamide, and dichlorphenamide. In some embodiments, the ligand is a small molecule selected from acetazolamide, brinzolamide, dorzolamide hydrochloride, dichlorphenamide, chlorthalidone, methazolamide, topiramate, indapamide, ambroxol hydrochloride, glimepiride, tetracaine hydrochloride and celecoxib. In some embodiments, the ligand is a small molecule selected from acetazolamide, brinzolamide, dorzolamide hydrochloride, dichlorphenamide, chlorthalidone, methazolamide or topiramate. In some embodiments, the ligand is a CA2 inhibitor selected from acetazolamide, brinzolamide, dorzolamide hydrochloride, dichlorphenamide or methazolamide. In some embodiments, the ligand is acetazolamide (ACZ).

In some embodiments, ligands that do not affect the activity of the immune cell, and/or the chimeric antigen receptor, in the absence of the SREs may be preferably selected.

In some embodiments, compositions of the disclosure comprise a promoter.

As used herein a promoter is defined as a DNA sequence recognized by transcription machinery of the cell, required to initiate specific transcription of the polynucleotide sequence of the present disclosure. Vectors can comprise native or non-native promoters operably linked to the polynucleotides of the disclosure. The promoters selected may be strong, weak, constitutive, inducible, tissue specific, development stage-specific, and/or organism specific. A strong constitutive promoter sequence is capable of driving high levels of expression of polynucleotide sequence that is operatively linked to it. Examples of strong constitutive promoters include, without limitation, immediate early cytomegalovirus (CMV) promoter and Elongation Growth Factor-1 Alpha (EF-1 alpha). Other constitutive promoters that may be used, include, but are not limited to, simian virus 40 (SV40), mouse mammary tumor virus (MMTV) promoter, human immunodeficiency virus (HIV) long terminal repeat (LTR) promoter, an avian leukemia virus promoter, a spleen focus forming virus (SFFV) promoter, a murine stem cell virus (MSCV) promoter, an Epstein-Barr virus immediate early promoter, a Rous sarcoma virus promoter, human gene promoters including, but not limited to, the phosphoglycerate kinase (PGK) promoter, an actin promoter, a myosin promoter, the hemoglobin promoter, the Ubiquitin C (Ubc) promoter, the human U6 small nuclear protein promoter and a creatine kinase promoter. Synthetic promoters include a MND promoter and a RPBSA promoter. In some instances, inducible promoters such as, but not limited to, metallothionine promoter, glucocorticoid promoter, a progesterone promoter, and a tetracycline promoter may be used.

In some embodiments, the optimal promoter may be selected based on its ability to achieve minimal expression of the SREs and payloads of the disclosure in the absence of the ligand and detectable expression in the presence of the ligand.

Additional promoter elements, e.g., enhancers may be used to regulate the frequency of transcriptional initiation. Such regions may be located 10-100 base pairs upstream or downstream of the start site. In some instances, two or more promoter elements may be used to cooperatively or independently activate transcription.

Biocircuits of the present disclosure may comprise at least one effector module which may comprise at least one SRE derived from CA2 (referred to as "CA2 SREs") which may be operably linked to at least one payload of interest. These types of biocircuits and effector modules are referred to as "CA2 biocircuits" and "CA2 effector modules". Additionally, the CA2 effector module may comprise additional features including, but not limited to, signal sequences, linker, spacers, tags, flags, cleavage sites, and IRES. Any of the exemplary SREs (e.g., DRDs), payloads of interest, signal sequences, linker, spacers, hinges, tags, flags, cleavage sites, and IRES taught herein or known in the art may be combined to create the CA2 effector modules of the present disclosure.

In one embodiment, the CA2 effector module comprises a payload of interest. The payload of interest may be a wild-type sequence, a fragment of a wild-type sequence and/or comprise one or more mutations. In one embodiment, the CA2 effector module produces regulated interleukin-15 (IL15). In some embodiments, an IL15 payload is N-terminal to the DRD. The CA2 effector module may include or be derived from any of the IL15-related sequences in Table 3. In some embodiments, at least one payload in the CA2 effector module is an IL15 (e.g. an IL15 payload) comprising an amino acid sequence that is at least 95%, or at least 96%, or at least 97%, or at least 98%, or at least 99%, or 100% identical to the amino acid sequence of SEQ ID NO: 8; the payload may be encoded by a nucleic acid sequence comprising the nucleotide sequence of SEQ ID NO: 9). In some embodiments, the payload is a membrane-bound form of IL15. In some embodiments, the payload is a membrane-bound form of IL15 comprising a transmembrane domain and an intracellular tail. In some embodiments, the payload is a membrane-bound form of IL15 comprising an IL15 polypeptide component comprising the amino acid sequence of SEQ ID NO: 8, a transmembrane domain and an intracellular tail, wherein the transmembrane domain is C-terminal to the IL15 polypeptide component and the intracellular tail is C-terminal to the transmembrane domain. In some embodiments, the payload is a membrane-bound form of IL15 comprising a transmembrane domain, intracellular tail and one or more linkers. In some embodiments, linkers are peptide domains that may be placed between the SRE or DRD and the payload, or between different domains within the payload. In some embodiments, linkers are peptide domains comprising glycine and serine amino acid residues. In some embodiments, peptide linkers comprising glycine and serine amino acid residues may be from 2-36 amino acids in length. In one embodiment, at least one payload in the CA2 effector module is a membrane-bound form of IL15 which further includes a linker (GS)15, a B7.1 Hinge, a B7.1 transmembrane domain, a B7.1 intracellular tail, and a linker (GS). The CA2 effector module may include a payload component of a transmembrane domain and/or cytoplasmic domain from another parent protein as well as the IL15 payload component. In one embodiment, at least one payload in the CA2 effector module includes at least one mutation as compared to the wild-type sequence. In one embodiment, at least one payload in the CA2 effector module includes at least one amino acid substitution as compared to the wild-type sequence.

Non-limiting examples of constructs and construct components are shown in Table 3.

TABLE 3

Constructs and construct components of interest.

| Description | Amino Acid Sequence (AA) | Nucleic Acid Sequence (NA) | Anti no Acid SEQ ID NO | Nucleic Acid SEQ ID NO |
|---|---|---|---|---|
| Leader sequence | MDMRVPAQLLGLLLLWL SGARC | ATGGACATGCGGGTGCCTGCACAACTTCTGGGCCTG CTGTTGTTGTGGCTGTCTGGAGCCCGGTGT | 6 | 7 |
| Interleukin-15 (IL15) | NWVNVISDLKKIEDLIQ SMHIDATLYTESDVHPS CKVTAMKCFLLELQVIS LANNSLSSNGNVTESGC KECEELEEKNIKEFLQS FVHIVQMFINTS | AATTGGGTAAATGTTATCAGTGATCTCAAGAAGATA GAGGATCTCATCCAGTCCATGCATATTGATGCCACG CTGTACACAGAAAGCGATGTGCATCCTAGCTGTAAG GTGACAGCGATGAAGTGTTTTCTTTTGGAGCTGCAG GTAATTAGTCTTGAGTCCGGCGATGCCAGCATTCAT GATACCGTAGAAAACTTGATTATCCTGGCCAACAAT TCTCTGTCCTCAAACGGAAACGTAACCGAGAGCGGT TGTAAAGAATGTGAAGAACTGGAAGAAAAGAACATC AAGGAGTTTCTGCAATCATTCGTTCACATCGTACAA ATGTTCATAAATACGTCA | 8 | 9 |
| Linker (GS)15 | GSGSGSGSGSGSGSGSG SGSGSGSGSGSGS | GGATCTGGTTCTGGTTCCGGAAGTGGATCTGGTTCA GGGTCCGGTAGTGGATCTGGGTCAGGAAGTGGAAGC GGTAGTGGGTCTGGATCT | 10 | 11 |
| Hinge | KQEHFPDN | AAACAAGAGCACTTTCCTGATAAC | 12 | 13 |
| Transmembrane | LLPSWAITLISVNGIFV ICCL | CTGTTGCCGAGCTGGGCGATTACGCTTATCAGTGTA AACGGCATCTTTGTAATATGCTGTCTG | 14 | 15 |
| Intracellular tail | TYCFAPRCRERRRNERL RRESVRPV | ACCTACTGCTTCGCACCAAGGTGCCGGGAGAGAAGG AGAAATGAAAGACTGAGAAGGGAGAGCGTGAGACCT GTG | 16 | 17 |
| Intracellular tail | TYCFAPRCRERARNERL RRETVRPV | ACCTACTGCTTCGCACCAAGGTGCCGGGAGAGAGCA AGAAATGAAAGACTGAGAAGGGAGACCGTGAGACCT GTG | 18 | 19 |
| Linker (GS) | GS | GGATCC | 20 | 21 |
| CA2 (M1del, L156H) | SHHWGYGKHNGPEHWHK DFPIAKGERQSPVDIDT HTAKYDPSLKPLSVSYD QATSLRILNNGHAFNVE FDDSQDKAVLKGGPLDG TYRLIQFHFHWGSLDGQ GSEHTVDKKKYAAELHL VHWNTKYGDFGKAVQQP DGLAVLGIFLKVGSAKP GHQKVVDVLDSIKTKGK SADFTNFDPRGLLPESL DYWTYPGSLTTPPLLEC VTWIVLKEPISVSSEQV LKFRKLNFNGEGEPEEL | TCCCATCACTGGGGGTACGGCAAACACAACGGACCT GAGCACTGGCATAAGGACTTCCCCATTGCCAAGGGA GAGCGCCAGTCCCCTGTTGACATCGACACTCATACA GCCAAGTATGACCCTTCCCTGAAGCCCCTGTCTGTT TCCTATGATCAAGCAACTTCCCTGAGAATCCTCAAC AATGGTCATGCTTTCAACGTGGAGTTTGATGACTCT CAGGACAAAGCAGTGCTCAAGGGAGGACCCCTGGAT GGCACTTACAGATTGATTCAGTTTCACTTTCACTGG GGTCACTTGATGGACAAGGTTCAGAGCATACTGTG GATAAAAGAAATATGCTGCAGAACTTCACTTGGTT CACTGGAACACCAAATATGGGGATTTGGGAAAGCT GTGCAGCAACCTGATGGACTGGCCGTTCTAGGTATT TTTTTGAAGGTTGGCAGCGCTAAACCGGGCCATCAG AAAGTTGTTGATGTGCTGGATTCCATTAAAACAAAG | 4 | 5 |

US 11,058,725 B2

TABLE 3-continued

Constructs and construct components of interest.

| Description | Amino Acid Sequence (AA) | Nucleic Acid Sequence (NA) | Anti no Acid SEQ ID NO | Nucleic Acid SEQ ID NO |
|---|---|---|---|---|
| | MVDNWRPAQPLKNRQIK ASFK | GGCAAGAGTGCTGACTTCACTAACTTCGATCCTCGT GGCCTCCTTCCTGAATCCCTGGATTACTGGACCTAC CCAGGCTCACTGACCACCCCTCCTCTTCTGGAATGT GTGACCTGGATTGTGCTCAAGGAACCCATCAGCGTC AGCAGCGAGCAGGTGTTGAAATTCCGTAAACTTAAC TTCAATGGGGAGGGTGAACCCGAAGAACTGATGGTG GACAACTGGCGCCCAGCTCAGCCACTGAAGAACAGG CAAATCAAAGCTTCCTTCAAA | | |
| IL15-292 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERRRNERLRRESVRPVG S | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAAGGAGAAATGAAAGACTGAGAAGGGAGAGC GTGAGACCTGTGGGATCC | 22 | 23 |
| OT-IL15-293 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERRRNERLRRESVRPVG SSHHWGYGKHNGPEHWH KDFPIAKGERQSPVDID THTAKYDPSLKPLSVSY DQATSLRILNNGHAFNV EFDDSQDKAVLKGGPLD GTYRLIQFHFHWGSLDG QGSEHTVDKKKYAAELH LVHWNTKYGDFGKAVQQ PDGLAVLGIFLKVGSAK PGHQKWDVLDSIKTKG KSADFTNFDPRGLLPES LDYWTYPGSLTTPPLLE CVTWIVLKEPISVSSEQ VLKFRKLNFNGEGEPEE LMVDNWRPAQPLKNRQI KASFK | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAAGGAGAAATGAAAGACTGAGAAGGGAGAGC GTGAGACCTGTGGGATCCTCCCATCACTGGGGGTAC GGCAAACACAACGGACCTGAGCACTGGCATAAGGAC TTCCCCATTGCCAAGGGAGAGCGCCAGTCCCCTGTT GACATCGACACTCATACAGCCAAGTATGACCCTTCC CTGAAGCCCCTGTCTGTTTCCTATGATCAAGCAACT TCCCTGAGAATCCTCAACAATGGTCATGCTTTCAAC GTGGAGTTTGATGACTCTCAGGACAAAGCAGTGCTC AAGGGAGGACCCCTGGATGGCACTTACAGATTGATT CAGTTTCACTTTCACTGGGGTTCACTTGATGGACAA GGTTCAGAGCATACTGTGGATAAAAAGAAATATGCT GCAGAACTTCACTTGGTTCACTGGAACACCAAATAT GGGGATTTTGGGAAAGCTGTGCAGCAACCTGATGGA CTGGCCGTTCTAGGTATTTTTTTGAAGGTTGGCAGC GCTAAACCGGGCCATCAGAAAGTTGTTGATGTGCTG GATTCCATTAAAACAAAGGGCAAGAGTGCTGACTTC ACTAACTTCGATCCTCGTGGCCTCCTTCCTGAATCC CTGGATTACTGGACCTACCCAGGCTCACTGACCACC CCTCCTCTTCTGGAATGTGTGACCTGGATTGTGCTC AAGGAACCCATCAGCGTCAGCAGCGAGCAGGTGTTG AAATTCCGTAAACTTAACTTCAATGGGGAGGGTGAA CCCGAAGAACTGATGGTGGACAACTGGCGCCCAGCT CAGCCACTGAAGAACAGGCAAATCAAAGCTTCCTTC AAA | 24 | 25 |
| OT-IL15-294 | MDMRVPAQLLGLLLLWL SGARCNWVNVISDLKKI | ATGGACATGCGGGTGCCTGCACAACTTCTGGGCCTG CTGTTGTTGTGGCTGTCTGGAGCCCGGTGTAATTGG | 26 | 27 |

TABLE 3-continued

Constructs and construct components of interest.

| Description | Amino Acid Sequence (AA) | Nucleic Acid Sequence (NA) | Anti no Acid SEQ ID NO | Nucleic Acid SEQ ID NO |
|---|---|---|---|---|
| | EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERARNERLRRETVRPVG S | GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAGCAAGAAATGAAAGACTGAGAAGGGAGACC GTGAGACCTGTGGGATCC | | |
| OT-IL15-295 | MDMRVPAQLLGLLLLWL SGARCNWVNVISDLKKI EDLIQSMHIDATLYTES DVHPSCKVTAMKCFLLE LQVISLESGDASIHDTV ENLIILANNSLSSNGNV TESGCKECEELEEKNIK EFLQSFVHIVQMFINTS GSGSGSGSGSGSGSGSG SGSGSGSGSGSGSKQEH FPDNLLPSWAITLISVN GIFVICCLTYCFAPRCR ERARNERLRRETVRPVG SSHHWGYGKHNGPEHWH KDFPIAKGERQSPVDID THTAKYDPSLKPLSVSY DQATSLRILNNGHAFNV EFDDSQDKAVLKGGPLD GTYRLIQFHFHWGSLDG QGSEHTVDKKKYAAELH LVHWNTKYGDFGKAVQQ PDGLAVLGIFLKVGSAK PGHQKWDVLDSIKTKG KSADFTNFDPRGLLPES LDYWTYPGSLTTPPLLE CVTWIVLKEPISVSSEQ VLKFRKLNFNGEGEPEE LMVDNWRPAQPLKNRQI KASFK | ATGGACATGCGGGTGCCTGCACAACTTCTGGGCCTG CTGTTGTTGTGGCTGTCTGGAGCCCGGTGTAATTGG GTAAATGTTATCAGTGATCTCAAGAAGATAGAGGAT CTCATCCAGTCCATGCATATTGATGCCACGCTGTAC ACAGAAAGCGATGTGCATCCTAGCTGTAAGGTGACA GCGATGAAGTGTTTTCTTTTGGAGCTGCAGGTAATT AGTCTTGAGTCCGGCGATGCCAGCATTCATGATACC GTAGAAAACTTGATTATCCTGGCCAACAATTCTCTG TCCTCAAACGGAAACGTAACCGAGAGCGGTTGTAAA GAATGTGAAGAACTGGAAGAAAAGAACATCAAGGAG TTTCTGCAATCATTCGTTCACATCGTACAAATGTTC ATAAATACGTCAGGATCTGGTTCTGGTTCCGGAAGT GGATCTGGTTCAGGGTCCGGTAGTGGATCTGGGTCA GGAAGTGGAAGCGGTAGTGGGTCTGGATCTAAACAA GAGCACTTTCCTGATAACCTGTTGCCGAGCTGGGCG ATTACGCTTATCAGTGTAAACGGCATCTTTGTAATA TGCTGTCTGACCTACTGCTTCGCACCAAGGTGCCGG GAGAGAGCAAGAAATGAAAGACTGAGAAGGGAGACC GTGAGACCTGTGGGATCCTCCCATCACTGGGGGTAC GGCAAACACAACGGACCTGAGCACTGGCATAAGGAC TTCCCCATTGCCAAGGGAGAGCGCCAGTCCCCTGTT GACATCGACACTCATACAGCCAAGTATGACCCTTCC CTGAAGCCCCTGTCTGTTTCCTATGATCAAGCAACT TCCCTGAGAATCCTCAACAATGGTCATGCTTTCAAC GTGGAGTTTGATGACTCTCAGGACAAAGCAGTGCTC AAGGGAGGACCCCTGGATGGCACTTACAGATTGATT CAGTTTCACTTTCACTGGGGTTCACTTGATGGACAA GGTTCAGAGCATACTGTGGATAAAAAGAAATATGCT GCAGAACTTCACTTGGTTCACTGGAACACCAAATAT GGGGATTTTGGGAAAGCTGTGCAGCAACCTGATGGA CTGGCCGTTCTAGGTATTTTTTTGAAGGTTGGCAGC GCTAAACCGGGCCATCAGAAAGTTGTTGATGTGCTG GATTCCATTAAAACAAAGGGCAAGAGTGCTGACTTC ACTAACTTCGATCCTCGTGGCCTCCTTCCTGAATCC CTGGATTACTGGACCTACCCAGGCTCACTGACCACC CCTCCTCTTCTGGAATGTGTGACCTGGATTGTGCTC AAGGAACCCATCAGCGTCAGCAGCGAGCAGGTGTTG AAATTCCGTAAACTTAACTTCAATGGGGAGGGTGAA CCCGAAGAACTGATGGTGGACAACTGGCGCCCAGCT CAGCCACTGAAGAACAGGCAAATCAAAGCTTCCTTC AAA | 28 | 29 |

In various embodiments, the effector module produces regulated membrane-bound interleukin-15 (IL15). In some embodiments, the effector module is IL15-293 or IL15-295 as described in Table 3. In various embodiments, the IL15 payload is expressed as a CA2 DRD fusion protein comprising a membrane-bound form of IL15.

The CA2 biocircuits and/or CA2 effector modules of the present disclosure may be monocistronic or multicistronic meaning one (monocistronic) or more than one (multicistronic) message (e.g., payload of interest) is produced. If two messages are produced, the CA2 biocircuit or CA2 effector module is considered bicistronic. In one embodiment, at least one CA2 effector module of the present disclosure is monocistronic.

Various embodiments of the present disclosure provide nucleic acid molecules comprising one or more of the polynucleotides described. In some embodiments, the nucleic acid molecule comprises a polynucleotide encoding a recombinant protein comprising a drug responsive domain (DRD) operably linked to an IL15 payload, wherein said DRD is derived from human carbonic anhydrase II (CA2) and comprises one, two, three, four or more mutations relative to SEQ ID NO:1 or SEQ ID NO:2. In some embodiments, the nucleic acid molecule further comprises a second polynucleotide encoding a chimeric antigen receptor (CAR) or T cell receptor (TCR), wherein the CAR or TCR comprises an antigen-binding domain specific to an antigen of interest. In some embodiments, the CAR or TCR comprises an antigen-binding domain specific to an antigen of interest for example, the CAR comprises an antigen-binding domain specific to CD19.

The present teachings further comprise pharmaceutical compositions comprising one or more of CA2 biocircuits, CA2 effector modules or systems of the present disclosure, and optionally at least one pharmaceutically acceptable excipient or inert ingredient.

As used herein the term "pharmaceutical composition" refers to a preparation of one or more of the CA2 biocircuits or components described herein, or pharmaceutically acceptable salts thereof, optionally with other chemical components such as physiologically suitable carriers and excipients.

The term "excipient" or "inactive ingredient" refers to an inert or inactive substance added to a pharmaceutical composition to further facilitate administration of a compound. Non-limiting examples of such inert ingredients are disclosed herein.

In some embodiments, compositions are administered to humans, such as human patients or subjects. For the purposes of the present disclosure, the phrase "active ingredient" generally refers to any one or more CA2 biocircuit components to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Subjects to which administration of the pharmaceutical compositions is contemplated include, but are not limited to, non-human mammals, including agricultural animals such as cattle, horses, chickens and pigs, domestic animals such as cats, dogs, or research animals such as mice, rats, rabbits, dogs and non-human primates.

A pharmaceutical composition in accordance with the disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient or inert ingredient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

Efficacy of treatment or amelioration of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of compositions of the present disclosure, "effective against" for example a cancer, indicates that administration in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating the particular type of cancer.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given composition or formulation of the present disclosure can also be judged using an experimental animal model for the given disease as known in the art. When using an experimental animal model, efficacy of treatment is evidenced when a statistically significant change is observed.

The compositions of the present disclosure may be formulated in any manner suitable for delivery. The formulation may be, but is not limited to, nanoparticles, poly (lactic-co-glycolic acid) (PLGA) microspheres, lipidoids, lipoplex, liposome, polymers, carbohydrates (including simple sugars), cationic lipids and combinations thereof.

In some embodiments, pharmaceutical or other formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present disclosure may be approved by the US Food and Drug Administration (FDA). The compositions of the disclosure may be delivered to a cell or a subject through one or more routes and modalities. The viral vectors containing one or more CA2 biocircuits, CA2 effector modules, SREs, payloads and other components described herein may be used to deliver them to a cell and/or a subject. Other modalities may also be used such as mRNAs, plasmids, and as recombinant proteins.

Pharmaceutical compositions, CA2 biocircuits, CA2 biocircuit components, CA2 effector modules including their SREs or payloads of the present disclosure may be delivered to cells, tissues, organs and/or organisms in naked form. As used herein in, the term "naked" refers to pharmaceutical compositions, CA2 biocircuits, CA2 biocircuit components, CA2 effector modules including their SREs or payloads delivered free from agents or modifications which promote transfection or permeability. The naked pharmaceutical compositions, CA2 biocircuits, CA2 biocircuit components, CA2 effector modules including their SREs or payloads may be delivered to the cells, tissues, organs and/or organisms using routes of administration known in the art and described herein. In some embodiments, naked delivery may include formulation in a simple buffer such as saline or PBS.

In some embodiments, pharmaceutical compositions, CA2 biocircuits, CA2 biocircuit components, CA2 effector modules including their SREs or payloads of the present disclosure may be formulated, using methods described herein. Formulations may comprise pharmaceutical compositions, CA2 biocircuits, CA2 biocircuit components, CA2 effector modules including their SREs or payloads which may be modified and/or unmodified. Formulations may further include, but are not limited to, cell penetration agents, pharmaceutically acceptable carriers, delivery agents, bioerodible or biocompatible polymers, solvents, and/or sustained-release delivery depots. Formulations of the present disclosure may be delivered to cells using routes of administration known in the art and described herein.

Pharmaceutical compositions, CA2 biocircuits, CA2 biocircuit components, CA2 effector modules including their SREs or payloads may also be formulated for direct delivery to organs or tissues in any of several ways in the art including, but not limited to, direct soaking or bathing, via a catheter, by gels, powder, ointments, creams, gels, lotions, and/or drops, by using substrates such as fabric or biodegradable materials coated or impregnated with compositions, and the like.

In another aspect of the disclosure, polynucleotides encoding CA2 biocircuits, CA2 effector modules, SREs (e.g., CA2 DRDs), payloads of interest (e.g., IL15) and compositions of the disclosure and vectors comprising said polynucleotides may be introduced into cells. As a non-limiting example, the cells may be effector immune cells.

In various embodiments, the present disclosure provides a cell comprising one or more nucleic acid molecules, one or more vectors or one or more recombinant proteins of the disclosure. In some embodiments, a method of modulating the expression, function, and/or level of an IL15 payload in the cell are provided, said method comprising administering to the cell a stimulus to which the DRD is responsive, wherein the stimulus is administered in an amount sufficient to modulate the expression, function and/or level of the IL15 payload. In some embodiments, the cell is isolated. In some embodiments, the cell is a bacterial cell. In some embodiments, the cell is a mammalian cell. The mammalian cell may be a human cell. The human cell may be a T cell, natural killer (NK) cell, or tumor infiltrating lymphocyte (TIL). In some embodiments, the cell is a CD4+ or CD8+ T cell. In some embodiments, the human T cell or the human NK cell further comprises a polynucleotide encoding a chimeric antigen receptor (CAR) or T cell receptor (TCR), wherein the CAR or TCR comprises an antigen-binding domain specific to an antigen of interest. In some embodiments, the CAR comprises antigen-binding domain specific to CD19.

In one aspect of the disclosure, polynucleotides encoding CA2 biocircuits, CA2 effector modules, SREs (e.g., CA2 DRDs), payloads of interest (e.g., IL15) and compositions of the disclosure, may be packaged into viral vectors or integrated into viral genomes allowing transient or stable expression of the polynucleotides. Preferable viral vectors are retroviral vectors including lentiviral vectors and gamma retroviral vectors. In order to construct a retroviral vector, a polynucleotide molecule encoding a CA2 biocircuit, a CA2 effector module, a CA2 DRD or a payload of interest (e.g., an immunotherapeutic agent) is inserted into the viral genome in the place of certain viral sequences to produce a virus that is replication-defective. The recombinant viral vector is then introduced into a packaging cell line containing the gag, pol, and env genes, but without the LTR (for lentiviral vectors) and packaging components. The recombinant retroviral particles are secreted into the culture media, then collected, optionally concentrated, and used for gene transfer. Lentiviral vectors are especially preferred as they are capable of infecting both dividing and non-dividing cells.

Vectors may also be transferred to cells by non-viral methods by physical methods such as needles, electroporation, sonoporation, hyrdoporation; chemical carriers such as inorganic particles (e.g. calcium phosphate, silica, gold) and/or chemical methods. In some embodiments, synthetic or natural biodegradable agents may be used for delivery such as cationic lipids, lipid nano emulsions, nanoparticles, peptide-based vectors, or polymer-based vectors.

The CA2 biocircuit systems, CA2 effector modules, SREs and/or payloads of the present disclosure may be delivered using one or more modalities. The present disclosure also provides vectors that package polynucleotides of the disclosure encoding CA2 biocircuits, CA2 effector modules, SREs (e.g., CA2 DRDs) and IL15 payloads of interest, and combinations thereof. Vectors of the present disclosure may also be used to deliver the packaged polynucleotides to a cell, a local tissue site or a subject. These vectors may be of any kind, including DNA vectors, RNA vectors, plasmids, viral vectors and particles. Viral vector technology is well known and described in Sambrook et al. (2001, Molecular Cloning: A Laboratory Manual, Cold Spring Harbor Laboratory, New York). Viruses, which are useful as vectors include, but are not limited to lentiviral vectors, adenoviral vectors, adeno-associated viral (AAV) vectors, herpes simplex viral vectors, retroviral vectors, oncolytic viruses, and the like. In some embodiments, a viral vector useful for introducing one or more nucleic acid molecules encoding a DRD and IL15 payload exemplified herein into a cell may be derived from an adenovirus, adeno-associated virus (AAV), alphavirus, flavivirus, herpes virus, measles virus, rhabdovirus, retrovirus, lentivirus, Newcastle disease virus (NDV), poxvirus, or picornavirus.

In general, vectors contain an origin of replication functional in at least one organism, a promoter sequence and convenient restriction endonuclease site, and one or more selectable markers e.g. a drug resistance gene.

In some embodiments, the recombinant expression vector may comprise regulatory sequences, such as transcription and translation initiation and termination codons, which are specific to the type of host cell into which the vector is to be introduced.

In some embodiments, the vector of the disclosure may comprise one or more payloads taught herein, wherein the two or more payloads may be included in one CA2 effector module. In this case, the two or more payloads are tuned by the same stimulus simultaneously. In other embodiments, the vector of the disclosure may comprise two or more CA2 effector modules, wherein each CA2 effector module comprises a different payload. In this case, the two or more CA2 effector modules and payloads are tuned by different stimuli, providing separately independent regulation of the two or more components. In other embodiments, the vector of the disclosure may comprise one or more CA2 effector modules and one or more non-CA2 effector modules, wherein each CA2 effector module comprises a different payload. In this case, the CA2 effector modules and payloads are tuned by different stimuli, providing separately independent regulation of the two or more components.

In some embodiments, lentiviral vehicles/particles may be used as delivery modalities. Lentiviruses are subgroup of the Retroviridae family of viruses, named because reverse transcription of viral RNA genomes to DNA is required before integration into the host genome. As such, the most important features of lentiviral vehicles/particles are the integration of their genetic material into the genome of a target/host cell. Some examples of lentivirus include the Human Immunodeficiency Viruses: HIV-1 and HIV-2, the Simian Immunodeficiency Virus (SIV), feline immunodeficiency virus (FIV), bovine immunodeficiency virus (BIV), Jembrana Disease Virus (JDV), equine infectious anemia virus (EIAV), equine infectious anemia virus, visna-maedi and caprine arthritis encephalitis virus (CAEV).

Typically, lentiviral particles making up the gene delivery vehicle are replication defective on their own (also referred to as "self-inactivating"). Lentiviruses are able to infect both dividing and non-dividing cells by virtue of the entry mechanism through the intact host nuclear envelope (Naldini L et al., Curr. Opin. Biotechnol, 1998, 9: 457-463). Recombinant lentiviral vehicles/particles have been generated by multiply attenuating the HIV virulence genes, for example, the genes Env, Vif, Vpr, Vpu, Nef and Tat are deleted making the vector biologically safe. Correspondingly, lentiviral vehicles, for example, derived from HIV-1/HIV-2 can mediate the efficient delivery, integration and long-term expression of transgenes into non-dividing cells. As used herein, the term "recombinant" refers to a vector or other nucleic acid containing both lentiviral sequences and non-lentiviral retroviral sequences.

Lentiviral particles may be generated by co-expressing the virus packaging elements and the vector genome itself in a producer cell such as human HEK293T cells. These elements are usually provided in three or four separate plasmids. The producer cells are co-transfected with plasmids that encode lentiviral components including the core (i.e. structural proteins) and enzymatic components of the virus, and the envelope protein(s) (referred to as the packaging systems), and a plasmid that encodes the genome including a foreign transgene, to be transferred to the target cell, the vehicle itself (also referred to as the transfer vector). In general, the plasmids or vectors are included in a producer cell line. The plasmids/vectors are introduced via transfection, transduction or infection into the producer cell line. Methods for transfection, transduction or infection are well known by those of skill in the art. As non-limiting example, the packaging and transfer constructs can be introduced into producer cell lines by calcium phosphate transfection, lipofection or electroporation, generally together with a dominant selectable marker, such as neo, DHFR, Gln synthetase or ADA, followed by selection in the presence of the appropriate drug and isolation of clones.

The producer cell produces recombinant viral particles that contain the foreign gene, for example, the CA2 effector module of the present disclosure. The recombinant viral particles are recovered from the culture media and titrated by standard methods used by those of skill in the art. The recombinant lentiviral vehicles can be used to infect target cells.

Cells that can be used to produce high-titer lentiviral particles may include, but are not limited to, HEK293T cells, 293G cells, STAR cells (Relander et al., Mol. Ther., 2005, 11: 452-459), FreeStyle™ 293 Expression System (ThermoFisher, Waltham, Mass.), and other HEK293T-based producer cell lines (e.g., Stewart et al., Hum Gene Ther. 2011, 22(3):357-369; Lee et al., Biotechnol Bioeng, 2012, 10996): 1551-1560; Throm et al., Blood. 2009, 113(21): 5104-5110; the contents of each of which are incorporated herein by reference in their entirety).

In some aspects, the envelope proteins may be heterologous envelop proteins from other viruses, such as the G protein of vesicular stomatitis virus (VSV G) or baculoviral gp64 envelop proteins. The VSV-G glycoprotein may especially be chosen among species classified in the vesiculovirus genus: Carajas virus (CJSV), Chandipura virus (CHPV), Cocal virus (COCV), Isfahan virus (ISFV), Maraba virus (MARAV), Piry virus (PIRYV), Vesicular stomatitis Alagoas virus (VSAV), Vesicular stomatitis Indiana virus (VSIV) and Vesicular stomatitis New Jersey virus (VSNJV) and/or stains provisionally classified in the vesiculovirus genus as Grass carp rhabdovirus, BeAn 157575 virus (BeAn 157575), Boteke virus (BTKV), Calchaqui virus (CQIV), Eel virus American (EVA), Gray Lodge virus (GLOV), Jurona virus (JURY), Klamath virus (KLAV), Kwatta virus (KWAV), La Joya virus (LJV), Malpais Spring virus (MSPV), Mount Elgon bat virus (MEBV), Perinet virus (PERV), Pike fry rhabdovirus (PFRV), Porton virus (PORV), Radi virus (RADIV), Spring viremia of carp virus (SVCV), Tupaia virus (TUPV), Ulcerative disease rhabdovirus (UDRV) and Yug Bogdanovac virus (YBV). The gp64 or other baculoviral env protein can be derived from *Autographa californica* nucleopolyhedrovirus (AcMNPV), *Anagrapha falcifera* nuclear polyhedrosis virus, *Bombyx mori* nuclear polyhedrosis virus, *Choristoneura fumiferana* nucleopolyhedrovirus, *Orgyia pseudotsugata* single capsid nuclear polyhedrosis virus, *Epiphyas postvittana* nucleopolyhedrovirus, *Hyphantria cunea* nucleopolyhedrovirus, *Galleria mellonella* nuclear polyhedrosis virus, Dhori virus, Thogoto virus, *Antheraea pemyi* nucleopolyhedrovirus or Batken virus.

Other elements provided in lentiviral particles may comprise retroviral LTR (long-terminal repeat) at either 5' or 3' terminus, a retroviral export element, optionally a lentiviral reverse response element (RRE), a promoter or active portion thereof, and a locus control region (LCR) or active portion thereof. The CA2 effector module is linked to the vector.

Methods for generating recombinant lentiviral particles are discussed in the art, for example, U.S. Pat. Nos. 8,846, 385; 7,745,179; 7,629,153; 7,575,924; 7,179,903; and 6,808,905; the contents of each of which are incorporated herein by reference in their entirety.

Lentivirus vectors used may be selected from, but are not limited to pLVX, pLenti, pLenti6, pLJM1, FUGW, pWPXL, pWPI, pLenti CMV puro DEST, pLJM1-EGFP, pULTRA, pInducer20, pHIV-EGFP, pCW57.1, pTRPE, pELPS, pRRL, and pLionII.

Lentiviral vectors are used for introducing transgenes into T cells (e.g., primary human T cells or Jurkat cells) for preclinical research and clinical applications, including recently approved products such as Tisagenlecleucel (KYMRIAH®) for relapsed/refractory B-cell lymphoma. VSV-G pseudotyped 3rd generation lentiviral vectors offer high titers, high transduction efficiency and safety, and have become the vectors of choice for T cell engineering. While not wishing to be bound by theory, T cell engineering usually involves T cell activation by CD3/CD28 antibodies, followed by lentivirus transduction, and then cell expansion which can last from 5 to 30 days (e.g., 9 to 14 days or 9 to 15 days). In general, lentivirus transgene integration may take over 7 days to fully stabilize in T cells (e.g., primary human T cells or Jurkat cells).

In some embodiments, to determine the transgene expression kinetics CD3/CD28 activated primary human T cells can be transduced with lentivirus carrying a transgene (e.g., IL15). The cells may be analyzed by methods described herein and/or known in the art for viability, viral genomic integration (e.g., by using quantitative PCR), transcript levels (e.g., by using quantitative RT-PCR), and cell surface expression of the transgene. The cells may be analyzed prior to transduction and/or after transduction such as 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, the cells may be analyzed at various time points between 3 to 14 days after transduction (e.g., 3 days, 4 days, 5 days, 6 days, 7 days, 8 days, 9 days, 10 days, 11 days, 12 days, 13 days, and/or 14 days). As a non-limiting example, the cells may be analyzed 3 to 15 days after transduction. As a non-limiting example, the cells may be analyzed 9 to 15 days after transduction.

In some embodiments, the CD3/CD28 activated primary human T cells can be reactivated with CD3/CD28 beads after transduction. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. The cells may be analyzed by methods described herein and/or known in the art for viability, viral genomic integration (e.g., by using quantitative PCR), transcript levels (e.g., by using quantitative RT-PCR), cell surface expression of the transgene, copy number, and/or mRNA levels.

In some embodiments, the cell viability of activated primary human T cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the cell viability of Jurkat cells transduced with lentivirus carrying a transgene is greater than 65%, 70%, 75%, 80%, 85%, 90%, 95%, 97%, or 99%. As a non-limiting example, the cell viability is greater than 90%. As a non-limiting example, the cell viability is greater than 85%.

In some embodiments, the integration of the transgene into the genome of the cell may be at or above the saturation point. As a non-limiting example, the saturation point may be 3 copies per cell.

In some embodiments, the integration of the transgene into the genome may be high in the initial timepoints evaluated and then decline to a lower integration value before becoming stable for the remainder of the culture. As a non-limiting example, the integration may be up to 20 copies per cell of the transgene into the genome during the early timepoints before declining to 2 copies per cell and being stable throughout the remainder of the culture.

In some embodiments, the transduction of ability of T cells may be evaluated. T cells from at least one donor may be transduced with a lentivirus containing a transgene at a dose that is predicted to reach the saturating levels (e.g., enough virus that each cell should contain a copy if a Poisson distribution is expected) and a higher lentivirus dose that exceeds saturation 5 times. Copies per cell, percentage and MFI of cells (or concentration in media of transgene) may be detected in order to determine if all cells are expressing transgene. As a non-limiting example, T cells from two distinct donors may be transduced with lentivirus which includes a transgene. The transduction may be at two doses, saturation and 5× saturation, and show that 5-10 days after transduction that all groups may reach or exceed a predicted saturating level of integrated transgene and similar expression intensity across groups but not all cells are expressing the transgene. Not all T cells may have equal transduction susceptibility, even when sourced from the same donor. The fraction of total cells that express GFP (above the detection threshold) may vary between donors, lots and/or viral dose.

In some embodiments, a percentage of the cultured T cells (e.g., primary human T cells and/or Jurkat cells) may express the transgene. The percentage of culture T cells expressing the transgene may be, but is not limited to, 5%, 10%, 15%, 20%, 25%, 30%, 35%, 40%, 45%, 50%, 55%, 60%, 65%, 70%, 75%, 80%, 85%, 90%, 95%, 97%, 99% or greater than 99%. As a non-limiting example, the percentage may be greater than 70%. As a non-limiting example, the percentage may be greater than 75%. As a non-limiting example, the percentage may be greater than 80%. As a non-limiting example, the percentage may be greater than 85%. As a non-limiting example, the percentage may be greater than 90%. As a non-limiting example, the percentage may be greater than 95%.

In some embodiments, the mRNA levels from the culture may decline over the duration of the study. The decline may not be limited to a specific transgene and the trend may be seen across multiple classes of expressed proteins. In order to increase the mRNA levels, the cells may be reactivated after the mRNA levels decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase mRNA levels in the culture, the cells may be reactivated with CD3/CD28 beads 13 days after transduction. As a non-limiting example, in order to increase mRNA levels in the culture, the cells may be reactivated with CD3/CD28 beads 14 days after transduction. As a non-limiting example, in order to increase mRNA levels in the culture, the cells may be reactivated with CD3/CD28 beads 15 days after transduction In some embodiments, the surface expression from the culture may decline over the duration of the study. For example, the surface expression may decline between days 3 to 13 days, 3 to 14 days, or 3 to 15 days after transduction. In order to increase the surface expression, the cells may be reactivated after the surface expression decrease from the initial levels. The cells may be reactivated 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 or more than 30 days after transduction. As a non-limiting example, in order to increase surface expression in the culture, the cells may be reactivated with CD3/CD28 beads 13 days after transduction. As a non-limiting example, in order to increase surface expression in the culture, the cells may be reactivated with CD3/CD28 beads 14 days after transduction. As a non-limiting example, in order to increase surface expression in the culture, the cells may be reactivated with CD3/CD28 beads 15 days after transduction.

In some embodiments, the transgene is IL15 (e.g., a membrane bound IL15 payload when combined with the other effector module components described in Table 3). The cell viability may be greater than 90% in cells transduced with IL15. The cell viability may be greater than 85% in cells transduced with IL15. If the cells are primary T cells transduced with IL15, the number of viable cells may increase over the initial timepoints before decreasing. If the cells are Jurkat cells transduced with IL15, the number of viable cells may increase for at least 10 days. The number of copies per cell for IL15 transduced cells may be higher for the initial timepoints before decreasing by 50% or more for the later timepoints. For IL15 transduced primary human T cells, the level of soluble IL15 in the media may drop steadily over the time course of the study with a slight increase visible in the restimulated group. For IL15 transduced Jurkat cells, the level of soluble IL15 in the media may have a drop in IL15 secretion in the first half of the culture with the levels remaining low through the second half of the culture time.

In some embodiments, lentivirally engineered cells described herein have genomic DNA integration that stabilizes after an initial decline of copy number, decreasing RNA and surface expression levels over time, and an increase in RNA and surface expression after restimulation.

In some embodiments, lentivirally engineering cells may be evaluated using the following 14-day method where samples are collected 5 times throughout the culture. On day −1 the T cells (e.g., primary human T cells or Jurkat cells) may be thawed and the CD3/CD28 beads are added. On day 0, the lentivirus for each of the conditions is added (e.g., 4 mL of cells at 0.5e6/mL) and there is a control of non-transduced cells. Double media to 8 mL on day 1 and then double the media to 16 mL on day 2. On day 3, harvest 4 mL and then double media to 24 mL on day 4. Harvest 4 mL on day 6 before doubling media to 40 mL. The cells can be split (e.g., 14 mL 0.5e6 cells/mL) on day 8 and then on day 6 harvest 4 mL before doubling media to 40 mL. 4 mL may be harvested on day 10 before the media is doubled to 20 mL. On day 13, 4 mL are harvested before doubling the media to 32 mL. The culture is split in half and half of the culture is activated (CD3/CD28 activation beads 1:1) and stimulated overnight. On day 14, 4 mL of each stimulated and non-stimulated cells are harvested and the culture is ended. Transgene copy number per cell are assayed by harvesting cells and extracting genomic DNA then quantifying with standard curve qPCR against the endogenous genome and against the transgene sequence, then converting the detected quantities to a ratio. Mean Fluorescence Intensity (MFI) is assayed by FLO on an Attune with appropriate staining for each group. Percent expressing may also be assayed by FLO on an attune quantifying the percent of cells fluorescing above threshold. Soluble payloads can be quantified by harvesting culture supernatant at each marked timepoint and running MesoScale Discovery plate assay (MSD) then normalizing for cell density.

In some embodiments, the CA2 effector modules of the disclosure may be designed as a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo.

The present disclosure provides methods comprising administering any one or more or components of a CA2 biocircuit system to a subject in need thereof. These may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

In some embodiments, the present disclosure provides a method of treating a disease or disorder responsive to regulated IL15 in a subject in need thereof, said method comprising: (a) administering to the subject a therapeutically effective amount of a nucleic acid molecule, vector, recombinant protein, cell, or pharmaceutical composition of the disclosure; and administering a therapeutically effective amount of a stimulus to the subject, wherein the DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus is acetazolamide.

In some embodiments, the present disclosure provides a method of treating a malignant tumor in a subject in need thereof, wherein said tumor expresses a tumor-associated antigen, said method comprising: (a) administering to the subject a therapeutically effective amount of a human T cell or a human NK cell of the disclosure, which further comprises a polynucleotide encoding a CAR or TCR, or a pharmaceutical composition thereof, wherein the CAR or TCR comprises an antigen-binding domain specific to the tumor-associated antigen; and (b) administering a therapeutically effective amount of a stimulus to the subject, wherein the CA2 DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus administered to the subject is acetazolamide.

In some embodiments, the present disclosure provides a method of treating a malignant tumor in a subject in need thereof, said method comprising: (a) administering to the subject a therapeutically effective amount of a human TIL of the disclosure; and (b) administering a therapeutically effective amount of a stimulus to the subject, wherein the CA2 DRD is responsive to the stimulus and wherein expression of the IL15 payload is modulated in response to the stimulus. In some embodiments, the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide. In some embodiments, the stimulus administered to the subject is acetazolamide.

Compositions in accordance with the disclosure are typically formulated in dosage unit form for ease of administration and uniformity of dosage. It will be understood, however, that the total daily usage of the compositions of the present disclosure may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Compositions of the disclosure may be used in varying doses to avoid T cell anergy, prevent cytokine release syndrome and minimize toxicity associated with immunotherapy. For example, low doses of the compositions of the present disclosure may be used to initially treat patients with high tumor burden, while patients with low tumor burden may be treated with high and repeated doses of the compositions of the disclosure to ensure recognition of a minimal tumor antigen load. In another instance, the compositions of the present disclosure may be delivered in a pulsatile fashion to reduce tonic T cell signaling and enhance persistence in vivo. In some aspects, toxicity may be minimized by initially using low doses of the compositions of the disclosure, prior to administering high doses. Dosing may be modified if serum markers such as ferritin, serum C-reactive protein, IL6, IFN-γ, and TNF-α are elevated.

Also provided herein are methods of administering ligands in accordance with the disclosure to a subject in need thereof. The ligand may be administered to a subject or to cells, using any amount and any route of administration effective for tuning the CA2 biocircuits of the present disclosure. The exact amount required will vary from subject to subject, depending on the species, age, and general condition of the subject, the severity of the disease, the particular composition, its mode of administration, its mode of activity, and the like. The subject may be a human, a mammal, or an animal. Compositions in accordance with the present disclosure are typically formulated in unit dosage form for ease of administration and uniformity of dosage. It will be understood, however, that the total daily usage of the compositions of the present disclosure may be decided by the attending physician within the scope of sound medical judgment. In certain embodiments, the ligands in accordance with the present disclosure may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, from about 10 mg/kg to about 100 mg/kg, from about 50 mg/kg to about 500 mg/kg, from about 100 mg/kg to about 1000 mg/kg, of subject body weight per day, one or more times a day, to obtain the desired effect. In some embodiments, the dosage levels may be 1 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg or mg/kg of subject body weight per day, or more times a day, to obtain the desired effect.

The present disclosure provides methods for delivering to a cell or tissue any of the ligands described herein, comprising contacting the cell or tissue with said ligand and can be accomplished in vitro, ex vivo, or in vivo. In certain embodiments, the ligands in accordance with the present disclosure may be administered to cells at dosage levels sufficient to deliver from about 1 nM to about 10 nM, from about 5 nM to about 50 nM, from about 10 nM to about 100 nM, from about 50 nM to about 500 nM, from about 100 nM to about 1000 nM, from about 1 μM to about 10 μM from about 5 μM to about 50 μM from about 1004 to about 10004 from about 2504 to about 25004 from about 50 μM to about 500 μM. In some embodiments, the ligand may be administered to cells at doses selected from but not limited to 0.00064 μM, 0.0032 μM, 0.016 μM, 0.08 μM, 0.4 μM, 1 μM, 2 μM, 10 μM, 50 μM, 75, 100 μM, 150 μM, 175 μM, 200 μM, 250 μM.

The desired dosage of the ligands of the present disclosure may be delivered only once, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of "single unit dose" or total daily dose into two or more doses, e.g., two or more administrations of the "single unit dose". As used herein, a "single unit dose" is a dose of any therapeutic administered in one dose/at one time/single route/single point of contact, i.e., single administration event. The desired dosage of the ligand of the present disclosure may be administered as a "pulse dose" or as a "continuous flow". As used herein, a "pulse dose" is a series of single unit doses of any therapeutic administered with a set frequency over a period of time. As used herein, a "continuous flow" is a dose of therapeutic administered continuously for a period of time in a single route/single point of contact, i.e., continuous administration event. A total daily dose, an amount given or prescribed in 24-hour period, may be administered by any of these methods, or as a combination of these methods, or by any other methods suitable for a pharmaceutical administration.

In some embodiments, the compositions for immunotherapy may be administered to cells ex vivo and subsequently administered to the subject. Immune cells can be isolated and expanded ex vivo using a variety of methods known in the art. For example, methods of isolating cytotoxic T cells are described in U.S. Pat. Nos. 6,805,861 and 6,531,451; the contents of each of which are incorporated herein by reference in their entirety. Isolation of NK cells is described in U.S. Pat. No. 7,435,596; the contents of which are incorporated by reference herein in its entirety.

In some embodiments, depending upon the nature of the cells, the cells may be introduced into a host organism e.g. a mammal, in a wide variety of ways including by injection, transfusion, infusion, local instillation or implantation. In some aspects, the cells described herein may be introduced at the site of the tumor. The number of cells that are employed will depend upon a number of circumstances, the purpose for the introduction, the lifetime of the cells, the protocol to be used, for example, the number of administrations, the ability of the cells to multiply, or the like. The cells may be in a physiologically-acceptable medium.

In some embodiments, the cells described herein may be administrated in multiple doses to subjects having a disease or condition. The administrations generally effect an improvement in one or more symptoms of cancer or a clinical condition and/or treat or prevent cancer or clinical condition or symptom thereof.

In some embodiments, the compositions for immunotherapy may be administered in vivo. In some embodiments, polypeptides of the present disclosure comprising CA2 biocircuits, CA2 effector molecules, SREs, payloads of interest (IL15) and compositions of the disclosure may be delivered in vivo to the subject. In vivo delivery of immunotherapeutic agents is well described in the art. For example, methods of delivery of cytokines are described in the EP Pat. No. EP0930892 A1, the contents of which are incorporated herein by reference.

The pharmaceutical compositions, CA2 biocircuits, CA2 biocircuit components, CA2 effector modules including their SREs (e.g., CA2 DRDs), payloads (e.g., IL15), vectors and cells of the present disclosure may be administered by any route to achieve a therapeutically effective outcome.

The pharmaceutical compositions, CA2 biocircuits, CA2 biocircuit components, CA2 effector modules including their SREs or payloads of the present disclosure may be administered by any route to achieve a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intra-epidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In some embodiments, pharmaceutical compositions, CA2 biocircuits, CA2 biocircuit components, CA2 effector modules including their SREs or payloads of the present disclosure may be administered parenterally. Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as CREMOPHOR®, alcohols, oils, modified oils, glycols, polysorbates, cyclodextrins, polymers, and/or combinations thereof. In other embodiments, surfactants are included such as hydroxypropylcellulose.

Injectable preparations, for example, sterile intravenous preparations or injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

The CA2 biocircuits, CA2 effector modules, SREs, stimuli, compositions or systems comprising one or more of the stimuli, CA2 biocircuits, CA2 effector modules of the present disclosure may be utilized in a large variety of applications including, but not limited to, therapeutics, diagnosis and prognosis, bioengineers, bioprocessing, biofactory, research agents, metabolomics, gene expression, enzyme replacement, etc.

According to the present disclosure, the CA2-IL15 biocircuits and systems may be used in the development and implementation of cell therapies such as adoptive cell therapy. The CA2-IL15 biocircuits and systems may be used to effect CAR T cell therapy, T cell receptor (TCR) cell therapy, CAR NK cell therapy, TCR NK cell therapy, TIL therapy, any of which may be used in combination therapy with other treatment lines (e.g. radiation, cytokines).

In some embodiments, CA2-IL15 biocircuits and systems may be used to engineer immune cells including T cells such as $CD8^+$ T cells and $CD4^+$ T cells, natural killer (NK) cells, NK T cells, Cytotoxic T lymphocytes (CTLs), tumor infiltrating lymphocytes (TIL), lymphokine activated killer (LAK) cells, memory T cells, regulatory T cells (Tregs), helper T cells, cytokine-induced killer (CIK) cells, and any combination thereof. In other embodiments, CA2-IL15 biocircuits and systems may be used to engineer immune stimulatory cells generated from embryonic stem cell (ESC) and induced pluripotent stem cell (iPSC) that may be used for ACT. In some embodiments, CA2-IL15 biocircuits and systems may be used to engineer autologous or allogeneic immune cells that may be used for ACT. In some embodiments, CA2-IL15 biocircuits and systems may be used to engineer T cells, TIL or NK cells. In some embodiments, the immune cells are NK cells derived from cord blood, iPSCs or peripheral blood mononuclear cells.

In some embodiments, CA2-IL15-engineered cells used for ACT may be T cells that also have been engineered to express a CAR or TCR comprising an antigen-binding domain specific to an antigen on tumor cells of interest. In other embodiments, CA2-IL15-engineered cells used for ACT may be NK cells engineered to express a CAR or TCR comprising an antigen-binding domain specific to an antigen on tumor cells of interest. In some embodiments, CA2-IL15-engineered cells used for ACT may be a mixture of T cells and NK cells, either or both of which may be expressing a CAR or TCR.

A chimeric antigen receptor (CAR), when transduced into immune cells (e.g., T cells and NK cells), can re-direct the immune cells against a target (e.g., a tumor cell) which expresses a molecule recognized by the extracellular target moiety of the CAR. As used herein, the term "chimeric antigen receptor (CAR)" refers to a synthetic receptor that mimics TCR on the surface of T cells. In general, a CAR is composed of an extracellular targeting domain, a transmembrane domain/region and an intracellular signaling/activation domain. In a standard CAR receptor, the extracellular targeting domain, transmembrane domain and intracellular signaling/activation domain, are linearly constructed as a single fusion protein. The extracellular region comprises a targeting domain/moiety (e.g., a scFv) that recognizes a specific tumor antigen (e.g., a tumor neoantigen) or other tumor cell-surface molecules. The intracellular region may contain a intracellular signaling domain (the immunoreceptor tyrosine-based activation motifs) of TCR complex (e.g., the signaling region of CD3), and/or one or more costimulatory signaling domains, such as those from CD28, 4-1BB (CD137) and OX-40 (CD134). A CAR, when expressed by a T cell or NK cell, endows the T cell or NK cell with antigen specificity determined by the extracellular targeting moiety of the CAR.

In some embodiments, the extracellular targeting domain is joined through the hinge (also called space domain or spacer) and transmembrane regions to an intracellular signaling domain. The hinge connects the extracellular targeting domain to the transmembrane domain which transverses the cell membrane and connects to the intracellular signaling domain. The hinge may need to be varied to optimize the potency of CAR transformed cells toward cancer cells due to the size of the target protein where the targeting moiety binds, and the size and affinity of the targeting domain itself. Upon recognition and binding of the targeting moiety to the target cell, the intracellular signaling domain leads to an activation signal to the CAR T cell or CAR NK cell, which is further amplified by the "second signal" from one or more intracellular costimulatory domains. The CAR T cell or CAR NK cell, once activated, can destroy the target cell.

In some embodiments, the present disclosure provides an immune cell comprising a CA2-IL15 effector module and further comprising a chimeric antigen receptor (CAR). The CAR may be regulated by a DRD or may be constitutively expressed. In some embodiments, the CAR is constitutively expressed.

In some embodiments, the constitutively expressed or regulated CAR and the CA2-IL15 effector module are encoded on different vectors. In some embodiments, a single vector comprises both the CA2-IL15 effector module and the constitutively expressed or regulated CAR to form a tandem construct. The CA2-IL15 effector module and the CAR may be separated from one another by an internal ribosome entry site (IRES); a ribosomal skipping sequence 2A peptide selected from foot-and-mouth disease virus (FMDV) 2A (F2A), equine rhinitis A virus (ERAV) 2A (E2A), porcine teschovirus-1 2A (P2A) or Thosea asigna virus 2A (T2A); or other ribosomal skipping sequence or ribosomal entry sequence, giving rise to a bicistronic construct. In some embodiments, the 2A sequence is a P2A sequence. The IRES, 2A sequence, or other ribosomal skipping sequence or ribosomal entry sequence leads to the expression of the upstream and downstream sequences expressed as two independent polypeptides. In some embodiments, a single vector comprises, in order, a sequence encoding a CAR, a P2A sequence, and a sequence encoding the CA2-IL15 effector module. The sequence encoding the CAR may be either 5' or 3' to the sequence encoding the CA2-IL15 effector module.

A T cell receptor (TCR) when transduced into immune cells (e.g., T cells and NK cells), can re-direct the immune cells against a target (e.g., a tumor cell) which expresses a molecule recognized by the TCR. A TCR is a molecule that contains a variable α and β chains (also known as TCRα and TCRβ, respectively) or a variable γ and δ chains (also known as TCRγ and TCRδ, respectively), or antigen-binding portions or fragments thereof, which is capable of specifically binding to a peptide bound to an WIC molecule. In some embodiments, the TCR is TCRαβ. Generally, a TCR is found on the surface of T cells where it is generally responsible for recognizing antigens bound to major histocompatibility complex (WIC) molecules.

As used herein, the term TCR encompasses full TCRs as well as antigen-binding portions or antigen-binding fragments thereof. In some embodiments, the TCR is a full-length TCR comprising both the α chain and β chain. In some embodiments, the TCR is an antigen-binding portion or fragment of a TCR, for example a portion of each of the α chain and β chain, that binds to a specific peptide bound in an WIC molecule. In some embodiments, the antigen-binding portion or fragment comprises the variable domains of a TCR, such as the variable α (Vα) chain and variable β (Vβ) chain, sufficient to bind to a specific WIC-peptide complex.

The variable domains of the TCR contain complementarity determining regions (CDRs), which primarily contribute to MHC-peptide antigen recognition, binding and specificity. The CDRs within a variable region of a TCR chain are separated by framework regions (FRs), which typically display less variability than the CDRs. In some embodiments, one or more CDRs of a TCR form all or substantially all of the antigen-binding site of a given TCR molecule. In some embodiments, CDR3 is the main CDR responsible for antigen binding or specificity and for interaction with the processed peptide portion of the peptide-MHC complex.

The α-chain and β-chain of a TCR also may contain a constant domain, a transmembrane domain and a short cytoplasmic tail. The cytoplasmic tail of a TCR, anchors the protein in the cell membrane, where it associates with invariant subunits of the CD3 complex, which are involved in the signaling capacity of the TCR complex.

In some embodiments, the present disclosure provides a CAR T cell or TCR T cell that is "armed" with a CA2-IL15 effector module to improve the engineered cells' efficacy and persistence.

In some embodiments, the present disclosure provides CAR NK cell or TCR NK cell that is "armed" with a CA2-IL15 effector module to improve the engineered cells' efficacy and persistence or prevent immune exhaustion and senescence.

In some embodiments, the present disclosure provides TIL engineered with a CA2-IL15 effector module to improve the engineered cells' efficacy and persistence.

In some embodiments, cells of the present disclosure may be autologous, allogeneic, syngeneic, or xenogeneic in relation to a particular individual subject. In some embodiments, cells of the present disclosure may be mammalian cells, particularly human cells. Cells described herein may be primary cells or immortalized cell lines.

Cancer immunotherapy aims at the induction or restoration of the reactivity of the immune system towards cancer. Adoptive cell therapy is a form of active immunotherapy that aims at induction of an endogenous, long-lasting tumor-antigen specific immune response. The response may be enhanced by non-specific stimulation of immune response modifiers such as cytokines but cytokine stimulation can cause toxicity or immune exhaustion.

Despite significant advances, the efficacy of current immunotherapy strategies is limited by associated toxicities. These are often related to the narrow therapeutic window associated with immunotherapy, which in part, emerges from the need to push therapy dose to the edge of potentially fatal toxicity to get a clinically meaningful treatment effect. Further, dose expands in vivo since adoptively transferred immune cells continue to proliferate within the patient, often unpredictably.

A major risk involved in immunotherapy is the on-target but off tumor side effects resulting from T cell activation in response to normal tissue expression of the tumor associated antigen (TAA).

Immunotherapy may also produce on target, on-tumor toxicities that emerge when tumor cells are killed in response to the immunotherapy. The adverse effects include tumor lysis syndrome, cytokine release syndrome and the related macrophage activation syndrome. Importantly, these adverse effects may occur during the destruction of tumors, and thus even a successful on-tumor immunotherapy might result in toxicity. Approaches to regulatably control immunotherapy are thus highly desirable since they have the potential to reduce toxicity and maximize efficacy.

The present disclosure provides systems, compositions, immunotherapeutic agents and methods for cancer immunotherapy. These compositions provide tunable regulation of gene expression and function in immunotherapy. The present disclosure also provides CA2 biocircuits, CA2 effector modules, stimulus response elements (SREs) and payloads, as well as polynucleotides encoding any of the foregoing. In one aspect, the systems, compositions, immunotherapeutic agents and other components of the disclosure can be controlled by a separately added stimulus, which provides a significant flexibility to regulate cancer immunotherapy. Further, the systems, compositions and the methods of the present disclosure may also be combined with therapeutic agents such as chemotherapeutic agents, small molecules, gene therapy, and antibodies.

The tunable nature of the systems and compositions of the disclosure has the potential to improve the potency and duration of the efficacy of immunotherapies. Reversibly silencing the biological activity of adoptively transferred cells using compositions of the present disclosure allows maximizing the potential of cell therapy without irretrievably killing and terminating the therapy.

The present disclosure provides methods for fine tuning of immunotherapy after administration to patients. This in turn improves the safety and efficacy of immunotherapy and increases the subject population that may benefit from immunotherapy.

In one embodiment, the CA2 biocircuits, CA2 effector modules, SREs, and components that tune expression levels and activities of any agents may be used for immunotherapy. As non-limiting examples, the immunotherapeutic agent used in the constructs of the present disclosure is IL15 that induces an immune response in a cell and a subject.

In some embodiments, the composition for inducing an immune response may comprise a CA2 effector module. In some embodiments, the CA2 effector module may comprise a stimulus response element (SRE) operably linked to a human IL15 comprising the amino acid sequence of SEQ ID NO: 8.

In some embodiments, CA2 biocircuits, CA2 effector modules, and compositions of the present disclosure relate to post-translational regulation of protein (payload) function anti-tumor immune responses of immunotherapeutic agents.

In some embodiments, cells which are genetically modified to express at least one CA2 biocircuit, CA2 effector module, SRE (e.g., CA2 DRD), and/or payload of interest (immunotherapeutic agent) may be used for adoptive cell therapy (ACT). As used herein, adoptive cell transfer refers to the administration of immune cells (from autologous, allogenic or genetically modified hosts) with direct anticancer activity. ACT has shown promise in clinical application against malignant and infectious disease.

According to the present disclosure, the CA2 biocircuits and systems may be used in the development and implementation of cell therapies such as adoptive cell therapy. The CA2 biocircuits, CA2 effector modules and their SREs and payloads may be used in cell therapies to effect immune cell therapies alone or in combination with other treatment lines (e.g. radiation, cytokines).

Provided herein are methods for use in adoptive cell therapy. In one embodiment, the method involves preconditioning a subject in need thereof, removing a portion of the subject's T cells, engineering the subject's T cells with a CA2 effector module of the present disclosure, and administering to the subject the engineered T cells expressing the CA2 effector module, wherein the engineered cells successfully engraft within the subject.

In another embodiment, the method involves preconditioning a subject in need thereof and administering to the subject allogeneic engineered T cells expressing the CA2 effector module, wherein the engineered cells successfully engraft within the subject.

In some embodiments, the method involves removing a malignant tumor from a subject, isolating TIL from the tumor, engineering the TIL with the CA2 effector module of the present disclosure, and administering to the subject the engineered TIL, wherein the TIL successfully infiltrate any remaining tumor or metastases in the subject.

In some embodiments, SREs, CA2 biocircuits and compositions of the present disclosure may be used to minimize preconditioning regimens associated with adoptive cell therapy. As used herein "preconditioning" refers to any therapeutic regimen administered to a subject to improve the outcome of adoptive cell therapy. Preconditioning strategies include but are not limited to total body irradiation and/or lymphodepleting chemotherapy. Adoptive therapy clinical trials without preconditioning have failed to demonstrate any clinical benefit, indicating its importance in ACT. Yet, preconditioning is associated with significant toxicity and limits the subject cohort that is suitable for ACT. In some instances, immune cells for ACT may be engineered to express cytokines such as IL15 as payload using SREs of the present disclosure to reduce the need for preconditioning.

In some embodiments, NK cells engineered to express the present compositions may be used for ACT. NK cell activation induces perforin/granzyme-dependent apoptosis in target cells. NK cell activation also induces cytokine secretion such as IFN γ, TNF-α and GM-CSF. These cytokines enhance the phagocytic function of macrophages and their antimicrobial activity and augment the adaptive immune response via up-regulation of antigen presentation by antigen presenting cells such as dendritic cells (DCs).

Immune cells can be isolated and expanded ex vivo using a variety of methods known in the art. For example, methods of isolating and expanding cytotoxic T cells are described in U.S. Pat. Nos. 6,805,861 and 6,531,451; US Patent Publication NO. US20160348072A1 and International Patent Publication NO. WO2016168595A1; the contents of each of which are incorporated herein by reference in their entirety. Isolation and expansion of NK cells is described in US Patent Publication NO. US20150152387A1, U.S. Pat. No. 7,435,596; and Oyer, J. L. (2016). Cytotherapy. 18(5):653-63; the contents of each of which are incorporated by reference herein in its entirety. Specifically, human primary NK cells may be expanded in the presence of feeder cells e.g. a myeloid cell line that has been genetically modified to express membrane bound IL15 and 4-1BBL.

In some embodiments, activation and expansion of T cells for ACT is achieved by antigenic stimulation of a transiently expressed Chimeric Antigen Receptor (CAR) on the cell surface. Such activation methods are taught in International Patent NO. WO2017015427, the content of which are incorporated herein by reference in their entirety.

In some embodiments, immune cells may be activated by antigens associated with antigen presenting cells (APCs). In some embodiments, the APCs may be dendritic cells, macrophages or B cells that antigen specific or nonspecific. The APCs may autologous or homologous in their organ. In some embodiments, the APCs may be artificial antigen presenting cells (aAPCs) such as cell based aAPCs or acellular aAPCs. Cell based aAPCs are may be selected from either genetically modified allogeneic cells such as human erythroleukemia cells or xenogeneic cells such as murine fibroblasts and *Drosophila* cells. Alternatively, the APCs maybe be acellular wherein the antigens or costimulatory domains are presented on synthetic surfaces such as latex beads, polystyrene beads, lipid vesicles or exosomes.

In some embodiments, adoptive cell therapy is carried out by autologous transfer, wherein the cells are derived from a subject in need of a treatment and the cells, following isolation and processing are administered to the same subject. In other instances, ACT may involve allogenic transfer wherein the cells are isolated and/or prepared from a donor subject other than the recipient subject who ultimately receives cell therapy. The donor and recipient subject may be genetically identical, or similar or may express the same HLA class or subtype.

Following genetic modulation using SREs, CA2 biocircuits and compositions of the disclosure, cells are administered to the subject in need thereof. Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338; the contents of each of which are incorporated herein by reference in their entirety.

In some embodiments, immune cells engineered with CA2-IL15 for ACT may be further modified to express one or more immunotherapeutic agents which facilitate immune cells activation, infiltration, expansion, survival and anti-tumor functions. The immunotherapeutic agents may be a CAR or TCR specific to a target molecule on a tumor cell; a second cytokine or a cytokine receptor; a chimeric switch receptor that converts an inhibitory signal to a stimulatory signal; a homing receptor that guides adoptively transferred cells to a target site such as the tumor tissue; an agent that optimizes the metabolism of the immune cell; or a safety switch gene (e.g., a suicide gene) that kills activated T cells when a severe event is observed after adoptive cell transfer or when the transferred immune cells are no-longer needed.

In some embodiments, immune cells used for adoptive cell transfer can be genetically manipulated to improve their persistence, cytotoxicity, tumor targeting capacity, and ability to home to disease sites in vivo, with the overall aim of further improving upon their capacity to kill tumors in cancer patients. One example is to introduce CA2 effector modules of the disclosure comprising IL15 into immune cells to promote immune cell proliferation and survival. Transduction of IL15 into cells will permit immune cells to propagate without addition of exogenous cytokines and cytokine-expressing NK cells may have enhanced tumor cytotoxicity.

In some embodiments, CA2 biocircuits, SREs or CA2 effector modules may be utilized to prevent T cell exhaustion. As used herein, "T cell exhaustion" refers to the stepwise and progressive loss of T cell function caused by chronic T cell activation. T cell exhaustion is a major factor limiting the efficacy of antiviral and antitumor immunotherapies. Exhausted T cells have low proliferative and cytokine producing capabilities concurrent with high rates of apoptosis and high surface expression of multiple inhibitory receptors. T cell activation leading to exhaustion may occur either in the presence or absence of the antigen.

In some embodiments, the CA2 biocircuits and their components may be utilized to prevent T cell exhaustion in the context of Chimeric Antigen Receptor-T cell therapy (CAR-T). In this context, exhaustion in some instances, may be caused by the oligomerization of the scFvs of the CAR on the cell surface which leads to continuous activation of the intracellular domains of the CAR. As a non-limiting example, CARs of the present disclosure may include scFvs that are unable to oligomerize. As another non-limiting example, CARs that are rapidly internalized and re-expressed following antigen exposure may also be selected to prevent chronic scFv oligomerization on cell surface. In one embodiment, the framework region of the scFvs may be modified to prevent constitutive CAR signaling.

Tunable CA2 biocircuits of the present disclosure may also be used to regulate the surface expression of the CAR on the T cell surface to prevent chronic T cell activation. The CARs of the disclosure may also be engineered to minimize exhaustion. As a non-limiting example, the 4-1-BB signaling domain may be incorporated into CAR design together with membrane bound IL15 expression regulated by CA2 biocircuits, SREs or CA2 effector modules, exemplified in Table 3 of the present disclosure, to ameliorate T cell exhaustion.

In some embodiments, the tunable nature of the CA2-IL15 biocircuits of the present disclosure may be utilized to reverse human T cell exhaustion observed with tonic CAR signaling. Reversibly silencing the biological activity of adoptively transferred cells using compositions of the present disclosure may be used to reverse tonic signaling which, in turn, may reinvigorate the T cells. Reversal of exhaustion may be measured by the downregulation of multiple inhibitory receptors associated with exhaustion.

In some embodiments, the compositions of the present disclosure may be utilized to alter TIL (tumor infiltrating lymphocyte) populations in a subject. In one embodiment, any of the payloads described herein may be utilized to change the ratio of CD4 positive cells to CD8 positive populations. In some embodiments, TIL may be sorted ex vivo and engineered to express any of the cytokines described herein. Payloads of the disclosure may be used to expand CD4 and/or CD8 populations of TIL to enhance TIL mediated immune response.

Provided in the present disclosure is a method of reducing a tumor volume or burden in a subject in need, the method comprising introducing into the subject a composition of the disclosure.

The present disclosure also provides methods for treating a cancer in a subject, comprising administering to the subject an effective amount of an effector immune cell genetically modified to express at least one CA2 effector module of the disclosure.

Various cancers may be treated with pharmaceutical compositions, CA2 biocircuits, CA2 biocircuit components, CA2 effector modules including their SREs and IL15 payloads of the present disclosure. As used herein, the term "cancer" refers to any of various malignant neoplasms characterized by the proliferation of anaplastic cells that tend to invade surrounding tissue and metastasize to new body sites and also refers to the pathological condition characterized by such malignant neoplastic growths. Cancers may be tumors or hematological malignancies, and include but are not limited to, all types of lymphomas/ leukemias, carcinomas and sarcomas, such as those cancers or tumors found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus.

Types of carcinomas which may be treated with the compositions of the present disclosure include, but are not limited to, papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma.

Types of carcinomas which may be treated with the compositions of the present disclosure include, but are not limited to, soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

As a non-limiting example, the carcinoma which may be treated may be Acute granulocytic leukemia, Acute lymphocytic leukemia, Acute myelogenous leukemia, Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma), Bile duct cancer, Bladder cancer, Bone cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia, Chronic myelogenous leukemia, Colon cancer, Colorectal cancer, Craniopharyngioma, Cutaneous lymphoma, Cutaneous melanoma, Diffuse astrocytoma, Ductal carcinoma in situ, Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, GallblaDRDer cancer, Gastric cancer, Gastrointestinal cancer, Gastrointestinal carcinoid cancer, Gastrointestinal stromal tumors, General, Germ cell tumor, Glioblastoma multiforme, Glioma, Hairy cell leukemia, Head and neck cancer, Hemangioendothelioma, Hodgkin lymphoma, Hodgkin's disease, Hodgkin's lymphoma, Hypopharyngeal cancer, Infiltrating ductal carcinoma, Infiltrating lobular carcinoma, Inflammatory breast cancer, Intestinal Cancer, Intrahepatic bile duct cancer, Invasive/infiltrating breast cancer, Islet cell cancer, Jaw cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Nasal cavity cancer, Nasopharyngeal cancer, Neck cancer, Neuroblastoma, Neuroendocrine tumors, Non-Hodgkin lymphoma, Non-Hodgkin's lymphoma, Non-small cell lung cancer, Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system lymphoma, Prostate cancer, Rectal cancer, Renal cell cancer, Renal pelvis cancer, Rhabdomyosarcoma, Salivary gland cancer, Sarcoma, Sarcoma, bone, Sarcoma, soft tissue, Sarcoma, uterine, Sinus cancer, Skin cancer, Small cell lung cancer, Small intestine cancer, Soft tissue sarcoma, Spinal cancer, Spinal column cancer, Spinal cord cancer, Spinal tumor, Squamous cell carcinoma, Stomach cancer, Synovial sarcoma, T cell lymphoma), Testicular cancer, Throat cancer, Thymoma/thymic carcinoma, Thyroid cancer, Tongue cancer, Tonsil cancer, Transitional cell cancer, Transitional cell cancer, Transitional cell cancer, Triple-negative breast cancer, Tubal cancer, Tubular carcinoma, Ureteral cancer, Ureteral cancer, Urethral cancer, Uterine adenocarcinoma, Uterine cancer, Uterine sarcoma, Vaginal cancer, and Vulvar cancer.

In some embodiments, pharmaceutical compositions, CA2 biocircuits, CA2 biocircuit components, CA2 effector modules including their SREs or payloads of the present disclosure may be used in the modulation or alteration or exploitation of the immune system to target one or more cancers. This approach may also be considered with other such biological approaches, e.g., immune response modifying therapies such as the administration of interferons, interleukins, colony-stimulating factors, other monoclonal antibodies, vaccines, gene therapy, and nonspecific immunomodulating agents are also envisioned as anti-cancer therapies to be combined with the pharmaceutical compositions, CA2 biocircuits, CA2 biocircuit components, CA2 effector modules including their SREs or payloads of the present disclosure.

Cancer immunotherapy refers to a diverse set of therapeutic strategies designed to induce the patient's own immune system to fight the cancer. In some embodiments, pharmaceutical compositions, CA2 biocircuits, CA2 biocircuit components, CA2 effector modules including their SREs or payloads of the present disclosure are designed as immune-oncology therapeutics.

There are several types of cellular immunotherapies, including NK cells, tumor infiltrating lymphocyte (TIL) therapy, and genetically engineered T cells bearing chimeric antigen receptors (CARs) or recombinant TCR technology.

In one embodiment, the CAR T cell or TCR T cell of the present disclosure may be an "armed" T cell which is transformed with a CA2-IL15 effector module to improve efficacy and persistence.

In one embodiment, patients may also be stratified according to the immunogenic peptides presented by their immune cells and may be utilized as a parameter to determine suitable patient cohorts that may therapeutically benefit for the compositions of the disclosure.

In some embodiments, cells of the disclosure may be autologous, allogeneic, syngeneic, or xenogeneic in relation to a particular individual subject.

In some embodiments, cells of the disclosure may be mammalian cells, particularly human cells. Cells of the disclosure may be primary cells or immortalized cell lines.

Engineered immune cells can be accomplished by transducing a cell composition with one or more polynucleotides encoding a polypeptide of a CA2 biocircuit, a CA2 effector module, an SRE and an IL15 payload, or a vector comprising said polynucleotide. The vector may be a viral vector such as a lentiviral vector or gamma retroviral vector. In some embodiments, immune cells of the disclosure are genetically modified to express at least one immunotherapeutic agent of the disclosure which is tunable using a stimulus.

Definitions

At various places in the present specification, features or functions of the compositions of the present disclosure are disclosed in groups or in ranges. It is specifically intended that the present disclosure include each and every individual sub combination of the members of such groups and ranges. The following is a non-limiting list of term definitions.

Activity: As used herein, the term "activity" refers to the condition in which things are happening or being done. Compositions of the disclosure may have activity and this activity may involve one or more biological events. In some embodiments, biological events may include cell signaling events. In some embodiments, biological events may include cell signaling events associated protein interactions with one or more corresponding proteins, receptors, small molecules or any of the biocircuit components described herein.

Adoptive cell therapy (ACT): The terms "Adoptive cell therapy" or "Adoptive cell transfer", as used herein, refer to a cell therapy involving in the transfer of cells into a patient, wherein cells may have originated from the patient, or from another individual, and are engineered (altered) before being transferred back into the patient. The therapeutic cells may be derived from the immune system, such as effector immune cells: CD4+ T cell; CD8+ T cell, Natural Killer cell (NK cell); and B cells and tumor infiltrating lymphocytes (TIL) derived from the resected tumors. Most commonly transferred cells are autologous anti-tumor T cells after ex vivo expansion or manipulation. For example, autologous peripheral blood lymphocytes can be genetically engineered to recognize specific tumor antigens by expressing T cell receptors (TCR) or chimeric antigen receptor (CAR).

Agent: As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a receptor, and soluble factor.

Antigen: the term "antigen" as used herein is defined as a molecule that provokes an immune response when it is introduced into a subject or produced by a subject such as tumor antigens which arise by the cancer development itself. This immune response may involve either antibody production, or the activation of specific immunologically-competent cells such as cytotoxic T lymphocytes and T helper cells, or both. An antigen can be derived from organisms, subunits of proteins/antigens, killed or inactivated whole cells or lysates. In the context of the disclosure, the terms "antigens of interest" or "desired antigens" refers to those proteins and/or other biomolecules provided herein that are immunospecifically bound or interact with antibodies of the present disclosure and/or fragments, mutants, variants, and/or alterations thereof described herein. In some embodiments, antigens of interest may comprise any of the polypeptides or payloads or proteins described herein, or fragments or portions thereof.

Associated with: As used herein, the terms "associated with," "conjugated," "linked," "attached," and "tethered," when used with respect to two or more moieties, mean that the moieties are physically associated or connected with one another, either directly or via one or more additional moieties that serve as linking agents, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization-based connectivity sufficiently stable such that the "associated" entities remain physically associated.

Autologous: the term "autologous" as used herein is meant to refer to any material derived from the same individual to which it is later to be re-introduced into the individual.

Cancer: the term "cancer" as used herein refers a broad group of various diseases characterized by the uncontrolled growth of abnormal cells in the body. Unregulated cell division and growth results in the formation of malignant tumors that invade neighboring tissues ultimately metastasize to distant parts of the body through the lymphatic system or bloodstream.

Co-stimulatory molecule: As used herein, in accordance with its meaning in immune T cell activation, refers to a group of immune cell surface receptor/ligands which engage between T cells and APCs and generate a stimulatory signal in T cells which combines with the stimulatory signal in T cells that results from T cell receptor (TCR) recognition of antigen/MHC complex (pMHC) on APCs Cytokines: the term "cytokines", as used herein, refers to a family of small soluble factors with pleiotropic functions that are produced by many cell types that can influence and regulate the function of the immune system.

Delivery: the term "delivery" as used herein refers to the act or manner of delivering a compound, substance, entity, moiety, cargo or payload. A "delivery agent" refers to any agent which facilitates, at least in part, the in vivo delivery of one or more substances (including, but not limited to a compound and/or composition of the present disclosure) to a cell, subject or other biological system cells.

Destabilized: As used herein, the term "destable," "destabilize," or "destabilizing region" means a region or molecule that is less stable than a starting, reference, wild-type or native form of the same region or molecule.

Engineered: As used herein, embodiments of the disclosure are "engineered" when they are designed to have a feature or property, whether structural or chemical, that varies from a starting point, wild type or native molecule.

Formulation: As used herein, a "formulation" includes at least a compound and/or composition of the present disclosure and a delivery agent.

Fragment: A "fragment," as used herein, refers to a portion of a molecule that is less than the entire molecule. For example, fragments of proteins may comprise polypeptides obtained by digesting full-length protein. In some embodiments, fragments of an antibody include portions of an antibody.

Functional: As used herein, a "functional" biological molecule is a biological entity with a structure and in a form in which it exhibits a property and/or activity by which it is characterized.

Immune cells: the term "an immune cell", as used herein, refers to any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a T γδ cell, a Tαβ cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

Immunotherapy: the term "immunotherapy" as used herein, refers to a type of treatment of a disease by the induction or restoration of the reactivity of the immune system towards the disease.

Immunotherapeutic agent: the term "immunotherapeutic agent" as used herein, refers to the treatment of disease by the induction or restoration of the reactivity of the immune system towards the disease with a biological, pharmaceutical, or chemical compound.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Linker: As used herein, a linker refers to a moiety that connects two or more domains, moieties or entities. In one embodiment, a linker may comprise 10 or more atoms. In a further embodiment, a linker may comprise a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. In some embodiments, a linker may comprise one or more nucleic acids comprising one or more nucleotides. In some embodiments, the linker may comprise an amino acid, peptide, polypeptide or protein. In some embodiments, a moiety bound by a linker may include, but is not limited to an atom, a chemical group, a nucleoside, a nucleotide, a nucleobase, a sugar, a nucleic acid, an amino acid, a peptide, a polypeptide, a protein, a protein complex, a payload (e.g., a therapeutic agent). or a marker (including, but not limited to a chemical, fluorescent, radioactive or bioluminescent marker). The linker can be used for any useful purpose, such as to form multimers or conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bonds include an amido bond which may be cleaved for example by the use of tris(2-carboxyethyl) phosphine (TCEP), or other reducing agents, and/or photolysis, as well as an ester bond which may be cleaved for example by acidic or basic hydrolysis.

Modified: As used herein, the term "modified" refers to a changed state or structure of a molecule or entity as compared with a parent or reference molecule or entity. Molecules may be modified in many ways including chemically, structurally, and functionally. In some embodiments, compounds and/or compositions of the present disclosure are modified by the introduction of non-natural amino acids.

Mutation: As used herein, the term "mutation" refers to a change and/or alteration. In some embodiments, mutations may be changes and/or alterations to proteins (including peptides and polypeptides) and/or nucleic acids (including polynucleic acids). In some embodiments, mutations comprise changes and/or alterations to a protein and/or nucleic acid sequence. Such changes and/or alterations may comprise the addition, substitution and or deletion of one or more amino acids (in the case of proteins and/or peptides) and/or nucleotides (in the case of nucleic acids and or polynucleic acids e.g., polynucleotides). In some embodiments, wherein mutations comprise the addition and/or substitution of amino acids and/or nucleotides, such additions and/or substitutions may comprise 1 or more amino acid and/or nucleotide residues and may include modified amino acids and/or nucleotides. The resulting construct, molecule or sequence of a mutation, change or alteration may be referred to herein as a mutant.

Neoantigen: the term "neoantigen", as used herein, refers to a tumor antigen that is present in tumor cells but not normal cells and do not induce deletion of their cognate antigen specific T cells in thymus (i.e., central tolerance). These tumor neoantigens may provide a "foreign" signal, similar to pathogens, to induce an effective immune response needed for cancer immunotherapy. A neoantigen may be restricted to a specific tumor. A neoantigen be a peptide/protein with a missense mutation (missense neoantigen), or a new peptide with long, completely novel stretches of amino acids from novel open reading frames (neoORFs). The neoORFs can be generated in some tumors by out-of-frame insertions or deletions (due to defects in DNA mismatch repair causing microsatellite instability), gene-fusion, read-through mutations in stop codons, or translation of improperly spliced RNA (e.g., Saeterdal et al., Proc Natl Acad Sci USA, 2001, 98: 13255-13260).

Off-target: As used herein, "off target" refers to any unintended effect on any one or more target, gene, cellular transcript, cell, and/or tissue.

Operably linked: As used herein, the phrase "operably linked" refers to a functional connection between two or more molecules, constructs, transcripts, entities, moieties or the like.

Payload or payload of interest (POI): the terms "payload" and "payload of interest (POI)", as used herein, are used interchangeable. A payload of interest (POI) refers to any protein or compound whose function is to be altered. In the context of the present disclosure, the POI is a component in the immune system, including both innate and adaptive immune systems. Payloads of interest may be a protein, a fusion construct encoding a fusion protein, or non-coding gene, or variant and fragment thereof. Payload of interest may, when amino acid based, may be referred to as a protein of interest.

Pharmaceutically acceptable excipients: the term "pharmaceutically acceptable excipient," as used herein, refers to any ingredient other than active agents (e.g., as described herein) present in pharmaceutical compositions and having the properties of being substantially nontoxic and non-inflammatory in subjects. In some embodiments, pharmaceutically acceptable excipients are vehicles capable of suspending and/or dissolving active agents. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: Pharmaceutically acceptable salts of the compounds described herein are forms of the disclosed compounds wherein the acid or base moiety is in its salt form (e.g., as generated by reacting a free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Pharmaceutically acceptable salts include the conventional non-toxic salts, for example, from non-toxic inorganic or organic acids. In some embodiments, a pharmaceutically acceptable salt is prepared from a parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, Pharmaceutical Salts: Properties, Selection, and Use, P. H. Stahl and C. G. Wermuth (eds.), Wiley-VCH, 2008, and Berge et al., Journal of Pharmaceutical Science, 66, 1-19 (1977), each of which is incorporated herein by reference in its entirety. Pharmaceutically acceptable solvate: The term "pharmaceutically acceptable solvate," as used herein, refers to a crystalline form of a compound wherein molecules of a suitable solvent are incorporated in the crystal lattice. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N, N'-dimethylformamide (DMF), N, N'-dimethyl acetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate." In some embodiments, the solvent incorporated into a solvate is of a type or at a level that is physiologically tolerable to an organism to which the solvate is administered (e.g., in a unit dosage form of a pharmaceutical composition).

Stable: As used herein "stable" refers to a compound or entity that is sufficiently robust to survive isolation to a useful degree of purity from a reaction mixture, and preferably capable of formulation into an efficacious therapeutic agent.

Stabilized: As used herein, the term "stabilize", "stabilized," "stabilized region" means to make or become stable. In some embodiments, stability is measured relative to an absolute value. In some embodiments, stability is measured relative to a secondary status or state or to a reference compound or entity.

Standard CAR: As used herein, the term "standard CAR" refers to the standard design of a chimeric antigen receptor. The components of a CAR fusion protein including the extracellular scFv fragment, transmembrane domain and one or more intracellular domains are linearly constructed as a single fusion protein.

Subject: As used herein, the term "subject" or "patient" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

T cell: A T cell is an immune cell that produces T cell receptors (TCRs). T cells can be naïve (not exposed to antigen; increased expression of CD62L, CCR7, CD28, CD3, CD127, and CD45RA, and decreased expression of CD45RO as compared to TCM), memory T cells (TM) (antigen-experienced and long-lived), and effector cells (antigen-experienced, cytotoxic). TM can be further divided into subsets of central memory T cells (TCM, increased expression of CD62L, CCR7, CD28, CD127, CD45RO, and CD95, and decreased expression of CD54RA as compared to naïve T cell and effector memory T cells (TEM, decreased expression of CD62L, CCR7, CD28, CD45RA, and increased expression of CD127 as compared to naïve T cells or TCM). Effector T cells (TE) refers to antigen-experienced CD8+ cytotoxic T lymphocytes that have decreased expression of CD62L, CCR7, CD28, and are positive for granzyme and perforin as compared to TCM. Other exemplary T cells include regulatory T cells, such as CD4+CD25+(Foxp3+) regulatory T cells and Treg17 cells, as well as Tr1, Th3, CD8+CD28−, and Qa-1 restricted T cells.

T cell receptor: T cell receptor (TCR) refers to an immunoglobulin superfamily member having a variable antigen binding domain, a constant domain, a transmembrane region, and a short cytoplasmic tail, which is capable of specifically binding to an antigen peptide bound to a MEW receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). The extracellular portion of TCR chains (e.g., α-chain, β-chain) contains two immunoglobulin domains, a variable domain (e.g., α-chain variable domain or Vα, β-chain variable domain or Vβ) at the N terminus, and one constant domain (e.g., α-chain constant domain or Cα and β-chain constant domain or Cβ) adjacent to the cell membrane. Similar to immunoglobulin, the variable domains contain complementary determining regions (CDRs) separated by framework regions (FRs). A TCR is usually associated with the CD3 complex to form a TCR complex. As used herein, the term "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD36 chain, two CD3ε chains, a homodimer of CD3ζ chains, a TCRγ chain, and a TCR chain. A "component of a TCR complex," as used herein, refers to a TCR chain (i.e., TCRα, TCRβ, TCRγ or TCRδ), a CD3 chain (i.e., CD3γ, CD3δ, CD3ε or CD3), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition. In some embodiments, a therapeutically effective amount is provided in a single dose. In some embodiments, a therapeutically effective amount is administered in a dosage regimen comprising a plurality of doses. Those skilled in the art will appreciate that in some embodiments, a unit dosage form may be considered to comprise a therapeutically effective amount of a particular agent or entity if it comprises an amount that is effective when administered as part of such a dosage regimen.

Treatment or treating: As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

Tune: As used herein, the term "tune" means to adjust, balance or adapt one thing in response to a stimulus or toward a particular outcome. In one non-limiting example, the SREs and/or DRDs of the present disclosure adjust, balance or adapt the function or structure of compositions to which they are appended, attached or associated with in response to particular stimuli and/or environments.

EQUIVALENTS AND SCOPE

Those skilled in the art will recognize or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or the entire group members are present in, employed in or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the disclosure (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the disclosure in its broader aspects.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure. The present disclosure is further illustrated by the following nonlimiting examples.

EXAMPLES

FIG. 1 depicts a representative procedure for in vitro characterization and/or validation of ACZ-regulated mbIL15 expression in T cells. As shown in FIG. 1, T cells may be transduced with an mbIL15 construct, for example, by following the procedures described in Example 1. Following transduction, T cells may be treated with control condition or ACZ and assayed for IL15 expression and/or antigen-independent cell expansion in vitro, for example, by following the procedures described in Example 2.

Figure 2:
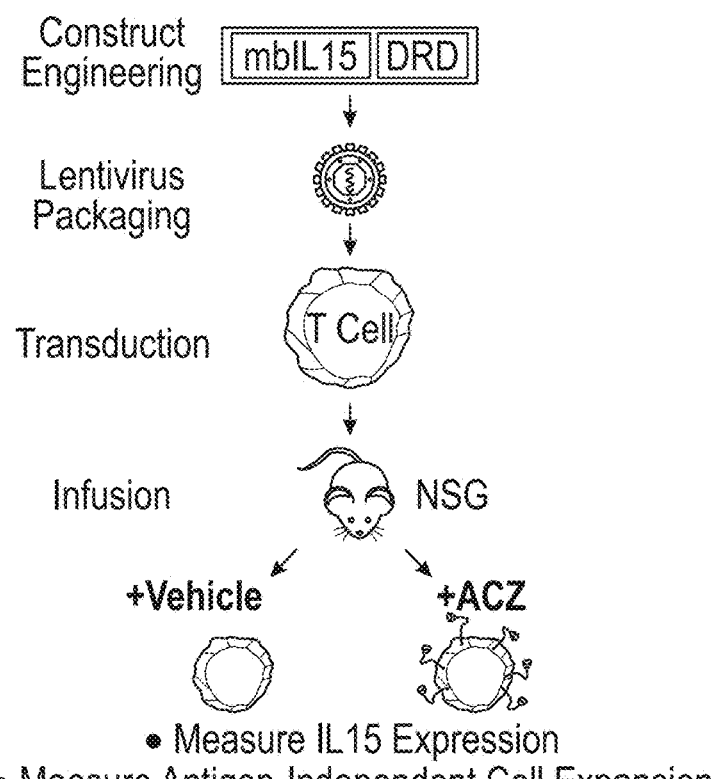
FIG. 2 depicts a representative procedure for in vivo characterization and/or validation of ACZ-regulated mbIL15 expression in T cells.

FIG. 2 depicts a representative procedure for in vivo characterization and/or validation of ACZ-regulated mbIL15 expression in T cells. As shown in FIG. 2, T cells may be transduced with an mbIL15 construct, for example, by following the procedures described in Example 1. Following transduction, T cells may be infused into a murine subject (e.g., an NSG mouse) and samples from mice treated with vehicle or ACZ may be assayed for IL15 expression and/or antigen-independent cell expansion, for example, by following the procedures described in Example 3.

Example 1. T Cell Transduction with Acetazolamide (ACZ)-Regulated mbIL15 Construct The present example demonstrates methods that may be used for preparing ACZ-regulated mbIL15 constructs and methods that may be used for transduction of T cells with ACZ-regulated mbIL15 constructs.

IL15 Construct Assembly

OT-IL15-292, OT-IL15-293, OT-IL15-294, and OT-IL15-295 were each constructed in a pELNS vector (a third-generation self-inactivating lentiviral expression vector) using standard molecular biology techniques. Gene fragments (Gblocks) encoding codon-optimized IL15, GS linker, B7-1 hinge, transmembrane domain and cytoplasmic tails were purchased from Integrated DNA Technologies, Inc. (IDT, Coralville, Iowa). The gene fragments were inserted into the pELNS vector and placed under the control of the EF1a promoter using Gibson assembly (NEBuilder Hifi). The assembled plasmid was transformed into E. coli (NEB stable) for amplification and sequence confirmed before proceeding with virus production.

Table 4 presents the nucleic acid and amino acid sequences for components of constitutive IL15 constructs (OT-IL15-292 and OT-IL15-294) and ACZ-regulated IL15 constructs (OT-IL15-293 and OT-IL15-295) disclosed herein. Bold and underlined amino acids in Table 4 indicate differences in the B7-1 cytoplasmic tail between constructs OT-IL15-292/OT-IL15-293 and OT-IL15-294/OT-IL15-295. Constructs OT-IL15-293 and OT-IL15-295 comprise a destabilizing domain labeled as CA2 (M1del, L156H) in Table 4.

TABLE 4 components of constitutive and ACZ-regulated IL15 constructs

| Description | DNA Sequence | DNA SEQ ID NO. | AA Sequence | AA SEQ ID NO. |
|---|---|---|---|---|
| Leader sequence | ATGGACATGCGGGTGCCTGCACAAC TTCTGGGCCTGCTGTTGTTGTGGCTG TCTGGAGCCCGGTGT | 7 | MDMRVPAQLLGLLLLWLSG ARC | 6 |

TABLE 4-continued components of constitutive and ACZ-regulated IL15 constructs

| Description | DNA Sequence | DNA NO. | AA Sequence | AA SEQ ID NO. |
|---|---|---|---|---|
| IL15 | AATTGGGTAAATGTTATCAGTGATCTC AAGAAGATAGAGGATCTCATCCAGTC CATGCATATTGATGCCACGCTGTACA CAGAAAGCGATGTGCATCCTAGCTGT AAGGTGACAGCGATGAAGTGTTTTCT TTTGGAGCTGCAGGTAATTAGTCTTG AGTCCGGCGATGCCAGCATTCATGAT ACCGTAGAAAACTTGATTATCCTGGC CAACAATTCTCTGTCCTCAAACGGAA ACGTAACCGAGAGCGGTTGTAAAGAA TGTGAAGAACTGGAAGAAAAGAACAT CAAGGAGTTTCTGCAATCATTCGTTC ACATCGTACAAATGTTCATAAATACGT CA | 9 | NWVNVISDLKKIEDLIQSMHI DATLYTESDVHPSCKVTAM KCFLLELQVISLESGDASIHD TVENLIILANNSLSSNGNVTE SGCKECEELEEKNIKEFLQS FVHIVQMFINTS | 8 |
| Linker (GS)15 | GGATCTGGTTCTGGTTCCGGAAGTG GATCTGGTTCAGGGTCCGGTAGTGG ATCTGGGTCAGGAAGTGGAAGCGGT AGTGGGTCTGGATCT | 11 | GSGSGSGSGSGSGSGSGS GSGSGSGSGSGS | 10 |
| Hinge | AAACAAGAGCACTTTCCTGATAAC | 13 | KQEHFPDN | 12 |
| Transmembrane domain | CTGTTGCCGAGCTGGGCGATTACGC TTATCAGTGTAAACGGCATCTTTGTAA TATGCTGTCTG | 15 | LLPSWAITLISVNGIFVICCL | 14 |
| Intracellular tail (OT-IL15-292 and OT-IL15-293) | ACCTACTGCTTCGCACCAAGGTGCCG GGAGAGAAGGAGAAATGAAAGACTG AGAAGGGAGAGCGTGAGACCTGTG | 17 | TYCFAPRCRERRRNERLRR ESVRPV | 16 |
| Intracellular tail (OT-IL15-294 and OT-IL15-295) | ACCTACTGCTTCGCACCAAGGTGCCG GGAGAGAGCAAGAAATGAAAGACTG AGAAGGGAGACCGTGAGACCTGTG | 19 | TYCFAPRCRERARNERLRR ETVRPV | 18 |
| Linker (GS) | GGATCC | 21 | GS | 20 |
| CA2 (M1 del, L156H) (OT-IL15-293 and OT-IL15-295) | TCCCATCACTGGGGGTACGGCAAAC ACAACGGACCTGAGCACTGGCATAA GGACTTCCCCATTGCCAAGGGAGAG CGCCAGTCCCCTGTTGACATCGACAC TCATACAGCCAAGTATGACCCTTCCC TGAAGCCCCTGTCTGTTTCCTATGAT CAAGCAACTTCCCTGAGAATCCTCAA CAATGGTCATGCTTTCAACGTGGAGT TTGATGACTCTCAGGACAAAGCAGTG CTCAAGGGAGGACCCCTGGATGGCA CTTACAGATTGATTCAGTTTCACTTTC ACTGGGGTTCACTTGATGGACAAGGT TCAGAGCATACTGTGGATAAAAAGAA ATATGCTGCAGAACTTCACTTGGTTC ACTGGAACACCAAATATGGGGATTTT GGGAAAGCTGTGCAGCAACCTGATG GACTGGCCGTTCTAGGTATTTTTTTG AAGGTTGGCAGCGCTAAACCGGGCC ATCAGAAAGTTGTTGATGTGCTGGAT TCCATTAAAACAAAGGGCAAGAGTGC TGACTTCACTAACTTCGATCCTCGTG GCCTCCTTCCTGAATCCCTGGATTAC TGGACCTACCCAGGCTCACTGACCAC CCCTCCTCTTCTGGAATGTGTGACCT GGATTGTGCTCAAGGAACCCATCAGC GTCAGCAGCGAGCAGGTGTTGAAATT CCGTAAACTTAACTTCAATGGGGAGG GTGAACCCGAAGAACTGATGGTGGA CAACTGGCGCCCAGCTCAGCCACTG AAGAACAGGCAAATCAAAGCTTCCTT CAAA | 5 | SHHWGYGKHNGPEHWHKD FPIAKGERQSPVDIDTHTAK YDPSLKPLSVSYDQATSLRI LNNGHAFNVEFDDSQDKAV LKGGPLDGTYRLIQFHFHW GSLDGQGSEHTVDKKKYAA ELHLVHWNTKYGDFGKAVQ QPDGLAVLGIFLKVGSAKPG HQKWDVLDSIKTKGKSADF TNFDPRGLLPESLDYWTYP GSLTTPPLLECVTWIVLKEPI SVSSEQVLKFRKLNFNGEG EPEELMVDNWRPAQPLKNR QIKASFK | 4 |

Table 5 presents the nucleic acid and amino acid sequences of the constitutive IL15 (IL15-292 and IL15-294) and ACZ-regulated IL15 (IL15-293 and IL15-295 constructs disclosed herein.

TABLE 5

| Constitutive and ACZ-regulated IL15 constructs | | | | |
|---|---|---|---|---|
| Description | DNA Sequence | DNA SEQ | AA Sequence | AA SEQ |
| IL15-292 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AAGAATGTGAAGAACTGGAAGAAAA GAACATCAAGGAGTTTCTGCAATCAT TCGTTCACATCGTACAAATGTTCATA AATACGTCAGGATCTGGTTCTGGTT CCGGAAGTGGATCTGGTTCAGGGTC CGGTAGTGGATCTGGGTCAGGAAGT GGAAGCGGTAGTGGGTCTGGATCTA AACAAGAGCACTTTCCTGATAACCT GTTGCCGAGCTGGGCGATTACGCTT ATCAGTGTAAACGGCATCTTTGTAAT ATGCTGTCTGACCTACTGCTTCGCA CCAAGGTGCCGGGAGAGAAGGAGA AATGAAAGACTGAGAAGGGAGAGCG TGAGACCTGTGGGATCC | 23 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSG SGSGSGSKQEHFPDNLLPSWAIT LISVNGIFVICCLTYCFAPRCRERR RNERLRRESVRPVGS | 22 |
| IL15-293 | ATGGACATGCGGGTGCCTG CACAACTTCTGGGCCTGCTGTTGTT GTGGCTGTCTGGAGCCCGGTGTAAT TGGGTAAATGTTATCAGTGATCTCAA GAAGATAGAGGATCTCATCCAGTCC ATGCATATTGATGCCACGCTGTACA CAGAAAGCGATGTGCATCCTAGCTG TAAGGTGACAGCGATGAAGTGTTTT CTTTTGGAGCTGCAGGTAATTAGTCT TGAGTCCGGCGATGCCAGCATTCAT GATACCGTAGAAAACTTGATTATCCT GGCCAACAATTCTCTGTCCTCAAAC GGAAACGTAACCGAGAGCGGTTGTA AAGAATGTGAAGAACTGGAAGAAAA GAACATCAAGGAGTTTCTGCAATCAT TCGTTCACATCGTACAAATGTTCATA AATACGTCAGGATCTGGTTCTGGTT CCGGAAGTGGATCTGGTTCAGGGTC CGGTAGTGGATCTGGGTCAGGAAGT GGAAGCGGTAGTGGGTCTGGATCTA AACAAGAGCACTTTCCTGATAACCT GTTGCCGAGCTGGGCGATTACGCTT ATCAGTGTAAACGGCATCTTTGTAAT ATGCTGTCTGACCTACTGCTTCGCA CCAAGGTGCCGGGAGAGAAGGAGA AATGAAAGACTGAGAAGGGAGAGCG TGAGACCTGTGGGATCCTCCCATCA CTGGGGGTACGGCAAACACAACGG ACCTGAGCACTGGCATAAGGACTTC CCCATTGCCAAGGGAGAGCGCCAG TCCCCTGTTGACATCGACACTCATA CAGCCAAGTATGACCCTTCCCTGAA GCCCCTGTCTGTTTCCTATGATCAA GCAACTTCCCTGAGAATCCTCAACA ATGGTCATGCTTTCAACGTGGAGTTT GATGACTCTCAGGACAAAGCAGTGC TCAAGGGAGGACCCCTGGATGGCA CTTACAGATTGATTCAGTTTCACTTT CACTGGGGTTCACTTGATGGACAAG GTTCAGAGCATACTGTGGATAAAAA GAAATATGCTGCAGAACTTCACTTG GTTCACTGGAACACCAAATATGGGG | 25 | MDMRVPAQLLGLLLLWL SGARCNWVNVISDLKKIEDLIQSM HIDATLYTESDVHPSCKVTAMKCF LLELQVISLESGDASIHDTVENLIIL ANNSLSSNGNVTESGCKECEELE EKNIKEFLQSFVHIVQMFINTSGS GSGSGSGSGSGSGSGSGSGSG SGSGSGSKQEHFPDNLLPSWAIT LISVNGIFVICCLTYCFAPRCRERR RNERLRRESVRPVGSSHHWGYG KHNGPEHWHKDFPIAKGERQSP VDIDTHTAKYDPSLKPLSVSYDQA TSLRILNNGHAFNVEFDDSQDKA VLKGGPLDGTYRLIQFHFHWGSL DGQGSEHTVDKKKYAAELHLVH WNTKYGDFGKAVQQPDGLAVLGI FLKVGSAKPGHQKVVDVLDSIKTK GKSADFTNFDPRGLLPESLDYWT YPGSLTTPPLLECVTWIVLKEPISV SSEQVLKFRKLNFNGEGEPEELM VDNWRPAQPLKNRQIKASFK | 24 |

TABLE 5 -continued

Constitutive and ACZ-regulated 1L15 constructs

| Description | DNA Sequence | DNA SEQ | AA Sequence | AA SEQ |
|---|---|---|---|---|
| | ATTTTGGGAAAGCTGTGCAGCAACC<br>TGATGGACTGGCCGTTCTAGGTATT<br>TTTTTGAAGGTTGGCAGCGCTAAAC<br>CGGGCCATCAGAAAGTTGTTGATGT<br>GCTGGATTCCATTAAAACAAAGGGC<br>AAGAGTGCTGACTTCACTAACTTCG<br>ATCCTCGTGGCCTCCTTCCTGAATC<br>CCTGGATTACTGGACCTACCCAGGC<br>TCACTGACCACCCCTCCTCTTCTGG<br>AATGTGTGACCTGGATTGTGCTCAA<br>GGAACCCATCAGCGTCAGCAGCGA<br>GCAGGTGTTGAAATTCCGTAAACTTA<br>ACTTCAATGGGAGGGTGAACCCGA<br>AGAACTGATGGTGGACAACTGGCGC<br>CCAGCTCAGCCACTGAAGAACAGGC<br>AAATCAAAGCTTCCTTCAAA | | | |
| IL15-294 | ATGGACATGCGGGTGCCTG<br>CACAACTTCTGGGCCTGCTGTTGTT<br>GTGGCTGTCTGGAGCCCGGTGTAAT<br>TGGGTAAATGTTATCAGTGATCTCAA<br>GAAGATAGAGGATCTCATCCAGTCC<br>ATGCATATTGATGCCACGCTGTACA<br>CAGAAAGCGATGTGCATCCTAGCTG<br>TAAGGTGACAGCGATGAAGTGTTTT<br>CllIIGGAGCTGCAGGTAATTAGTCT<br>TGAGTCCGGCGATGCCAGCATTCAT<br>GATACCGTAGAAAACTTGATTATCCT<br>GGCCAACAATTCTCTGTCCTCAAAC<br>GGAAACGTAACCGAGAGCGGTTGTA<br>AAGAATGTGAAGAACTGGAAGAAAA<br>GAACATCAAGGAGTTTCTGCAATCAT<br>TCGTTCACATCGTACAAATGTTCATA<br>AATACGTCAGGATCTGGTTCTGGTT<br>CCGGAAGTGGATCTGGTTCAGGGTC<br>CGGTAGTGGATCTGGGTCAGGAAGT<br>GGAAGCGGTAGTGGGTCTGGATCTA<br>AACAAGAGCACTTTCCTGATAACCT<br>GTTGCCGAGCTGGGCGATTACGCTT<br>ATCAGTGTAAACGGCATCTTTGTAAT<br>ATGCTGTCTGACCTACTGCTTCGCA<br>CCAAGGTGCCGGGAGAGAGCAAGA<br>AATGAAAGACTGAGAAGGGAGAGCG<br>TGAGACCTGTGGGATCC | 27 | MDMRVPAQLLGLLLLWL<br>SGARCNWVNVISDLKKIEDLIQSM<br>HIDATLYTESDVHPSCKVTAMKCF<br>LLELQVISLESGDASIHDTVENLIIL<br>ANNSLSSNGNVTESGCKECEELE<br>EKNIKEFLQSFVHIVQMFINTSGS<br>GSGSGSGSGSGSGSGSGSGSG<br>SGSGSGSKQEHFPDNLLPSWAIT<br>LISVNGIFVICCLTYCFAPRCRERA<br>RNERLRRETVRPVGS | 26 |
| IL15-295 | ATGGACATGCGGGTGCCTG<br>CACAACTTCTGGGCCTGCTGTTGTT<br>GTGGCTGTCTGGAGCCCGGTGTAAT<br>TGGGTAAATGTTATCAGTGATCTCAA<br>GAAGATAGAGGATCTCATCCAGTCC<br>ATGCATATTGATGCCACGCTGTACA<br>CAGAAAGCGATGTGCATCCTAGCTG<br>TAAGGTGACAGCGATGAAGTGTTTT<br>CTTTTGGAGCTGCAGGTAATTAGTCT<br>TGAGTCCGGCGATGCCAGCATTCAT<br>GATACCGTAGAAAACTTGATTATCCT<br>GGCCAACAATTCTCTGTCCTCAAAC<br>GGAAACGTAACCGAGAGCGGTTGTA<br>AAGAATGTGAAGAACTGGAAGAAAA<br>GAACATCAAGGAGTTTCTGCAATCAT<br>TCGTTCACATCGTACAAATGTTCATA<br>AATACGTCAGGATCTGGTTCTGGTT<br>CCGGAAGTGGATCTGGTTCAGGGTC<br>CGGTAGTGGATCTGGGTCAGGAAGT<br>GGAAGCGGTAGTGGGTCTGGATCTA<br>AACAAGAGCACTTTCCTGATAACCT<br>GTTGCCGAGCTGGGCGATTACGCTT<br>ATCAGTGTAAACGGCATCTTTGTAAT<br>ATGCTGTCTGACCTACTGCTTCGCA<br>CCAAGGTGCCGGGAGAGAGCAAGA<br>AATGAAAGACTGAGAAGGGAGAGCG<br>TGAGACCTGTGGGATCCTCCCATCA<br>CTGGGGGTACGGCAAACACAACGG<br>ACCTGAGCACTGGCATAAGGACTTC<br>CCCATTGCCAAGGGAGAGCGCCAG<br>TCCCCTGTTGACATCGACACTCATA | 29 | MDMRVPAQLLGLLLLWL<br>SGARCNWVNVISDLKKIEDLIQSM<br>HIDATLYTESDVHPSCKVTAMKCF<br>LLELQVISLESGDASIHDTVENLIIL<br>ANNSLSSNGNVTESGCKECEELE<br>EKNIKEFLQSFVHIVQMFINTSGS<br>GSGSGSGSGSGSGSGSGSGSG<br>SGSGSGSKQEHFPDNLLPSWAIT<br>LISVNGIFVICCLTYCFAPRCRERA<br>RNERLRRETVRPVGSSHHWGYG<br>KHNGPEHWHKDFPIAKGERQSP<br>VDIDTHTAKYDPSLKPLSVSYDQA<br>TSLRILNNGHAFNVEFDDSQDKA<br>VLKGGPLDGTYRLIQFHFHWGSL<br>DGQGSEHTVDKKKYAAELHLVH<br>WNTKYGDFGKAVQQPDGLAVLGI<br>FLKVGSAKPGHQKVVDVLDSIKTK<br>GKSADFTNFDPRGLLPESLDYWT<br>YPGSLTTPPLLECVTWIVLKEPISV<br>SSEQVLKFRKLNFNGEGEPEELM<br>VDNWRPAQPLKNRQIKASFK | 28 |

TABLE 5 -continued

Constitutive and ACZ-regulated 1L15 constructs

| Description | DNA Sequence | DNA SEQ | AA Sequence | AA SEQ |
|---|---|---|---|---|
| | CAGCCAAGTATGACCCTTCCCTGAA | | | |
| | GCCCCTGTCTGTTTCCTATGATCAA | | | |
| | GCAACTTCCCTGAGAATCCTCAACA | | | |
| | ATGGTCATGCTTTCAACGTGGAGTTT | | | |
| | GATGACTCTCAGGACAAAGCAGTGC | | | |
| | TCAAGGGAGGACCCCTGGATGGCA | | | |
| | CTTACAGATTGATTCAGTTTCACTTT | | | |
| | CACTGGGGTTCACTTGATGGACAAG | | | |
| | GTTCAGAGCATACTGTGGATAAAAA | | | |
| | GAAATATGCTGCAGAACTTCACTTG | | | |
| | GTTCACTGGAACACCAAATATGGGG | | | |
| | ATTTTGGGAAAGCTGTGCAGCAACC | | | |
| | TGATGGACTGGCCGTTCTAGGTATT | | | |
| | TTTTTGAAGGTTGGCAGCGCTAAAC | | | |
| | CGGGCCATCAGAAAGTTGTTGATGT | | | |
| | GCTGGATTCCATTAAAACAAAGGGC | | | |
| | AAGAGTGCTGACTTCACTAACTTCG | | | |
| | ATCCTCGTGGCCTCCTTCCTGAATC | | | |
| | CCTGGATTACTGGACCTACCCAGGC | | | |
| | TCACTGACCACCCCTCCTCTTCTGG | | | |
| | AATGTGTGACCTGGATTGTGCTCAA | | | |
| | GGAACCCATCAGCGTCAGCAGCGA | | | |
| | GCAGGTGTTGAAATTCCGTAAACTTA | | | |
| | ACTTCAATGGGGAGGGTGAACCCGA | | | |
| | AGAACTGATGGTGGACAACTGGCGC | | | |
| | CCAGCTCAGCCACTGAAGAACAGGC | | | |
| | AAATCAAAGCTTCCTTCAAA | | | |

Lentivirus Production

HEK293T cells were seeded on collagen coated tissue culture plates until 70% confluent. Cells were transfected with pELNS transfer vector carrying constitutive (IL15-292 or IL15-294) or regulated (IL15-293 or IL15-295) IL15 constructs, as well as packaging plasmids (pRSV.REV, pMDLg/p.RRE and pMD2.G) using Lipofectamine 3000 transfection reagent in Opti-MEM media. Media was replaced 6-8 hrs post-transfection with serum-free media. Supernatants containing virus were harvested 24 hr post-transfection, fresh media was added, and supernatants were harvested again at 48 hr post-transfection. Viral supernatants were filtered to remove debris and concentrated by ultracentrifugation in 20% sucrose gradient. Virus were resuspended, aliquoted and stored at −80 C freezer.

The nucleotide sequences of the pELNS transfer vectors OT-IL15-292, OT-IL15-293, OT-IL15-294 and OT-IL15-295 are SEQ ID NO: 34, SEQ ID NO: 35, SEQ ID NO: 36 and SEQ ID NO: 37, respectively.

As used herein, the lentiviruses used to transduce cells are referred to by their construct name (e.g., IL15-292, IL15-293, IL15-294, IL15-295, CD19-IL15-057, CD19-IL15-058 or CD19-063) or their transfer vector name (e.g., OT-IL15-292, OT-IL15-293, OT-IL15-294, OT-IL15-295, OT-CD19-IL15-057, OT-CD19-IL15-058 or OT-CD19-063).

T Cell Stocks

T cells were isolated from Leukopaks collected from human healthy donors. After PBMC isolation with Ficoll gradients, T cells were isolated using negative selection kit (StemCell Technologies) according to manufacturer's protocol. T cells were resuspended in cell freezing media (Bambanker), aliquoted and stored in liquid nitrogen.

Lentivirus Transduction of T Cells

T cells were thawed, cells were washed and counted. T cells were mixed with CD3/CD28 beads (Invitrogen cat#11141D) at 3:1 bead to T cell ratio. 5×10$^5$ cells/well were added to 24-well plates in 500 µL media. Cells were activated for 24 hrs. Next day, lentivirus was thawed and added to each well at different volumes. After 24 hrs, 500 µL of fresh media was added to wells, and cells were expanded by adding equal volume of fresh media every 2-3 days to keep cell density at 0.5-1×10$^6$/mL. Cells were analyzed by flow cytometry to confirm expression on day 5 or 6. Cells were expanded for 9-10 days.

Example 2. In Vitro Analysis of ACZ-Regulated mbIL15 Expression and ACZ-Regulated T Cell Expansion The present example demonstrates in vitro validation of (i) ACZ-regulated mbIL15 expression in T cells and (ii) ACZ-regulated expansion of T cells expressing ACZ-regulated mbIL15.

Human primary T cells capable of expressing constitutive mbIL15 or ACZ-regulated mbIL15 were prepared in accordance with methods described in Example 1 above. See FIG. 1.

After T cell transduction and expansion, CD3/CD28 beads were removed using magnets, cells were washed twice, resuspended in fresh media and counted. Cells were plated in 12-well plates at 1×10$^6$ in 2 mL. One well of untransduced cells was cultured in the presence of 2 ng/mL IL15 as a control. T cells expressing regulated constructs were cultured in the absence or presence of acetazolamide (ACZ, 30, 10, 3, 1, 0.3 µM). Cell numbers were monitored by flow cytometry every 3-4 days and cells were cultured for 10-12 days. At each time point 100 µL of cells were collected from wells and analyzed by flow cytometry. Cells were split as needed. Cell cultures were maintained in 12-well plates by taking a portion and adding media in a new plate. Volumes for each well were recorded before and after split to calculate final volume in cell number assessment. IL15 or ACZ were replenished at final concentration of the fresh media added during each split. See FIG. 1.

Figure 3A:
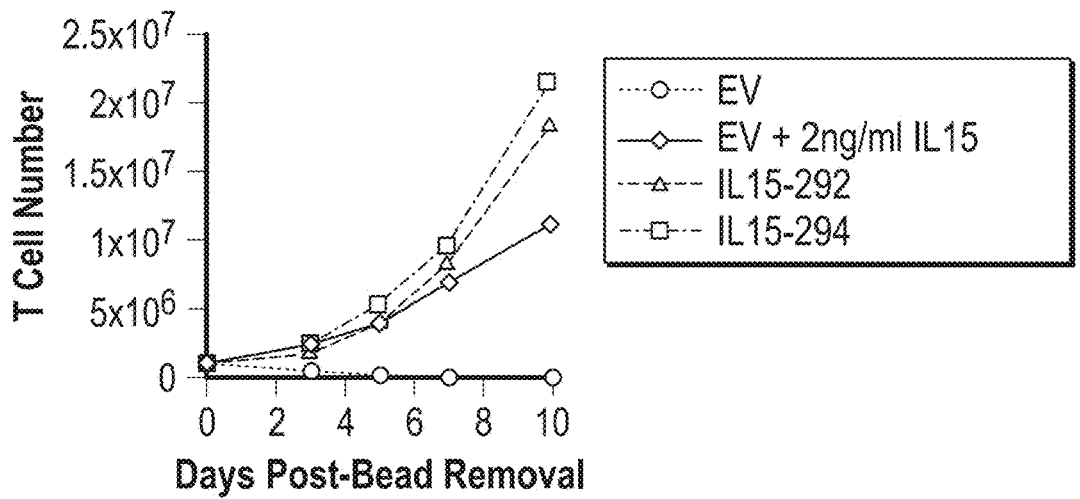
FIG. 3A-FIG. 3C shows in vitro expansion of T cells expressing constitutive IL15-292 and IL15-294 (FIG. 3A), and regulated IL15-293 (FIG. 3B) and IL15-295 (FIG. 3C) constructs in the presence of different concentrations of ACZ. Empty vector (EV) transduced cells cultured in the absence or presence of exogenous IL15 (2 ng/mL) were used as controls.
Figure 3B:
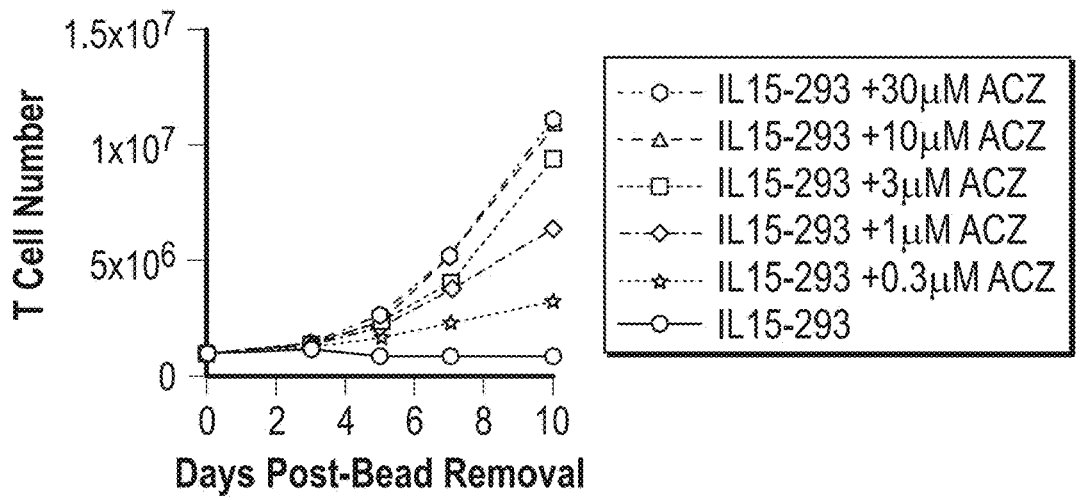
Figure 3C:
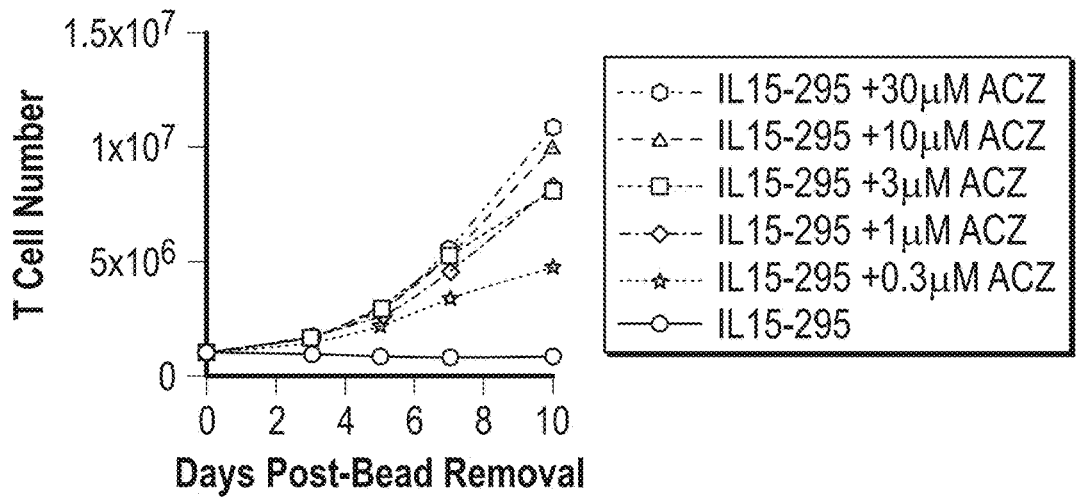

T cell numbers were determined by flow cytometry. Empty vector (EV) transduced cell numbers decreased to background levels between 3-5 days in the absence of IL15, and cells expanded 11-fold in the presence of 2 ng/mL exogenous IL15 (FIG. 3A). T cells expressing constitutive IL15-292 and IL15-294 expanded between 18 and 21-fold, respectively, in 10 days (FIG. 3A). In T cells expressing IL15-293, maximum expansion was 9.5-11× with 30, 10, 3 µM (FIG. 3B). At the lowest concentration tested (0.3 µM), cells expanded 3.3×. These cells survived longer (0.8×) compared to EV cells without drug treatment (0.8×). In T cells expressing IL15-295, maximum expansion was 8.2-10× with 30, 10, 3 µM and cells expanded 4.9× at the lowest concentration (0.3 µM) tested (FIG. 3C). Without drug treatment, these cells survived (0.9×) longer compared to EV.

Figure 4A:
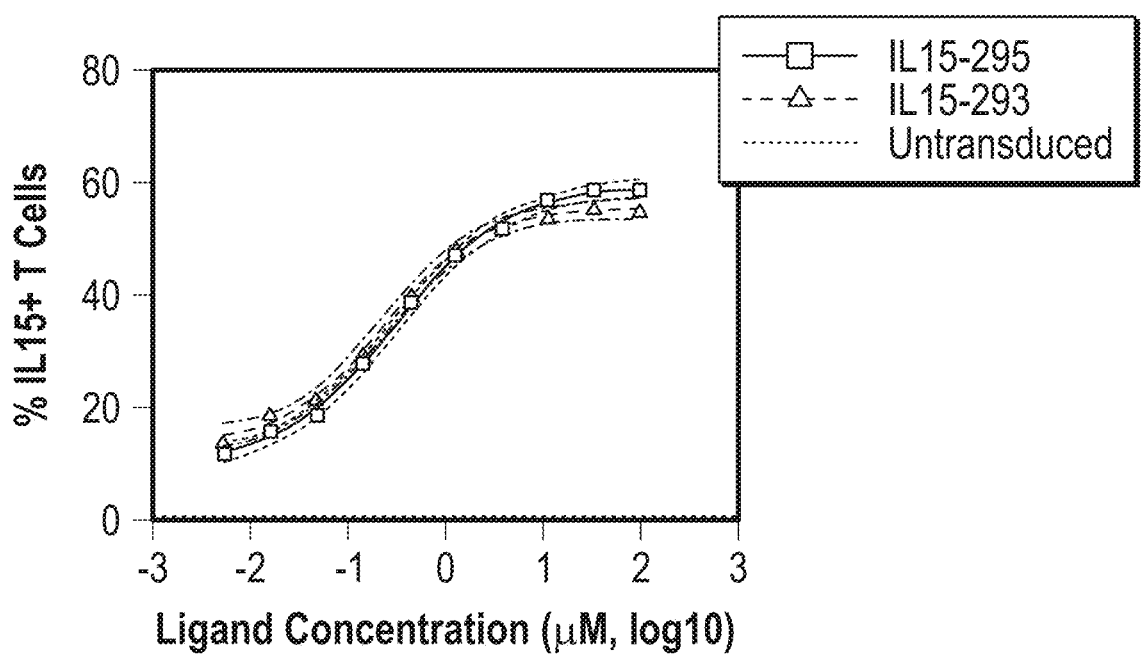
FIG. 4A-FIG. 4B shows acetazolamide dose response and IL15 expression on T cells. Cells were treated with different concentrations of ACZ (ligand) starting at 100 μM for 24 hrs. Graphs show % IL15+ T Cells (FIG. 4A) and mean fluorescence intensity (MFI) of IL15 (FIG. 4B).
Figure 4B:
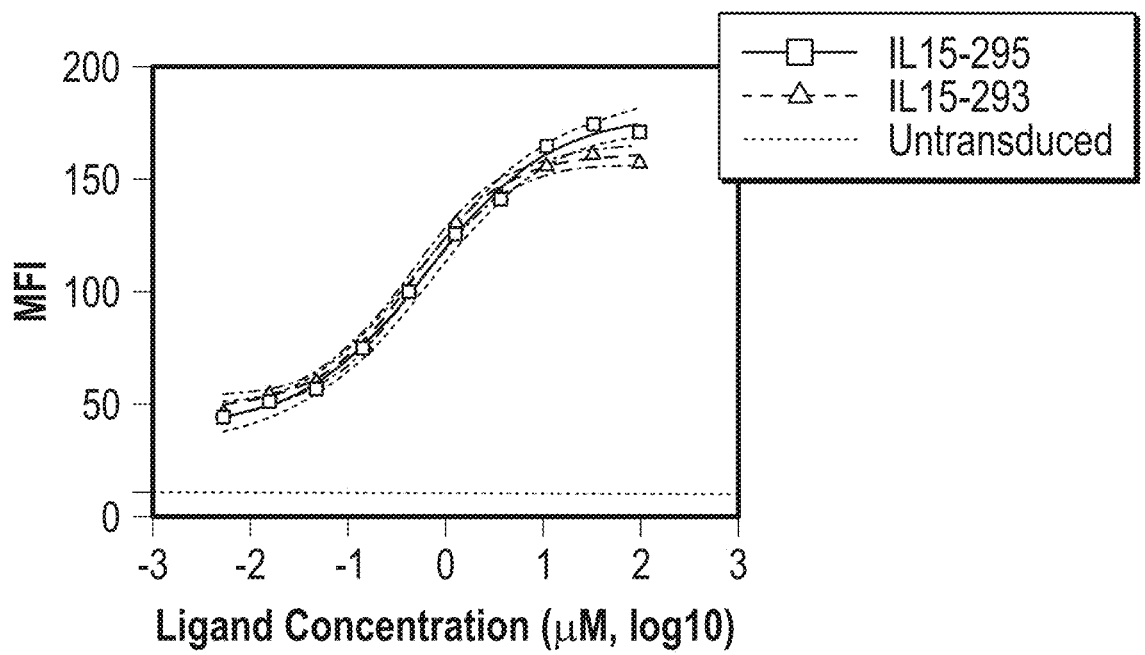

The effect of different concentrations of ACZ on IL15 expression was tested. T cells were treated with ACZ for 24 hrs starting at 100 µM, diluted 3-fold for 9 points. Both % IL15+ T Cells (FIG. 4A) and IL15 Mean Fluorescence Intensity (MFI) (FIG. 4B) analysis indicated similar dose curves for OT-IL15-293 and OT-IL15-295. There was 4-5-fold increase in expression (both % IL15+ T cells and IL15 MFI) between highest and lowest concentrations of ACZ. $EC_{50}$ values were 0.29 µM and 0.22 µM EC50 based on % IL15+ T Cells, 0.65 µM and 0.44 µM based on MFI of IL15 for OT-IL15-293 and OT-IL15-295, respectively.

Example 3. In Vivo Analysis of ACZ-Regulated mbIL15 Expression and ACZ-Regulated T Cell Expansion The present example demonstrates in vivo validation of (i) ACZ-regulated mbIL15 expression in T cells and (ii) ACZ-regulated expansion of T cells expressing ACZ-regulated mbIL15.

NK Cell Expansion

A portion of the PBMCs isolated from Leukopaks were used to enrich NK cells using negative selection kits (StemCell Technologies) according to manufacturer's protocol. Cells were cultured in 1:1 ratio with feeder K562 cells expressing 4-1BB-L and membrane-bound IL21, and recombinant IL2 (100 U/mL) for 7-14 days. Expansion was monitored by cell counts and purity was evaluated by flow cytometry.

In Vivo Analysis

Human primary T cells capable of expressing constitutive mbIL15 or ACZ-regulated mbIL15 were prepared in accordance with methods described in Example 1 above. After T cell transduction and expansion, CD3/CD28 beads were removed using magnets, cells were washed twice, resuspended in fresh media and counted. T cells were mixed with expanded NK cells and each animal received $5 \times 10^6$ T cells and $2 \times 10^6$ expanded NK cells. Cells were infused by intravenous injections into NSG mice. Animals infused with T cells expressing regulated constructs were dosed daily with 200 mg/kg ACZ or vehicle by PO injections. Every 3-4 days, 50 µL blood was analyzed by flow cytometry for presence of T cells and NK cells using antibodies against mouse and human CD45, CD3 and CD56. IL15 expression on day 25 was analyzed using IL15Ra-Fc and fluorochrome conjugated anti-human IgG antibody. See FIG. 2.

Figure 5A:
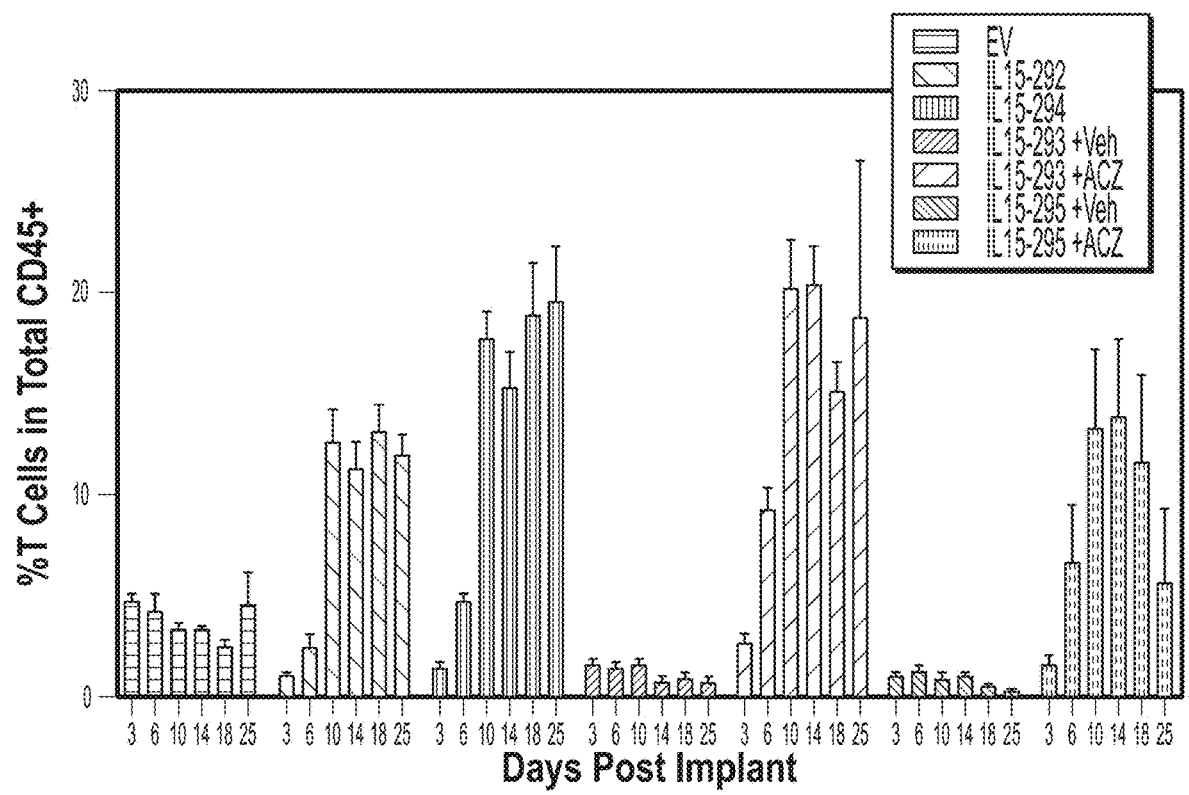
FIG. 5A-FIG. 5C shows in vivo analyses of T cells expressing constitutive and regulated IL15 constructs and their effects on NK cells.
Figure 5B:
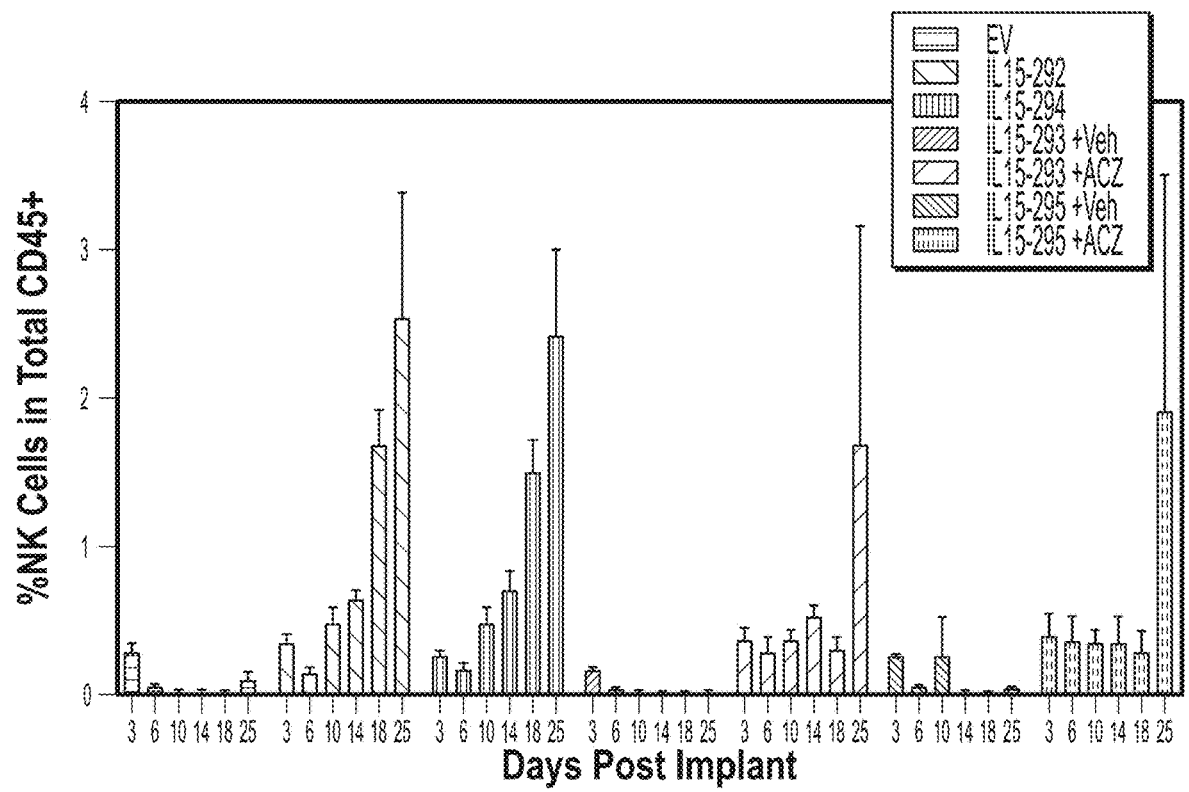

Expansion of T cells expressing constitutive and regulated IL15 constructs, and their effects on bystander NK cells were evaluated in vivo in NSG mice over a course of 25 days (FIG. 5A-FIG. 5B). Empty vector (EV) transduced cell numbers slowly declined over time. T cells expressing constitutive IL15-292 and IL15-294 expanded up to 13× compared to the frequencies on day 3. In mice infused with T cells expressing regulated constructs, cell frequencies decreased in the presence of vehicle treatment. In groups treated with daily ACZ, cells expanded up to 7-8× compared to the frequencies on day 3. Bystander NK cells survived and expanded in the presence of T cells expressing constitutive IL15 constructs, or in the presence of T cells expressing regulated IL15 constructs treated daily with ACZ.

Figures 5C, 6:
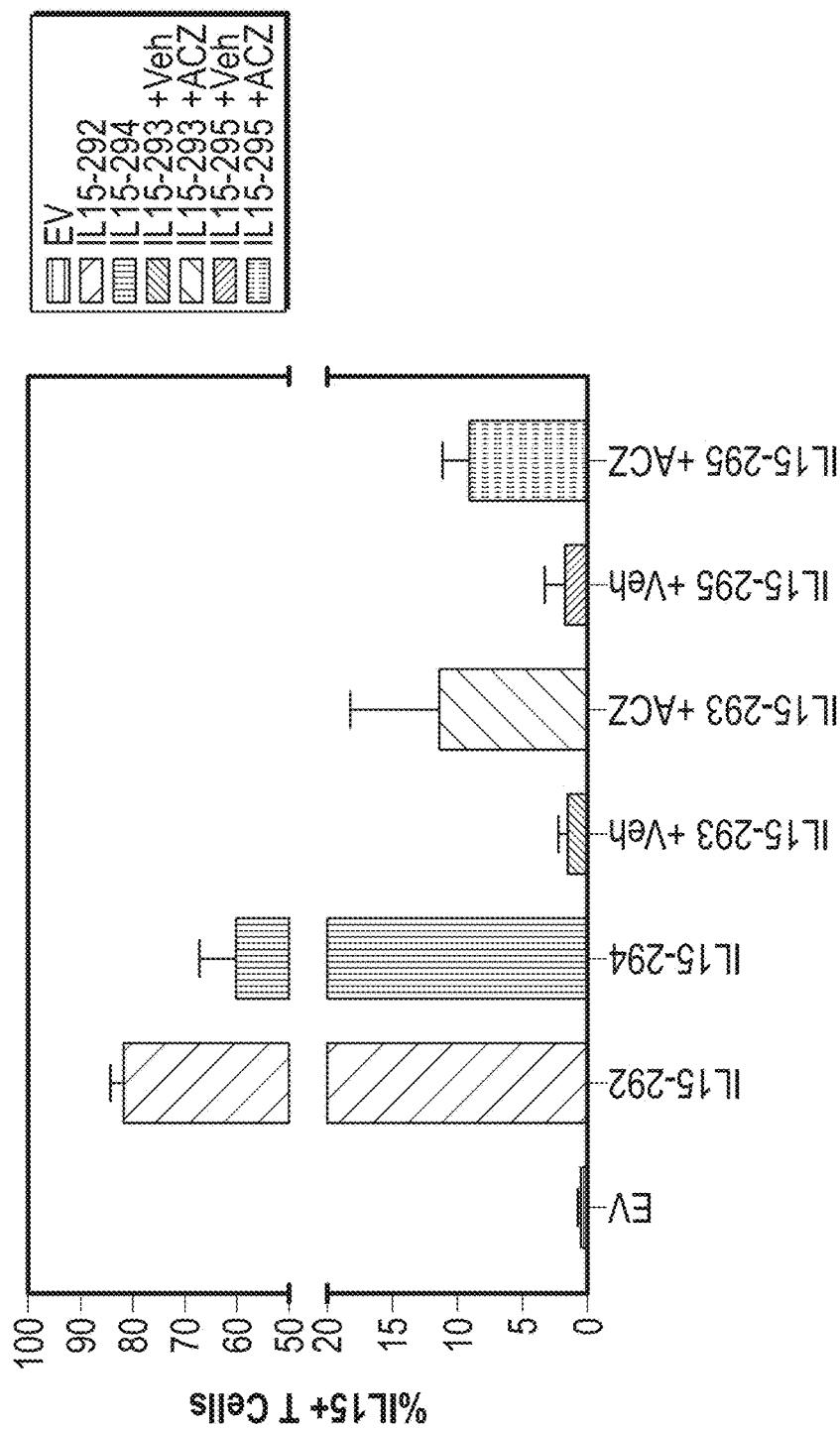
FIG. 6 depicts schematic representations of tandem CD19 CAR and mbIL15 constructs encoding a constitutively expressed mbIL15 (CD19-IL15-057) or a regulated mbIL15 (CD19-IL15-058). Each construct comprises polynucleotide sequences encoding a regulated or constitutive mbIL15 that comprises an IgKv leader sequence (IgKv LS), an IL15 polypeptide component, a GS linker, a B7-1 hinge, a transmembrane domain (TM), and a tail. The constitutive construct encodes the mbIL15 operably linked to a CA2 wild-type sequence (CA2 (WT)). The regulated construct encodes the mbIL15 operably linked to a CA2(L156H) DRD. Each construct also comprises a P2A sequence and polynucleotide sequences encoding an anti-CD19 CAR that comprises a CD8a leader sequence (CD8a LS), a CD19 scFv, a CD8α transmembrane domain and hinge, a costimulatory domain derived from 4-1BB and a CD3ζ signaling domain.

IL15 expression on T cells in vivo on day 25 was analyzed by flow cytometry (FIG. 5C). T cells transduced with constitutive constructs IL15-292 and IL15-294 expressed high levels of IL15 (82% and 61%). IL15 expression was <1.5% in vehicle-treated IL15-293 and IL15-295 as well as EV groups. IL15 expression levels were 11% and 9% on T cells transduced with IL15-293 and IL15-295 in groups treated with ACZ.

Example 4: In Vivo Analysis of Efficacy and Expansion in CART Cells Expressing Constitutive and Regulated mbIL15

The present example demonstrates that regulated mbIL15 coupled to ACZ dosing enhances anti-tumor efficacy and expansion of CD19 CART cells in the presence of CD19-positive tumors.

Generation of Tandem CD19 CAR and mbIL15 Constructs and Lentivirus Stocks

Lentiviral vector constructs and lentivirus stocks that co-express CD19 CAR and mbIL15 were generated essentially as described in Example 1. A CD19 CAR sequence (AA sequence: SEQ ID NO: 38; NA sequence: SEQ ID NO: 39) was constructed consisting of a CD8a leader sequence (aa1-21 in Uniprot ID P01732), FMC63 (anti-CD19) single chain variable fragment (scFv), a hinge and transmembrane domain derived from CD8 (aa138-206 in Uniprot ID P01732), a costimulatory domain derived from 4-1BB (aa214-255 in Uniprot ID Q07011) and CD3zeta signaling domains (aa52-164 in Uniprot IDP20963).

The bicistronic transgene expression cassette (5' to 3' as described) was comprised of a regulated or constitutive mbIL15, a P2A sequence (AA sequence: SEQ ID NO: 40; NA sequence: SEQ ID NO: 41), and the anti-CD19 CAR downstream from the P2A (see FIG. 6). For the regulated construct (CD19-IL15-058; AA Sequence: SEQ ID NO: 42; NA Sequence: SEQ ID NO: 43), the IL15-293 construct comprising mbIL15 operably linked to the CA2(L156H) DRD was used (AA sequence: SEQ ID NO: 24, NA sequence: SEQ ID NO: 25). For the constitutive construct (CD19-IL15-057; AA Sequence: SEQ ID NO: 45; NA Sequence: SEQ ID NO: 46), a construct comprising mbIL15 operably linked to the CA2 wildtype sequence was used (See FIG. 6). The nucleotide sequence of lentivirus OT-CD19-IL15-058 is SEQ ID NO:44; the nucleotide sequence of lentivirus OT-CD19-IL15-057 is SEQ ID NO:45.

Expression of mbIL15-CAR Constructs in Peripheral Blood T Cells

Figure 7A:
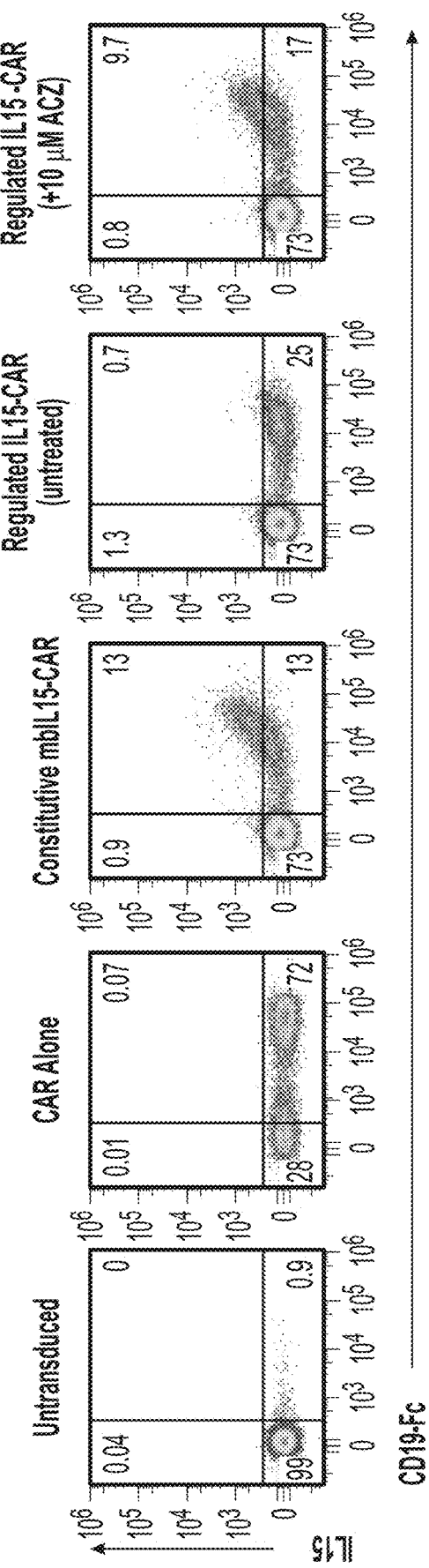
FIG. 7A-FIG. 7E show T cells transduced with tandem CD19 CAR and mbIL15 constructs evaluated for regulated mbIL15 expression and anti-tumor effects in vivo.

Peripheral blood T cells were activated, transduced, expanded for up to 10 days, and frozen in cell freezing medium essentially as described in Example 1 to be used in the in vivo human Nalm6-Luc xenograft tumor model. mbIL15 and CAR expression were analyzed by flow cytometry using anti-IL15 antibody and recombinant protein comprised of the extracellular domain of human CD19 fused to human IgG1 Fc domain (CD19-Fc), respectively. CD19 CAR-only transduced cell or untransduced cells were used as controls. 72% of cells transduced with control CD19 CAR construct were CAR+ mbIL15- (FIG. 7A). For cells transduced with lentiviral vector expressing constitutive mbIL15 and CAR (CD19-IL15-057), 26% of the cells were CAR+ and 13% were double positive for CAR+ mbIL15+. For cells transduced with vector expressing regulated mbIL15 and CAR (CD19-IL15-058), 25% were CAR+ mbIL15− in the absence of ACZ and 9.7% were CAR+ mbIL15+ double positive after a 24-hr exposure to 10 µM ACZ. These results confirmed expression of both CAR and mbIL15 after transduction of T cells with lentiviral vector expressing CD19CAR in combination with constitutive or regulated mbIL15.

Evaluation of mbIL15-CART Cells in Nalm6-Luc Xenograft Model

To evaluate the effect of mbIL15 on anti-tumor activity of CART cells, T cells that were transduced with lentiviral vectors expressing CD19 CAR with or without constitutive or regulated mbIL15 were infused into mice after implantation of CD19+ Nalm6-Luc tumors. CD19+ Nalm6 cells expressing luciferase (Nalm6-Luc) were injected by intravenous route ($1\times10^6$/mouse) into NSG mice and tumor growth was measured once or twice per week by bioluminescence imaging measurement (total flux units in photons per second (p/s)) after intraperitoneal injections of D-luciferin. On day 6, animals were randomized into new cages (N=8 for each group) when average tumor size reached approximately $10^6$ total p/s. CD19 CART cells (engineered with or without constitutive or regulated mbIL15) were thawed for infusion into tumor bearing mice. CAR expression in T cells was determined post-thaw and after 24-hr restimulation with anti-CD3/CD28 beads. CART cells across different groups were normalized based on % CAR+ cells. Each mouse received $0.3\times10^6$ CAR+ cells and the total number of T cells in the infusion product was adjusted to $7\times10^6$ T cells by addition of EV-transduced T cells.

The first group received T cells engineered with EV as a negative control, the second group received control CART cells without mbIL15 (CD19-063; AA Sequence: SEQ ID NO: 48; NA Sequence: SEQ ID NO: 49; vector sequence: SEQ ID NO: 50) and the third group received CART cells expressing constitutive mbIL5 (CD19-IL15-057). Groups 4 and 5 received CART cells that co-expressed regulated mbIL15 (CD19-IL15-058), and while one group was treated daily PO with 200 mg/kg ACZ, the other group was treated daily with vehicle until the end of the study (~50 days). To monitor T cell expansion, additional animals were included in each group (n=4 for blood, and n=4 for bone marrow). Blood (50 µL) was withdrawn from submandibular veins on days 7, 14, and 21, and bone marrow (from femur) was harvested on day 14 after T cell infusion. Red blood cells were lysed, stained with fluorochrome-conjugated antibodies against human CD45, CD3 and mouse CD45, and cells were analyzed by flow cytometry. Tumor growth was measured up to 55 days after tumor implantation; endpoints included $10^{10}$ total flux units as well as effects on animal health such as hind-limb paralysis and decrease in body weight.

Figure 7B:
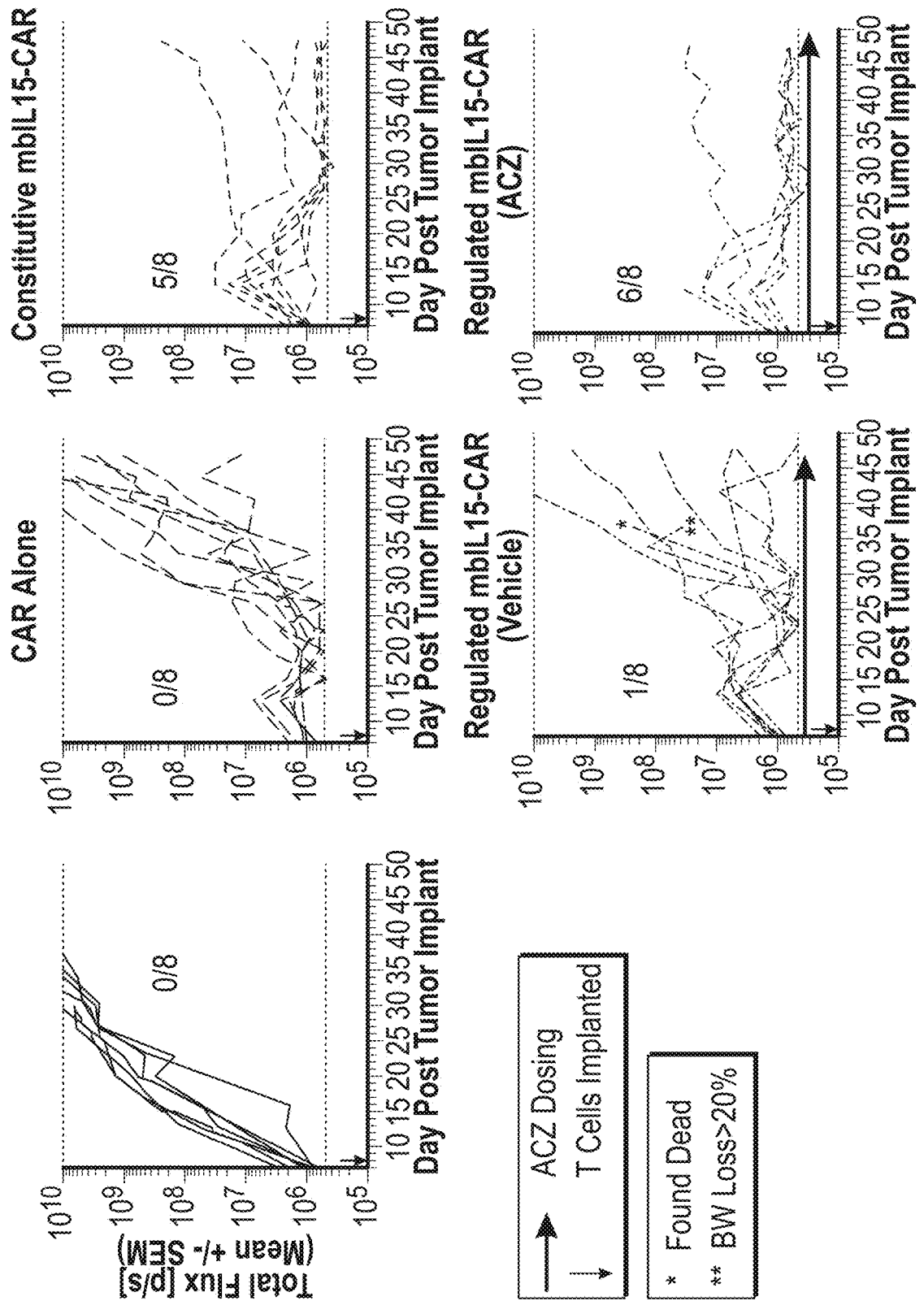
Figure 7C:
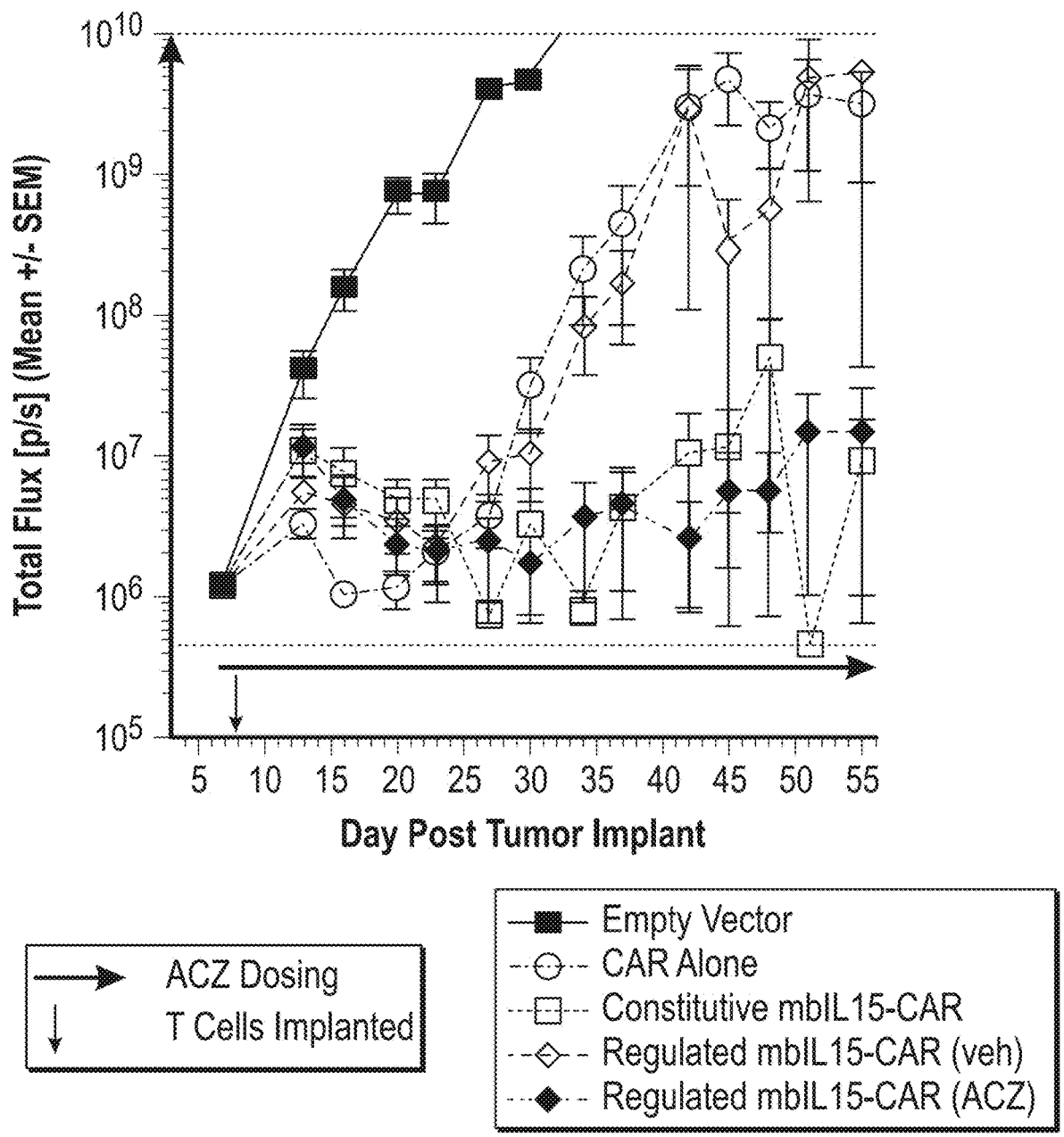
Figure 7D:
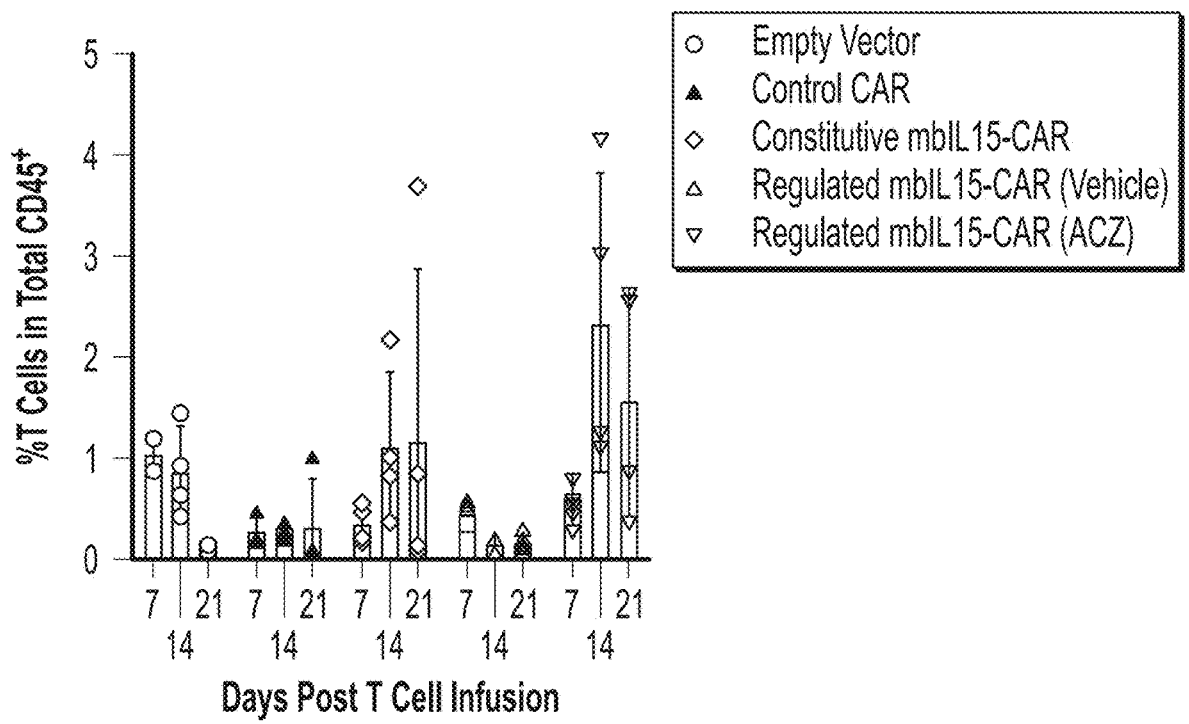
Figure 7E:
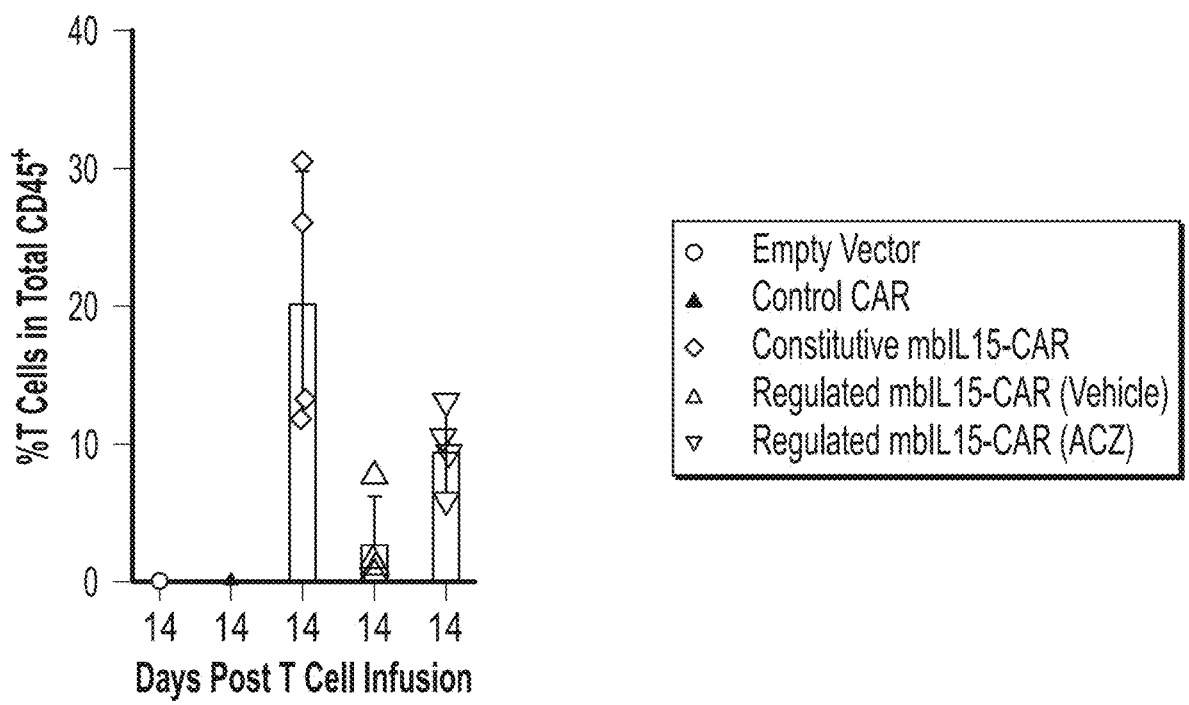

Tumor growth in individual mice in each group is shown in FIG. 7B and group averages are shown in FIG. 7C. Rapid tumor growth was observed in all animals in group 2 treated with EV-transduced T cells, and tumor growth was delayed up to ~25 days upon treatment with control CART cells with no complete response. Tumor growth rate in mice treated with CART cells expressing regulated mbIL15 and vehicle treatment were similar to control CART group. In contrast, tumors regressed to background levels in 5 and 6 of 8 animals in groups treated with CART cells expressing constitutive mbIL15 and CART cells expressing regulated mbIL15 plus ACZ, respectively. T cells numbers were reduced over time in blood (<0.2% on day 21, FIG. 7D) and were low in bone marrow (<1% on day 14, FIG. 7E) from mice treated with control T cells, control CART, and CART expressing regulated mbIL15 with vehicle treatment. In contrast, in mice treated with CART expressing constitutive mbIL15 or regulated mbIL15 with ACZ, T cell numbers increased in blood over time (>1% on day 21, FIG. 7D) and were high in bone marrow (20% for constitutive, 10% for regulated plus ACZ, FIG. 7E). These results demonstrate that regulated mbIL15 coupled to ACZ treatment enhanced CART anti-tumor responses compared to T cells expressing CAR alone after infusion of a suboptimal CART cell dose, and promoted CAR engineered T cell expansion post-tumor clearance.

Example 5: Isolation of TIL From Patient Tumor Samples

Head and neck tumor samples were obtained from Cooperative Human Tissue Network. Tumor samples were cut into 1-3 mm fragments in Hanks' Balanced Salt Solution (HBSS) buffer and fragments were placed in 24-well plates at 1 fragment/well in 2 ml of culture media (RPMI-1640 supplemented with 1× Penicillin/Streptomycin, 1 mM Sodium Pyruvate, 1× HEPES, 50 µM 2-Mercaptoethanol (Invitrogen) and 10% heat-inactivated human AB serum (Valley Bio)) containing 6000 IU/mL IL2. Half of the media was replaced with fresh media containing IL2 starting on day 5 and cells were split into multiple wells as they became confluent for a duration of 3 weeks. This culture process is referred to as pre-rapid expansion protocol (REP). TIL from other tumor types have been isolated using essentially the same process.

Figure 8A:
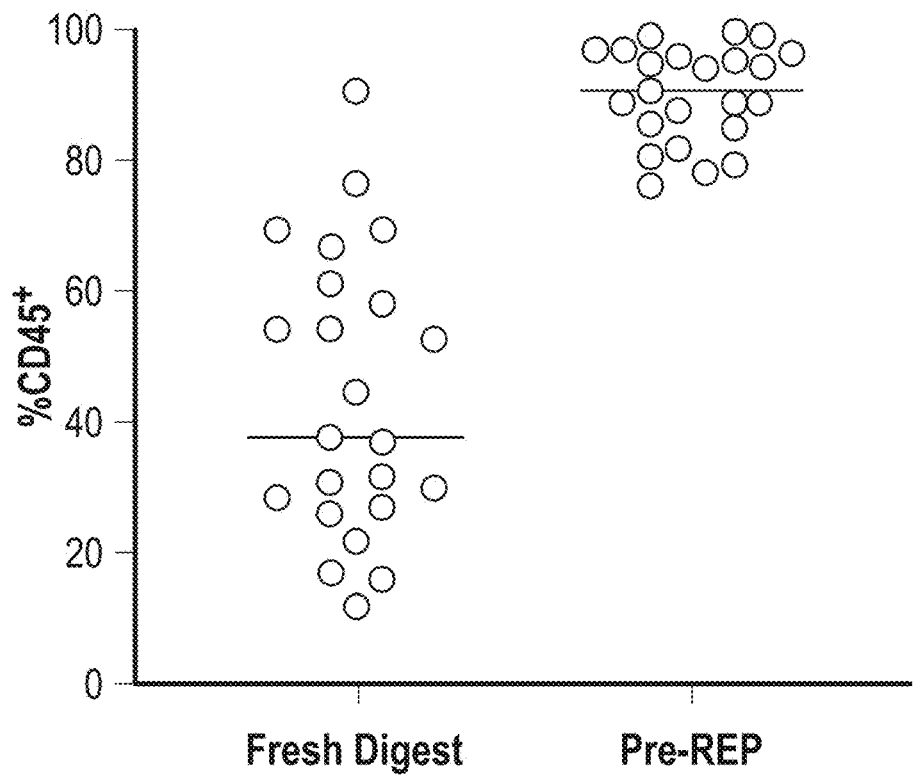
FIG. 8A shows frequency of $CD45^+$ cells (top) and $CD3^+$ T cells within $CD45^+$ cells (bottom) in fresh tumor digest and after 3 weeks of pre-REP TIL culture.
Figure 8A:
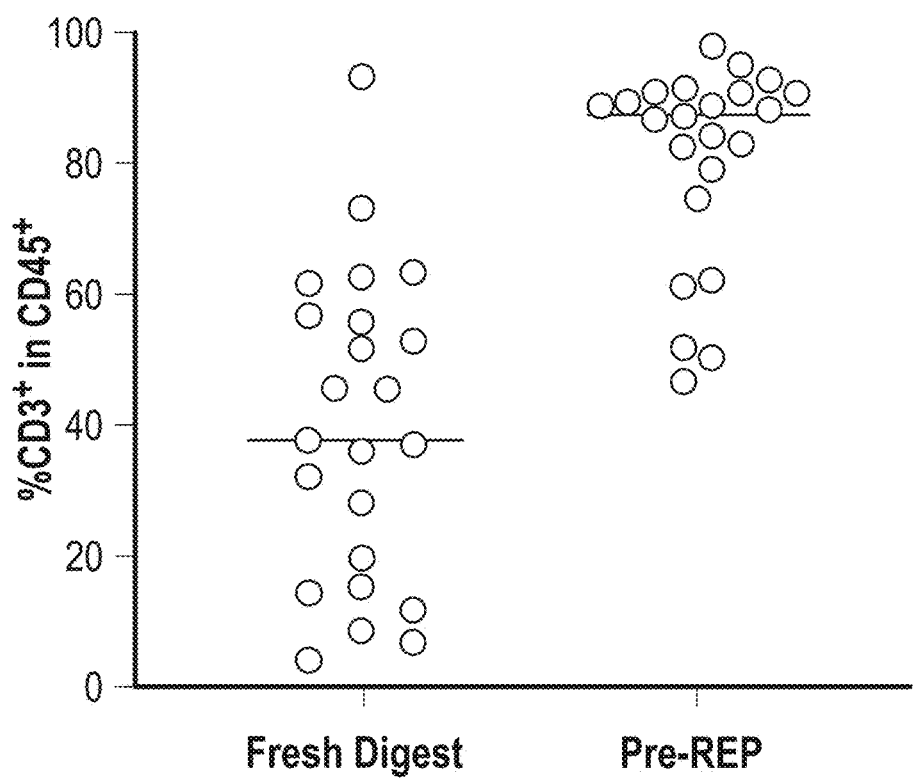

In order to determine the change in frequency of T cells before and after pre-REP culture, a portion of tumor fragments were digested with collagenase and DNase I to generate single cell suspension prior to the pre-REP culture and compared to cells obtained after the pre-REP culture. Frequency of T cells were analyzed by flow cytometry using fluorochrome conjugated anti-CD45 and anti-CD3 antibodies. As shown in FIG. 8A, nearly half of the cells (44.29±21.67%) in the pre-culture tumor cell suspension were CD45+ and among these only ~39.85±23.69% were CD3+ T cells. After 3 weeks of culture in the presence of IL2 (pre-REP), the majority of the cells were CD45+ (90.35±7.28%), indicating an enrichment of hematopoietic cells, and CD3+(80.64±15.19%), indicating an enrichment of T cells.

TIL from numerous other human tumor types, including melanoma tumors and malignant tumors from breast, lung, kidney, endometrium, liver, pancreas and ovary, have been isolated in the same manner.

Example 6. In Vitro Analysis of Regulated mbIL15 Expression by ACZ in TIL

BaEV-Pseudotyped Lentivirus Production

HEK293T cells were seeded on collagen coated tissue culture plates until 70% confluent. Cells were transfected with pELNS transfer vector carrying constitutive (IL15-292) or regulated (IL15-293) IL15 constructs, as well as packaging plasmids (pRSV.REV, pMDLg/pRRE and OT-BaEVg-002 (SEQ ID NO: 51)) using Lipofectamine 3000 transfection reagent in Opti-MEM media. Media was replaced 6-8 hrs post-transfection with serum-free media. Supernatants containing virus were harvested 24 hr post-transfection, fresh media was added, and supernatants were harvested again at 48 hr post-transfection. Viral supernatants were filtered to remove debris and concentrated by low speed ultracentrifugation. Virus were resuspended, aliquoted and stored at −80 C freezer.

Transduction of TIL with Lentivirus 96-well non-coated tissue culture plates were incubated with 35 µg per mL RetroNectin (Takara Bio) in PBS for 2 h at 37° C. or overnight at 4° C. RetroNectin was removed and the plates washed with PBS. BaEV-pseudotyped lentivirus, prepared as described above, and TIL cell media, at a total volume of 50 µL per well, were added to each well and the plates were centrifuged at low speed for 2 hours at 32° C. TIL generated from a head and neck tumor sample prepared as described in Example 5 were engineered after 3 weeks in the pre-REP culture. TIL were activated for 24 hrs in 24-well plates with anti-CD3/CD28 beads at 3:1 bead to T cell ratio. Activated TIL were placed in virus-coated plates and centrifuged at 800 g for 2 hrs and incubated at 37° C. for 4 days in culture media. One well of cells was processed similarly without virus addition and used as negative control ("untransduced"). Cells that were transduced with the regulated mbIL15 construct were treated either with 10 µM ACZ or DMSO for 24 hrs.

Figure 8B:
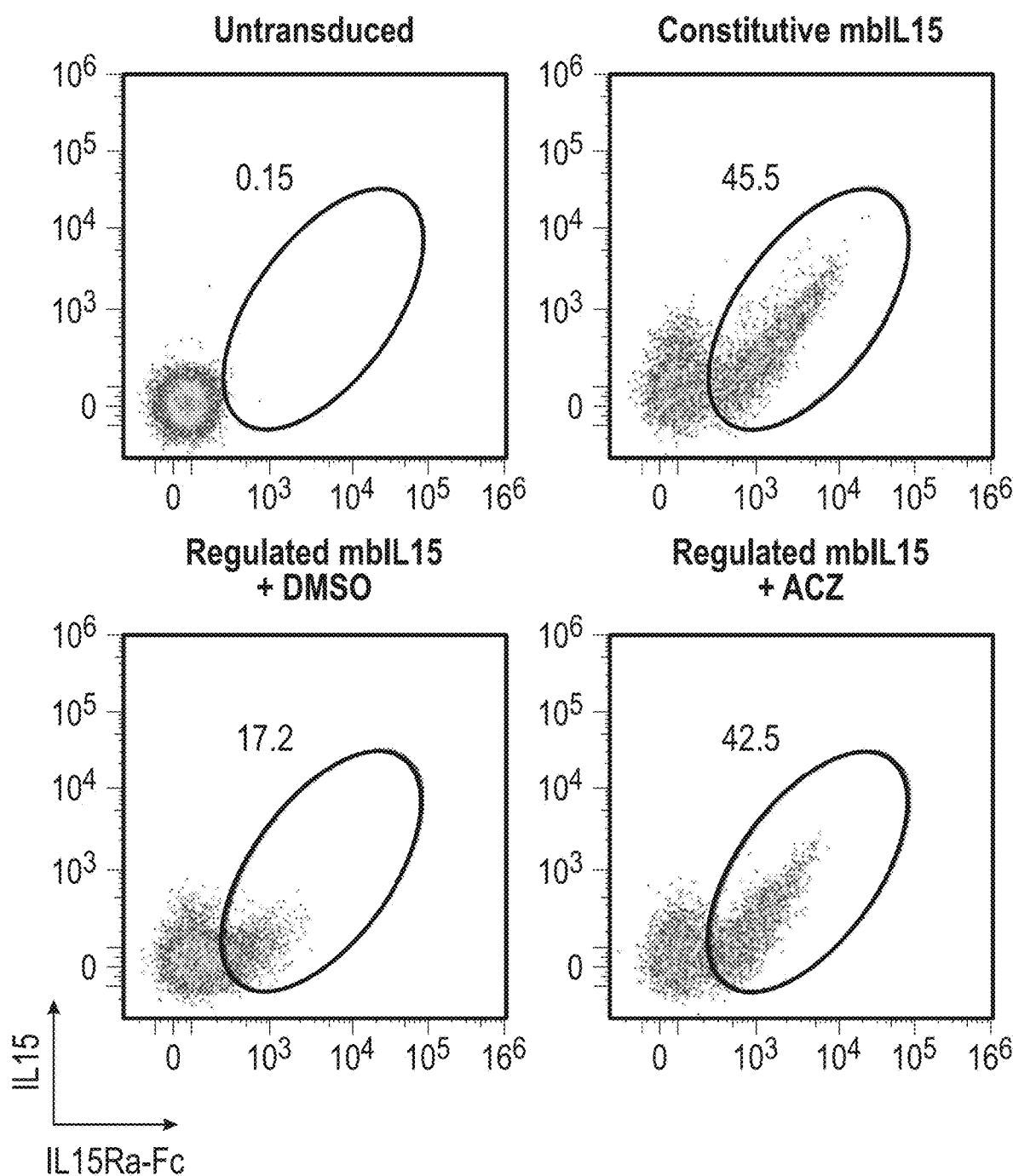
FIG. 8B shows mbIL15 expression determined by flow cytometry for TILs transduced with constitutive or regulated mbIL15 constructs. TILs transduced with the regulated mbIL15 construct were treated with 10 μM ACZ or DMSO for 24 hrs. Untransduced cells were evaluated as a negative control.

Expression of Regulated mbIL15 in TIL in Response to ACZ mbIL15 expression was determined by flow cytometry using two staining reagents: fluorochrome-conjugated anti-IL15 antibody as well as a recombinant protein comprised of extracellular domain of IL15Ra fused to human IgG1 Fc domain (IL15Ra-Fc). mbIL15+ cell frequency was determined based on co-staining with anti-IL15 and IL15Ra-Fc (identified as the IL15+IL15Ra-Fc+ double positive population). As shown in FIG. 8B, 45.5% of TIL expressed constitutive mbIL15 (IL15-292). In the presence of DMSO, regulated mbIL15 (IL15-293) expression was 17.1% with low MFI. In contrast, in the presence of ACZ, regulated mbIL15 expression increased to 42.5% with high MFI. These data indicate that ACZ induces CA2 DRD-regulated mbIL15 in transduced TIL.

Example 7: In Vivo Analysis of TIL Expressing Constitutive and Regulated mbIL15

To evaluate the effect of regulated mbIL15 on the anti-tumor activity of tumor infiltrating lymphocytes (TIL), a human PDX (hPDX) model is used. TIL are isolated from a patient tumor sample, for example, a head and neck tumor sample, as described in Example 6. TIL are transduced with BaEV-pseudotyped lentiviral vectors containing either the IL15-292 construct or the IL15-293 construct, as described in Example 6, or with BaEV-pseudotyped lentiviral empty vector (EV), and then optionally frozen. TIL-matched patient-derived xenografts (hPDX) from the tumor sample are established via subcutaneous implant into the right flank of NSG mice. Tumor growth is measured once or twice per week using calipers. On study start, tumors are measured, and mice are randomized and placed in cohorts based on similar mean tumor volume across all groups into new cages (N=8 for each group). The engineered matched TIL are thawed if necessary, stimulated with PMA, and then infused into the tumor-bearing mice. Each mouse receives an equal number of engineered TIL.

Group 1 receives untransduced TIL supplemented with recombinant human IL2 (hIL2) as benchmark control, and group 2 receives TIL transduced with constitutive mbIL15 (IL15-292). Groups 3 and 4 receive TIL transduced with regulated mbIL15 (IL15-293). Group 3 is treated daily PO with 200 mg/kg ACZ, and group 4 is treated daily with vehicle until the end of the study. To monitor TIL persistence, additional animals are included in each group (n=4 for blood). Blood (50 µL) was withdrawn from submandibular veins on pre-determined days. Red blood cells are lysed, stained with fluorochrome-conjugated antibodies against human CD45, CD3 and mouse CD45, and cells are analyzed by flow cytometry. Tumor growth is measured for up to approximately 90 days; endpoints include maximal caliper measurements as well as effects on animal health, such as tumor necrosis and decrease in body weight.

Tumor growth in individual mice in each group is followed and group averages are collected. Delayed tumor growth is expected in animals in group 1 treated with untransduced TIL plus hIL2. No tumor growth inhibition will be observed in group 4 because little or no mbIL15 will be expressed by the TIL. In contrast, tumors will substantially regress, in some cases to baseline, in groups 2 and 3 because both groups have TIL expressing mbIL15, which will enhance their persistence and correlated anti-tumor activity.

Example 8: Isolation of NK Cells from Cord Blood

Cryopreserved mononuclear cell-fractionated cord blood units were obtained from BioBridge Global. Cord blood was diluted 1:1 with phosphate-buffered saline (PBS) and centrifuged over a cushion of Ficoll-Paque+(Sigma Cat. No. GE17-1440-02). The buffy coat comprising mononuclear cells (MNC) was collected, and the MNC were washed and counted. NK cells were isolated from MNC using EasySep Human NK Cell Isolation Kit (Stemcell Technologies Cat. No. 17955). NK cells were counted and checked for purity by FACS using CD56, CD16, CD3 and viability stain.

Example 9: In Vitro Analysis of Regulated mbIL15 Expression by ACZ in NK Cells NK Cell Expansion One day prior to NK cell isolation as described in Example 8, feeder cells (K562 cells expressing 4-1BBL and mbIL-21) were thawed in complete NK cell media (RPMI with Glutamax (ThermoFisher), 10% heat-inactivated fetal bovine serum (Gibco), 1× Penicillin/Streptomycin, 1 mM Sodium Pyruvate, 1×HEPES, 50 µM 2-Mercaptoethanol). On the day of NK cell isolation, $10 \times 10^6$ feeder cells were treated with mitomycin C to inhibit their proliferation and washed to remove excess drug. NK cells were added to the feeder cells at a 1:2 effector to target ratio in NK cell media with 200 U/mL recombinant human IL2 (rhIL2; PeproTech). NK cell cultures were expanded by replenishing cell cultures with NK cell media and rhIL2 every two days, and analyzed by FACS for NK cell expansion.

Transduction of NK Cells with Lentivirus 96-well non-coated tissue culture plates were incubated with 35 µg per mL RetroNectin (Takara Bio) in PBS for 2 h at 37° C. or overnight at 4° C. RetroNectin was removed and the plates washed with PBS. BaEV-pseudotyped lentivirus, prepared as described in Example 6, and NK cell media, at a total volume of 50 µL per well, were added to each well and the plates were centrifuged at low speed for 2 hours at 32° C. $1 \times 10^5$ NK cells in 100 µL NK cell transduction media (NK cell media with 1 mg/mL Synperonic F 108 (Sigma-Aldrich) and 200 U/mL rhIL2) were added to each well and the cells were expanded for four days in NK cell media.

Regulation of mbIL15 Construct with ACZ

Figure 9:
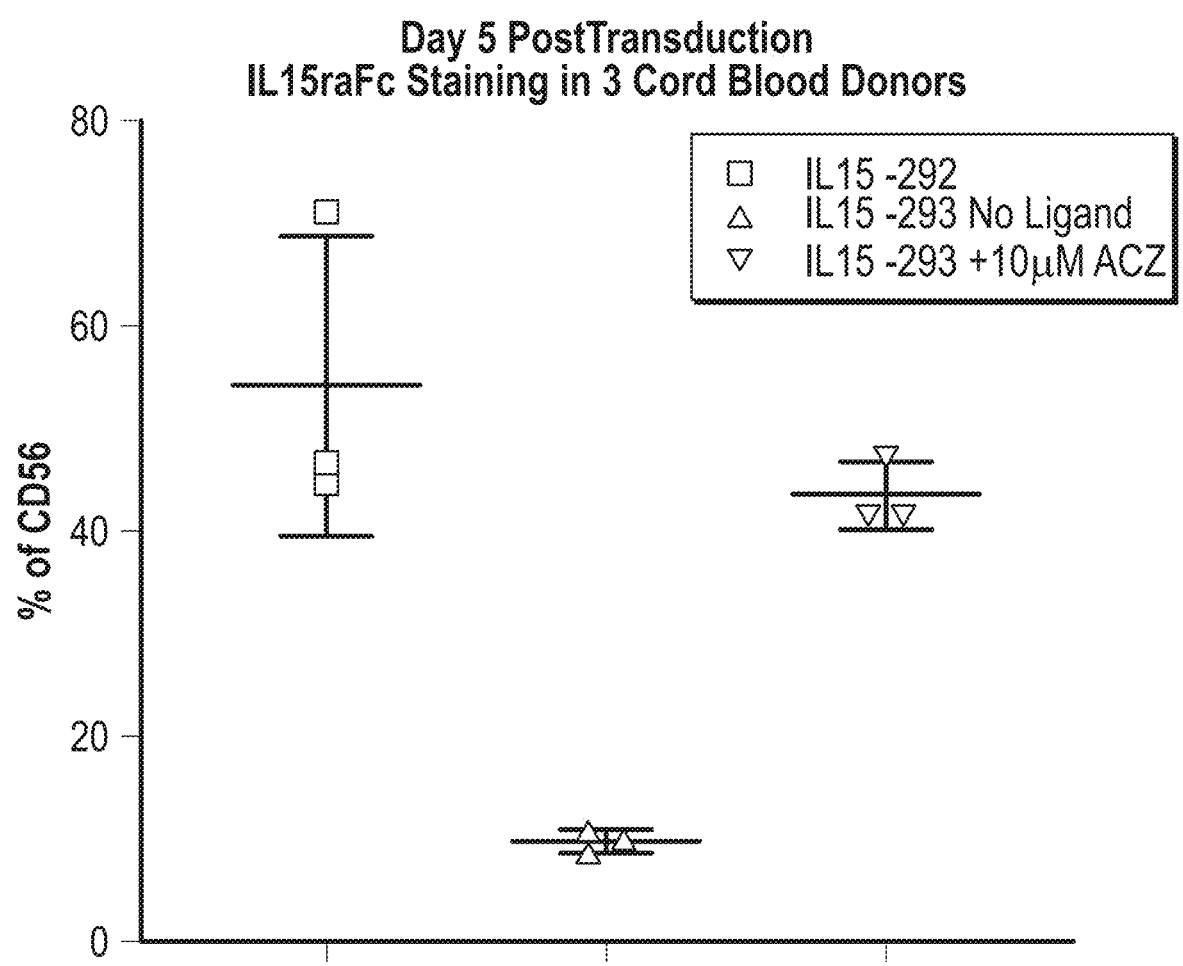
FIG. 9 shows expression of constitutive and regulated mbIL15 in NK cells. Each symbol on the graph (squares and triangles) represents one of three donors. Error bars represent standard deviation for the three donors for each indicated transduction/treatment group.

NK cells from three different donors were isolated, expanded and transduced with BaEV-pseudotyped lentivirus containing either the IL15-292 construct or the IL15-293 construct. The titer of the IL15-292 lentivirus was $2.38 \times 10^8$ TU/mL while the titer for the IL15-293 lentivirus was $6.51 \times 10^8$ TU/mL (as measured by a Jurkat qPCR titer), and 4 µL lentivirus and 46 µL NK cell media were added to each well. After cells were expanded for four days, 10 µM ACZ or vehicle (DMSO) was added and the cells were incubated overnight. Expression of mbIL15 was anayzed via FACS the following day (five days post-transduction).

mbIL15 expression was determined by flow cytometry using two staining reagents: IL15Ra-Fc and an anti-CD56 antibody. mbIL15+ cell frequency was determined relative to the number of NK cells as determined by the anti-CD56 antibody. As shown in FIG. 9, greater than 40% of cord blood-derived NK cells from two of the three donors expressed mbIL15, and approximately 70% of cord blood-derived NK cells from one of the three donors expressed mbIL15. In the presence of DMSO, regulated mbIL15 expression was 10% or less in NK cells regardless of donor. In contrast, in the presence of ACZ, regulated mbIL15 expression increased to greater than 40% in NK cells regardless of donor. These data indicate that ACZ induces CA2 DRD-regulated mbIL15 in transduced NK.

Example 10: In Vivo Analysis of NK Cells Expressing Constitutive and Regulated mbIL15

To evaluate the effect of regulated mbIL15 on the anti-tumor activity of NK cells, an HL-60 animal model of acute myeloid leukemia is used. Cord blood NK cells are transduced with BaEV-pseudotyped lentiviral vectors containing either the IL15-292 construct or the IL15-293 construct, as described in Example 9, or with BaEV-pseudotyped lentiviral empty vector (EV), and optionally frozen after transduction. HL-60 cells expressing luciferase (HL-60-luc) are injected intravenously ($1 \times 10^6$/mouse) into NSG mice and tumor growth is measured once or twice per week by bioluminescence imaging measurement (total flux units in photons per second (p/s) after intraperitoneal injections of D-luciferin). On day 6, animals are randomized into new cages (N=8 for each group) when average tumor size reaches approximately $10^6$ total p/s. The engineered NK cells are thawed if necessary and infused into the HL-60 tumor-bearing mice. Each mouse receives an equal number of mbIL15+ cells and the total number of NK cells in the infusion product is adjusted by addition of EV-transduced NK cells.

Group 1 receives NK cells engineered with EV as a negative control, and group 2 receives NK cells transduced with constitutive mbIL5 (construct IL15-292). Groups 3 and 4 receive NK cells transduced with regulated mbIL15 (construct IL15-293). Group 3 is treated daily PO with 200 mg/kg ACZ, and group 4 is treated daily with vehicle until the end of the study. To monitor NK expansion, additional animals are included in each group (n=4 for blood analyses). Blood (50 µL) is withdrawn from submandibular veins on days 7, 14, and 21. Red blood cells are lysed, stained with fluorochrome-conjugated antibodies against human CD45, CD3 and mouse CD45, and cells are analyzed by flow cytometry. Tumor growth is measured up to approximately 30 days; endpoints include maximal total flux units ($10^{10}$) as well as effects on animal health such as hind-limb paralysis and decrease in body weight.

Tumor growth in individual mice in each group is measured and group averages are collected. Rapid tumor growth is expected in all animals in group 1 infused with EV-transduced NK cells. Tumor growth rate in group 4 mice will be similar to the control EV group because little or no mbIL15 will be expressed. In contrast, tumors will regress substantially in groups 2 and 3 because both groups of mice express mbIL15 on NK cells such that these cells will exhibit higher expansion and persistence compared to NK cells from groups 1 and 4. This example will demonstrate that ACZ can induce expression in vivo of mbIL15 in transduced NK cells, leading to enhanced NK anti-tumor responses, compared to transduced vehicle-treated NK cells that express little or no mbIL15.

In the foregoing detailed description, the invention has been described with reference to specific embodiments. However, it may be appreciated that various modifications and changes can be made without departing from the scope of the invention as set forth in the appended claims.

The following Items are illustrative of various embodiments of the present disclosure.

Item 1. A nucleic acid molecule comprising a polynucleotide encoding a recombinant protein comprising a drug responsive domain (DRD) operably linked to an IL15 payload, wherein said DRD is derived from human carbonic anhydrase II (CA2) and comprises one, two, three, four or more mutations relative to SEQ ID NO:1 or SEQ ID NO:2.

Item 2. The nucleic acid molecule of Item 1, wherein the DRD comprises one, two, three or four amino acid additions, substitutions and/or deletions relative to SEQ ID NO:1 or SEQ ID NO:2.

Item 3. The nucleic acid molecule of Item 2, wherein the DRD comprises the amino acid sequence of SEQ ID NO:4.

Item 4. The nucleic acid molecule of Item 3, wherein the DRD consists of the amino acid sequence of SEQ ID NO:4.

Item 5. The nucleic acid molecule of any of Items 1-4, wherein the IL15 payload comprises the amino acid sequence of SEQ ID NO:8.

Item 6. The nucleic acid molecule of any one of Items 1-5, wherein the IL15 payload is N-terminal to the DRD.

Item 7. The nucleic acid molecule of Item 6, wherein the IL15 payload is a membrane-bound IL15 polypeptide.

Item 8. The nucleic acid molecule of Item 7, wherein the membrane-bound IL15 polypeptide comprises an IL15 polypeptide component comprising the amino acid sequence of SEQ ID NO:8, a transmembrane domain and an intracellular tail, wherein the transmembrane domain is C-terminal to the IL15 polypeptide component and the intracellular tail is C-terminal to the transmembrane domain.

Item 9. The nucleic acid molecule of Item 8, wherein the membrane-bound IL15 polypeptide further comprises a linker between the IL15 polypeptide component and the transmembrane domain.

Item 10. The nucleic acid molecule of any one of Items 1-7, wherein the IL15 payload further comprises one or more components selected from the group consisting of: (a) a leader sequence; (b) a GS linker; (c) a hinge domain; (d) a transmembrane domain; and (e) an intracellular tail.

Item 11. The nucleic acid molecule of any one of Items 1-7, wherein the IL15 payload further comprises: (a) a leader sequence; (b) a GS linker; (c) a hinge domain; (d) a transmembrane domain; and (e) an intracellular tail.

Item 12. The nucleic acid molecule of Item 11, wherein the polynucleotide encodes the amino acid sequence of SEQ ID NO:24.

Item 13. The nucleic acid molecule of Item 12, wherein the polynucleotide comprises the nucleic acid sequence of SEQ ID NO:25.

Item 14. The nucleic acid molecule of Item 11, wherein the polynucleotide encodes the amino acid sequence of SEQ ID NO:28.

Item 15. The nucleic acid molecule of Item 14, wherein the polynucleotide comprises the nucleic acid sequence of SEQ ID NO:29.

Item 16. The nucleic acid molecule of any one of Items 1-15, wherein the nucleic acid molecule further comprises a second polynucleotide encoding a chimeric antigen receptor (CAR) or T cell receptor (TCR), wherein the CAR or TCR comprises an antigen-binding domain specific to an antigen of interest.

Item 17. The nucleic acid molecule of Item 16, wherein the second polynucleotide encodes a CAR comprising an antigen-binding domain specific to an antigen of interest.

Item 18. The nucleic acid molecule of Item 17, wherein the CAR comprises an antigen-binding domain specific to CD19.

Item 19. A vector comprising the nucleic acid molecule of any one of Items 1-19.

Item 20. The vector of Item 19, wherein the vector is a plasmid or a viral vector.

Item 21. The vector of Item 20, wherein the vector is a viral vector derived from an adenovirus, adeno-associated virus (AAV), alphavirus, flavivirus, herpes virus, measles virus, rhabdovirus, retrovirus, lentivirus, Newcastle disease virus (NDV), poxvirus, or picornavirus.

Item 22. The vector of Item 21, wherein the viral vector is selected from a lentiviral vector, adenoviral vector, AAV vector, herpes simplex viral vector, retroviral vector or oncolytic viral vector.

Item 23. The vector of Item 22, wherein the viral vector is selected from a lentiviral vector or a gamma retroviral vector.

Item 24. A recombinant protein encoded by the nucleic acid molecule of any one of Items 1-15.

Item 25. A cell comprising the nucleic acid molecule of any one of Items 1-18, the vector of any one of Items 18-23, or the recombinant protein of Item 24.

Item 26. The cell of Item 25, wherein the cell is a bacterial cell.

Item 27. The cell of Item 25, wherein the cell is a mammalian cell.

Item 28. The cell of Item 27, wherein the mammalian cell is a human cell.

Item 29. The cell of Item 28, wherein the human cell is a T cell, natural killer (NK) cell, or tumor infiltrating lymphocyte (TIL).

Item 30. The cell of Item 29, wherein the cell is a CD4+ or CD8+ T cell.

Item 31. The cell of Item 29, wherein the cell is isolated.

Item 32. The cell of Item 29, wherein the human cell is a T cell or an NK cell, and wherein the human T cell or the human NK cell further comprises a second polynucleotide encoding a chimeric antigen receptor (CAR) or T cell receptor (TCR), wherein the CAR or TCR comprises an antigen-binding domain specific to an antigen of interest.

Item 33. The cell of Item 32, wherein the second polynucleotide encodes a CAR comprising an antigen-binding domain specific to an antigen of interest.

Item 34. The cell of Item 33, wherein the CAR comprises an antigen-binding domain specific to CD19.

Item 35. A pharmaceutical composition comprising the cell of any one of Items 25-34 and a pharmaceutically acceptable carrier.

Item 36. The pharmaceutical composition of Item 35, wherein the cell is a human T cell, human NK cell or human TIL.

Item 37. A method of modulating the expression, function, and/or level of IL15 in the cell of any one of Items 25-34, said method comprising administering to the cell a stimulus to which the DRD is responsive, wherein the stimulus is administered in an amount sufficient to modulate the expression, function and/or level of IL15.

Item 38. The method of Item 37, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 39. The method of Item 38, wherein the stimulus is acetazolamide.

Item 40. The method of Item 37, wherein the cell is a human T cell or a human NK cell, and wherein the human T cell or the human NK cell further comprises a second polynucleotide encoding a chimeric antigen receptor (CAR) or T cell receptor (TCR), wherein the CAR or TCR comprises an antigen-binding domain specific to an antigen of interest.

Item 41. The method of Item 40, wherein the second polynucleotide encodes a CAR comprising an antigen-binding domain specific to an antigen of interest.

Item 42. The method of Item 41, wherein the CAR comprises an antigen-binding domain specific to CD19.

Item 43. A method of treating a disease or disorder responsive to regulated IL15 in a subject in need thereof, said method comprising: (a) administering to the subject a therapeutically effective amount of the nucleic acid molecule of any one of Items 1-18, the vector of any one of Items 19-23, the recombinant protein of Item 24, the cell of any one of Items 25-34 or the pharmaceutical composition of any one of Items 35-36; and (b) administering a therapeutically effective amount of a stimulus to the subject, wherein the DRD is responsive to the stimulus and wherein expression of the IL15 payload is modulated in response to the stimulus.

Item 44. The method of Item 43, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 45. The method of Item 44, wherein the stimulus is acetazolamide.

Item 46. The method of any of Items 43-45, wherein the disease or disorder is cancer.

Item 47. A method of treating a malignant tumor in a subject in need thereof, wherein said tumor expresses a tumor-associated antigen, said method comprising: (a) administering to the subject a therapeutically effective amount of the human T cell or the human NK cell of any one of Items 32-34, or a pharmaceutical composition thereof, wherein the CAR or TCR comprises an antigen-binding domain specific to the tumor-associated antigen; and (b) administering a therapeutically effective amount of a stimulus to the subject, wherein the DRD is responsive to the stimulus and wherein expression of the IL15 payload is modulated in response to the stimulus.

Item 48. The method according to Item 48, wherein the subject is administered a therapeutically effective amount of the human T cell comprising a CAR, or a pharmaceutical composition thereof.

Item 49. The method according to either of Items 47 or 48, wherein the stimulus is selected from acetazolamide, celecoxib, valdecoxib, rofecoxib, methazolamide, dorzolamide, brinzolamide, diclofenamide, ethoxzolamide, zonisamide, dansylamide, or dichlorphenamide.

Item 50. The method of Item 49, wherein the stimulus is acetazolamide.

Item 51. A method of producing a genetically engineered T cell, natural killer (NK) cell or tumor infiltrating lymphocyte (TIL), comprising introducing into the T cell, NK cell or TIL a polynucleotide encoding a protein comprising a drug responsive domain (DRD) operably linked to an IL15 payload, wherein the polynucleotide encodes an amino acid sequence of SEQ ID NOS:24 or 28.

Item 52. The method of Item 51, wherein the polynucleotide comprises a nucleotide sequence of SEQ ID NOS:25 or 29.

Item 53. The method of Item 52, wherein the polynucleotide is introduced into the T cell, NK cell or TIL by lentiviral transduction.

Item 54. The method of Item 52, wherein the polynucleotide is introduced into the T cell, NK cell or TIL by a non-viral vector delivery method.

Item 55. A modified cell comprising a recombinant protein, said recombinant protein comprising: (i) an effector module, wherein said effector module comprises a stimulus response element (SRE) that comprises a drug responsive domain (DRD), wherein said DRD is derived from a parent protein or a mutant protein having one or more amino acid mutations in the amino acid sequence of human carbonic anhydrase 2 (CA2) (SEQ ID NO: 1) and comprises the amino acid sequence of SEQ ID NO:4; and (ii) a recombinant IL15 linked to the SRE.

Item 56. The cell of Item 55, wherein the recombinant IL15 comprises the amino acid sequence of SEQ ID NO:8.

Item 57. The cell of Item 55 or 56, wherein the recombinant IL15 can be expressed on the cell surface.

Item 58. The cell of Item 55 or 56, wherein the recombinant IL15 is a membrane bound IL15 (mbIL15).

Item 59. The cell of any of Items 55-58, wherein the recombinant protein comprises the whole or a portion of SEQ ID NO: 16.

Item 60. The cell of any of Items 55-59, wherein the recombinant protein comprises the whole or a portion of SEQ ID NO: 18.

Item 61. The cell of Item 55, wherein the recombinant protein further comprises one or more components selected from the group consisting of: (a) a leader sequence; (b) a GS linker; (c) a hinge domain; (d) a transmembrane domain; and (e) a cytoplasmic tail domain.

Item 62. The cell of Item 55, wherein the recombinant protein comprises the amino acid sequence of SEQ ID NO:24.

Item 63. The cell of Item 55, wherein the recombinant protein comprises the amino acid sequence of SEQ ID NO:28.

Item 64. The cell of any one of Items 55-63, wherein the recombinant IL15 is further linked to at least one of: (a) a leader sequence; (b) a signal peptide; (c) a linker; (d) a spacer; (e) a cleavage site; (f) a tag; (g) a co-stimulatory domain; (h) a fluorescence protein; and (i) a hinge.

Item 65. The cell of any of Items 55-64, wherein the SRE is responsive to or interacts with Acetazolamide (ACZ).

Item 66. The cell of Item 55, wherein the cell is a T cell, a natural killer cell (NK cell), or a tumor infiltrating lymphocyte (TIL).

Item 67. A nucleic acid molecule, comprising: a polynucleotide, optionally a first expression cassette, encoding a first recombinant protein comprising a stimulus response element (SRE) linked to an IL15 polypeptide; wherein the SRE comprises a DRD, wherein said DRD comprises an amino acid sequence of SEQ ID NO:4.

Item 68. The nucleic acid molecule of Item 67, wherein the IL15 is under control of the SRE.

Item 69. The nucleic acid molecule of Item 67, wherein the polynucleotide further encodes: (a) a leader sequence; (b) a GS linker; (c) a hinge domain; (d) a transmembrane domain; and (e) a cytoplasmic tail domain.

Item 70. The nucleic acid molecule of Item 67, wherein the polynucleotide comprises the nucleic acid sequence of SEQ ID NO:25.

Item 71. The nucleic acid molecule of Item 67, wherein the polynucleotide comprises the nucleic acid sequence of SEQ ID NO:29.

Item 72. The nucleic acid molecule of any of Items 67-71 that is isolated.

Item 73. A recombinant protein encoded by a nucleic acid molecule of any one of Items 67-72.

Item 74. The recombinant protein of Item 73, wherein the recombinant protein comprises an amino acid sequence of SEQ ID NO:24 or 28.

Item 75. A vector comprising a nucleic acid molecule of any one of Items 67-72.

Item 76. The vector of Item 75, wherein the vector is a plasmid, or lentiviral vector.

Item 77. The vector of Item 76 that is integrase defective.

Item 78. A T cell, NK cell or TIL, comprising the nucleic acid molecule of any one of Items 67-72, a recombinant protein of Items 73-74, or a vector of any one of Items 75-77.

Item 79. The T cell of Item 78 that is a CD4+ or CD8+ T cell.

Item 80. The T cell of Item 79 or Item 42 that is a human T cell.

Item 81. The T cell of any of Items 78-80 that is isolated.

Item 82. A pharmaceutical composition, comprising the cell, T cell, NK cell or TIL of any one of Items 55-66 or 78-81 and a pharmaceutically acceptable carrier.

Item 83. A method of producing a genetically engineered T cell, NK cell or TIL, comprising: introducing into a T cell, NK cell or TIL: a first polynucleotide encoding a stimulus response element comprising a CA2 DRD linked to an IL15 polypeptide payload, wherein the first polynucleotide has a nucleotide sequence of SEQ ID NO:25 or 29.

Item 84. The method of Item 83, wherein the first polynucleotide is introduced into the T cell, NK cell or TIL via a lentiviral virus transfection of said T cell, NK cell or TIL.

While the present disclosure has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the disclosure.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A nucleic acid molecule comprising a polynucleotide encoding a recombinant protein comprising a drug responsive domain (DRD) operably linked to an IL15 payload, wherein said DRD is derived from human carbonic anhydrase II (CA2) and comprises the amino acid sequence of SEQ ID NO:4 and said IL15 payload is a membrane-bound IL15 polypeptide.

2. The nucleic acid molecule of claim 1, wherein the DRD consists of the amino acid sequence of SEQ ID NO:4.

3. The nucleic acid molecule of claim 1, wherein the membrane-bound IL15 polypeptide comprises the amino acid sequence of SEQ ID NO:8.

4. The nucleic acid molecule of claim 3, wherein the membrane-bound IL15 polypeptide is N-terminal to the DRD.

5. The nucleic acid molecule of claim 4, wherein the membrane-bound IL15 polypeptide comprises an IL15 polypeptide component comprising the amino acid sequence of SEQ ID NO:8, a transmembrane domain and an intracellular tail, wherein the transmembrane domain is C-terminal to the IL15 polypeptide component and the intracellular tail is C-terminal to the transmembrane domain.

6. The nucleic acid molecule of claim 5, wherein the membrane-bound IL15 polypeptide further comprises a linker between the IL15 polypeptide component and the transmembrane domain and a leader sequence N-terminal to the IL15 polypeptide component.

7. The nucleic acid molecule of claim 6, wherein the polynucleotide encodes the amino acid sequence of SEQ ID NO:24.

8. The nucleic acid molecule of claim 7, wherein the polynucleotide comprises the nucleic acid sequence of SEQ ID NO:25.

9. A vector comprising the nucleic acid molecule of claim 7.

10. The vector of claim 9, wherein the vector is a plasmid or a viral vector.

11. The vector of claim 10, wherein the viral vector is selected from a lentiviral vector, adenoviral vector, AAV vector, herpes simplex viral vector, retroviral vector or oncolytic viral vector.

12. The vector of claim 11, wherein the viral vector is a lentiviral vector.

13. A method of producing a genetically engineered T cell, natural killer (NK) cell or tumor infiltrating lymphocyte (TIL), comprising transducing the T cell, NK cell or TIL with the lentiviral vector of claim 12.

14. An isolated genetically engineered T cell, NK cell or TIL made by the method of claim 13.

15. An isolated cell comprising the nucleic acid molecule of claim 7.

16. The isolated cell of claim 15, wherein the cell is a mammalian cell.

17. The isolated cell of claim 16, wherein the mammalian cell is a human cell.

18. The isolated cell of claim 17, wherein the human cell is a T cell, natural killer (NK) cell, or tumor infiltrating lymphocyte (TIL).

19. A pharmaceutical composition comprising the cell of claim 18, and a pharmaceutically acceptable carrier.

20. A method of modulating the expression, function, and/or level of IL15 in the cell of claim 18, said method comprising administering acetazolamide to the cell, wherein the acetazolamide is administered in an amount sufficient to modulate the expression, function and/or level of IL15.

21. A recombinant protein encoded by the nucleic acid molecule of claim 7.

* * * * *

UNITED STATES PATENT AND TRADEMARK OFFICE
CERTIFICATE OF CORRECTION

PATENT NO. : 11,058,725 B2
APPLICATION NO. : 17/017670
DATED : July 13, 2021
INVENTOR(S) : Kutlu Goksu Elpek et al.

Page 1 of 1

It is certified that error appears in the above-identified patent and that said Letters Patent is hereby corrected as shown below:

On the Title Page

On page 3, in Column 1, item (56), under "FOREIGN PATENT DOCUMENTS" in Line 8, please delete:
"WO 2016212770 A1 11/2018"

And insert:
--WO 2018212770 A1 11/2018--.

On page 3, in Column 1, item (56), under "FOREIGN PATENT DOCUMENTS" in Line 9, please delete:
"WO 2018213328 A1 11/2018"

And insert:
--WO 2018213828 A1 11/2018--.

Signed and Sealed this
Seventeenth Day of October, 2023

Katherine Kelly Vidal
*Director of the United States Patent and Trademark Office*

SEQUENCE LISTING

<160> NUMBER OF SEQ ID NOS: 51

<210> SEQ ID NO 1
<211> LENGTH: 260
<212> TYPE: PRT
<213> ORGANISM: Homo sapiens

<400> SEQUENCE: 1

Met Ser His His Trp Gly Tyr Gly Lys His Asn Gly Pro Glu His Trp
1               5                   10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
        35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
            100                 105                 110

Lys Tyr Ala Ala Glu Leu His Leu Val His Trp Asn Thr Lys Tyr Gly
        115                 120                 125

Asp Phe Gly Lys Ala Val Gln Gln Pro Asp Gly Leu Ala Val Leu Gly
    130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
    210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 2
<211> LENGTH: 259
<212> TYPE: PRT
<213> ORGANISM: Homo sapiens

<400> SEQUENCE: 2

Ser His His Trp Gly Tyr Gly Lys His Asn Gly Pro Glu His Trp His
1               5                   10                  15

Lys Asp Phe Pro Ile Ala Lys Gly Glu Arg Gln Ser Pro Val Asp Ile
            20                  25                  30

Asp Thr His Thr Ala Lys Tyr Asp Pro Ser Leu Lys Pro Leu Ser Val

|  |  |  |  | 35 |  |  |  |  | 40 |  |  |  |  | 45 |  |  |
|---|---|---|---|---|---|---|---|---|---|---|---|---|---|---|---|---|

Ser Tyr Asp Gln Ala Thr Ser Leu Arg Ile Leu Asn Asn Gly His Ala
 50                              55                              60

Phe Asn Val Glu Phe Asp Asp Ser Gln Asp Lys Ala Val Leu Lys Gly
 65                  70                              75                              80

Gly Pro Leu Asp Gly Thr Tyr Arg Leu Ile Gln Phe His Phe His Trp
                         85                              90                              95

Gly Ser Leu Asp Gly Gln Gly Ser Glu His Thr Val Asp Lys Lys Lys
                 100                             105                             110

Tyr Ala Ala Glu Leu His Leu Val His Trp Asn Thr Lys Tyr Gly Asp
             115                             120                             125

Phe Gly Lys Ala Val Gln Gln Pro Asp Gly Leu Ala Val Leu Gly Ile
     130                             135                             140

Phe Leu Lys Val Gly Ser Ala Lys Pro Gly Leu Gln Lys Val Val Asp
145                             150                             155                             160

Val Leu Asp Ser Ile Lys Thr Lys Gly Lys Ser Ala Asp Phe Thr Asn
                     165                             170                             175

Phe Asp Pro Arg Gly Leu Leu Pro Glu Ser Leu Asp Tyr Trp Thr Tyr
                 180                             185                             190

Pro Gly Ser Leu Thr Thr Pro Pro Leu Leu Glu Cys Val Thr Trp Ile
             195                             200                             205

Val Leu Lys Glu Pro Ile Ser Val Ser Ser Glu Gln Val Leu Lys Phe
     210                             215                             220

Arg Lys Leu Asn Phe Asn Gly Glu Gly Glu Pro Glu Glu Leu Met Val
225                             230                             235                             240

Asp Asn Trp Arg Pro Ala Gln Pro Leu Lys Asn Arg Gln Ile Lys Ala
                     245                             250                             255

Ser Phe Lys

<210> SEQ ID NO 3
<211> LENGTH: 780
<212> TYPE: DNA
<213> ORGANISM: Homo sapiens

<400> SEQUENCE: 3

```
atgtcccatc actgggggta cggcaaacac aacggacctg agcactggca taaggacttc      60
cccattgcca agggagagcg ccagtcccct gttgacatcg acactcatac agccaagtat     120
gaccccttcc ctgaagcccct gtctgtttcc tatgatcaag caacttccct gaggatcctc     180
aacaatggtc atgctttcaa cgtggagttt gatgactctc aggacaaagc agtgctcaag     240
ggaggacccc tggatggcac ttacagattg attcagtttc actttcactg gggttcactt     300
gatggacaag gttcagagca tactgtggat aaaaagaaat atgctgcaga acttcacttg     360
gttcactgga acaccaaata tggggatttt gggaaagctg tgcagcaacc tgatggactg     420
gccgttctag gtatttttt gaaggttggc agcgctaaac cgggccttca gaaagttgtt     480
gatgtgctgg attccattaa acaaagggc aagagtgctg acttcactaa cttcgatcct     540
cgtggcctcc ttcctgaatc cctggattac tggacctacc caggctcact gaccaccct     600
cctcttctgg aatgtgtgac ctggattgtg ctcaaggaac ccatcagcgt cagcagcgag     660
caggtgttga aattccgtaa acttaacttc aatggggagg gtgaaccga agaactgatg     720
gtggacaact ggcgcccagc tcagccactg aagaacaggc aaatcaaagc ttccttcaaa     780
```

<210> SEQ ID NO 4

<211> LENGTH: 259
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ser His His Trp Gly Tyr Gly Lys His Asn Gly Pro Glu His Trp His
1               5                   10                  15

Lys Asp Phe Pro Ile Ala Lys Gly Glu Arg Gln Ser Pro Val Asp Ile
            20                  25                  30

Asp Thr His Thr Ala Lys Tyr Asp Pro Ser Leu Lys Pro Leu Ser Val
        35                  40                  45

Ser Tyr Asp Gln Ala Thr Ser Leu Arg Ile Leu Asn Asn Gly His Ala
    50                  55                  60

Phe Asn Val Glu Phe Asp Asp Ser Gln Asp Lys Ala Val Leu Lys Gly
65                  70                  75                  80

Gly Pro Leu Asp Gly Thr Tyr Arg Leu Ile Gln Phe His Phe His Trp
                85                  90                  95

Gly Ser Leu Asp Gly Gln Gly Ser Glu His Thr Val Asp Lys Lys Lys
            100                 105                 110

Tyr Ala Ala Glu Leu His Leu Val His Trp Asn Thr Lys Tyr Gly Asp
        115                 120                 125

Phe Gly Lys Ala Val Gln Gln Pro Asp Gly Leu Ala Val Leu Gly Ile
    130                 135                 140

Phe Leu Lys Val Gly Ser Ala Lys Pro Gly His Gln Lys Val Val Asp
145                 150                 155                 160

Val Leu Asp Ser Ile Lys Thr Lys Gly Lys Ser Ala Asp Phe Thr Asn
                165                 170                 175

Phe Asp Pro Arg Gly Leu Leu Pro Glu Ser Leu Asp Tyr Trp Thr Tyr
            180                 185                 190

Pro Gly Ser Leu Thr Thr Pro Pro Leu Leu Glu Cys Val Thr Trp Ile
        195                 200                 205

Val Leu Lys Glu Pro Ile Ser Val Ser Ser Glu Gln Val Leu Lys Phe
    210                 215                 220

Arg Lys Leu Asn Phe Asn Gly Glu Gly Glu Pro Glu Glu Leu Met Val
225                 230                 235                 240

Asp Asn Trp Arg Pro Ala Gln Pro Leu Lys Asn Arg Gln Ile Lys Ala
                245                 250                 255

Ser Phe Lys
```

<210> SEQ ID NO 5
<211> LENGTH: 777
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
tcccatcact gggggtacgg caaacacaac ggacctgagc actggcataa ggacttcccc      60
attgccaagg gagagcgcca gtcccctgtt gacatcgaca ctcatacagc caagtatgac     120
ccttccctga gcccctgtc tgtttcctat gatcaagcaa cttccctgag aatcctcaac     180
aatggtcatg ctttcaacgt ggagtttgat gactctcagg acaaagcagt gctcaaggga     240
ggacccctgg atggcactta cagattgatt cagtttcact ttcactgggg ttcacttgat     300
```

```
ggacaaggtt cagagcatac tgtggataaa agaaatatg ctgcagaact tcacttggtt    360
cactggaaca ccaaatatgg ggattttggg aaagctgtgc agcaacctga tggactggcc    420
gttctaggta ttttttttgaa ggttggcagc gctaaaccgg ccatcagaa agttgttgat    480 gtgctggatt ccattaaaac aaagggcaag agtgctgact tcactaactt cgatcctcgt    540
ggcctccttc ctgaatccct ggattactgg acctacccag gctcactgac caccccctcct    600 cttctggaat gtgtgacctg gattgtgctc aaggaaccca tcagcgtcag cagcgagcag    660
gtgttgaaat ccgtaaaact taacttcaat ggggagggtg aacccgaaga actgatggtg    720
gacaactggc gcccagctca gccactgaag aacaggcaaa tcaaagcttc cttcaaa      777
```

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Met Asp Met Arg Val Pro Ala Gln Leu Leu Gly Leu Leu Leu Leu Trp
1               5                   10                  15

Leu Ser Gly Ala Arg Cys
            20
```

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
atggacatgc gggtgcctgc acaacttctg ggcctgctgt tgttgtggct gtctggagcc    60
cggtgt                                                                66
```

<210> SEQ ID NO 8
<211> LENGTH: 114
<212> TYPE: PRT
<213> ORGANISM: Homo sapiens

<400> SEQUENCE: 8

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 9
<211> LENGTH: 342
<212> TYPE: DNA
<213> ORGANISM: Homo sapiens

<400> SEQUENCE: 9

```
aattgggtaa atgttatcag tgatctcaag aagatagagg atctcatcca gtccatgcat    60
attgatgcca cgctgtacac agaaagcgat gtgcatccta gctgtaaggt gacagcgatg   120
aagtgttttc ttttggagct gcaggtaatt agtcttgagt ccggcgatgc cagcattcat   180
gataccgtag aaaacttgat tatcctggcc aacaattctc tgtcctcaaa cggaaacgta   240
accgagagcg gttgtaaaga atgtgaagaa ctggaagaaa agaacatcaa ggagtttctg   300
caatcattcg ttcacatcgt acaaatgttc ataaatacgt ca                      342
```

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Gly Ser Gly Ser Gly Ser Gly Ser Gly Ser Gly Ser Gly Ser
1               5                   10                  15
Gly Ser Gly Ser Gly Ser Gly Ser Gly Ser Gly Ser Gly Ser
            20                  25                  30

<210> SEQ ID NO 11
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

```
ggatctggtt ctggttccgg aagtggatct ggttcagggt ccggtagtgg atctgggtca    60
ggaagtggaa gcggtagtgg gtctggatct                                     90
```

<210> SEQ ID NO 12
<211> LENGTH: 8
<212> TYPE: PRT
<213> ORGANISM: Homo sapiens

<400> SEQUENCE: 12

Lys Gln Glu His Phe Pro Asp Asn
1               5

<210> SEQ ID NO 13
<211> LENGTH: 24
<212> TYPE: DNA
<213> ORGANISM: Homo sapiens

<400> SEQUENCE: 13

```
aaacaagagc actttcctga taac                                           24
```

<210> SEQ ID NO 14
<211> LENGTH: 21
<212> TYPE: PRT
<213> ORGANISM: Homo sapiens

<400> SEQUENCE: 14

Leu Leu Pro Ser Trp Ala Ile Thr Leu Ile Ser Val Asn Gly Ile Phe
1               5                   10                  15

Val Ile Cys Cys Leu
            20

<210> SEQ ID NO 15
<211> LENGTH: 63
<212> TYPE: DNA
<213> ORGANISM: Homo sapiens

<400> SEQUENCE: 15
ctgttgccga gctgggcgat tacgcttatc agtgtaaacg gcatctttgt aatatgctgt    60
ctg                                                                  63

<210> SEQ ID NO 16
<211> LENGTH: 25
<212> TYPE: PRT
<213> ORGANISM: Homo sapiens

<400> SEQUENCE: 16

Thr Tyr Cys Phe Ala Pro Arg Cys Arg Glu Arg Arg Asn Glu Arg
1               5                   10                  15

Leu Arg Arg Glu Ser Val Arg Pro Val
            20                  25

<210> SEQ ID NO 17
<211> LENGTH: 75
<212> TYPE: DNA
<213> ORGANISM: Homo sapiens

<400> SEQUENCE: 17
acctactgct tcgcaccaag gtgccggag agaaggagaa atgaaagact gagaagggag     60
agcgtgagac ctgtg                                                     75

<210> SEQ ID NO 18
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Tyr Cys Phe Ala Pro Arg Cys Arg Glu Arg Ala Arg Asn Glu Arg
1               5                   10                  15

Leu Arg Arg Glu Thr Val Arg Pro Val
            20                  25

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acctactgct tcgcaccaag gtgccggag agagcaagaa atgaaagact gagaagggag     60
accgtgagac ctgtg                                                     75

<210> SEQ ID NO 20
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gly Ser
1

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21 ggatcc                                                              6

<210> SEQ ID NO 22
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Gly Ser Gly Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg
        195                 200                 205

Asn Glu Arg Leu Arg Arg Glu Ser Val Arg Pro Val Gly Ser
    210                 215                 220

<210> SEQ ID NO 23
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atggacatgc gggtgcctgc acaacttctg ggcctgctgt tgttgtggct gtctggagcc    60
cggtgtaatt gggtaaatgt tatcagtgat ctcaagaaga tagaggatct catccagtcc   120
atgcatattg atgccacgct gtacacagaa agcgatgtgc atcctagctg taaggtgaca   180
gcgatgaagt gttttctttt ggagctgcag gtaattagtc ttgagtccgg cgatgccagc   240
attcatgata ccgtagaaaa cttgattatc ctggccaaca attctctgtc ctcaaacgga   300
aacgtaaccg agagcggttg taagaatgt gaagaactgg aagaaaagaa catcaaggag   360
tttctgcaat cattcgttca catcgtacaa atgttcataa atacgtcagg atctggttct   420
ggttccggaa gtggatctgg ttcagggtcc ggtagtggat ctgggtcagg aagtggaagc   480
ggtagtgggt ctggatctaa acaagagcac tttcctgata acctgttgcc gagctgggcg   540
attacgctta tcagtgtaaa cggcatcttt gtaatatgct gtctgaccta ctgcttcgca   600
ccaaggtgcc gggagagaag gagaaatgaa agactgagaa gggagagcgt gagacctgtg   660
ggatcc                                                              666
```

<210> SEQ ID NO 24
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

```
Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg Arg
        195                 200                 205

Asn Glu Arg Leu Arg Arg Glu Ser Val Arg Pro Val Gly Ser Ser His
    210                 215                 220

His Trp Gly Tyr Gly Lys His Asn Gly Pro Glu His Trp Lys Asp
225                 230                 235                 240

Phe Pro Ile Ala Lys Gly Arg Gln Ser Pro Val Asp Ile Asp Thr
                245                 250                 255

His Thr Ala Lys Tyr Asp Pro Ser Leu Lys Pro Leu Ser Val Ser Tyr
            260                 265                 270

Asp Gln Ala Thr Ser Leu Arg Ile Leu Asn Asn Gly His Ala Phe Asn
        275                 280                 285

Val Glu Phe Asp Asp Ser Gln Asp Lys Ala Val Leu Lys Gly Gly Pro
    290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Lys Tyr Ala
                325                 330                 335

Ala Glu Leu His Leu Val His Trp Asn Thr Lys Tyr Gly Asp Phe Gly
            340                 345                 350

Lys Ala Val Gln Gln Pro Asp Gly Leu Ala Val Leu Gly Ile Phe Leu
        355                 360                 365

Lys Val Gly Ser Ala Lys Pro Gly His Gln Lys Val Val Asp Val Leu
    370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415

Ser Leu Thr Thr Pro Pro Leu Leu Glu Cys Val Thr Trp Ile Val Leu
            420                 425                 430

Lys Glu Pro Ile Ser Val Ser Ser Glu Gln Val Leu Lys Phe Arg Lys
        435                 440                 445

Leu Asn Phe Asn Gly Glu Gly Glu Pro Glu Glu Leu Met Val Asp Asn
    450                 455                 460

Trp Arg Pro Ala Gln Pro Leu Lys Asn Arg Gln Ile Lys Ala Ser Phe
465                 470                 475                 480

Lys

<210> SEQ ID NO 25
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggacatgc gggtgcctgc acaacttctg ggcctgctgt tgttgtggct gtctggagcc    60
cggtgtaatt gggtaaatgt tatcagtgat ctcaagaaga tagaggatct catccagtcc   120
atgcatattg atgccacgct gtacacagaa agcgatgtgc atcctagctg taagggtgaca  180 gcgatgaagt gttttctttt ggagctgcag gtaattagtc ttgagtccgg cgatgccagc   240
```

```
attcatgata  ccgtagaaaa  cttgattatc  ctggccaaca  attctctgtc  ctcaaacgga      300
aacgtaaccg  agagcggttg  taaagaatgt  gaagaactgg  aagaaaagaa  catcaaggag      360
tttctgcaat  cattcgttca  catcgtacaa  atgttcataa  atacgtcagg  atctggttct      420
ggttccggaa  gtggatctgg  ttcagggtcc  ggtagtggat  ctgggtcagg  aagtggaagc      480
ggtagtgggt  ctggatctaa  acaagagcac  tttcctgata  acctgttgcc  gagctgggcg      540
attacgctta  tcagtgtaaa  cggcatcttt  gtaatatgct  gtctgaccta  ctgcttcgca      600
ccaaggtgcc  gggagagaag  gagaaatgaa  agactgagaa  gggagagcgt  gagacctgtg      660
ggatcctccc  atcactgggg  gtacggcaaa  cacaacggac  ctgagcactg  gcataaggac      720
ttccccattg  ccaagggaga  gcgccagtcc  cctgttgaca  tcgacactca  tacagccaag      780
tatgacccct  ccctgaagcc  cctgtctgtt  tcctatgatc  aagcaacttc  cctgagaatc      840
ctcaacaatg  gtcatgcttt  caacgtggag  tttgatgact  tcaggacaa  agcagtgctc      900 aagggaggac  ccctgatgg  cacttacaga  ttgattcagt  ttcactttca  ctggggttca      960
cttgatggac  aaggttcaga  gcatactgtg  gataaaaaga  aatatgctgc  agaacttcac     1020
ttggttcact  ggaacaccaa  atatgggat   tttgggaaag  ctgtgcagca  acctgatgga     1080
ctggccgttc  taggtatttt  tttgaaggtt  ggcagcgcta  aaccgggcca  tcagaaagtt     1140
gttgatgtgc  tggattccat  taaaacaaag  ggcaagagtg  ctgacttcac  taacttcgat     1200
cctcgtggcc  tccttcctga  atccctggat  tactggacct  acccaggctc  actgaccacc     1260
cctcctcttc  tggaatgtgt  gacctggatt  gtgctcaagg  aacccatcag  cgtcagcagc     1320
gagcaggtgt  tgaaattccg  taaacttaac  ttcaatgggg  agggtgaacc  cgaagaactg     1380
atggtggaca  ctggcgccc   agctcagcca  ctgaagaaca  ggcaaatcaa  agcttccttc     1440
aaa                                                                        1443
```

```
<210> SEQ ID NO 26
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser Gly Ser
    130                 135                 140
```

Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Ala Arg
        195                 200                 205

Asn Glu Arg Leu Arg Arg Glu Thr Val Arg Pro Val Gly Ser
    210                 215                 220

<210> SEQ ID NO 27
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taagaatgt gaagaactgg aagaaagaa catcaaggag      360 tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagagc aagaaatgaa agactgagaa gggagaccgt gagacctgtg     660
ggatcc                                                                666

<210> SEQ ID NO 28
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

-continued

```
Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser Gly Ser
130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Ala Arg
        195                 200                 205

Asn Glu Arg Leu Arg Arg Glu Thr Val Arg Pro Val Gly Ser Ser His
    210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
                245                 250                 255

His Thr Ala Lys Tyr Asp Pro Ser Leu Lys Pro Leu Ser Val Ser Tyr
            260                 265                 270

Asp Gln Ala Thr Ser Leu Arg Ile Leu Asn Asn Gly His Ala Phe Asn
        275                 280                 285

Val Glu Phe Asp Asp Ser Gln Asp Lys Ala Val Leu Lys Gly Gly Pro
    290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Tyr Ala
                325                 330                 335

Ala Glu Leu His Leu Val His Trp Asn Thr Lys Tyr Gly Asp Phe Gly
            340                 345                 350

Lys Ala Val Gln Gln Pro Asp Gly Leu Ala Val Leu Gly Ile Phe Leu
        355                 360                 365

Lys Val Gly Ser Ala Lys Pro Gly His Gln Lys Val Val Asp Val Leu
    370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415

Ser Leu Thr Thr Pro Pro Leu Leu Glu Cys Val Thr Trp Ile Val Leu
            420                 425                 430

Lys Glu Pro Ile Ser Val Ser Ser Glu Gln Val Leu Lys Phe Arg Lys
        435                 440                 445

Leu Asn Phe Asn Gly Glu Gly Glu Pro Glu Glu Leu Met Val Asp Asn
    450                 455                 460

Trp Arg Pro Ala Gln Pro Leu Lys Asn Arg Gln Ile Lys Ala Ser Phe
465                 470                 475                 480

Lys
```

<210> SEQ ID NO 29
<211> LENGTH: 1443
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 29

```
atggacatgc gggtgcctgc acaacttctg ggcctgctgt tgttgtggct gtctggagcc     60
cggtgtaatt gggtaaatgt tatcagtgat ctcaagaaga tagaggatct catccagtcc    120
atgcatattg atgccacgct gtacacagaa agcgatgtgc atcctagctg taaggtgaca    180
gcgatgaagt gttttctttt ggagctgcag gtaattagtc ttgagtccgg cgatgccagc    240
attcatgata ccgtagaaaa cttgattatc ctggccaaca attctctgtc ctcaaacgga    300
aacgtaaccg agagcggttg taaagaatgt gaagaactgg aagaaagaa catcaaggag    360
tttctgcaat cattcgttca catcgtacaa atgttcataa atacgtcagg atctggttct    420
ggttccggaa gtggatctgg ttcagggtcc ggtagtggat ctgggtcagg aagtggaagc    480
ggtagtgggg ctggatctaa acaagagcac tttcctgata acctgttgcc gagctgggcg    540
attacgctta tcagtgtaaa cggcatcttt gtaatatgct gtctgaccta ctgcttcgca    600
ccaaggtgcc gggagagagc aagaaatgaa agactgagaa gggagaccgt gagacctgtg    660
ggatcctccc atcactgggg gtacggcaaa cacaacggac ctgagcactg cataaggac    720
ttcccccattg ccaagggaga cgccagtcc cctgttgaca tcgacactca tacagccaag    780
tatgacccctt ccctgaagcc cctgtctgtt tcctatgatc aagcaacttc cctgagaatc    840
ctcaacaatg tcatgctttt caacgtggag tttgatgact ctcaggacaa agcagtgctc    900
aagggaggac ccctggatgg cacttacaga ttgattcagt tcactttca ctgggggttca    960
cttgatggac aaggttcaga gcatactgtg gataaaaaga aatatgctgc agaacttcac   1020
ttggttcact ggaacaccaa atatggggat tttgggaaag ctgtgcagca acctgatgga   1080
ctggccgttc taggtatttt tttgaaggtt ggcagcgcta aaccgggcca tcagaaagtt   1140
gttgatgtgc tggattccat taaaacaaag ggcaagagtg ctgacttcac taacttcgat   1200
cctcgtggcc tccttcctga atccctggat tactggacct acccaggctc actgaccacc   1260
cctcctcttc tggaatgtgt gacctggatt gtgctcaagg aacccatcag cgtcagcagc   1320
gagcaggtgt tgaaattccg taaacttaac ttcaatgggg agggtgaacc cgaagaactg   1380
atggtggaca ctggcgcccc agctcagcca ctgaagaaca ggcaaatcaa agcttccttc   1440
aaa                                                                1443
```

<210> SEQ ID NO 30
<211> LENGTH: 200
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60
```

```
Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
        115                 120                 125

Gly Ser Gly Ser Gly Ser Gly Ser Gly Ser Gly Ser Gly Ser Gly Ser
    130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
                165                 170                 175

Phe Ala Pro Arg Cys Arg Glu Arg Arg Arg Asn Glu Arg Leu Arg Arg
            180                 185                 190

Glu Ser Val Arg Pro Val Gly Ser
        195                 200

<210> SEQ ID NO 31
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
        115                 120                 125

Gly Ser Gly Ser Gly Ser Gly Ser Gly Ser Gly Ser Gly Ser Gly Ser
    130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
                165                 170                 175

Phe Ala Pro Arg Cys Arg Glu Arg Arg Arg Asn Glu Arg Leu Arg Arg
            180                 185                 190

Glu Ser Val Arg Pro Val Gly Ser Ser His His Trp Gly Tyr Gly Lys
        195                 200                 205

His Asn Gly Pro Glu His Trp His Lys Asp Phe Pro Ile Ala Lys Gly
```

-continued

```
                210                 215                 220
Glu Arg Gln Ser Pro Val Asp Ile Asp Thr His Thr Ala Lys Tyr Asp
225                 230                 235                 240

Pro Ser Leu Lys Pro Leu Ser Val Ser Tyr Asp Gln Ala Thr Ser Leu
                245                 250                 255

Arg Ile Leu Asn Asn Gly His Ala Phe Asn Val Glu Phe Asp Asp Ser
            260                 265                 270

Gln Asp Lys Ala Val Leu Lys Gly Gly Pro Leu Asp Gly Thr Tyr Arg
        275                 280                 285

Leu Ile Gln Phe His Phe His Trp Gly Ser Leu Asp Gly Gln Gly Ser
    290                 295                 300

Glu His Thr Val Asp Lys Lys Tyr Ala Ala Glu Leu His Leu Val
305                 310                 315                 320

His Trp Asn Thr Lys Tyr Gly Asp Phe Gly Lys Ala Val Gln Gln Pro
                325                 330                 335

Asp Gly Leu Ala Val Leu Gly Ile Phe Leu Lys Val Gly Ser Ala Lys
            340                 345                 350

Pro Gly His Gln Lys Val Val Asp Val Leu Asp Ser Ile Lys Thr Lys
        355                 360                 365

Gly Lys Ser Ala Asp Phe Thr Asn Phe Asp Pro Arg Gly Leu Leu Pro
    370                 375                 380

Glu Ser Leu Asp Tyr Trp Thr Tyr Pro Gly Ser Leu Thr Thr Pro Pro
385                 390                 395                 400

Leu Leu Glu Cys Val Thr Trp Ile Val Leu Lys Glu Pro Ile Ser Val
                405                 410                 415

Ser Ser Glu Gln Val Leu Lys Phe Arg Lys Leu Asn Phe Asn Gly Glu
            420                 425                 430

Gly Glu Pro Glu Glu Leu Met Val Asp Asn Trp Arg Pro Ala Gln Pro
        435                 440                 445

Leu Lys Asn Arg Gln Ile Lys Ala Ser Phe Lys
    450                 455

<210> SEQ ID NO 32
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110
```

```
Thr Ser Gly Ser Gly Ser Gly Ser Gly Ser Gly Ser
        115                 120                 125

Gly Ser Gly Ser Gly Ser Gly Ser Gly Ser Gly Ser
        130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
                165                 170                 175

Phe Ala Pro Arg Cys Arg Glu Arg Ala Arg Asn Glu Arg Leu Arg Arg
                180                 185                 190

Glu Thr Val Arg Pro Val Gly Ser
        195                 200
```

<210> SEQ ID NO 33
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser Gly Ser Gly Ser Gly Ser Gly Ser Gly Ser Gly Ser Gly Ser
        115                 120                 125

Gly Ser Gly Ser Gly Ser Gly Ser Gly Ser Gly Ser Gly Ser Gly Ser
        130                 135                 140

Lys Gln Glu His Phe Pro Asp Asn Leu Leu Pro Ser Trp Ala Ile Thr
145                 150                 155                 160

Leu Ile Ser Val Asn Gly Ile Phe Val Ile Cys Cys Leu Thr Tyr Cys
                165                 170                 175

Phe Ala Pro Arg Cys Arg Glu Arg Ala Arg Asn Glu Arg Leu Arg Arg
                180                 185                 190

Glu Thr Val Arg Pro Val Gly Ser Ser His His Trp Gly Tyr Gly Lys
        195                 200                 205

His Asn Gly Pro Glu His Trp His Lys Asp Phe Pro Ile Ala Lys Gly
    210                 215                 220

Glu Arg Gln Ser Pro Val Asp Ile Asp Thr His Thr Ala Lys Tyr Asp
225                 230                 235                 240

Pro Ser Leu Lys Pro Leu Ser Val Ser Tyr Asp Gln Ala Thr Ser Leu
                245                 250                 255

Arg Ile Leu Asn Asn Gly His Ala Phe Asn Val Glu Phe Asp Asp Ser
            260                 265                 270
```

Gln Asp Lys Ala Val Leu Lys Gly Gly Pro Leu Asp Gly Thr Tyr Arg
        275                 280                 285

Leu Ile Gln Phe His Phe His Trp Gly Ser Leu Asp Gly Gln Gly Ser
        290                 295                 300

Glu His Thr Val Asp Lys Lys Tyr Ala Ala Glu Leu His Leu Val
305                 310                 315                 320

His Trp Asn Thr Lys Tyr Gly Asp Phe Gly Lys Ala Val Gln Gln Pro
                325                 330                 335

Asp Gly Leu Ala Val Leu Gly Ile Phe Leu Lys Val Gly Ser Ala Lys
                340                 345                 350

Pro Gly His Gln Lys Val Val Asp Val Leu Asp Ser Ile Lys Thr Lys
                355                 360                 365

Gly Lys Ser Ala Asp Phe Thr Asn Phe Asp Pro Arg Gly Leu Leu Pro
370                 375                 380

Glu Ser Leu Asp Tyr Trp Thr Tyr Pro Gly Ser Leu Thr Thr Pro Pro
385                 390                 395                 400

Leu Leu Glu Cys Val Thr Trp Ile Val Leu Lys Glu Pro Ile Ser Val
                405                 410                 415

Ser Ser Glu Gln Val Leu Lys Phe Arg Lys Leu Asn Phe Asn Gly Glu
                420                 425                 430

Gly Glu Pro Glu Glu Leu Met Val Asp Asn Trp Arg Pro Ala Gln Pro
                435                 440                 445

Leu Lys Asn Arg Gln Ile Lys Ala Ser Phe Lys
450                 455

<210> SEQ ID NO 34
<211> LENGTH: 8384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
tttgagtgag ctgataccgc tcgccgcagc cgaacgaccg agcgcagcga gtcagtgagc        60
gaggaagcgg aagagcgccc aatacgcaaa ccgcctctcc ccgcgcgttg gccgattcat       120
taatgcagct ggcacgacag gtttcccgac tggaaagcgg gcagtgagcg caacgcaatt       180
aatgtgagtt agctcactca ttaggcaccc caggctttac actttatgct tccggctcgt       240
atgttgtgtg gaattgtgag cggataacaa tttcacacag gaaacagcta tgaccatgat       300
tacgccaagc gcgcaattaa ccctcactaa agggaacaaa agctggagct gcaagcttaa       360
tgtagtctta tgcaatactc ttgtagtctt gcaacatggt aacgatgagt tagcaacatg       420
ccttacaagg agagaaaaag caccgtgcat gccgattggt ggaagtaagg tggtacgatc       480
gtgccttatt aggaaggcaa cagacgggtc tgacatggat tggacgaacc actgaattgc       540
cgcattgcag agatattgta tttaagtgcc tagctcgata caataaacgg gtctctctgg       600
ttagaccaga tctgagcctg ggagctctct ggctaactag ggaacccact gcttaagcct       660
caataaagct tgccttgagt gcttcaagta gtgtgtgccc gtctgttgtg tgactctggt       720
aactagagat ccctcagacc cttttagtca gtgtggaaaa tctctagcag tggcgcccga       780
acagggacct gaaagcgaaa gggaaaccag agctctctcg acgcaggact cggcttgctg       840
aagcgcgcac ggcaagaggc gaggggcggc gactggtgag tacgccaaaa attttgacta       900
gcggaggcta gaaggagaga gatgggtgcg agagcgtcag tattaagcgg gggagaatta       960

```
gatcgcgatg ggaaaaaatt cggttaaggc caggggaaa  gaaaaatat aaattaaaac    1020 atatagtatg ggcaagcagg gagctagaac gattcgcagt taatcctggc ctgttagaaa    1080
catcagaagg ctgtagacaa atactgggac agctacaacc atcccttcag acaggatcag    1140
aagaacttag atcattatat aatacagtag caaccctcta ttgtgtgcat caaaggatag    1200
agataaaaga caccaaggaa gctttagaca agatagagga agagcaaaac aaaagtaaga    1260
ccaccgcaca gcaagcggcc gctgatcttc agacctggag gaggagatat gagggacaat    1320
tggagaagtg aattatataa ataaaagta gtaaaaattg aaccattagg agtagcaccc    1380
accaaggcaa agagaagagt ggtgcagaga gaaaaaagag cagtgggaat aggagctttg    1440
ttccttgggt tcttgggagc agcaggaagc actatgggcg cagcctcaat gacgctgacg    1500
gtacaggcca gacaattatt gtctggtata gtgcagcagc agaacaattt gctgagggct    1560
attgaggcgc aacagcatct gttgcaactc acagtctggg gcatcaagca gctccaggca    1620
agaatcctgg ctgtggaaag atacctaaag gatcaacagc tcctggggat ttggggttgc    1680
tctggaaaac tcatttgcac cactgctgtg ccttggaatg ctagttggag taataaatct    1740
ctggaacaga ttggaatcac acgacctgga tggagtggga cagagaaatt aacaattaca    1800
caagcttaat acactcctta ttgaagaat  cgcaaaacca gcaagaaaag aatgaacaag    1860
aattattgga attagataaa tgggcaagtt tgtggaattg gtttaacata acaaattggc    1920
tgtggtatat aaaattattc ataatgatag taggaggctt ggtaggttta agaatagttt    1980
ttgctgtact ttctatagtg aatagagtta ggcaggata ttcaccatta tcgtttcaga    2040
cccacctccc aaccccgagg ggacccgaca ggcccgaagg aatagaagaa gaaggtggag    2100
agagagacag agacagatcc attcgattag tgaacggatc tcgacggtat cgattagact    2160
gtagcccagg aatatggcag ctagattgta cacatttaga aggaaaagtt atcttggtag    2220
cagttcatgt agccagtgga tatatagaag cagaagtaat tccagcagag acagggcaag    2280
aaacagcata cttcctctta aaattagcag gaagatggcc agtaaaaaca gtacatacag    2340
acaatggcag caatttcacc agtactacag ttaaggccgc ctgttggtgg gcggggatca    2400
agcaggaatt tggcattccc tacaatcccc aaagtcaagg agtaatagaa tctatgaata    2460
aagaattaaa gaaaattata ggacaggtaa gagatcaggc tgaacatctt aagacagcag    2520
tacaaatggc agtattcatc cacaatttta aaagaaaagg ggggattggg gggtacagtg    2580
caggggaaag aatagtagac ataatagcaa cagacataca aactaaagaa ttacaaaaac    2640
aaattacaaa aattcaaaat tttcgggttt attacaggga cagcagagat ccagtttggc    2700
tgcatacgcg tcgtgaggct ccggtgcccg tcagtgggca gagcgcacat cgcccacagt    2760
ccccgagaag ttggggggag gggtcggcaa ttgaaccggt gcctagaaa  ggtggcgcgg    2820 ggtaaactgg gaaagtgatg tcgtgtactg gctccgcctt tttcccgagg gtggggagg    2880 accgtatata agtgcagtag tcgccgtgaa cgttcttttt cgcaacgggt ttgccgccag    2940
aacacaggta agtgccgtgt gtggttcccg cgggcctggc ctctttacgg gttatggccc    3000
ttgcgtgcct tgaattactt ccacctggct gcagtacgtg attcttgatc ccgagcttcg    3060
ggttggaagt gggtgggaga gttcgaggcc ttgcgcttaa ggagcccctt cgcctcgtgc    3120
ttgagttgag gcctggcctg ggcgctgggg ccgccgcgtg cgaatctggt ggcaccttcg    3180
cgcctgtctc gctgctttcg ataagtctct agccatttaa aattttttgat gacctgctgc    3240 gacgcttttt ttctggcaag atagtcttgt aaatgcgggc caagatctgc acactggtat    3300
```

```
ttcggttttt ggggccgcgg gcggcgacgg ggcccgtgcg tcccagcgca catgttcggc    3360
gaggcgggc  ctgcgagcgc ggccaccgag aatcggacgg gggtagtctc aagctggccg    3420
gcctgctctg gtgcctggcc tcgcgccgcc gtgtatcgcc ccgccctggg cggcaaggct    3480
ggcccggtcg gcaccagttg cgtgagcgga aagatggccg cttcccggcc ctgctgcagg    3540
gagctcaaaa tggaggacgc ggcgctcggg agagcgggcg ggtgagtcac ccacacaaag    3600
gaaaagggcc tttccgtcct cagccgtcgc ttcatgtgac tccactgagt accgggcgcc    3660
gtccaggcac ctcgattagt tctcgtgctt ttggagtacg tcgtctttag gttgggggga    3720
ggggttttat gcgatggagt ttccccacac tgagtgggtg gagactgaag ttaggccagc    3780
ttggcacttg atgtaattct ccttggaatt tgccctttt  gagtttggat cttggttcat    3840
tctcaagcct cagacagtgg ttcaaagttt ttttcttcca tttcaggtgt cgtgagctag    3900
actagtacca tggacatgcg ggtgcctgca caacttctgg gcctgctgtt gttgtggctg    3960
tctggagccc ggtgtaattg ggtaaatgtt atcagtgatc tcaagaagat agaggatctc    4020
atccagtcca tgcatattga tgccacgctg tacacagaaa gcgatgtgca tcctagctgt    4080
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagaagg agaaatgaaa gactgagaag ggagagcgtg    4560
agacctgtgg gatcctaagc tagcgtcggc aatcaacctc tggattacaa aatttgtgaa    4620
agattgactg gtattcttaa ctatgttgct ccttttacgc tatgtggata cgctgcttta    4680
atgcctttgt atcatgctat tgcttcccgt atggctttca ttttctcctc cttgtataaa    4740
tcctggttgc tgtctcttta tgaggagttg tggcccgttg tcaggcaacg tggcgtggtg    4800
tgcactgtgt ttgctgacgc aaccccact  ggttgggca  ttgccaccac ctgtcagctc    4860
ctttccggga ctttcgcttt ccccctccct attgccacgg cggaactcat cgccgcctgc    4920
cttgcccgct gctggacagg ggctcggctg ttgggcactg acaattccgt ggtgttgtcg    4980
gggaagctga cgtcctttcc atggctgctc gcctgtgttg ccacctggat tctgcgcggg    5040
acgtccttct gctacgtccc ttcggccctc aatccagcgg accttccttc ccgcggcctg    5100
ctgccggctc tgcggcctct tccgcgtctt cgccttcgcc ctcagacgag tcggatctcc    5160
ctttgggccg cctccccgcc tggaattcga gctcggtacc tttaagacca atgacttaca    5220
aggcagctgt agatcttagc cacttttta  aagaaaaggg gggactggaa gggctaattc    5280
actcccaacg aagacaagat ctgcttttg  cttgtactgg gtctctctgg ttagaccaga    5340
tctgagcctg ggagctctct ggctaactag ggaacccact gcttaagcct caataaagct    5400
tgccttgagt gcttcaagta gtgtgtgccc gtctgttgtg tgactctggt aactagagat    5460
ccctcagacc cttttagtca gtgtggaaaa tctctagcag tagtagttca tgtcatctta    5520
ttattcagta tttataactt gcaaagaaat gaatatcaga gagtgagagg aacttgttta    5580
ttgcagctta taatggttac aaataaagca atagcatcac aaatttcaca aataaagcat    5640
tttttcact  gcattctagt tgtggtttgt ccaaactcat caatgtatct tatcatgtct    5700
```

```
ggctctagct atcccgcccc taactccgcc cagttccgcc cattctccgc cccatggctg    5760
actaattttt tttatttatg cagaggccga ggccgcctcg gcctctgagc tattccagaa    5820
gtagtgagga ggcttttttg gaggcctagg cttttgcgtc gagacgtacc caattcgccc    5880
tatagtgagt cgtattacgc gcgctcactg gccgtcgttt tacaacgtcg tgactgggaa    5940
aaccctggcg ttacccaact taatcgcctt gcagcacatc cccctttcgc cagctggcgt    6000
aatagcgaag aggcccgcac cgatcgccct tcccaacagt tgcgcagcct gaatggcgaa    6060
tggcgcgacg cgcccgtag cggcgcatta agcgcggcgg gtgtggtggt tacgcgcagc    6120
gtgaccgcta cacttgccag cgccctagcg cccgctcctt tcgctttctt cccttccttt    6180
ctcgccacgt tcgccggctt tccccgtcaa gctctaaatc gggggctccc tttagggttc    6240
cgatttagtg ctttacggca cctcgacccc aaaaaacttg attagggtga tggttcacgt    6300
agtgggccat cgccctgata acggtttttc gccctttga cgttggagtc cacgttcttt    6360
aatagtggac tcttgttcca aactggaaca acactcaacc ctatctcggt ctattctttt    6420
gatttataag ggattttgcc gatttcggcc tattggttaa aaaatgagct gatttaacaa    6480
aaatttaacg cgaattttaa caaaatatta acgtttacaa tttcccaggt ggcacttttc    6540
ggggaaatgt gcgcggaacc cctatttgtt tatttttcta aatacattca aatatgtatc    6600
cgctcatgag acaataaccc tgataaatgc ttcaataata ttgaaaaagg aagagtatga    6660
gtattcaaca tttccgtgtc gcccttattc cttttttgc ggcattttgc cttcctgttt    6720
ttgctcaccc agaaacgctg gtgaaagtaa aagatgctga agatcagttg ggtgcacgag    6780
tgggttacat cgaactggat ctcaacagcg gtaagatcct tgagagtttt cgccccgaag    6840
aacgttttcc aatgatgagc acttttaaag ttctgctatg tggcgcggta ttatcccgta    6900
ttgacgccgg gcaagagcaa ctcggtcgcc gcatacacta ttctcagaat gacttggttg    6960
agtactcacc agtcacagaa aagcatctta cggatggcat gacagtaaga gaattatgca    7020
gtgctgccat aaccatgagt gataacactg cggccaactt acttctgaca acgatcggag    7080
gaccgaagga gctaaccgct ttttgcaca acatggggga tcatgtaact cgccttgatc    7140
gttgggaacc ggagctgaat gaagccatac caaacgacga gcgtgacacc acgatgcctg    7200
tagcaatggc aacaacgttg cgcaaactat taactggcga actacttact ctagcttccc    7260
ggcaacaatt aatagactgg atggaggcgg ataaagttgc aggaccactt ctgcgctcgg    7320
cccttccggc tggctggttt attgctgata atctggagc cggtgagcgt gggtctcgcg    7380
gtatcattgc agcactgggg ccagatggta agccctcccg tatcgtagtt atctacacga    7440
cggggagtca ggcaactatg gatgaacgaa atagacagat cgctgagata ggtgcctcac    7500
tgattaagca ttggtaactg tcagaccaag tttactcata tatactttag attgatttaa    7560
aacttcattt ttaatttaaa aggatctagg tgaagatcct ttttgataat ctcatgacca    7620
aaatccctta acgtgagttt tcgttccact gagcgtcaga ccccgtagaa aagatcaaag    7680
gatcttcttg agatcctttt tttctgcgcg taatctgctg cttgcaaaca aaaaaaccac    7740
cgctaccagc ggtggtttgt ttgccggatc aagagctacc aactcttttt ccgaaggtaa    7800
ctggcttcag cagagcgcag ataccaaata ctgtccttct agtgtagccg tagttaggcc    7860
accacttcaa gaactctgta gcaccgccta catacctcgc tctgctaatc ctgttaccag    7920
tggctgctgc cagtggcgat aagtcgtgtc ttaccgggtt ggactcaaga cgatagttac    7980
cggataaggc gcagcggtcg ggctgaacgg ggggttcgtg cacacagccc agcttggagc    8040
```

| | |
|---|---|
| gaacgaccta caccgaactg agatacctac agcgtgagct atgagaaagc gccacgcttc | 8100 |
| ccgaagggag aaaggcggac aggtatccgg taagcggcag ggtcggaaca ggagagcgca | 8160 |
| cgagggagct tccaggggga aacgcctggt atctttatag tcctgtcggg tttcgccacc | 8220 |
| tctgacttga gcgtcgattt tgtgatgct cgtcaggggg gcggagccta tggaaaaacg | 8280 |
| ccagcaacgc ggccttttta cggttcctgg ccttttgctg gccttttgct cacatgttct | 8340 |
| ttcctgcgtt atcccctgat tctgtggata accgtattac cgcc | 8384 |

```
<210> SEQ ID NO 35
<211> LENGTH: 9161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
```

| | |
|---|---|
| tttgagtgag ctgataccgc tcgccgcagc cgaacgaccg agcgcagcga gtcagtgagc | 60 |
| gaggaagcgg aagagcgccc aatacgcaaa ccgcctctcc ccgcgcgttg gccgattcat | 120 |
| taatgcagct ggcacgacag gtttcccgac tggaaagcgg gcagtgagcg caacgcaatt | 180 |
| aatgtgagtt agctcactca ttaggcaccc caggctttac actttatgct tccggctcgt | 240 |
| atgttgtgtg gaattgtgag cggataacaa tttcacacag gaaacagcta tgaccatgat | 300 |
| tacgccaagc gcgcaattaa ccctcactaa agggaacaaa agctggagct gcaagcttaa | 360 |
| tgtagtctta tgcaatactc ttgtagtctt gcaacatggt aacgatgagt tagcaacatg | 420 |
| ccttacaagg agagaaaaag caccgtgcat gccgattggt ggaagtaagg tggtacgatc | 480 |
| gtgccttatt aggaaggcaa cagacgggtc tgacatggat tggacgaacc actgaattgc | 540 |
| cgcattgcag agatattgta tttaagtgcc tagctcgata caataaacgg gtctctctgg | 600 |
| ttagaccaga tctgagcctg ggagctctct ggctaactag ggaacccact gcttaagcct | 660 |
| caataaagct tgccttgagt gcttcaagta gtgtgtgccc gtctgttgtg tgactctggt | 720 |
| aactagagat ccctcagacc cttttagtca gtgtggaaaa tctctagcag tggcgcccga | 780 |
| acagggacct gaaagcgaaa gggaaaccag agctctctcg acgcaggact cggcttgctg | 840 |
| aagcgcgcac ggcaagaggc gaggggcggc gactggtgag tacgccaaaa attttgacta | 900 |
| gcggaggcta agaggagaga gatgggtgcg agagcgtcag tattaagcgg gggagaatta | 960 |
| gatcgcgatg ggaaaaaatt cggttaaggc caggggaaa gaaaaaatat aaattaaaac | 1020 |
| atatagtatg ggcaagcagg gagctagaac gattcgcagt taatcctggc ctgttagaaa | 1080 |
| catcagaagg ctgtagacaa atactgggac agctacaacc atcccttcag acaggatcag | 1140 |
| aagaacttag atcattatat aatacagtag caaccctcta ttgtgtgcat caaaggatag | 1200 |
| agataaaaga caccaaggaa gctttagaca agatagagga gagcaaaac aaaagtaaga | 1260 |
| ccaccgcaca gcaagcggcc gctgatcttc agacctggag gaggagatat gagggacaat | 1320 |
| tggagaagtg aattatataa atataaagta gtaaaaattg aaccattagg agtagcaccc | 1380 |
| accaaggcaa agagaagagt ggtgcagaga gaaaaaagag cagtgggaat aggagctttg | 1440 |
| ttccttgggt tcttgggagc agcaggaagc actatgggcg cagcctcaat gacgctgacg | 1500 |
| gtacaggcca gacaattatt gtctggtata gtgcagcagc agaacaattt gctgagggct | 1560 |
| attgaggcgc aacagcatct gttgcaactc acagtctggg gcatcaagca gctccaggca | 1620 |
| agaatcctgg ctgtggaaag atacctaaag gatcaacagc tcctggggat ttggggttgc | 1680 |

-continued

```
tctggaaaac tcatttgcac cactgctgtg ccttggaatg ctagttggag taataaatct      1740
ctggaacaga ttggaatcac acgacctgga tggagtggga cagagaaatt aacaattaca      1800
caagcttaat acactcctta attgaagaat cgcaaaacca gcaagaaaag aatgaacaag      1860
aattattgga attagataaa tgggcaagtt tgtggaattg gtttaacata acaaattggc      1920
tgtggtatat aaaattattc ataatgatag taggaggctt ggtaggttta agaatagttt      1980
ttgctgtact ttctatagtg aatagagtta ggcaggata ttcaccatta tcgtttcaga       2040
cccacctccc aaccccgagg ggacccgaca ggcccgaagg aatagaagaa gaaggtggag      2100
agagagacag agacagatcc attcgattag tgaacggatc tcgacggtat cgattagact      2160
gtagcccagg aatatggcag ctagattgta cacatttaga aggaaaagtt atcttggtag      2220
cagttcatgt agccagtgga tatatagaag cagaagtaat tccagcagag acagggcaag      2280
aaacagcata cttcctctta aaattagcag gaagatggcc agtaaaaaca gtacatacag      2340
acaatggcag caatttcacc agtactacag ttaaggccgc ctgttggtgg gcggggatca      2400
agcaggaatt tggcattccc tacaatcccc aaagtcaagg agtaatagaa tctatgaata      2460
aagaattaaa gaaaattata ggacaggtaa gagatcaggc tgaacatctt aagacagcag      2520
tacaaatggc agtattcatc cacaatttta aaagaaaagg ggggattggg gggtacagtg      2580
caggggaaag aatagtagac ataatagcaa cagacataca aactaaagaa ttacaaaaac      2640
aaattacaaa aattcaaaat tttcgggttt attacaggga cagcagagat ccagtttggc      2700
tgcatacgcg tcgtgaggct ccggtgcccg tcagtgggca gagcgcacat cgcccacagt      2760
ccccgagaag ttgggggggag gggtcggcaa ttgaaccggt gcctagagaa ggtggcgcgg      2820
ggtaaactgg gaaagtgatg tcgtgtactg gctccgcctt tttcccgagg gtgggggaga      2880
accgtatata agtgcagtag tcgccgtgaa cgttcttttt cgcaacgggt ttgccgccag      2940
aacacaggta agtgccgtgt gtggttcccg cgggcctggc ctctttacgg gttatggccc      3000
ttgcgtgcct tgaattactt ccacctggct gcagtacgtg attcttgatc ccagagcttcg     3060 ggttggaagt gggtgggaga gttcgaggcc ttgcgcttaa ggagccccct cgcctcgtgc      3120
ttgagttgag gcctggcctg ggcgctgggg ccgccgcgtg cgaatctggt ggcaccttcg      3180
cgcctgtctc gctgctttcg ataagtctct agccatttaa aatttttgat gacctgctgc      3240
gacgcttttt ttctggcaag atagtcttgt aaatgcgggc caagatctgc acactggtat      3300
ttcggttttt ggggccgcgg gcggcgacgg ggcccgtgcg tcccagcgca catgttcggc      3360
gaggcggggc ctgcgagcgc ggccaccgag aatcggacgg gggtagtctc aagctggccg      3420
gcctgctctg gtgcctggcc tcgcgccgcc gtgtatcgcc ccgccctggg cggcaaggct      3480
ggcccggtcg gcaccagttg cgtgagcgga aagatggccg cttcccggcc ctgctgcagg      3540
gagctcaaaa tggaggacgc ggcgctcggg agagcgggcg ggtgagtcac ccacacaaag      3600
gaaaagggcc tttccgtcct cagccgtcgc ttcatgtgac tccactgagt accgggcgcc      3660
gtccaggcac ctcgattagt tctcgtgctt ttggagtacg tcgtctttag gttgggggga      3720
ggggttttat gcgatggagt ttccccacac tgagtgggtg gagactgaag ttaggccagc      3780
ttggcacttg atgtaattct ccttggaatt tgcccttttt gagtttggat cttggttcat      3840
tctcaagcct cagacagtgg ttcaaagttt ttttcttcca tttcaggtgt cgtgagctag      3900
actagtacca tggacatgcg ggtgcctgca caacttctgg gcctgctgtt gttgtggctg      3960
tctggagccc ggtgtaattg ggtaaatgtt atcagtgatc tcaagaagat agaggatctc      4020
atccagtcca tgcatattga tgccacgctg tacacagaaa gcgatgtgca tcctagctgt      4080
```

```
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagaagg agaaatgaaa gactgagaag ggagagcgtg    4560
agacctgtgg gatcctccca tcactggggg tacggcaaac acaacggacc tgagcactgg    4620
cataaggact tccccattgc caaggggagag cgccagtccc ctgttgacat cgacactcat    4680
acagccaagt atgacccttc cctgaagccc ctgtctgttt cctatgatca agcaacttcc    4740
ctgagaatcc tcaacaatgg tcatgctttc aacgtggagt ttgatgactc tcaggacaaa    4800
gcagtgctca agggaggacc cctggatggc acttacagat tgattcagtt tcactttcac    4860
tggggttcac ttgatggaca aggttcagag catactgtgg ataaaaagaa atatgctgca    4920
gaacttcact tggttcactg gaacaccaaa tatggggatt ttgggaaagc tgtgcagcaa    4980
cctgatggac tggccgttct aggtattttt ttgaaggttg gcagcgctaa accgggccat    5040
cagaaagttg ttgatgtgct ggattccatt aaaacaaagg gcaagagtgc tgacttcact    5100
aacttcgatc ctcgtggcct ccttcctgaa tccctggatt actggaccta cccaggctca    5160
ctgaccaccc ctcctcttct ggaatgtgtg acctggattg tgctcaagga acccatcagc    5220
gtcagcagcg agcaggtgtt gaaattccgt aaacttaact tcaatgggga gggtgaaccc    5280
gaagaactga tggtggacaa ctggcgccca gctcagccac tgaagaacag gcaaatcaaa    5340
gcttccttca aataagctag cgtcgacaat caacctctgg attacaaaat ttgtgaaaga    5400
ttgactggta ttcttaacta tgttgctcct tttacgctat gtggatacgc tgctttaatg    5460
cctttgtatc atgctattgc ttcccgtatg gctttcattt tctcctcctt gtataaatcc    5520
tggttgctgt ctctttatga ggagttgtgg cccgttgtca ggcaacgtgg cgtggtgtgc    5580
actgtgtttg ctgacgcaac ccccactggt tggggcattg ccaccacctg tcagctcctt    5640
tccgggactt tcgctttccc cctccctatt gccacggcgg aactcatcgc cgcctgcctt    5700
gcccgctgct ggacaggggc tcggctgttg ggcactgaca attccgtggt gttgtcgggg    5760
aagctgacgt ccttttccatg gctgctcgcc tgtgttgcca cctggattct gcgcgggacg    5820
tccttctgct acgtcccttc ggccctcaat ccagcggacc ttccttcccg cggcctgctg    5880
ccggctctgc ggcctcttcc gcgtcttcgc cttcgccctc agacgagtcg atctccctt    5940 tgggccgcct ccccgcctgg aattcgagct cggtaccttt aagaccaatg acttacaagg    6000
cagctgtaga tcttagccac ttttttaaaag aaaagggggg actggaaggg ctaattcact    6060
cccaacgaag acaagatctg cttttttgctt gtactgggtc tctctggtta gaccagatct    6120
gagcctggga gctctctggc taactaggga acccactgct taagcctcaa taaagcttgc    6180
cttgagtgct tcaagtagtg tgtgcccgtc tgttgtgtga ctctggtaac tagagatccc    6240
tcagaccctt ttagtcagtg tggaaaatct ctagcagtag tagttcatgt catcttatta    6300
ttcagtattt ataacttgca aagaaatgaa tatcagagag tgagaggaac ttgtttattg    6360
cagcttataa tggttacaaa taaagcaata gcatcacaaa tttcacaaat aaagcatttt    6420
```

| | |
|---|---|
| tttcactgca ttctagttgt ggtttgtcca aactcatcaa tgtatcttat catgtctggc | 6480 |
| tctagctatc ccgcccctaa ctccgcccag ttccgcccat tctccgcccc atggctgact | 6540 |
| aatttttttt atttatgcag aggccgaggc cgcctcggcc tctgagctat tccagaagta | 6600 |
| gtgaggaggc ttttttggag gcctaggctt ttgcgtcgag acgtacccaa ttcgccctat | 6660 |
| agtgagtcgt attacgcgcg ctcactggcc gtcgttttac aacgtcgtga ctgggaaaac | 6720 |
| cctggcgtta cccaacttaa tcgccttgca gcacatcccc ctttcgccag ctggcgtaat | 6780 |
| agcgaagagg cccgcaccga tcgcccttcc caacagttgc gcagcctgaa tggcgaatgg | 6840 |
| cgcgacgcgc cctgtagcgg cgcattaagc gcggcgggtg tggtggttac gcgcagcgtg | 6900 |
| accgctacac ttgccagcgc cctagcgccc gctcctttcg ctttcttccc ttcctttctc | 6960 |
| gccacgttcg ccggctttcc ccgtcaagct ctaaatcggg gctcccttt agggttccga | 7020 |
| tttagtgctt tacggcacct cgaccccaaa aaacttgatt agggtgatgg ttcacgtagt | 7080 |
| gggccatcgc cctgatagac ggttttcgc cctttgacgt tggagtccac gttctttaat | 7140 |
| agtggactct tgttccaaac tggaacaaca ctcaaccta tctcggtcta ttcttttgat | 7200 |
| ttataaggga ttttgccgat ttcggcctat tggttaaaaa atgagctgat ttaacaaaaa | 7260 |
| tttaacgcga attttaacaa atattaacg tttacaattt cccaggtggc acttttcggg | 7320 |
| gaaatgtgcg cggaacccct atttgtttat ttttctaaat acattcaaat atgtatccgc | 7380 |
| tcatgagaca ataaccctga taaatgcttc aataatattg aaaaggaag agtatgagta | 7440 |
| ttcaacattt ccgtgtcgcc cttattccct tttttgcggc attttgcctt cctgttttg | 7500 |
| ctcacccaga aacgctggtg aaagtaaaag atgctgaaga tcagttgggt gcacgagtgg | 7560 |
| gttacatcga actggatctc aacagcggta agatccttga gttttcgc ccgaagaac | 7620 |
| gttttccaat gatgagcact tttaaagttc tgctatgtgg cgcggtatta tcccgtattg | 7680 |
| acgccgggca agagcaactc ggtcgccgca tacactattc tcagaatgac ttggttgagt | 7740 |
| actcaccagt cacagaaaag catcttacg atggcatgac agtaagagaa ttatgcagtg | 7800 |
| ctgccataac catgagtgat aacactgcgg ccaacttact tctgacaacg atcggaggac | 7860 |
| cgaaggagct aaccgctttt ttgcacaaca tgggggatca tgtaactcgc cttgatcgtt | 7920 |
| gggaaccgga gctgaatgaa gccataccaa acgacgagcg tgacaccacg atgcctgtag | 7980 |
| caatggcaac aacgttgcgc aaactattaa ctggcgaact acttactcta gcttcccggc | 8040 |
| aacaattaat agactggatg gaggcggata aagttgcagg accacttctg cgctcggccc | 8100 |
| ttccggctgg ctggtttatt gctgataaat ctggagccgg tgagcgtggg tctcgcggta | 8160 |
| tcattgcagc actggggcca gatggtaagc cctcccgtat cgtagttatc tacacgacgg | 8220 |
| ggagtcaggc aactatggat gaacgaaata gacagatcgc tgagataggt gcctcactga | 8280 |
| ttaagcattg gtaactgtca gaccaagttt actcatatat actttagatt gatttaaaac | 8340 |
| ttcatttta atttaaaagg atctaggtga agatccttt tgataatctc atgaccaaaa | 8400 |
| tcccttaacg tgagttttcg ttccactgag cgtcagaccc cgtagaaaag atcaaaggat | 8460 |
| cttcttgaga tcctttttt ctgcgcgtaa tctgctgctt gcaaacaaaa aaaccaccgc | 8520 |
| taccagcggt ggtttgtttg ccggatcaag agctaccaac tctttttccg aaggtaactg | 8580 |
| gcttcagcag agcgcagata ccaaatactg tccttctagt gtagccgtag ttaggccacc | 8640 |
| acttcaagaa ctctgtagca ccgcctacat acctcgctct gctaatcctg ttaccagtgg | 8700 |
| ctgctgccag tggcgataag tcgtgtctta ccgggttgga ctcaagacga tagttaccgg | 8760 |
| ataaggcgca gcggtcgggc tgaacggggg gttcgtgcac acagcccagc ttggagcgaa | 8820 |

| | |
|---|---|
| cgacctacac cgaactgaga tacctacagc gtgagctatg agaaagcgcc acgcttcccg | 8880 |
| aagggagaaa ggcggacagg tatccggtaa gcggcagggt cggaacagga gagcgcacga | 8940 |
| gggagcttcc aggggaaac gcctggtatc tttatagtcc tgtcgggttt cgccacctct | 9000 |
| gacttgagcg tcgattttg tgatgctcgt caggggggcg gagcctatgg aaaaacgcca | 9060 |
| gcaacgcggc cttttacgg ttcctggcct tttgctggcc ttttgctcac atgttctttc | 9120 |
| ctgcgttatc ccctgattct gtggataacc gtattaccgc c | 9161 |

<210> SEQ ID NO 36
<211> LENGTH: 8384
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 36

| | |
|---|---|
| tttgagtgag ctgataccgc tcgccgcagc cgaacgaccg agcgcagcga gtcagtgagc | 60 |
| gaggaagcgg aagagcgccc aatacgcaaa ccgcctctcc ccgcgcgttg gccgattcat | 120 |
| taatgcagct ggcacgacag gtttcccgac tggaaagcgg gcagtgagcg caacgcaatt | 180 |
| aatgtgagtt agctcactca ttaggcaccc caggctttac actttatgct tccggctcgt | 240 |
| atgttgtgtg gaattgtgag cggataacaa tttcacacag gaaacagcta tgaccatgat | 300 |
| tacgccaagc gcgcaattaa ccctcactaa agggaacaaa agctggagct gcaagcttaa | 360 |
| tgtagtctta tgcaatactc ttgtagtctt gcaacatggt aacgatgagt tagcaacatg | 420 |
| ccttacaagg agagaaaaag caccgtgcat gccgattggt ggaagtaagg tggtacgatc | 480 |
| gtgccttatt aggaaggcaa cagacgggtc tgacatggat tggacgaacc actgaattgc | 540 |
| cgcattgcag agatattgta tttaagtgcc tagctcgata caataaacgg gtctctctgg | 600 |
| ttagaccaga tctgagcctg ggagctctct ggctaactag ggaacccact gcttaagcct | 660 |
| caataaagct tgccttgagt gcttcaagta gtgtgtgccc gtctgttgtg tgactctggt | 720 |
| aactagagat ccctcagacc cttttagtca gtgtggaaaa tctctagcag tggcgcccga | 780 |
| acagggacct gaaagcgaaa gggaaaccag agctctctcg acgcaggact cggcttgctg | 840 |
| aagcgcgcac ggcaagaggc gaggggcggc gactggtgag tacgccaaaa attttgacta | 900 |
| gcggaggcta agaggagaga tgggtgcg agagcgtcag tattaagcgg gggagaatta | 960 |
| gatcgcgatg ggaaaaaatt cggttaaggc caggggaaa gaaaaaatat aaattaaaac | 1020 |
| atatagtatg ggcaagcagg gagctagaac gattcgcagt taatcctggc ctgttagaaa | 1080 |
| catcagaagg ctgtagacaa atactgggac agctacaacc atcccttcag acaggatcag | 1140 |
| aagaacttag atcattatat aatacagtag caaccctcta ttgtgtgcat caaaggatag | 1200 |
| agataaaaga caccaaggaa gctttagaca agatagagga agagcaaaac aaaagtaaga | 1260 |
| ccaccgcaca gcaagcggcc gctgatcttc agacctggag gaggagatat gagggacaat | 1320 |
| tggagaagtg aattatataa atataaagta gtaaaaattg aaccattagg agtagcaccc | 1380 |
| accaaggcaa agagaagagt ggtgcagaga gaaaaaagag cagtgggaat aggagctttg | 1440 |
| ttccttgggt tcttgggagc agcaggaagc actatgggcg cagcctcaat gacgctgacg | 1500 |
| gtacaggcca gacaattatt gtctggtata gtgcagcagc agaacaattt gctgagggct | 1560 |
| attgaggcgc aacagcatct gttgcaactc acagtctggg gcatcaagca gctccaggca | 1620 |
| agaatcctgg ctgtggaaag atacctaaag gatcaacagc tcctgggat ttggggttgc | 1680 |

```
tctggaaaac tcatttgcac cactgctgtg ccttggaatg ctagttggag taataaatct   1740
ctggaacaga ttggaatcac acgacctgga tggagtggga cagagaaatt aacaattaca   1800
caagcttaat acactcctta attgaagaat cgcaaaacca gcaagaaaag aatgaacaag   1860
aattattgga attagataaa tgggcaagtt tgtggaattg gtttaacata acaaattggc   1920
tgtggtatat aaaattattc ataatgatag taggaggctt ggtaggttta agaatagttt   1980
ttgctgtact ttctatagtg aatagagtta ggcagggata ttcaccatta tcgtttcaga   2040
cccacctccc aaccccgagg ggacccgaca ggcccgaagg aatagaagaa gaaggtggag   2100
agagagacag agacagatcc attcgattag tgaacggatc tcgacggtat cgattagact   2160
gtagcccagg aatatggcag ctagattgta cacatttaga aggaaaagtt atcttggtag   2220
cagttcatgt agccagtgga tatatagaag cagaagtaat tccagcagag acagggcaag   2280
aaacagcata cttcctctta aaattagcag gaagatggcc agtaaaaaca gtacatacag   2340
acaatggcag caatttcacc agtactacag ttaaggccgc ctgttggtgg gcggggatca   2400
agcaggaatt tggcattccc tacaatcccc aaagtcaagg agtaatagaa tctatgaata   2460
aagaattaaa gaaaattata ggacaggtaa gagatcaggc tgaacatctt aagacagcag   2520
tacaaatggc agtattcatc cacaatttta aaagaaaagg ggggattggg gggtacagtg   2580
caggggaaag aatagtagac ataatagcaa cagacataca aactaaagaa ttacaaaaac   2640
aaattacaaa aattcaaaat tttcgggttt attacaggga cagcagagat ccagtttggc   2700
tgcatacgcg tcgtgaggct ccggtgcccg tcagtgggca gagcgcacat cgcccacagt   2760
ccccgagaag ttgggggggag gggtcggcaa ttgaaccggt gcctagagaa ggtggcgcgg   2820
ggtaaactgg gaaagtgatg tcgtgtactg gctccgcctt tttcccgagg gtgggggaga   2880
accgtatata agtgcagtag tcgccgtgaa cgttcttttt cgcaacgggt ttgccgccag   2940
aacacaggta agtgccgtgt gtggttcccg cgggcctggc ctctttacgg gttatggccc   3000
ttgcgtgcct tgaattactt ccacctggct gcagtacgtg attcttgatc ccgagcttcg   3060
ggttggaagt gggtgggaga gttcgaggcc ttgcgcttaa ggagcccctt cgcctcgtgc   3120
ttgagttgag gcctggcctg ggcgctgggg ccgccgcgtg cgaatctggt ggcaccttcg   3180
cgcctgtctc gctgctttcg ataagtctct agccatttaa aattttttgat gacctgctgc   3240
gacgcttttt ttctggcaag atagtcttgt aaatgcgggc caagatctgc acactggtat   3300
ttcggttttt ggggccgcgg gcggcgacgg ggcccgtgcg tcccagcgca catgttcggc   3360
gaggcggggc ctgcgagcgc ggccaccgag aatcggacgg gggtagtctc aagctggccg   3420
gcctgctctg gtgcctggcc tcgcgccgcc gtgtatcgcc ccgccctggg cggcaaggct   3480
ggcccggtcg gcaccagttg cgtgagcgga aagatggccg cttcccggcc ctgctgcagg   3540
gagctcaaaa tggaggacgc ggcgctcggg agagcgggcg ggtgagtcac ccacacaaag   3600
gaaaagggcc tttccgtcct cagccgtcgc ttcatgtgac tccactgagt accgggcgcc   3660
gtccaggcac ctcgattagt tctcgtgctt ttggagtacg tcgtctttag gttgggggga   3720
ggggttttat gcgatggagt ttccccacac tgagtgggtg gagactgaag ttaggccagc   3780
ttggcacttg atgtaattct ccttggaatt tgccctttt gagtttggat cttggttcat   3840
tctcaagcct cagacagtgg ttcaaagttt ttttcttcca tttcaggtgt cgtgagctag   3900
actagtacca tggacatgcg ggtgcctgca caacttctgg gcctgctgtt gttgtggctg   3960
tctggagccc ggtgtaattg ggtaaatgtt atcagtgatc tcaagaagat agaggatctc   4020
```

```
atccagtcca tgcatattga tgccacgctg tacacagaaa gcgatgtgca tcctagctgt    4080
aaggtgacag cgatgaagtg ttttcttttg gagctgcagg taattagtct tgagtccggc    4140
gatgccagca ttcatgatac cgtagaaaac ttgattatcc tggccaacaa ttctctgtcc    4200
tcaaacggaa acgtaaccga gagcggttgt aaagaatgtg aagaactgga agaaaagaac    4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagagca agaaatgaaa gactgagaag ggagaccgtg    4560
agacctgtgg gatcctaagc tagcgtcgac aatcaacctc tggattacaa aatttgtgaa    4620
agattgactg gtattcttaa ctatgttgct ccttttacgc tatgtggata cgctgcttta    4680
atgcctttgt atcatgctat tgcttcccgt atggctttca ttttctcctc cttgtataaa    4740
tcctggttgc tgtctcttta tgaggagttg tggcccgttg tcaggcaacg tggcgtggtg    4800
tgcactgtgt ttgctgacgc aacccccact ggttggggca ttgccaccac ctgtcagctc    4860
ctttccggga ctttcgcttt ccccctccct attgccacgg cggaactcat cgccgcctgc    4920
cttgcccgct gctggacagg ggctcggctg ttgggcactg acaattccgt ggtgttgtcg    4980
gggaagctga cgtcctttcc atggctgctc gcctgtgttg ccacctggat tctgcgcggg    5040
acgtccttct gctacgtccc ttcggccctc aatccagcgg accttccttc ccgcggcctg    5100
ctgccggctc tgcggcctct tccgcgtctt cgccttcgcc ctcagacgag tcggatctcc    5160
ctttgggccg cctccccgcc tggaattcga gctcggtacc tttaagacca atgacttaca    5220
aggcagctgt agatcttagc cactttttaa agaaaaggg gggactggaa gggctaattc    5280
actcccaacg aagacaagat ctgctttttg cttgtactgg gtctctctgg ttagaccaga    5340
tctgagcctg ggagctctct ggctaactag ggaacccact gcttaagcct caataaagct    5400
tgccttgagt gcttcaagta gtgtgtgccc gtctgttgtg tgactctggt aactagagat    5460
ccctcagacc cttttagtca gtgtggaaaa tctctagcag tagtagttca tgtcatctta    5520
ttattcagta tttataactt gcaaagaaat gaatatcaga gagtgagagg aacttgttta    5580
ttgcagctta taatggttac aaataaagca atagcatcac aaatttcaca aataaagcat    5640
ttttttcact gcattctagt tgtggtttgt ccaaactcat caatgtatct tatcatgtct    5700
ggctctagct atcccgcccc taactccgcc cagttccgcc cattctccgc cccatggctg    5760
actaattttt tttatttatg cagaggccga ggccgcctcg gcctctgagc tattccagaa    5820
gtagtgagga ggcttttttg gaggcctagg cttttgcgtc gagacgtacc caattcgccc    5880
tatagtgagt cgtattacgc gcgctcactg gccgtcgttt tacaacgtcg tgactgggaa    5940
aaccctggcg ttacccaact taatcgcctt gcagcacatc cccctttcgc cagctggcgt    6000
aatagcgaag aggcccgcac cgatcgccct tcccaacagt tgcgcagcct gaatggcgaa    6060
tggcgcgacg cgccctgtag cggcgcatta agcgcggcgg gtgtggtggt tacgcgcagc    6120
gtgaccgcta cacttgccag cgccctagcg cccgctcctt tcgctttctt cccttccttt    6180
ctcgccacgt tcgccggctt tccccgtcaa gctctaaatc ggggggctccc tttagggttc    6240 cgatttagtg ctttacggca cctcgacccc aaaaaacttg attagggtga tggttcacgt    6300
agtgggccat cgccctgata gacggttttt cgccctttga cgttggagtc cacgttcttt    6360
aatagtggac tcttgttcca aactggaaca acactcaacc ctatctcggt ctattctttt    6420
```

```
gattttataag ggattttgcc gatttcggcc tattggttaa aaaatgagct gatttaacaa    6480
aaatttaacg cgaattttaa caaaatatta acgtttacaa tttcccaggt ggcacttttc    6540
ggggaaatgt gcgcggaacc cctatttgtt tattttctta aatacattca aatatgtatc    6600
cgctcatgag acaataaccc tgataaatgc ttcaataata ttgaaaaagg aagagtatga    6660
gtattcaaca tttccgtgtc gcccttattc cttttttgc ggcattttgc cttcctgttt    6720
ttgctcaccc agaaacgctg gtgaaagtaa aagatgctga agatcagttg ggtgcacgag    6780
tgggttacat cgaactggat ctcaacagcg gtaagatcct tgagagtttt cgccccgaag    6840
aacgttttcc aatgatgagc acttttaaag ttctgctatg tggcgcggta ttatcccgta    6900
ttgacgccgg gcaagagcaa ctcggtcgcc gcatacacta ttctcagaat gacttggttg    6960
agtactcacc agtcacagaa aagcatctta cggatggcat gacagtaaga gaattatgca    7020
gtgctgccat aaccatgagt gataacactg cggccaactt acttctgaca acgatcggag    7080
gaccgaagga gctaaccgct ttttttgcaca catgggggga tcatgtaact cgccttgatc    7140
gttgggaacc ggagctgaat gaagccatac caaacgacga gcgtgacacc acgatgcctg    7200
tagcaatggc aacaacgttg cgcaaactat taactggcga actacttact ctagcttccc    7260
ggcaacaatt aatagactgg atggaggcgg ataaagttgc aggaccactt ctgcgctcgg    7320
cccttccggc tggctggttt attgctgata aatctggagc cggtgagcgt gggtctcgcg    7380
gtatcattgc agcactgggg ccagatggta agccctcccg tatcgtagtt atctacacga    7440
cggggagtca ggcaactatg gatgaacgaa atagacagat cgctgagata ggtgcctcac    7500
tgattaagca ttggtaactg tcagaccaag tttactcata tatactttag attgatttaa    7560
aacttcattt ttaatttaaa aggatctagg tgaagatcct ttttgataat ctcatgacca    7620
aaatccctta acgtgagttt tcgttccact gagcgtcaga ccccgtagaa aagatcaaag    7680
gatcttcttg agatcctttt tttctgcgcg taatctgctg cttgcaaaca aaaaaaccac    7740
cgctaccagc ggtggtttgt ttgccggatc aagagctacc aactcttttt ccgaaggtaa    7800
ctggcttcag cagagcgcag ataccaaata ctgtccttct agtgtagccg tagttaggcc    7860
accacttcaa gaactctgta gcaccgccta catacctcgc tctgctaatc ctgttaccag    7920
tggctgctgc cagtggcgat aagtcgtgtc ttaccgggtt ggactcaaga cgatagttac    7980
cggataaggc gcagcggtcg ggctgaacgg ggggttcgtg cacacagccc agcttggagc    8040
gaacgaccta caccgaactg agatacctac agcgtgagct atgagaaagc gccacgcttc    8100
ccgaagggag aaaggcggac aggtatccgg taagcggcag ggtcggaaca ggagagcgca    8160
cgagggagct tccaggggga aacgcctggt atctttatag tcctgtcggg tttcgccacc    8220
tctgacttga gcgtcgattt ttgtgatgct cgtcaggggg gcggagccta tggaaaaacg    8280
ccagcaacgc ggccttttta cggttcctgg ccttttgctg gccttttgct cacatgttct    8340
ttcctgcgtt atcccctgat tctgtggata accgtattac cgcc                     8384
```

<210> SEQ ID NO 37
<211> LENGTH: 9161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
tttgagtgag ctgataccgc tcgccgcagc cgaacgaccg agcgcagcga gtcagtgagc    60
```

```
gaggaagcgg aagagcgccc aatacgcaaa ccgcctctcc ccgcgcgttg gccgattcat    120
taatgcagct ggcacgacag gtttcccgac tggaaagcgg gcagtgagcg caacgcaatt    180
aatgtgagtt agctcactca ttaggcaccc caggctttac actttatgct tccggctcgt    240
atgttgtgtg gaattgtgag cggataacaa tttcacacag gaaacagcta tgaccatgat    300
tacgccaagc gcgcaattaa ccctcactaa agggaacaaa agctggagct gcaagcttaa    360
tgtagtctta tgcaatactc ttgtagtctt gcaacatggt aacgatgagt tagcaacatg    420
ccttacaagg agagaaaaag caccgtgcat gccgattggt ggaagtaagg tggtacgatc    480
gtgccttatt aggaaggcaa cagacgggtc tgacatggat tggacgaacc actgaattgc    540
cgcattgcag agatattgta tttaagtgcc tagctcgata caataaacgg gtctctctgg    600
ttagaccaga tctgagcctg ggagctctct ggctaactag ggaacccact gcttaagcct    660
caataaagct tgccttgagt gcttcaagta gtgtgtgccc gtctgttgtg tgactctggt    720
aactagagat ccctcagacc cttttagtca gtgtggaaaa tctctagcag tggcgcccga    780
acagggacct gaaagcgaaa gggaaaccag agctctctcg acgcaggact cggcttgctg    840
aagcgcgcac ggcaagaggc gaggggcggc gactggtgag tacgccaaaa attttgacta    900
gcggaggcta aaggagaga gatgggtgcg agagcgtcag tattaagcgg gggagaatta    960
gatcgcgatg ggaaaaaatt cggttaaggc caggggggaaa gaaaaaatat aaattaaaac   1020
atatagtatg ggcaagcagg gagctagaac gattcgcagt taatcctggc ctgttagaaa   1080
catcagaagg ctgtagacaa atactgggac agctacaacc atcccttcag acaggatcag   1140
aagaacttag atcattatat aatacagtag caaccctcta ttgtgtgcat caaaggatag   1200
agataaaaga caccaaggaa gctttagaca agatagagga agagcaaaac aaaagtaaga   1260
ccaccgcaca gcaagcggcc gctgatcttc agacctggag gaggagatat gagggacaat   1320
tggagaagtg aattatataa atataaagta gtaaaaattg aaccattagg agtagcaccc   1380
accaaggcaa agagaagagt ggtgcagaga gaaaaaagag cagtgggaat aggagctttg   1440
ttccttgggt tcttgggagc agcaggaagc actatgggcg cagcctcaat gacgctgacg   1500
gtacaggcca gacaattatt gtctggtata gtgcagcagc agaacaattt gctgagggct   1560
attgaggcgc aacagcatct gttgcaactc acagtctggg gcatcaagca gctccaggca   1620
agaatcctgg ctgtggaaag atacctaaag gatcaacagc tcctgggat ttggggttgc   1680 tctggaaaac tcatttgcac cactgctgtg ccttggaatg ctagttggag taataaatct   1740
ctggaacaga ttggaatcac acgacctgga tggagtggga cagagaaatt aacaattaca   1800
caagcttaat acactcctta attgaagaat cgcaaaacca gcaagaaaag aatgaacaag   1860
aattattgga attagataaa tgggcaagtt tgtggaattg gtttaacata acaaattggc   1920
tgtggtatat aaaattattc ataatgatag taggaggctt ggtaggttta agaatagttt   1980
ttgctgtact ttctatagtg aatagagtta ggcaggata ttcaccatta tcgtttcaga   2040
cccacctccc aaccccgagg ggacccgaca ggcccgaagg aatagaagaa gaaggtggag   2100
agagagacag agacagatcc attcgattag tgaacggatc tcgacggtat cgattagact   2160
gtagcccagg aatatggcag ctagattgta cacatttaga aggaaaagtt atcttggtag   2220
cagttcatgt agccagtgga tatatagaag cagaagtaat tccagcagag acagggcaag   2280
aaacagcata cttcctctta aaattagcag gaagatggcc agtaaaaaca gtacatacag   2340
acaatggcag caatttcacc agtactacag ttaaggccgc ctgttggtgg gcggggatca   2400
```

```
agcaggaatt tggcattccc tacaatcccc aaagtcaagg agtaatagaa tctatgaata    2460
aagaattaaa gaaaattata ggacaggtaa gagatcaggc tgaacatctt aagacagcag    2520
tacaaatggc agtattcatc cacaatttta aaagaaaagg ggggattggg gggtacagtg    2580
caggggaaag aatagtagac ataatagcaa cagacataca aactaaagaa ttacaaaaac    2640
aaattacaaa aattcaaaat tttcgggttt attacaggga cagcagagat ccagtttggc    2700
tgcatacgcg tcgtgaggct ccggtgcccg tcagtgggca gagcgcacat cgcccacagt    2760
ccccgagaag ttgggggggag gggtcggcaa ttgaaccggt gcctagagaa ggtggcgcgg    2820
ggtaaactgg gaaagtgatg tcgtgtactg gctccgcctt tttcccgagg gtgggggaga    2880
accgtatata agtgcagtag tcgccgtgaa cgttctttt cgcaacgggt ttgccgccag     2940
aacacaggta agtgccgtgt gtggttcccg cgggcctggc ctctttacgg gttatggccc    3000
ttgcgtgcct tgaattactt ccacctggct gcagtacgtg attcttgatc ccgagcttcg    3060
ggttggaagt gggtgggaga gttcgaggcc ttgcgcttaa ggagccccctt cgcctcgtgc   3120
ttgagttgag gcctggcctg ggcgctgggg ccgccgcgtg cgaatctggt ggcaccttcg    3180
cgcctgtctc gctgctttcg ataagtctct agccatttaa aatttttgat gacctgctgc    3240
gacgcttttt ttctggcaag atagtcttgt aaatgcgggc caagatctgc acactggtat    3300
ttcggtttt ggggccgcgg gcggcgacgg ggcccgtgcg tcccagcgca catgttcggc     3360
gaggcggggc ctgcgagcgc ggccaccgag aatcggacgg gggtagtctc aagctggccg    3420
gcctgctctg gtgcctggcc tcgcgccgcc gtgtatcgcc ccgccctggg cggcaaggct    3480
ggcccggtcg gcaccagttg cgtgagcgga aagatggccg cttcccggcc ctgctgcagg    3540
gagctcaaaa tggaggacgc ggcgctcggg agagcgggcg ggtgagtcac ccacacaaag    3600
gaaaagggcc tttccgtcct cagccgtcgc ttcatgtgac tccactgagt accgggcgcc    3660
gtccaggcac ctcgattagt tctcgtgctt ttggagtacg tcgtctttag gttgggggga    3720
ggggttttat gcgatggagt ttccccacac tgagtgggtg gagactgaag ttaggccagc    3780
ttggcacttg atgtaattct ccttggaatt tgccctttt gagtttggat cttggttcat     3840
tctcaagcct cagacagtgg ttcaaagttt ttttcttcca tttcaggtgt cgtgagctag    3900
actagtacca tggacatgcg ggtgcctgca caacttctgg gcctgctgtt gttgtggctg    3960
tctggagccc ggtgtaattg ggtaaatgtt atcagtgatc tcaagaagat agaggatctc    4020
atccagtcca tgcatattga tgccacgctg tacacagaaa gcgatgtgca tcctagctgt    4080
aaggtgacag cgatgaagtg ttttctttg gagctgcagg taattagtct tgagtccggc     4140
gatgccagca ttcatgatac cgtagaaaac ttgattatcc tggccaacaa ttctctgtcc    4200
tcaaacggaa acgtaaccga gagcggttgt aagaatgtg aagaactgga agaaaagaac      4260
atcaaggagt ttctgcaatc attcgttcac atcgtacaaa tgttcataaa tacgtcagga    4320
tctggttctg gttccggaag tggatctggt tcagggtccg gtagtggatc tgggtcagga    4380
agtggaagcg gtagtgggtc tggatctaaa caagagcact ttcctgataa cctgttgccg    4440
agctgggcga ttacgcttat cagtgtaaac ggcatctttg taatatgctg tctgacctac    4500
tgcttcgcac caaggtgccg ggagagagca agaaatgaaa gactgagaag ggagaccgtg    4560
agacctgtgg gatcctccca tcactggggg tacggcaaac acaacggacc tgagcactgg    4620
cataaggact tccccattgc caagggagag cgccagtccc ctgttgacat cgacactcat    4680
acagccaagt atgacccttc cctgaagccc ctgtctgttt cctatgatca agcaacttcc    4740
ctgagaatcc tcaacaatgg tcatgctttc aacgtggagt ttgatgactc tcaggacaaa    4800
```

| | |
|---|---|
| gcagtgctca agggaggacc cctggatggc acttacagat tgattcagtt tcactttcac | 4860 |
| tggggttcac ttgatggaca aggttcagag catactgtgg ataaaaagaa atatgctgca | 4920 |
| gaacttcact tggttcactg aacaccaaa tatggggatt ttgggaaagc tgtgcagcaa | 4980 |
| cctgatggac tggccgttct aggtattttt ttgaaggttg gcagcgctaa accgggccat | 5040 |
| cagaaagttg ttgatgtgct ggattccatt aaaacaaagg gcaagagtgc tgacttcact | 5100 |
| aacttcgatc ctcgtggcct ccttcctgaa tccctggatt actggaccta cccaggctca | 5160 |
| ctgaccaccc ctcctcttct ggaatgtgtg acctggattg tgctcaagga acccatcagc | 5220 |
| gtcagcagcg agcaggtgtt gaaattccgt aaacttaact tcaatgggga gggtgaaccc | 5280 |
| gaagaactga tggtggacaa ctggcgccca gctcagccac tgaagaacag gcaaatcaaa | 5340 |
| gcttccttca aataagctag cgtcgacaat caacctctgg attacaaaat tgtgaaaga | 5400 |
| ttgactggta ttcttaacta tgttgctcct tttacgctat gtggatacgc tgctttaatg | 5460 |
| cctttgtatc atgctattgc ttcccgtatg gctttcattt tctcctcctt gtataaatcc | 5520 |
| tggttgctgt ctctttatga ggagttgtgg cccgttgtca ggcaacgtgg cgtggtgtgc | 5580 |
| actgtgtttg ctgacgcaac ccccactggt tggggcattg ccaccacctg tcagctcctt | 5640 |
| tccgggactt tcgctttccc cctccctatt gccacggcgg aactcatcgc cgcctgcctt | 5700 |
| gcccgctgct ggacagggc tcggctgttg gcactgaca attccgtggt gttgtcgggg | 5760 |
| aagctgacgt cctttccatg gctgctcgcc tgtgttgcca cctggattct gcgcgggacg | 5820 |
| tccttctgct acgtcccttc ggccctcaat ccagcggacc ttccttcccg cggcctgctg | 5880 |
| ccggctctgc ggcctcttcc gcgtcttcgc cttcgccctc agacgagtcg atctccctt | 5940 |
| tgggccgcct ccccgcctgg aattcgagct cggtaccttt aagaccaatg acttacaagg | 6000 |
| cagctgtaga tcttagccac ttttttaaaag aaaagggggg actggaaggg ctaattcact | 6060 |
| cccaacgaag acaagatctg cttttttgctt gtactgggtc tctctggtta gaccagatct | 6120 |
| gagcctggga gctctctggc taactaggga acccactgct taagcctcaa taaagcttgc | 6180 |
| cttgagtgct tcaagtagtg tgtgcccgtc tgttgtgtga ctctggtaac tagagatccc | 6240 |
| tcagaccctt ttagtcagtg tggaaaatct ctagcagtag tagttcatgt catcttatta | 6300 |
| ttcagtattt ataacttgca aagaaatgaa tatcagagag tgagaggaac ttgtttattg | 6360 |
| cagcttataa tggttacaaa taagcaata gcatcacaaa tttcacaaat aaagcatttt | 6420 |
| tttcactgca ttctagttgt ggtttgtcca aactcatcaa tgtatcttat catgtctggc | 6480 |
| tctagctatc ccgcccctaa ctccgcccag ttccgcccat tctccgcccc atggctgact | 6540 |
| aattttttt atttatgcag aggccgaggc cgcctcggcc tctgagctat tccagaagta | 6600 |
| gtgaggaggc tttttggag cctaggctt ttgcgtcgag acgtacccaa ttcgccctat | 6660 |
| agtgagtcgt attacgcgcg ctcactggcc gtcgttttac aacgtcgtga ctgggaaaac | 6720 |
| cctggcgtta cccaacttaa tcgccttgca gcacatcccc ctttcgccag ctggcgtaat | 6780 |
| agcgaagagg cccgcaccga tcgcccttcc caacagttgc gcagcctgaa tggcgaatgg | 6840 |
| cgcgacgcgc cctgtagcgg cgcattaagc gcggcgggtg tggtggttac gcgcagcgtg | 6900 |
| accgctacac ttgccagcgc cctagcgccc gctcctttcg ctttcttccc ttcctttctc | 6960 |
| gccacgttcg ccggctttcc ccgtcaagct ctaaatcggg gctcccttt agggttccga | 7020 |
| tttagtgctt tacggcacct cgaccccaaa aaacttgatt agggtgatgg ttcacgtagt | 7080 |
| gggccatcgc cctgatagac ggtttttcgc cctttgacgt tggagtccac gttctttaat | 7140 |

| | |
|---|---|
| agtggactct tgttccaaac tggaacaaca ctcaaccctacc tctcggtcta ttcttttgat | 7200 |
| ttataaggga ttttgccgat ttcggcctat tggttaaaaa atgagctgat ttaacaaaaa | 7260 |
| tttaacgcga atttaacaa aatattaacg tttacaattt cccaggtggc acttttcggg | 7320 |
| gaaatgtgcg cggaacccct atttgtttat ttttctaaat acattcaaat atgtatccgc | 7380 |
| tcatgagaca ataaccctga taaatgcttc aataatattg aaaaaggaag agtatgagta | 7440 |
| ttcaacattt ccgtgtcgcc cttattccct tttttgcggc attttgcctt cctgtttttg | 7500 |
| ctcacccaga aacgctggtg aaagtaaaag atgctgaaga tcagttgggt gcacgagtgg | 7560 |
| gttacatcga actggatctc aacagcggta agatccttga gagttttcgc cccgaagaac | 7620 |
| gttttccaat gatgagcact tttaaagttc tgctatgtgg cgcggtatta tcccgtattg | 7680 |
| acgccgggca agagcaactc ggtcgccgca tacactattc tcagaatgac ttggttgagt | 7740 |
| actcaccagt cacagaaaag catcttacgg atggcatgac agtaagagaa ttatgcagtg | 7800 |
| ctgccataac catgagtgat aacactgcgg ccaacttact tctgacaacg atcggaggac | 7860 |
| cgaaggagct aaccgctttt ttgcacaaca tgggggatca tgtaactcgc cttgatcgtt | 7920 |
| gggaaccgga gctgaatgaa gccataccaa acgacgagcg tgacaccacg atgcctgtag | 7980 |
| caatggcaac aacgttgcgc aaactattaa ctggcgaact acttactcta gcttcccggc | 8040 |
| aacaattaat agactggatg gaggcggata aagttgcagg accacttctg cgctcggccc | 8100 |
| ttccggctgg ctggtttatt gctgataaat ctggagccgg tgagcgtggg tctcgcggta | 8160 |
| tcattgcagc actggggcca gatggtaagc cctcccgtat cgtagttatc tacacgacgg | 8220 |
| ggagtcaggc aactatggat gaacgaaata gacagatcgc tgagataggt gcctcactga | 8280 |
| ttaagcattg gtaactgtca gaccaagttt actcatatat actttagatt gatttaaaac | 8340 |
| ttcatttta atttaaaagg atctaggtga agatcctttt tgataatctc atgaccaaaa | 8400 |
| tcccttaacg tgagttttcg ttccactgag cgtcagaccc cgtagaaaag atcaaaggat | 8460 |
| cttcttgaga tccttttttt ctgcgcgtaa tctgctgctt gcaaacaaaa aaaccaccgc | 8520 |
| taccagcggt ggtttgtttg ccggatcaag agctaccaac tcttttttccg aaggtaactg | 8580 |
| gcttcagcag agcgcagata ccaaatactg tccttctagt gtagccgtag ttaggccacc | 8640 |
| acttcaagaa ctctgtagca ccgcctacat acctcgctct gctaatcctg ttaccagtgg | 8700 |
| ctgctgccag tggcgataag tcgtgtctta ccgggttgga ctcaagacga tagttaccgg | 8760 |
| ataaggcgca gcggtcgggc tgaacggggg gttcgtgcac acagcccagc ttggagcgaa | 8820 |
| cgacctacac cgaactgaga tacctacagc gtgagctatg agaaagcgcc acgcttcccg | 8880 |
| aagggagaaa ggcggacagg tatccggtaa gcggcagggt cggaacagga gagcgcacga | 8940 |
| gggagcttcc agggggaaac gcctggtatc tttatagtcc tgtcgggttt cgccacctct | 9000 |
| gacttgagcg tcgatttttg tgatgctcgt caggggggcg gagcctatgg aaaaacgcca | 9060 |
| gcaacgcggc cttttacgg ttcctggcct tttgctggcc ttttgctcac atgttctttc | 9120 |
| ctgcgttatc ccctgattct gtggataacc gtattaccgc c | 9161 |

<210> SEQ ID NO 38
<211> LENGTH: 485
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Ala Leu Pro Val Thr Ala Leu Leu Leu Pro Leu Ala Leu Leu His
1               5                   10                  15

Ala Ala Arg Pro Asp Ile Gln Met Thr Gln Thr Thr Ser Ser Leu Ser
            20                  25                  30

Ala Ser Leu Gly Asp Arg Val Thr Ile Ser Cys Arg Ala Ser Gln Asp
            35                  40                  45

Ile Ser Lys Tyr Leu Asn Trp Tyr Gln Gln Lys Pro Asp Gly Thr Val
50                  55                  60

Lys Leu Leu Ile Tyr His Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Thr Leu Pro Tyr Thr Phe Gly Gly Gly Thr Lys Leu Glu Ile Thr Gly
        115                 120                 125

Gly Gly Gly Ser Gly Gly Gly Ser Gly Gly Gly Ser Glu Val
130                 135                 140

Lys Leu Gln Glu Ser Gly Pro Gly Leu Val Ala Pro Ser Gln Ser Leu
145                 150                 155                 160

Ser Val Thr Cys Thr Val Ser Gly Val Ser Leu Pro Asp Tyr Gly Val
                165                 170                 175

Ser Trp Ile Arg Gln Pro Pro Arg Lys Gly Leu Glu Trp Leu Gly Val
            180                 185                 190

Ile Trp Gly Ser Glu Thr Thr Tyr Tyr Asn Ser Ala Leu Lys Ser Arg
        195                 200                 205

Leu Thr Ile Ile Lys Asp Asn Ser Lys Ser Gln Val Phe Leu Lys Met
210                 215                 220

Asn Ser Leu Gln Thr Asp Asp Thr Ala Ile Tyr Tyr Cys Ala Lys His
225                 230                 235                 240

Tyr Tyr Tyr Gly Gly Ser Tyr Ala Met Asp Tyr Trp Gly Gln Gly Thr
            245                 250                 255

Ser Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
            325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu
        355                 360                 365

Gly Gly Cys Glu Leu Arg Val Lys Phe Ser Arg Ser Ala Asp Ala Pro
370                 375                 380

Ala Tyr Lys Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
```

```
                420             425             430
Asn Glu Leu Gln Lys Asp Lys Met Ala Glu Ala Tyr Ser Glu Ile Gly
            435                 440                 445

Met Lys Gly Glu Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 39
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gccttaccag tgaccgcctt gctcctgccg ctggccttgc tgctccacgc cgccaggccg      60
gacatccaga tgacacagac tacatcctcc ctgtctgcct ctctgggaga cagagtcacc     120
atcagttgca gggcaagtca ggacattagt aaatatttaa attggtatca gcagaaacca     180
gatggaactg ttaaactcct gatctaccat acatcaagat acactcagg agtcccatca      240 aggttcagtg gcagtgggtc tggaacagat tattctctca ccattagcaa cctggagcaa     300
gaagatattg ccacttactt tgccaacag gtaatacgc ttccgtacac gttcggaggg       360
gggaccaagc tggagatcac aggtggcggt ggctcgggcg gtggtgggtc gggtggcggc     420
ggatctgagg tgaaactgca ggagtcagga cctggcctgg tggcgccctc acagagcctg     480
tccgtcacat gcactgtctc aggggtctca ttacccgact atggtgtaag ctggattcgc     540
cagcctccac gaaagggtct ggagtggctg gagtaatat ggggtagtga aaccacatac      600
tataattcag ctctcaaatc cagactgacc atcatcaagg acaactccaa gagccaagtt     660
ttcttaaaaa tgaacagtct gcaaactgat gacacagcca tttactactg tgccaaacat     720
tattactacg gtggtagcta tgctatggac tactggggcc aaggaacctc agtcaccgtc     780
tcctcaacca cgacgccagc gccgcgacca ccaacaccgg cgcccaccat cgcgtcgcag     840 ccctgtccc tgcgcccaga ggcgtgccgg ccagcggcgg ggggcgcagt gcacacgagg     900
gggctggact cgcctgtga tatctacatc tgggcgccct tggccgggac ttgtgggggtc     960 cttctcctgt cactggttat ccccttac tgcaaacggg gcagaaagaa actcctgtat      1020
atattcaaac aaccatttat gagaccagta caaactactc aagaggaaga tggctgtagc    1080
tgccgatttc cagaagaaga agaaggagga tgtgaactga gagtgaagtt cagcaggagc    1140
gcagacgccc ccgcgtacaa gcagggccag aaccagctct ataacgagct caatctagga    1200
cgaagagagg agtacgatgt tttggacaag agacgtggcc gggaccctga gatgggggga    1260
aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgc                                                    1455

<210> SEQ ID NO 40
<211> LENGTH: 19
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 40

Ala Thr Asn Phe Ser Leu Leu Lys Gln Ala Gly Asp Val Glu Asn
1               5                   10                  15

Pro Gly Pro

<210> SEQ ID NO 41
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
gctactaact tcagcctgct gaagcaggct ggagacgtgg aggagaaccc tggacct      57

<210> SEQ ID NO 42
<211> LENGTH: 989
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
                20                  25                  30

Lys Ile Glu Asp Leu Ile Gln Ser Met His Ile Asp Ala Thr Leu Tyr
            35                  40                  45

Thr Glu Ser Asp Val His Pro Ser Cys Lys Val Thr Ala Met Lys Cys
        50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg Arg
        195                 200                 205

Asn Glu Arg Leu Arg Arg Glu Ser Val Arg Pro Val Gly Ser Ser His
    210                 215                 220

His Trp Gly Tyr Gly Lys His Asn Gly Pro Glu His Trp His Lys Asp

```
                225                 230                 235                 240

Phe Pro Ile Ala Lys Gly Glu Arg Gln Ser Pro Val Asp Ile Asp Thr
                         245                 250                 255

His Thr Ala Lys Tyr Asp Pro Ser Leu Lys Pro Leu Ser Val Ser Tyr
                         260                 265                 270

Asp Gln Ala Thr Ser Leu Arg Ile Leu Asn Asn Gly His Ala Phe Asn
                         275                 280                 285

Val Glu Phe Asp Asp Ser Gln Asp Lys Ala Val Leu Lys Gly Gly Pro
                 290                 295                 300

Leu Asp Gly Thr Tyr Arg Leu Ile Gln Phe His Phe His Trp Gly Ser
         305                 310                 315                 320

Leu Asp Gly Gln Gly Ser Glu His Thr Val Asp Lys Lys Tyr Ala
                         325                 330                 335

Ala Glu Leu His Leu Val His Trp Asn Thr Lys Tyr Gly Asp Phe Gly
                         340                 345                 350

Lys Ala Val Gln Gln Pro Asp Gly Leu Ala Val Leu Gly Ile Phe Leu
                         355                 360                 365

Lys Val Gly Ser Ala Lys Pro Gly His Gln Lys Val Val Asp Val Leu
                 370                 375                 380

Asp Ser Ile Lys Thr Lys Gly Lys Ser Ala Asp Phe Thr Asn Phe Asp
         385                 390                 395                 400

Pro Arg Gly Leu Leu Pro Glu Ser Leu Asp Tyr Trp Thr Tyr Pro Gly
                         405                 410                 415

Ser Leu Thr Thr Pro Pro Leu Leu Glu Cys Val Thr Trp Ile Val Leu
                         420                 425                 430

Lys Glu Pro Ile Ser Val Ser Ser Glu Gln Val Leu Lys Phe Arg Lys
                         435                 440                 445

Leu Asn Phe Asn Gly Glu Gly Glu Pro Glu Glu Leu Met Val Asp Asn
                 450                 455                 460

Trp Arg Pro Ala Gln Pro Leu Lys Asn Arg Gln Ile Lys Ala Ser Phe
         465                 470                 475                 480

Lys Gly Ser Gly Ala Thr Asn Phe Ser Leu Leu Lys Gln Ala Gly Asp
                         485                 490                 495

Val Glu Glu Asn Pro Gly Pro Met Ala Leu Pro Val Thr Ala Leu Leu
                 500                 505                 510

Leu Pro Leu Ala Leu Leu Leu His Ala Ala Arg Pro Asp Ile Gln Met
                 515                 520                 525

Thr Gln Thr Thr Ser Ser Leu Ser Ala Ser Leu Gly Asp Arg Val Thr
                 530                 535                 540

Ile Ser Cys Arg Ala Ser Gln Asp Ile Ser Lys Tyr Leu Asn Trp Tyr
         545                 550                 555                 560

Gln Gln Lys Pro Asp Gly Thr Val Lys Leu Leu Ile Tyr His Thr Ser
                         565                 570                 575

Arg Leu His Ser Gly Val Pro Ser Arg Phe Ser Gly Ser Gly Ser Gly
                         580                 585                 590

Thr Asp Tyr Ser Leu Thr Ile Ser Asn Leu Glu Gln Glu Asp Ile Ala
                         595                 600                 605

Thr Tyr Phe Cys Gln Gln Gly Asn Thr Leu Pro Tyr Thr Phe Gly Gly
                         610                 615                 620

Gly Thr Lys Leu Glu Ile Thr Gly Gly Gly Ser Gly Gly Gly Gly
         625                 630                 635                 640

Ser Gly Gly Gly Gly Ser Glu Val Lys Leu Gln Glu Ser Gly Pro Gly
                         645                 650                 655
```

Leu Val Ala Pro Ser Gln Ser Leu Ser Val Thr Cys Thr Val Ser Gly
            660                 665                 670

Val Ser Leu Pro Asp Tyr Gly Val Ser Trp Ile Arg Gln Pro Pro Arg
        675                 680                 685

Lys Gly Leu Glu Trp Leu Gly Val Ile Trp Gly Ser Glu Thr Thr Tyr
    690                 695                 700

Tyr Asn Ser Ala Leu Lys Ser Arg Leu Thr Ile Ile Lys Asp Asn Ser
705                 710                 715                 720

Lys Ser Gln Val Phe Leu Lys Met Asn Ser Leu Gln Thr Asp Asp Thr
                725                 730                 735

Ala Ile Tyr Tyr Cys Ala Lys His Tyr Tyr Gly Gly Ser Tyr Ala
            740                 745                 750

Met Asp Tyr Trp Gly Gln Gly Thr Ser Val Thr Val Ser Ser Thr Thr
        755                 760                 765

Thr Pro Ala Pro Arg Pro Pro Thr Pro Ala Pro Thr Ile Ala Ser Gln
    770                 775                 780

Pro Leu Ser Leu Arg Pro Glu Ala Cys Arg Pro Ala Ala Gly Gly Ala
785                 790                 795                 800

Val His Thr Arg Gly Leu Asp Phe Ala Cys Asp Ile Tyr Ile Trp Ala
                805                 810                 815

Pro Leu Ala Gly Thr Cys Gly Val Leu Leu Leu Ser Leu Val Ile Thr
            820                 825                 830

Leu Tyr Cys Lys Arg Gly Arg Lys Lys Leu Leu Tyr Ile Phe Lys Gln
        835                 840                 845

Pro Phe Met Arg Pro Val Gln Thr Thr Gln Glu Glu Asp Gly Cys Ser
    850                 855                 860

Cys Arg Phe Pro Glu Glu Glu Glu Gly Gly Cys Glu Leu Arg Val Lys
865                 870                 875                 880

Phe Ser Arg Ser Ala Asp Ala Pro Ala Tyr Lys Gln Gly Gln Asn Gln
                885                 890                 895

Leu Tyr Asn Glu Leu Asn Leu Gly Arg Arg Glu Glu Tyr Asp Val Leu
            900                 905                 910

Asp Lys Arg Arg Gly Arg Asp Pro Glu Met Gly Gly Lys Pro Arg Arg
        915                 920                 925

Lys Asn Pro Gln Glu Gly Leu Tyr Asn Glu Leu Gln Lys Asp Lys Met
    930                 935                 940

Ala Glu Ala Tyr Ser Glu Ile Gly Met Lys Gly Glu Arg Arg Arg Gly
945                 950                 955                 960

Lys Gly His Asp Gly Leu Tyr Gln Gly Leu Ser Thr Ala Thr Lys Asp
                965                 970                 975

Thr Tyr Asp Ala Leu His Met Gln Ala Leu Pro Pro Arg
            980                 985

<210> SEQ ID NO 43
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120

```
atgcatattg atgccacgct gtacacagaa agcgatgtgc atcctagctg taaggtgaca      180
gcgatgaagt gttttctttt ggagctgcag gtaattagtc ttgagtccgg cgatgccagc      240
attcatgata ccgtagaaaa cttgattatc ctggccaaca attctctgtc ctcaaacgga      300
aacgtaaccg agagcggttg taaagaatgt gaagaactgg aagaaaagaa catcaaggag      360
tttctgcaat cattcgttca catcgtacaa atgttcataa atacgtcagg atctggttct      420
ggttccggaa gtggatctgg ttcagggtcc ggtagtggat ctgggtcagg aagtggaagc      480
ggtagtgggt ctggatctaa acaagagcac tttcctgata acctgttgcc gagctgggcg      540
attacgctta tcagtgtaaa cggcatcttt gtaatatgct gtctgaccta ctgcttcgca      600
ccaaggtgcc gggagagaag gagaaatgaa agactgagaa gggagagcgt gagacctgtg      660
ggatcctccc atcactgggg gtacggcaaa acaacggac ctgagcactg gcataaggac       720
ttccccattg ccaagggaga gcgccagtcc cctgttgaca tcgacactca tacagccaag      780 tatgacccctt ccctgaagcc cctgtctgtt tcctatgatc aagcaacttc cctgagaatc     840
ctcaacaatg gtcatgcttt caacgtggag tttgatgact tcaggacaa agcagtgctc      900 aagggaggac ccctggatgg cacttacaga ttgattcagt ttcactttca ctggggttca     960
cttgatggac aaggttcaga gcatactgtg gataaaaaga aatatgctgc agaacttcac     1020
ttggttcact ggaacaccaa atatggggat tttgggaaag ctgtgcagca acctgatgga     1080
ctggccgttc taggtatttt tttgaaggtt ggcagcgcta aaccgggcca tcagaaagtt     1140
gttgatgtgc tggattccat taaaacaaag ggcaagagtg ctgacttcac taacttcgat     1200
cctcgtggcc tccttcctga atccctggat tactggaccc acccaggctc actgaccacc     1260
cctcctcttc tggaatgtgt gacctggatt gtgctcaagg aacccatcag cgtcagcagc     1320
gagcaggtgt tgaaattccg taaacttaac ttcaatgggg agggtgaacc cgaagaactg     1380
atggtggaca actggcgccc agctcagcca ctgaagaaca ggcaaatcaa agcttccttc     1440
aaaggatccg gagctactaa cttcagcctg ctgaagcagg ctggagacgt ggaggagaac     1500
cctggaccta tggccttacc agtgaccgcc ttgctcctgc cgctggcctt gctgctccac     1560
gccgccaggc cggacatcca gatgacacag actacatcct ccctgtctgc ctctctggga     1620
gacagagtca ccatcagttg cagggcaagt caggacatta gtaaatattt aaattggtat     1680
cagcagaaac cagatggaac tgttaaactc ctgatctacc atacatcaag attacactca     1740
ggagtcccat caaggttcag tggcagtggg tctggaacag attattctct caccattagc     1800
aacctggagc aagaagatat tgccacttac ttttgccaac agggtaatac gcttccgtac     1860
acgttcggag ggggaccaa gctggagatc acaggtggcg gtggctcggg cggtggtggg      1920
tcgggtggcg gcggatctga ggtgaaactg caggagtcag gacctggcct ggtggcgccc     1980
tcacagagcc tgtccgtcac atgcactgtc tcaggggtct cattacccga ctatggtgta     2040
agctggattc gccagcctcc acgaaagggt ctggagtggc tgggagtaat atgggggtagt     2100 gaaaccacat actataattc agctctcaaa tccagactga ccatcatcaa ggacaactcc     2160
aagagccaag ttttcttaaa aatgaacagt ctgcaaactg atgacacagc catttactac     2220
tgtgccaaac attattacta cggtggtagc tatgctatgg actactgggg ccaaggaacc     2280
tcagtcaccg tctcctcaac cacgacgcca gcgccgcgac caccaacacc ggcgcccacc     2340
atcgcgtcgc agcccctgtc cctgcgccca gaggcgtgcc ggccagcggc gggggggcgca    2400 gtgcacacga gggggctgga cttcgcctgt gatatctaca tctgggcgcc cttggccggg     2460
acttgtgggg tccttctcct gtcactggtt atcacccttt actgcaaacg gggcagaaag     2520
```

```
aaactcctgt atatattcaa acaaccattt atgagaccag tacaaactac tcaagaggaa    2580
gatggctgta gctgccgatt tccagaagaa gaagaaggag gatgtgaact gagagtgaag    2640
ttcagcagga gcgcagacgc ccccgcgtac aagcagggcc agaaccagct ctataacgag    2700
ctcaatctag gacgaagaga ggagtacgat gttttggaca agagacgtgg ccgggaccct    2760
gagatggggg gaaagccgag aaggaagaac cctcaggaag gcctgtacaa tgaactgcag    2820
aaagataaga tggcggaggc ctacagtgag attgggatga aggcgagcg ccggaggggc     2880 aaggggcacg atggccttta ccagggtctc agtacagcca ccaaggacac ctacgacgcc    2940
cttcacatgc aggccctgcc ccctcgctaa                                     2970
```

<210> SEQ ID NO 44
<211> LENGTH: 10685
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
tttgagtgag ctgataccgc tcgccgcagc cgaacgaccg agcgcagcga gtcagtgagc      60
gaggaagcgg aagagcgccc aatacgcaaa ccgcctctcc ccgcgcgttg gccgattcat     120
taatgcagct ggcacgacag gtttcccgac tggaaagcgg gcagtgagcg caacgcaatt     180
aatgtgagtt agctcactca ttaggcaccc caggctttac actttatgct tccggctcgt     240
atgttgtgtg gaattgtgag cggataacaa tttcacacag gaaacagcta tgaccatgat     300
tacgccaagc gcgcaattaa ccctcactaa agggaacaaa agctggagct gcaagcttaa     360
tgtagtctta tgcaatactc ttgtagtctt gcaacatggt aacgatgagt tagcaacatg     420
ccttacaagg agagaaaaag caccgtgcat gccgattggt ggaagtaagg tggtacgatc     480
gtgccttatt aggaaggcaa cagacgggtc tgacatggat tggacgaacc actgaattgc     540
cgcattgcag agatattgta tttaagtgcc tagctcgata cataaacggg tctctctggt     600
tagaccagat ctgagcctgg gagctctctg gctaactagg gaacccactg cttaagcctc     660
aataaagctt gccttgagtg cttcaagtag tgtgtgcccg tctgttgtgt gactctggta     720
actagagatc cctcagaccc ttttagtcag tgtggaaaat ctctagcagt ggcgcccgaa     780
cagggacttg aaagcgaaag ggaaaccaga ggagctctct cgacgcagga ctcggcttgc     840
tgaagcgcgc acggcaagag gcgaggggcg cgactggtg agtacgccaa aattttgac      900 tagcggaggc tagaaggaga gagatgggtg cgagagcgtc agtattaagc gggggagaat     960
tagatcgcga tgggaaaaaa ttcggttaag gccagggga aagaaaaaat ataaattaaa     1020
acatatagta tgggcaagca gggagctaga acgattcgca gttaatcctg gcctgttaga    1080
aacatcagaa ggctgtagac aaatactggg acagctacaa ccatcccttc agacaggatc    1140
agaagaactt agatcattat ataatacagt agcaaccctc tattgtgtgc atcaaaggat    1200
agagataaaa gacaccaagg aagctttaga caagatagag gaagagcaaa acaaaagtaa    1260
gaccaccgca cagcaagcgg ccgctgatct tcagacctgg aggaggagat atgagggaca    1320
attggagaag tgaattatat aaatataaag tagtaaaaat tgaaccatta ggagtagcac    1380
ccaccaaggc aaagaagaaga gtggtgcaga gagaaaaaag agcagtggga ataggagctt    1440
tgttccttgg gttcttggga gcagcaggaa gcactatggg cgcagcgtca atgacgctga    1500
cggtacaggc cagacaatta ttgtctggta tagtgcagca gcagaacaat ttgctgaggg    1560
```

```
ctattgaggc gcaacagcat ctgttgcaac tcacagtctg gggcatcaag cagctccagg    1620
caagaatcct ggctgtggaa agatacctaa aggatcaaca gctcctgggg atttggggtt    1680
gctctggaaa actcatttgc accactgctg tgccttggaa tgctagttgg agtaataaat    1740
ctctggaaca gatttggaat cacacgacct ggatggagtg ggacagagaa attaacaatt    1800
acacaagctt aatacactcc ttaattgaag aatcgcaaaa ccagcaagaa aagaatgaac    1860
aagaattatt ggaattagat aaatgggcaa gtttgtggaa ttggtttaac ataacaaatt    1920
ggctgtggta tataaaatta ttcataatga tagtaggagg cttggtaggt ttaagaatag    1980
tttttgctgt actttctata gtgaatagag ttaggcaggg atattcacca ttatcgtttc    2040
agacccacct cccaaccccg aggggacccg acaggcccga aggaatagaa gaagaaggtg    2100
gagagagaga cagagacaga tccattcgat tagtgaacgg atctcgacgg tatcgattag    2160
actgtagccc aggaatatgg cagctagatt gtacacattt agaaggaaaa gttatcttgg    2220
tagcagttca tgtagccagt ggatatatag aagcagaagt aattccagca gagacagggc    2280
aagaaacagc atacttcctc ttaaaattag caggaagatg gccagtaaaa acagtacata    2340
cagacaatgg cagcaatttc accagtacta cagttaaggc cgcctgttgg tgggcgggga    2400
tcaagcagga atttggcatt ccctacaatc cccaaagtca aggagtaata gaatctatga    2460
ataaagaatt aaagaaaatt ataggacagg taagagatca ggctgaacat cttaagacag    2520
cagtacaaat ggcagtattc atccacaatt ttaaaagaaa agggggggatt gggggtaca    2580 gtgcagggga agaatagta gacataatag caacagacat acaaactaaa gaattacaaa    2640
aacaaattac aaaaattcaa aattttcggg tttattacag ggacagcaga gatccagttt    2700
ggctgcattg atcacgtgag gctccggtgc ccgtcagtgg gcagagcgca catcgcccac    2760
agtccccgag aagttggggg gaggggtcgg caattgaacc ggtgcctaga aaggtggcg    2820 cggggtaaac tgggaaagtg atgtcgtgta ctggctccgc cttttttccg agggtggggg    2880
agaaccgtat ataagtgcag tagtcgccgt gaacgttctt tttcgcaacg ggtttgccgc    2940
cagaacacag gtaagtgccg tgtgtggttc ccgcgggcct ggcctcttta cgggttatgg    3000
cccttgcgtg ccttgaatta cttccacctg gctgcagtac gtgattcttg atcccgagct    3060
tcgggttgga agtgggtggg agagttcgag gccttgcgct taaggagccc cttcgcctcg    3120
tgcttgagtt gaggcctggc ctgggcgctg gggccgccgc gtgcgaatct ggtggcacct    3180
tcgcgcctgt ctcgctgctt tcgataagtc tctagccatt taaaattttt gatgacctgc    3240
tgcgacgctt ttttttctggc aagatagtct tgtaaatgcg ggccaagatc tgcacactgg    3300
tatttcggtt tttggggccg cgggcggcga cggggcccgt gcgtcccagc gcacatgttc    3360
ggcgaggcgg ggcctgcgag cgcggccacc gagaatcgga cggggggtagt ctcaagctgg    3420 ccggcctgct ctggtgcctg gcctcgcgcc gccgtgtatc gccccgccct gggcggcaag    3480
gctgccccgg tcggcaccag ttgcgtgagc ggaaagatgg ccgcttcccg gccctgctgc    3540
agggagctca aaatggagga cgcggcgctc gggagagcgg gcgggtgagt cacccacaca    3600
aaggaaaagg gccttttccgt cctcagccgt cgcttcatgt gactccactg agtaccgggc    3660
gccgtccagg cacctcgatt agttctcgag cttttggagt acgtcgtctt taggttgggg    3720
ggaggggttt tatgcgatgg agtttccca cactgagtgg gtggagactg aagttaggcc    3780
agcttggcac ttgatgtaat tctccttgga atttgccctt tttgagtttg gatcttggtt    3840
cattctcaag cctcagacag tggttcaaag ttttttttctt ccatttcagg tgtcgtgagc    3900
```

| | |
|---|---|
| tagactagta ccatggacat gcgggtgcct gcacaacttc tgggcctgct gttgttgtgg | 3960 |
| ctgtctggag cccggtgtaa ttgggtaaat gttatcagtg atctcaagaa gatagaggat | 4020 |
| ctcatccagt ccatgcatat tgatgccacg ctgtacacag aaagcgatgt gcatcctagc | 4080 |
| tgtaaggtga cagcgatgaa gtgttttctt ttggagctgc aggtaattag tcttgagtcc | 4140 |
| ggcgatgcca gcattcatga taccgtagaa aacttgatta tcctggccaa caattctctg | 4200 |
| tcctcaaacg gaaacgtaac cgagagcggt tgtaaagaat gtgaagaact ggaagaaaag | 4260 |
| aacatcaagg agtttctgca atcattcgtt cacatcgtac aaatgttcat aaatacgtca | 4320 |
| ggatctggtt ctggttccgg aagtggatct ggttcagggt ccggtagtgg atctgggtca | 4380 |
| ggaagtggaa gcggtagtgg gtctggatct aaacaagagc actttcctga taacctgttg | 4440 |
| ccgagctggg cgattacgct tatcagtgta acggcatct ttgtaatatg ctgtctgacc | 4500 |
| tactgcttcg caccaaggtg ccgggagaga aggagaaatg aaagactgag aagggagagc | 4560 |
| gtgagacctg tgggatcctc ccatcactgg gggtacggca acacaacgg acctgagcac | 4620 |
| tggcataagg acttccccat tgccaaggga gagcgccagt cccctgttga catcgacact | 4680 |
| catacagcca agtatgaccc ttccctgaag cccctgtctg tttcctatga tcaagcaact | 4740 |
| tccctgagaa tcctcaacaa tggtcatgct ttcaacgtgg agtttgatga ctctcaggac | 4800 |
| aaagcagtgc tcaagggagg acccctggat ggcacttaca gattgattca gtttcacttt | 4860 |
| cactggggtt cacttgatgg acaaggttca gagcatactg tggataaaaa gaaatatgct | 4920 |
| gcagaacttc acttggttca ctggaacacc aaatatgggg attttgggaa agctgtgcag | 4980 |
| caacctgatg gactggccgt tctaggtatt tttttgaagg ttggcagcgc taaaccgggc | 5040 |
| catcagaaag ttgttgatgt gctggattcc attaaaacaa agggcaagag tgctgacttc | 5100 |
| actaacttcg atcctcgtgg cctccttcct gaatccctgg attactggac ctacccaggc | 5160 |
| tcactgacca cccctcctct tctggaatgt gtgacctgga ttgtgctcaa ggaacccatc | 5220 |
| agcgtcagca gcgagcaggt gttgaaattc cgtaaactta acttcaatgg ggagggtgaa | 5280 |
| cccgaagaac tgatggtgga caactggcgc ccagctcagc cactgaagaa caggcaaatc | 5340 |
| aaagcttcct tcaaaggatc cggagctact aacttcagcc tgctgaagca ggctggagac | 5400 |
| gtggaggaga accctggacc tatggcctta ccagtgaccg ccttgctcct gccgctggcc | 5460 |
| ttgctgctcc acgccgccag gccggacatc cagatgacac agactacatc ctccctgtct | 5520 |
| gcctctctgg gagacagagt caccatcagt tgcagggcaa gtcaggacat tagtaaatat | 5580 |
| ttaaattggt atcagcagaa accagatgga actgttaaac tcctgatcta ccatacatca | 5640 |
| agattacact caggagtccc atcaaggttc agtggcagtg ggtctggaac agattattct | 5700 |
| ctcaccatta gcaacctgga gcaagaagat attgccactt acttttgcca acagggtaat | 5760 |
| acgcttccgt acacgttcgg aggggggacc aagctggaga tcacaggtgg cggtggctcg | 5820 |
| ggcggtggtg ggtcgggtgg cggcggatct gaggtgaaac tgcaggagtc aggacctggc | 5880 |
| ctggtggcgc cctcacagag cctgtccgtc acatgcactg tctcagggt ctcattaccc | 5940 |
| gactatggtg taagctggat tcgccagcct ccacgaaagg gtctggagtg gctgggagta | 6000 |
| atatggggta gtgaaaccac atactataat tcagctctca atccagact gaccatcatc | 6060 |
| aaggacaact ccaagagcca agttttctta aaaatgaaca gtctgcaaac tgatgacaca | 6120 |
| gccatttact actgtgccaa acattattac tacggtggta gctatgctat ggactactgg | 6180 |
| ggccaaggaa cctcagtcac cgtctcctca accacgacgc cagcgccgcg accaccaaca | 6240 |
| ccggcgccca ccatcgcgtc gcagcccctg tccctgcgcc cagaggcgtg ccggccagcg | 6300 |

```
gcggggggcg cagtgcacac gagggggctg gacttcgcct gtgatatcta catctgggcg    6360
cccttggccg ggacttgtgg ggtccttctc ctgtcactgg ttatcaccct ttactgcaaa    6420
cggggcagaa agaaactcct gtatatattc aaacaaccat ttatgagacc agtacaaact    6480
actcaagagg aagatggctg tagctgccga tttccagaag aagaagaagg aggatgtgaa    6540
ctgagagtga agttcagcag gagcgcagac gcccccgcgt acaagcaggg ccagaaccag    6600
ctctataacg agctcaatct aggacgaaga gaggagtacg atgttttgga caagagacgt    6660
ggccgggacc ctgagatggg gggaaagccg agaaggaaga accctcagga aggcctgtac    6720
aatgaactgc agaaagataa gatggcgagc gcctacagtg agattgggat gaaaggcgag    6780
cgccggaggg gcaaggggca cgatggcctt taccagggtc tcagtacagc caccaaggac    6840
acctacgacg cccttcacat gcaggccctg cccctcgct aagtcgacaa tcaacctctg     6900
gattacaaaa tttgtgaaag attgactggt attcttaact atgttgctcc ttttacgcta    6960
tgtggatacg ctgctttaat gcctttgtat catgctattg cttcccgtat ggctttcatt    7020
ttctcctcct tgtataaatc ctggttgctg tctctttatg aggagttgtg gcccgttgtc    7080
aggcaacgtg gcgtggtgtg cactgtgttt gctgacgcaa cccccactgg ttggggcatt    7140
gccaccacct gtcagctcct ttccgggact ttcgctttcc cctccctat tgccacggcg     7200 gaactcatcg ccgcctgcct tgcccgctgc tggacagggg ctcggctgtt gggcactgac    7260
aattccgtgg tgttgtcggg aagctgacg tccctttccat ggctgctcgc ctgtgttgcc     7320
acctggattc tgcgcgggac gtccttctgc tacgtccctt cggccctcaa tccagcggac    7380
cttccttccc gcggcctgct gccggctctg cggcctcttc cgcgtcttcg ccttcgccct    7440
cagacgagtc ggatctccct ttgggccgcc tccccgcctg gaattcgagc tcggtacctt    7500
taagaccaat gacttacaag gcagctgtag atcttagcca cttttaaaa gaaaaggggg     7560 gactggaagg gctaattcac tcccaacgaa gacaagatct gcttttgct tgtactgggt     7620 ctctctggtt agaccagatc tgagcctggg agctctctgg ctaactaggg aacccactgc    7680
ttaagcctca ataaagcttg ccttgagtgc ttcaagtagt gtgtgcccgt ctgttgtgtg    7740
actctggtaa ctagagatcc ctcagaccct tttagtcagt gtggaaaatc tctagcagta    7800
gtagttcatg tcatcttatt attcagtatt tataacttgc aaagaaatga atatcagaga    7860
gtgagaggaa cttgttttatt gcagcttata atggttacaa ataaagcaat agcatcacaa    7920
atttcacaaa taaagcattt ttttcactgc attctagttg tggtttgtcc aaactcatca    7980
atgtatctta tcatgtctgg ctctagctat cccgccccta actccgccca tcccgcccct    8040
aactccgccc agttccgccc attctccgcc ccatggctga ctaatttttt ttatttatgc    8100
agaggccgag gccgcctcgg cctctgagct attccagaag tagtgaggag ctttttttgg    8160
aggcctaggg acgtacccaa ttcgccctat agtgagtcgt attacgcgcg ctcactggcc    8220
gtcgttttac aacgtcgtga ctgggaaaac cctggcgtta cccaacttaa tcgccttgca    8280
gcacatcccc ctttcgccag ctggcgtaat agcgaagagg cccgcaccga tcgcccttcc    8340
caacagttgc gcagcctgaa tggcgaatgg gacgcgccct gtagcggcgc attaagcgcg    8400
gcgggtgtgg tggttacgcg cagcgtgacc gctacacttg ccagcgccct agcgcccgct    8460
cctttcgctt tcttcccttc ctttctcgcc acgttcgccg gctttccccg tcaagctcta    8520
aatcgggggc tccctttagg gttccgattt agtgctttac ggcacctcga ccccaaaaaa    8580
cttgattagg gtgatggttc acgtagtggg ccatcgccct gatagacggt ttttcgccct    8640
```

| | | | |
|---|---|---|---|
| ttgacgttgg | agtccacgtt | ctttaatagt ggactcttgt tccaaactgg aacaacactc | 8700 |
| aaccctatct | cggtctattc | ttttgattta aagggatttt tgccgatttc ggcctattgg | 8760 |
| ttaaaaaatg | agctgattta | acaaaaattt aacgcgaatt ttaacaaaat attaacgctt | 8820 |
| acaatttagg | tggcactttt | cggggaaatg tgcgcggaac ccctatttgt ttatttttct | 8880 |
| aaatacattc | aaatatgtat | ccgctcatga caataaacc ctgataaatg cttcaataat | 8940 |
| attgaaaaag | gaagagtatg | agtattcaac atttccgtgt cgcccttatt ccctttttg | 9000 |
| cggcattttg | ccttcctgtt | tttgctcacc cagaaacgct ggtgaaagta aaagatgctg | 9060 |
| aagatcagtt | gggtgcacga | gtgggttaca tcgaactgga tctcaacagc ggtaagatcc | 9120 |
| ttgagagttt | tcgccccgaa | gaacgttttc caatgatgag cacttttaaa gttctgctat | 9180 |
| gtggcgcggt | attatcccgt | attgacgccg ggcaagagca actcggtcgc cgcatacact | 9240 |
| attctcagaa | tgacttggtt | gagtactcac cagtcacaga aaagcatctt acggatggca | 9300 |
| tgacagtaag | agaattatgc | agtgctgcca taaccatgag tgataacact gcggccaact | 9360 |
| tacttctgac | aacgatcgga | ggaccgaagg agctaaccgc ttttttgcac aacatggggg | 9420 |
| atcatgtaac | tcgccttgat | cgttgggaac cggagctgaa tgaagccata ccaaacgacg | 9480 |
| agcgtgacac | cacgatgcct | gtagcaatgg caacaacgtt gcgcaaacta ttaactggcg | 9540 |
| aactacttac | tctagcttcc | cggcaacaat taatagactg gatggaggcg gataaagttg | 9600 |
| caggaccact | tctgcgctcg | gcccttccgg ctggctggtt tattgctgat aaatctggag | 9660 |
| ccggtgagcg | tgggtctcgc | ggtatcattg cagcactggg gccagatggt aagccctccc | 9720 |
| gtatcgtagt | tatctacacg | acggggagtc aggcaactat ggatgaacga atagacaga | 9780 |
| tcgctgagat | aggtgcctca | ctgattaagc attggtaact gtcagaccaa gtttactcat | 9840 |
| atatacttta | gattgattta | aaacttcatt tttaatttaa aaggatctag gtgaagatcc | 9900 |
| tttttgataa | tctcatgacc | aaaatccctt aacgtgagtt ttcgttccac tgagcgtcag | 9960 |
| accccgtaga | aaagatcaaa | ggatcttctt gagatccttt ttttctgcgc gtaatctgct | 10020 |
| gcttgcaaac | aaaaaaacca | ccgctaccag cggtggtttg tttgccggat caagagctac | 10080 |
| caactctttt | tccgaaggta | actggcttca gcagagcgca gataccaaat actgttcttc | 10140 |
| tagtgtagcc | gtagttaggc | caccacttca agaactctgt agcaccgcct acatacctcg | 10200 |
| ctctgctaat | cctgttacca | gtggctgctg ccagtggcga taagtcgtgt cttaccgggt | 10260 |
| tggactcaag | acgatagtta | ccggataagg cgcagcggtc gggctgaacg gggggttcgt | 10320 |
| gcacacagcc | cagcttggag | cgaacgacct acaccgaact gagatcccta cagcgtgagc | 10380 |
| tatgagaaag | cgccacgctt | cccgaaggga gaaaggcgga caggtatccg gtaagcggca | 10440 |
| gggtcggaac | aggagagcgc | acgagggagc ttccaggggg aaacgcctgg tatctttata | 10500 |
| gtcctgtcgg | gtttcgccac | ctctgacttg agcgtcgatt tttgtgatgc tcgtcagggg | 10560 |
| ggcggagcct | atgaaaaaac | gccagcaacg cggccttttt acggttcctg gccttttgct | 10620 |
| ggccttttgc | tcacatgttc | tttcctgcgt tatcccctga ttctgtggat aaccgtatta | 10680 |
| ccgcc | | | 10685 |

<210> SEQ ID NO 45
<211> LENGTH: 989
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 45

Met Asp Met Arg Val Pro Ala Gln Leu Leu Gly Leu Leu Leu Leu Trp
1               5                   10                  15

Leu Ser Gly Ala Arg Cys Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser Gly Ser Gly Ser Gly Ser
    130                 135                 140

Gly Ser Gly Ser Gly Ser Gly Ser Gly Ser Gly Ser Gly Ser Gly Ser
145                 150                 155                 160

Gly Ser Gly Ser Gly Ser Lys Gln Glu His Phe Pro Asp Asn Leu Leu
                165                 170                 175

Pro Ser Trp Ala Ile Thr Leu Ile Ser Val Asn Gly Ile Phe Val Ile
            180                 185                 190

Cys Cys Leu Thr Tyr Cys Phe Ala Pro Arg Cys Arg Glu Arg Arg Arg
        195                 200                 205

Asn Glu Arg Leu Arg Arg Glu Ser Val Arg Pro Val Gly Ser Ser His
    210                 215                 220

His Trp Gly Tyr Gly Lys His Asn Gly Pro Glu His Trp His Lys Asp
225                 230                 235                 240

Phe Pro Ile Ala Lys Gly Glu Arg Gln Ser Pro Val Asp Ile Asp Thr
                245                 250                 255

His Thr Ala Lys Tyr Asp Pro Ser Leu Lys Pro Leu Ser Val Ser Tyr
            260                 265                 270

Asp Gln Ala Thr Ser Leu Arg Ile Leu Asn Asn Gly His Ala Phe Asn
        275                 280                 285

Val Glu Phe Asp Asp Ser Gln Asp Lys Ala Val Leu Lys Gly Gly Pro
    290                 295                 300

Leu Asp Gly Thr Tyr Arg Leu Ile Gln Phe His Phe His Trp Gly Ser
305                 310                 315                 320

Leu Asp Gly Gln Gly Ser Glu His Thr Val Asp Lys Lys Lys Tyr Ala
                325                 330                 335

Ala Glu Leu His Leu Val His Trp Asn Thr Lys Tyr Gly Asp Phe Gly
            340                 345                 350

Lys Ala Val Gln Gln Pro Asp Gly Leu Ala Val Leu Gly Ile Phe Leu
        355                 360                 365

Lys Val Gly Ser Ala Lys Pro Gly Leu Gln Lys Val Val Asp Val Leu
    370                 375                 380

Asp Ser Ile Lys Thr Lys Gly Lys Ser Ala Asp Phe Thr Asn Phe Asp
385                 390                 395                 400

Pro Arg Gly Leu Leu Pro Glu Ser Leu Asp Tyr Trp Thr Tyr Pro Gly
                405                 410                 415
```

```
Ser Leu Thr Thr Pro Pro Leu Leu Glu Cys Val Thr Trp Ile Val Leu
            420                 425                 430

Lys Glu Pro Ile Ser Val Ser Ser Glu Gln Val Leu Lys Phe Arg Lys
            435                 440                 445

Leu Asn Phe Asn Gly Glu Gly Glu Pro Glu Leu Met Val Asp Asn
450                 455                 460

Trp Arg Pro Ala Gln Pro Leu Lys Asn Arg Gln Ile Lys Ala Ser Phe
465                 470                 475                 480

Lys Gly Ser Gly Ala Thr Asn Phe Ser Leu Leu Lys Gln Ala Gly Asp
                    485                 490                 495

Val Glu Glu Asn Pro Gly Pro Met Ala Leu Pro Val Thr Ala Leu Leu
                500                 505                 510

Leu Pro Leu Ala Leu Leu Leu His Ala Ala Arg Pro Asp Ile Gln Met
            515                 520                 525

Thr Gln Thr Thr Ser Ser Leu Ser Ala Ser Leu Gly Asp Arg Val Thr
            530                 535                 540

Ile Ser Cys Arg Ala Ser Gln Asp Ile Ser Lys Tyr Leu Asn Trp Tyr
545                 550                 555                 560

Gln Gln Lys Pro Asp Gly Thr Val Lys Leu Leu Ile Tyr His Thr Ser
                565                 570                 575

Arg Leu His Ser Gly Val Pro Ser Arg Phe Ser Gly Ser Gly Ser Gly
            580                 585                 590

Thr Asp Tyr Ser Leu Thr Ile Ser Asn Leu Glu Gln Glu Asp Ile Ala
            595                 600                 605

Thr Tyr Phe Cys Gln Gln Gly Asn Thr Leu Pro Tyr Thr Phe Gly Gly
            610                 615                 620

Gly Thr Lys Leu Glu Ile Thr Gly Gly Gly Gly Ser Gly Gly Gly Gly
625                 630                 635                 640

Ser Gly Gly Gly Gly Ser Glu Val Lys Leu Gln Glu Ser Gly Pro Gly
                645                 650                 655

Leu Val Ala Pro Ser Gln Ser Leu Ser Val Thr Cys Thr Val Ser Gly
            660                 665                 670

Val Ser Leu Pro Asp Tyr Gly Val Ser Trp Ile Arg Gln Pro Pro Arg
            675                 680                 685

Lys Gly Leu Glu Trp Leu Gly Val Ile Trp Gly Ser Glu Thr Thr Tyr
            690                 695                 700

Tyr Asn Ser Ala Leu Lys Ser Arg Leu Thr Ile Ile Lys Asp Asn Ser
705                 710                 715                 720

Lys Ser Gln Val Phe Leu Lys Met Asn Ser Leu Gln Thr Asp Asp Thr
                725                 730                 735

Ala Ile Tyr Tyr Cys Ala Lys His Tyr Tyr Tyr Gly Gly Ser Tyr Ala
            740                 745                 750

Met Asp Tyr Trp Gly Gln Gly Thr Ser Val Thr Val Ser Ser Thr Thr
            755                 760                 765

Thr Pro Ala Pro Arg Pro Pro Thr Pro Ala Pro Thr Ile Ala Ser Gln
            770                 775                 780

Pro Leu Ser Leu Arg Pro Glu Ala Cys Arg Pro Ala Ala Gly Gly Ala
785                 790                 795                 800

Val His Thr Arg Gly Leu Asp Phe Ala Cys Asp Ile Tyr Ile Trp Ala
                805                 810                 815

Pro Leu Ala Gly Thr Cys Gly Val Leu Leu Leu Ser Leu Val Ile Thr
            820                 825                 830
```

| | | | | | | | | | | | | |
|---|---|---|---|---|---|---|---|---|---|---|---|---|
|Leu|Tyr|Cys|Lys|Arg|Gly|Arg|Lys|Lys|Leu|Leu|Tyr|Ile|Phe|Lys|Gln|
| |835| | | |840| | | |845| | | |

Pro Phe Met Arg Pro Val Gln Thr Thr Gln Glu Glu Asp Gly Cys Ser
    850                 855                 860

Cys Arg Phe Pro Glu Glu Glu Gly Gly Cys Glu Leu Arg Val Lys
865             870                 875                 880

Phe Ser Arg Ser Ala Asp Ala Pro Ala Tyr Lys Gln Gly Gln Asn Gln
                885                 890                 895

Leu Tyr Asn Glu Leu Asn Leu Gly Arg Arg Glu Glu Tyr Asp Val Leu
            900                 905                 910

Asp Lys Arg Arg Gly Arg Asp Pro Glu Met Gly Gly Lys Pro Arg Arg
            915                 920                 925

Lys Asn Pro Gln Glu Gly Leu Tyr Asn Glu Leu Gln Lys Asp Lys Met
            930                 935                 940

Ala Glu Ala Tyr Ser Glu Ile Gly Met Lys Gly Glu Arg Arg Arg Gly
945                 950                 955                 960

Lys Gly His Asp Gly Leu Tyr Gln Gly Leu Ser Thr Ala Thr Lys Asp
                965                 970                 975

Thr Tyr Asp Ala Leu His Met Gln Ala Leu Pro Pro Arg
            980                 985

<210> SEQ ID NO 46
<211> LENGTH: 2970
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
atggacatgc gggtgcctgc acaacttctg ggcctgctgt tgttgtggct gtctggagcc      60
cggtgtaatt gggtaaatgt tatcagtgat ctcaagaaga tagaggatct catccagtcc     120
atgcatattg atgccacgct gtacacagaa agcgatgtgc atcctagctg taaggtgaca     180
gcgatgaagt gttttctttt ggagctgcag gtaattagtc ttgagtccgg cgatgccagc     240
attcatgata ccgtagaaaa cttgattatc ctggccaaca attctctgtc ctcaaacgga     300
aacgtaaccg agagcggttg taaagaatgt gaagaactgg aagaaaagaa catcaaggag     360
tttctgcaat cattcgttca catcgtacaa atgttcataa atacgtcagg atctggttct     420
ggttccggaa gtggatctgg ttcagggtcc ggtagtggat ctgggtcagg aagtggaagc     480
ggtagtgggt ctggatctaa acaagagcac tttcctgata acctgttgcc gagctgggcg     540
attacgctta tcagtgtaaa cggcatcttt gtaatatgct gtctgaccta ctgcttcgca     600
ccaaggtgcc gggagagaag gagaaatgaa agactgagaa gggagagcgt gagacctgtg     660
ggatcctccc atcactgggg gtacggcaaa cacaacggac tgagcactg gcataaggac     720
ttccccattg ccaagggaga gcgccagtcc cctgttgaca tcgacactca tacagccaag     780
tatgaccctt ccctgaagcc cctgtctgtt cctatgatc aagcaacttc cctgagaatc     840
ctcaacaatg gtcatgcttt caacgtggag tttgatgact ctcaggacaa agcagtgctc     900
aagggaggac ccctggatgg cacttacaga ttgattcagt tcactttca ctgggggttca     960
cttgatggac aaggttcaga gcatactgtg gataaaaaga aatatgctgc agaacttcac    1020
ttggttcact ggaacaccaa atatgggat tttgggaaag ctgtgcagca acctgatgga    1080
ctggccgttc taggtatttt tttgaaggtt ggcagcgcta accgggcct tcagaaagtt    1140
```

```
gttgatgtgc tggattccat taaaacaaag gcaagagtg ctgacttcac taacttcgat    1200
cctcgtggcc tccttcctga atccctggat tactggacct acccaggctc actgaccacc    1260
cctcctcttc tggaatgtgt gacctggatt gtgctcaagg aacccatcag cgtcagcagc    1320
gagcaggtgt tgaaattccg taaacttaac ttcaatgggg agggtgaacc cgaagaactg    1380
atggtggaca actggcgccc agctcagcca ctgaagaaca ggcaaatcaa agcttccttc    1440
aaaggatccg gagctactaa cttcagcctg ctgaagcagg ctggagacgt ggaggagaac    1500
cctggaccta tggccttacc agtgaccgcc ttgctcctgc cgctggcctt gctgctccac    1560
gccgccaggc cggacatcca gatgacacag actacatcct ccctgtctgc ctctctggga    1620
gacagagtca ccatcagttg cagggcaagt caggacatta gtaaatattt aaattggtat    1680
cagcagaaac cagatggaac tgttaaactc ctgatctacc atacatcaag attacactca    1740
ggagtcccat caaggttcag tggcagtggg tctggaacag attattctct caccattagc    1800
aacctggagc aagaagatat tgccacttac ttttgccaac agggtaatac gcttccgtac    1860
acgttcggag gggggaccaa gctggagatc acaggtggcg tggctcgggg cggtggtggg    1920
tcgggtggcg gcggatctga ggtgaaactg caggagtcag gacctggcct ggtggcgccc    1980
tcacagagcc tgtccgtcac atgcactgtc tcaggggtct cattacccga ctatggtgta    2040
agctggattc gccagcctcc acgaaagggt ctggagtggc tgggagtaat atggggtagt    2100
gaaaccacat actataattc agctctcaaa tccagactga ccatcatcaa ggacaactcc    2160
aagagccaag ttttcttaaa aatgaacagt ctgcaaactg atgacacagc catttactac    2220
tgtgccaaac attattacta cggtggtagc tatgctatgg actactgggg ccaaggaacc    2280
tcagtcaccg tctcctcaac cacgacgcca gcgccgcgac caccaacacc ggcgcccacc    2340
atcgcgtcgc agcccctgtc cctgcgccca gaggcgtgcc ggccagcggc ggggggcgca    2400
gtgcacacga gggggctgga cttcgcctgt gatatctaca tctgggcgcc cttggccggg    2460
acttgtgggg tccttctcct gtcactggtt atcacccttt actgcaaacg gggcagaaag    2520
aaactcctgt atatattcaa acaaccattt atgagaccag tacaaactac tcaagaggaa    2580
gatggctgta gctgccgatt tccagaagaa gaagaaggag gatgtgaact gagagtgaag    2640
ttcagcagga gcgcagacgc ccccgcgtac aagcagggcc agaaccagct ctataacgag    2700
ctcaatctag gacgaagaga ggagtacgat gttttggaca gagacgtggg ccgggaccct    2760
gagatggggg gaaagccgag aaggaagaac cctcaggaag gcctgtacaa tgaactgcag    2820
aaagataaga tggcggaggc ctacagtgag attgggatga aggcgagcg ccggaggggc    2880 aagggcacg atggccttta ccagggtctc agtacagcca ccaaggacac ctacgacgcc    2940
cttcacatgc aggccctgcc ccctcgctaa                                      2970
```

<210> SEQ ID NO 47
<211> LENGTH: 10685
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
tttgagtgag ctgataccgc tcgccgcagc cgaacgaccg agcgcagcga gtcagtgagc    60
gaggaagcgg aagagcgccc aatacgcaaa ccgcctctcc ccgcgcgttg gccgattcat    120
taatgcagct ggcacgacag gtttcccgac tggaaagcgg gcagtgagcg caacgcaatt    180
```

-continued

```
aatgtgagtt agctcactca ttaggcaccc caggctttac actttatgct tccggctcgt    240
atgttgtgtg gaattgtgag cggataacaa tttcacacag gaaacagcta tgaccatgat    300
tacgccaagc gcgcaattaa ccctcactaa agggaacaaa agctggagct gcaagcttaa    360
tgtagtctta tgcaatactc ttgtagtctt gcaacatggt aacgatgagt tagcaacatg    420
ccttacaagg agagaaaaag caccgtgcat gccgattggt ggaagtaagg tggtacgatc    480
gtgccttatt aggaaggcaa cagacgggtc tgacatggat tggacgaacc actgaattgc    540
cgcattgcag agatattgta tttaagtgcc tagctcgata cataaacggg tctctctggt    600
tagaccagat ctgagcctgg gagctctctg gctaactagg gaacccactg cttaagcctc    660
aataaagctt gccttgagtg cttcaagtag tgtgtgcccg tctgttgtgt gactctggta    720
actagagatc cctcagaccc ttttagtcag tgtggaaaat ctctagcagt ggcgcccgaa    780
cagggacttg aaagcgaaag ggaaaccaga ggagctctct cgacgcagga ctcggcttgc    840
tgaagcgcgc acggcaagag gcgaggggcg gcgactggtg agtacgccaa aaattttgac    900
tagcggaggc tagaaggaga gagatgggtg cgagagcgtc agtattaagc gggggagaat    960
tagatcgcga tgggaaaaaa ttcggttaag gccaggggga agaaaaaat ataaattaaa    1020 acatatagta tgggcaagca gggagctaga acgattcgca gttaatcctg gcctgttaga    1080
aacatcagaa ggctgtagac aaatactggg acagctacaa ccatcccttc agacaggatc    1140
agaagaactt agatcattat ataatacagt agcaaccctc tattgtgtgc atcaaaggat    1200
agagataaaa gacaccaagg aagctttaga caagatagag gaagagcaaa acaaaagtaa    1260
gaccaccgca cagcaagcgg ccgctgatct tcagacctgg aggaggagat atgagggaca    1320
attggagaag tgaattatat aaatataaag tagtaaaaat tgaaccatta ggagtagcac    1380
ccaccaaggc aaagagaaga gtggtgcaga gagaaaaaag agcagtggga ataggagctt    1440
tgttccttgg gttcttggga gcagcaggaa gcactatggg cgcagcgtca atgacgctga    1500
cggtacaggc cagacaatta ttgtctggta tagtgcagca gcagaacaat ttgctgaggg    1560
ctattgaggc gcaacagcat ctgttgcaac tcacagtctg gggcatcaag cagctccagg    1620
caagaatcct ggctgtggaa agatacctaa aggatcaaca gctcctgggg atttggggtt    1680
gctctggaaa actcatttgc accactgctg tgccttggaa tgctagttgg agtaataaat    1740
ctctggaaca gatttggaat cacacgacct ggatggagtg ggacagagaa attaacaatt    1800
acacaagctt aatacactcc ttaattgaag aatcgcaaaa ccagcaagaa aagaatgaac    1860
aagaattatt ggaattagat aaatgggcaa gtttgtggaa ttggtttaac ataacaaatt    1920
ggctgtggta tataaaatta ttcataatga tagtaggagg cttggtaggt ttaagaatag    1980
tttttgctgt actttctata gtgaatagag ttaggcaggg atattcacca ttatcgtttc    2040
agacccacct cccaaccccg aggggacccg acaggcccga aggaatagaa gaagaaggtg    2100
gagagagaga cagagacaga tccattcgat tagtgaacgg atctcgacgg tatcgattag    2160
actgtagccc aggaatatgg cagctagatt gtacacattt agaaggaaaa gttatcttgg    2220
tagcagttca tgtagccagt ggatatatag aagcagaagt aattccagca gagacagggc    2280
aagaaacagc atacttcctc ttaaaattag caggaagatg gccagtaaaa acagtacata    2340
cagacaatgg cagcaatttc accagtacta cagttaaggc cgcctgttgg tgggcgggga    2400
tcaagcagga atttggcatt ccctacaatc cccaaagtca aggagtaata gaatctatga    2460
ataaagaatt aaagaaaatt ataggacagg taagagatca ggctgaacat cttaagacag    2520
cagtacaaat ggcagtattc atccacaatt ttaaaagaaa aggggggatt ggggggtaca    2580
```

```
gtgcaggga   aagaatagta   gacataatag   caacagacat   acaaactaaa   gaattacaaa   2640
aacaaattac  aaaaattcaa   aattttcggg   tttattacag   ggacagcaga   gatccagttt   2700
ggctgcattg  atcacgtgag   gctccggtgc   ccgtcagtgg   gcagagcgca   catcgcccac   2760
agtccccgag  aagttggggg   gagggtcgg    caattgaacc   ggtgcctaga   gaaggtggcg   2820
cggggtaaac  tgggaaagtg   atgtcgtgta   ctggctccgc   cttttcccg    agggtggggg   2880 agaaccgtat  ataagtgcag   tagtcgccgt   gaacgttctt   tttcgcaacg   ggtttgccgc   2940
cagaacacag  gtaagtgccg   tgtgtggttc   ccgcgggcct   ggcctcttta   cgggttatgg   3000
cccttgcgtg  ccttgaatta   cttccacctg   gctgcagtac   gtgattcttg   atcccgagct   3060
tcgggttgga  agtgggtggg   agagttcgag   gccttgcgct   taaggagccc   cttcgcctcg   3120
tgcttgagtt  gaggcctggc   ctgggcgctg   ggccgccgc    gtgcgaatct   ggtggcacct   3180
tcgcgcctgt  ctcgctgctt   tcgataagtc   tctagccatt   taaaatttt    gatgacctgc   3240 tgcgacgctt  tttttctggc   aagatagtct   tgtaaatgcg   ggccaagatc   tgcacactgg   3300
tatttcggtt  tttggggccg   cgggcggcga   cggggcccgt   gcgtcccagc   gcacatgttc   3360
ggcgaggcgg  ggcctgcgag   cgcggccacc   gagaatcgga   cggggtagt    ctcaagctgg   3420 ccggcctgct  ctggtgcctg   gcctcgcgcc   gccgtgtatc   gccccgccct   gggcggcaag   3480
gctggcccgg  tcggcaccag   ttgcgtgagc   ggaaagatgg   ccgcttcccg   gccctgctgc   3540
agggagctca  aaatggagga   cgcggcgctc   gggagagcgg   gcgggtgagt   cacccacaca   3600
aaggaaaagg  gcctttccgt   cctcagccgt   cgcttcatgt   gactccactg   agtaccgggc   3660
gccgtccagg  cacctcgatt   agttctcgag   cttttggagt   acgtcgtctt   taggttgggg   3720
ggaggggttt  tatgcgatgg   agtttcccca   cactgagtgg   gtggagactg   aagttaggcc   3780
agcttggcac  ttgatgtaat   tctccttgga   atttgccctt   tttgagtttg   gatcttggtt   3840
cattctcaag  cctcagacag   tggttcaaag   tttttttctt   ccatttcagg   tgtcgtgagc   3900
tagactagta  ccatggacat   gcgggtgcct   gcacaacttc   tgggcctgct   gttgttgtgg   3960
ctgtctggag  cccggtgtaa   ttgggtaaat   gttatcagtg   atctcaagaa   gatagaggat   4020
ctcatccagt  ccatgcatat   tgatgccacg   ctgtacacag   aaagcgatgt   gcatcctagc   4080
tgtaaggtga  cagcgatgaa   gtgttttctt   ttggagctgc   aggtaattag   tcttgagtcc   4140
ggcgatgcca  gcattcatga   taccgtagaa   aacttgatta   tcctggccaa   caattctctg   4200
tcctcaaacg  gaaacgtaac   cgagagcggt   tgtaaagaat   gtgaagaact   ggaagaaaag   4260
aacatcaagg  agtttctgca   atcattcgtt   cacatcgtac   aaatgttcat   aaatacgtca   4320
ggatctggtt  ctggttccgg   aagtggatct   ggttcagggt   ccggtagtgg   atctgggtca   4380
ggaagtggaa  gcggtagtgg   gtctggatct   aaacaagagc   actttcctga   taacctgttg   4440
ccgagctggg  cgattacgct   tatcagtgta   aacggcatct   ttgtaatatg   ctgtctgacc   4500
tactgcttcg  caccaaggtg   ccgggagaga   aggagaaatg   aaagactgag   aagggagagc   4560
gtgagacctg  tgggatcctc   ccatcactgg   gggtacggca   aacacaacgg   acctgagcac   4620
tggcataagg  acttccccat   tgccaaggga   gagcgccagt   ccctgttga    catcgacact   4680 catacagcca  agtatgaccc   ttccctgaag   ccctgtctg    tttcctatga   tcaagcaact   4740
tccctgagaa  tcctcaacaa   tggtcatgct   ttcaacgtgg   agtttgatga   ctctcaggac   4800
aaagcagtgc  tcaagggagg   acccctggat   ggcacttaca   gattgattca   gtttcacttt   4860
cactggggtt  cacttgatgg   acaaggttca   gagcatactg   tggataaaaa   gaaatatgct   4920
```

```
gcagaacttc acttggttca ctggaacacc aaatatgggg attttgggaa agctgtgcag    4980
caacctgatg gactggccgt tctaggtatt tttttgaagg ttggcagcgc taaaccgggc    5040
cttcagaaag ttgttgatgt gctggattcc attaaaacaa agggcaagag tgctgacttc    5100
actaacttcg atcctcgtgg cctccttcct gaatccctgg attactggac ctacccaggc    5160
tcactgacca cccctcctct tctggaatgt gtgacctgga ttgtgctcaa ggaacccatc    5220
agcgtcagca gcgagcaggt gttgaaattc cgtaaactta acttcaatgg ggagggtgaa    5280
cccgaagaac tgatggtgga caactggcgc ccagctcagc cactgaagaa caggcaaatc    5340
aaagcttcct tcaaaggatc cggagctact aacttcagcc tgctgaagca ggctggagac    5400
gtggaggaga accctggacc tatggcctta ccagtgaccg ccttgctcct gccgctggcc    5460
ttgctgctcc acgccgccag gccggacatc cagatgacac agactacatc ctccctgtct    5520
gcctctctgg agacagagt caccatcagt tgcagggcaa gtcaggacat tagtaaatat    5580
ttaaattggt atcagcagaa accagatgga actgttaaac tcctgatcta ccatacatca    5640
agattacact caggagtccc atcaaggttc agtggcagtg gtctggaac agattattct    5700 ctcaccatta gcaacctgga gcaagaagat attgccactt acttttgcca acagggtaat    5760
acgcttccgt acacgttcgg agggggggacc aagctggaga tcacaggtgg cggtggctcg    5820
ggcggtggtg ggtcgggtgg cggcggatct gaggtgaaac tgcaggagtc aggacctggc    5880
ctggtggcgc cctcacagag cctgtccgtc acatgcactg tctcaggggt ctcattaccc    5940
gactatggtg taagctggat tcgccagcct ccacgaaagg gtctggagtg gctgggagta    6000
atatggggta gtgaaaccac atactataat tcagctctca atccagact gaccatcatc    6060 aaggacaact ccaagagcca gttttcttta aaaatgaaca gtctgcaaac tgatgacaca    6120
gccatttact actgtgccaa acattattac tacggtggta gctatgctat ggactactgg    6180
ggccaaggaa cctcagtcac cgtctcctca accacgacgc cagcgccgcg accaccaaca    6240
ccggcgccca catcgcgtc gcagcccctg tccctgcgcc cagaggcgtg ccggccagcg    6300
gcggggggcg cagtgcacac gagggggctg gacttcgcct gtgatatcta catctgggcg    6360
cccttggccg ggacttgtgg ggtccttctc ctgtcactgg ttatcaccct ttactgcaaa    6420
cggggcagaa agaaactcct gtatatattc aaacaaccat ttatgagacc agtacaaact    6480
actcaagagg aagatggctg tagctgccga tttccagaag aagaagaagg aggatgtgaa    6540
ctgagagtga agttcagcag gagcgcagac gcccccgcgt acaagcaggg ccagaaccag    6600
ctctataacg agctcaatct aggacgaaga gaggagtacg atgttttgga caagagacgt    6660
ggccgggacc ctgagatggg gggaaagccg agaaggaaga accctcagga aggcctgtac    6720
aatgaactgc agaaagataa gatggcggag gcctacagtg agattgggat gaaaggcgag    6780
cgccggaggg gcaaggggca cgatggcctt taccagggtc tcagtacagc caccaaggac    6840
acctacgacg cccttcacat gcaggccctg ccccctcgct aagtcgacaa tcaacctctg    6900
gattacaaaa tttgtgaaag attgactggt attcttaact atgttgctcc ttttacgcta    6960
tgtggatacg ctgctttaat gcctttgtat catgctattg cttcccgtat ggctttcatt    7020
ttctcctcct tgtataaatc ctggttgctg tctctttatg aggagttgtg gcccgttgtc    7080
aggcaacgtg gcgtggtgtg cactgtgttt gctgacgcaa cccccactgg ttggggcatt    7140
gccaccacct gtcagctcct ttccgggact ttcgctttcc cctcccctat gccacggcg    7200 gaactcatcg ccgcctgcct tgcccgctgc tggacagggg ctcggctgtt gggcactgac    7260
aattccgtgg tgttgtcggg gaagctgacg tccttccat ggctgctcgc ctgtgttgcc    7320
```

```
acctggattc tgcgcgggac gtccttctgc tacgtccctt cggccctcaa tccagcggac   7380
cttccttccc gcggcctgct gccggctctg cggcctcttc cgcgtcttcg ccttcgccct   7440
cagacgagtc ggatctccct ttgggccgcc tccccgcctg gaattcgagc tcggtacctt   7500
taagaccaat gacttacaag gcagctgtag atcttagcca cttttaaaa gaaaagggg   7560 gactggaagg gctaattcac tcccaacgaa gacaagatct gcttttgct tgtactgggt   7620 ctctctggtt agaccagatc tgagcctggg agctctctgg ctaactaggg aacccactgc   7680
ttaagcctca ataaagcttg ccttgagtgc ttcaagtagt gtgtgcccgt ctgttgtgtg   7740
actctggtaa ctagagatcc ctcagaccct tttagtcagt gtggaaaatc tctagcagta   7800
gtagttcatg tcatcttatt attcagtatt tataacttgc aaagaaatga atatcagaga   7860
gtgagaggaa cttgtttatt gcagcttata atggttacaa ataaagcaat agcatcacaa   7920
atttcacaaa taaagcattt ttttcactgc attctagttg tggtttgtcc aaactcatca   7980
atgtatctta tcatgtctgg ctctagctat cccgccccta actccgccca tcccgccct   8040 aactccgccc agttccgccc attctccgcc ccatggctga ctaatttttt ttatttatgc   8100
agaggccgag gccgcctcgg cctctgagct attccagaag tagtgaggag cttttttgg   8160 aggcctaggg acgtacccaa ttcgccctat agtgagtcgt attacgcgcg ctcactggcc   8220
gtcgttttac aacgtcgtga ctgggaaaac cctggcgtta cccaacttaa tcgccttgca   8280
gcacatcccc ctttcgccag ctggcgtaat agcgaagagg cccgcaccga tcgcccttcc   8340
caacagttgc gcagcctgaa tggcgaatgg gacgcgccct gtagcggcgc attaagcgcg   8400
gcgggtgtgg tggttacgcg cagcgtgacc gctacacttg ccagcgccct agcgcccgct   8460
cctttcgctt tcttcccttc ctttctcgcc acgttcgccg gctttccccg tcaagctcta   8520
aatcgggggc tccctttagg gttccgattt agtgctttac ggcacctcga ccccaaaaaa   8580
cttgattagg gtgatggttc acgtagtggg ccatcgccct gatagacggt ttttcgccct   8640
ttgacgttgg agtccacgtt ctttaatagt ggactcttgt tccaaactgg aacaacactc   8700
aaccctatct cggtctattc ttttgattta agggattt tgccgatttc ggcctattgg   8760
ttaaaaaatg agctgattta acaaaaattt aacgcgaatt ttaacaaaat attaacgctt   8820
acaatttagg tggcactttt cggggaaatg tgcgcggaac ccctatttgt ttatttttct   8880
aaatacattc aaatatgtat ccgctcatga cacaataacc ctgataaatg cttcaataat   8940
attgaaaaag gaagagtatg agtattcaac atttccgtgt cgcccttatt ccctttttg   9000 cggcatttg ccttcctgtt tttgctcacc cagaaacgct ggtgaaagta aaagatgctg   9060
aagatcagtt gggtgcacga gtgggttaca tcgaactgga tctcaacagc ggtaagatcc   9120
ttgagagttt tcgccccgaa gaacgttttc caatgatgag cacttttaaa gttctgctat   9180
gtggcgcggt attatcccgt attgacgccg ggcaagagca actcggtcgc cgcatacact   9240
attctcagaa tgacttggtt gagtactcac cagtcacaga aaagcatctt acggatggca   9300
tgacagtaag agaattatgc agtgctgcca taaccatgag tgataacact gcggccaact   9360
tacttctgac aacgatcgga ggaccgaagg agctaaccgc ttttttgcac aacatggggg   9420
atcatgtaac tcgccttgat cgttgggaac cggagctgaa tgaagccata ccaaacgacg   9480
agcgtgacac cacgatgcct gtagcaatgg caacaacgtt gcgcaaacta ttaactggcg   9540
aactacttac tctagcttcc cggcaacaat taatagactg gatggaggcg gataaagttg   9600
caggaccact tctgcgctcg gcccttccgg ctggctggtt tattgctgat aaatctggag   9660
```

```
ccggtgagcg tgggtctcgc ggtatcattg cagcactggg gccagatggt aagccctccc    9720
gtatcgtagt tatctacacg acggggagtc aggcaactat ggatgaacga aatagacaga    9780
tcgctgagat aggtgcctca ctgattaagc attggtaact gtcagaccaa gtttactcat    9840
atatacttta gattgattta aaacttcatt tttaatttaa aaggatctag gtgaagatcc    9900 ttttttgataa tctcatgacc aaaatccctt aacgtgagtt ttcgttccac tgagcgtcag    9960
accccgtaga aaagatcaaa ggatcttctt gagatccttt ttttctgcgc gtaatctgct    10020
gcttgcaaac aaaaaaacca ccgctaccag cggtggtttg tttgccggat caagagctac    10080
caactctttt tccgaaggta actggcttca gcagagcgca gataccaaat actgttcttc    10140
tagtgtagcc gtagttaggc caccacttca agaactctgt agcaccgcct acatacctcg    10200
ctctgctaat cctgttacca gtggctgctg ccagtggcga taagtcgtgt cttaccgggt    10260
tggactcaag acgatagtta ccggataagg cgcagcggtc gggctgaacg ggggggttcgt    10320 gcacacagcc cagcttggag cgaacgacct acaccgaact gagataccta cagcgtgagc    10380
tatgagaaag cgccacgctt cccgaaggga gaaaggcgga caggtatccg gtaagcggca    10440
gggtcggaac aggagagcgc acgagggagc ttccaggggg aaacgcctgg tatctttata    10500
gtcctgtcgg gtttcgccac ctctgacttg agcgtcgatt tttgtgatgc tcgtcagggg    10560
ggcggagcct atggaaaaac gccagcaacg cggccttttt acggttcctg gccttttgct    10620
ggccttttgc tcacatgttc tttcctgcgt tatcccctga ttctgtggat aaccgtatta    10680
ccgcc                                                               10685

<210> SEQ ID NO 48
<211> LENGTH: 486
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175
```

```
Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
            210                 215                 220

Met Asn Ser Leu Gln Thr Asp Asp Thr Ala Ile Tyr Tyr Cys Ala Lys
225                 230                 235                 240

His Tyr Tyr Tyr Gly Ser Tyr Ala Met Asp Tyr Trp Gly Gln Gly
                245                 250                 255

Thr Ser Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Lys Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
            405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 49
<211> LENGTH: 1461
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
atggccttac cagtgaccgc cttgctcctg ccgctggcct tgctgctcca cgccgccagg    60
ccggacatcc agatgacaca gactacatcc tccctgtctg cctctctggg agacagagtc   120
accatcagtt gcagggcaag tcaggacatt agtaaatatt taaattggta tcagcagaaa   180
ccagatggaa ctgttaaact cctgatctac catacatcaa gattacactc aggagtccca   240
```

```
tcaaggttca gtggcagtgg gtctggaaca gattattctc tcaccattag caacctggag      300
caagaagata ttgccactta cttttgccaa cagggtaata cgcttccgta cacgttcgga      360
gggggaccca agctggagat cacaggtggc ggtggctcgg gcggtggtgg gtcgggtggc      420
ggcggatctg aggtgaaact gcaggagtca ggacctggcc tggtggcgcc ctcacagagc      480
ctgtccgtca catgcactgt ctcagggtc tcattaccg actatggtgt aagctggatt        540
cgccagcctc cacgaaaggg tctggagtgg ctgggagtaa tatggggtag tgaaaccaca      600
tactataatt cagctctcaa atccagactg accatcatca aggacaactc caagagccaa      660
gttttcttaa aaatgaacag tctgcaaact gatgacacag ccatttacta ctgtgccaaa      720
cattattact acggtggtag ctatgctatg gactactggg gccaaggaac ctcagtcacc      780
gtctcctcaa ccacgacgcc agcgccgcga ccaccaacac cggcgcccac catcgcgtcg      840
cagcccctgt ccctgcgccc agaggcgtgc cggccagcgg cggggggcgc agtgcacacg      900
agggggctgg acttcgcctg tgatatctac atctgggcgc ccttggccgg acttgtgggg      960
gtccttctcc tgtcactggt tatcacccct tactgcaaac ggggcagaaa gaaactcctg     1020
tatatattca acaaccatt tatgagacca gtacaaacta ctcaagagga agatggctgt       1080
agctgccgat tccagaaga agaagaagga ggatgtgaac tgagagtgaa gttcagcagg      1140
agcgcagacg cccccgcgta caagcagggc cagaaccagc tctataacga gctcaatcta      1200
ggacgaagag aggagtacga tgttttggac aagagacgtg gccgggaccc tgagatgggg     1260
ggaaagccga aaggaagaa ccctcaggaa ggcctgtaca atgaactgca gaaagataag      1320
atggcggagg cctacagtga gattgggatg aaaggcgagc gccggagggg caaggggcac    1380
gatggccttt accagggtct cagtacagcc accaaggaca cctacgacgc ccttcacatg      1440
caggccctgc cccctcgcta a                                                1461
```

<210> SEQ ID NO 50
<211> LENGTH: 9174
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 50

```
gcgcgctcac tggccgtcgt tttacaacgt cgtgactggg aaaaccctgg cgttacccaa       60
cttaatcgcc ttgcagcaca tccccctttc gccagctggc gtaatagcga agaggcccgc      120
accgatcgcc cttcccaaca gttgcgcagc ctgaatggcg aatgggacgc gccctgtagc      180
ggcgcattaa gcgcggcggg tgtggtggtt acgcgcagcg tgaccgctac acttgccagc      240
gccctagcgc ccgctccttt cgctttcttc ccttcctttc tcgccacgtt cgccggcttt      300
ccccgtcaag ctctaaatcg ggggctccct ttagggttcc gatttagtgc tttacggcac      360
ctcgacccca aaaaacttga ttagggtgat ggttcacgta gtgggccatc gccctgatag      420
acggtttttc gccctttgac gttggagtcc acgttcttta atagtggact cttgttccaa      480
actggaacaa cactcaaccc tatctcggtc tattcttttg atttataagg gattttgccg      540
atttcggcct attggttaaa aaatgagctg atttaacaaa aatttaacgc gaattttaac      600
aaaatattaa cgcttacaat ttaggtggca cttttcgggg aaatgtgcgc ggaacccta      660 tttgtttatt tttctaaata cattcaaata tgtatccgct catgagacaa taaccctgat      720
aaatgcttca ataatattga aaaggaaga gtatgagtat tcaacatttc cgtgtcgccc      780
```

```
ttattccctt ttttgcggca ttttgccttc ctgttttgc tcacccagaa acgctggtga      840
aagtaaaaga tgctgaagat cagttgggtg cacgagtggg ttacatcgaa ctggatctca      900
acagcggtaa gatccttgag agttttcgcc ccgaagaacg ttttccaatg atgagcactt      960
ttaaagttct gctatgtggc gcggtattat cccgtattga cgccgggcaa gagcaactcg     1020
gtcgccgcat acactattct cagaatgact tggttgagta ctcaccagtc acagaaaagc     1080
atcttacgga tggcatgaca gtaagagaat tatgcagtgc tgccataacc atgagtgata     1140
acactgcggc caacttactt ctgacaacga tcggaggacc gaaggagcta accgcttttt     1200
tgcacaacat gggggatcat gtaactcgcc ttgatcgttg ggaaccggag ctgaatgaag     1260
ccataccaaa cgacgagcgt gacaccacga tgcctgtagc aatggcaaca cgttgcgca      1320 aactattaac tggcgaacta cttactctag cttcccggca acaattaata gactggatgg     1380
aggcggataa agttgcagga ccacttctgc gctcggccct tccggctggc tggtttattg     1440
ctgataaatc tggagccggt gagcgtgggt ctcgcggtat cattgcagca ctggggccag     1500
atggtaagcc ctcccgtatc gtagttatct acacgacggg gagtcaggca actatggatg     1560
aacgaaatag acagatcgct gagataggtg cctcactgat taagcattgg taactgtcag     1620
accaagttta ctcatatata ctttagattg atttaaaact tcattttaa tttaaaagga      1680 tctaggtgaa gatcctttt gataatctca tgaccaaaat cccttaacgt gagttttcgt      1740
tccactgagc gtcagacccc gtagaaaaga tcaaggatc ttcttgagat cctttttttc      1800
tgcgcgtaat ctgctgcttg caaacaaaaa aaccaccgct accagcggtg tttgtttgc      1860 cggatcaaga gctaccaact cttttttccga aggtaactgg cttcagcaga gcgcagatac     1920
caaatactgt tcttctagtg tagccgtagt taggccacca cttcaagaac tctgtagcac     1980
cgcctacata cctcgctctg ctaatcctgt taccagtggc tgctgccagt ggcgataagt     2040
cgtgtcttac cgggttggac tcaagacgat agttaccgga taaggcgcag cggtcgggct     2100
gaacgggggg ttcgtgcaca cagcccagct tggagcgaac gacctacacc gaactgagat     2160
acctacagcg tgagctatga gaaagcgcca cgcttcccga agggagaaag gcggacaggt     2220
atccggtaag cggcagggtc ggaacaggag agcgcacgag ggagcttcca gggggaaacg     2280
cctggtatct ttatagtcct gtcgggtttc gccacctctg acttgagcgt cgatttttgt     2340
gatgctcgtc aggggggcgg agcctatgga aaaacgccag caacgcggcc ttttttacggt     2400 tcctggcctt tgctggcct tttgctcaca tgttctttcc tgcgttatcc cctgattctg      2460
tggataaccg tattaccgcc tttgagtgag ctgataccgc tcgccgcagc cgaacgaccg     2520
agcgcagcga gtcagtgagc gaggaagcgg aagagcgccc aatacgcaaa ccgcctctcc     2580
ccgcgcgttg gccgattcat taatgcagct ggcacgacag gtttcccgac tggaaagcgg     2640
gcagtgagcg caacgcaatt aatgtgagtt agctcactca ttaggcaccc caggctttac     2700
actttatgct tccggctcgt atgttgtgtg gaattgtgag cggataacaa tttcacacag     2760
gaaacagcta tgaccatgat tacgccaagc gcgcaattaa ccctcactaa agggaacaaa     2820
agctggagct gcaagcttaa tgtagtctta tgcaatactc ttgtagtctt gcaacatggt     2880
aacgatgagt tagcaacatg ccttacaagg agagaaaaag caccgtgcat gccgattggt     2940
ggaagtaagg tggtacgatc gtgccttatt aggaaggcaa cagacgggtc tgacatggat     3000
tggacgaacc actgaattgc cgcattgcag agatattgta tttaagtgcc tagctcgata     3060
cataaacggg tctctctggt tagaccagat ctgagcctgg gagctctctg gctaactagg     3120
```

```
gaacccactg cttaagcctc aataaagctt gccttgagtg cttcaagtag tgtgtgcccg    3180
tctgttgtgt gactctggta actagagatc cctcagaccc ttttagtcag tgtggaaaat    3240
ctctagcagt ggcgcccgaa cagggacttg aaagcgaaag ggaaaccaga ggagctctct    3300
cgacgcagga ctcggcttgc tgaagcgcgc acggcaagag gcgaggggcg cgactggtg    3360 agtacgccaa aaattttgac tagcggaggc tagaaggaga gagatgggtg cgagagcgtc    3420
agtattaagc gggggagaat tagatcgcga tgggaaaaaa ttcggttaag gccaggggga    3480
aagaaaaaat ataaattaaa acatatagta tgggcaagca gggagctaga acgattcgca    3540
gttaatcctg gcctgttaga aacatcagaa ggctgtagac aaatactggg acagctacaa    3600
ccatcccttc agacaggatc agaagaactt agatcattat ataatacagt agcaaccctc    3660
tattgtgtgc atcaaaggat agagataaaa gacaccaagg aagctttaga caagatagag    3720
gaagagcaaa acaaaagtaa gaccaccgca cagcaagcgg ccgctgatct tcagacctgg    3780
aggaggagat atgagggaca attggagaag tgaattatat aaatataaag tagtaaaaat    3840
tgaaccatta ggagtagcac ccaccaaggc aaagagaaga gtggtgcaga gagaaaaaag    3900
agcagtggga ataggagctt tgttccttgg gttcttggga gcagcaggaa gcactatggg    3960
cgcagcgtca atgacgctga cggtacaggc cagacaatta ttgtctggta tagtgcagca    4020
gcagaacaat ttgctgaggg ctattgaggc gcaacagcat ctgttgcaac tcacagtctg    4080
gggcatcaag cagctccagg caagaatcct ggctgtggaa agatacctaa aggatcaaca    4140
gctcctgggg atttggggtt gctctggaaa actcatttgc accactgctg tgccttggaa    4200
tgctagttgg agtaataaat ctctggaaca gatttggaat cacacgacct ggatggagtg    4260
ggacagagaa attaacaatt acacaagctt aatacactcc ttaattgaag aatcgcaaaa    4320
ccagcaagaa aagaatgaac aagaattatt ggaattagat aaatgggcaa gtttgtggaa    4380
ttggtttaac ataacaaatt ggctgtggta tataaaatta ttcataatga tagtaggagg    4440
cttggtaggt ttaagaatag ttttgctgt actttctata gtgaatagag ttaggcaggg    4500
atattcacca ttatcgtttc agacccacct cccaaccccg aggggacccg acaggcccga    4560
aggaatagaa gaagaaggtg gagagagaga cagagacaga tccattcgat tagtgaacgg    4620
atctcgacgg tatcgattag actgtagccc aggaatatgg cagctagatt gtacacattt    4680
agaaggaaaa gttatcttgg tagcagttca tgtagccagt ggatatatag aagcagaagt    4740
aattccagca gagacagggc aagaaacagc atacttcctc ttaaaattag caggaagatg    4800
gccagtaaaa acagtacata cagacaatgg cagcaatttc accagtacta cagttaaggc    4860
cgcctgttgg tgggcgggga tcaagcagga atttggcatt ccctacaatc cccaaagtca    4920
aggagtaata gaatctatga ataaagaatt aagaaaaatt ataggacagg taagagatca    4980
ggctgaacat cttaagacag cagtacaaat ggcagtattc atccacaatt ttaaaagaaa    5040 agggggatt ggggggtaca gtgcagggga aagaatagta gacataatag caacagacat    5100
acaaactaaa gaattacaaa aacaaattac aaaaattcaa aattttcggg tttattacag    5160
ggacagcaga gatccagttt ggctgcattg atcacgtgag gctccggtgc ccgtcagtgg    5220
gcagagcgca catcgcccac agtccccgag aagttggggg gaggggtcgg caattgaacc    5280
ggtgcctaga gaaggtggcg cggggtaaac tgggaaagtg atgtcgtgta ctggctccgc    5340
ctttttcccg agggtggggg agaaccgtat ataagtgcag tagtcgccgt gaacgttctt    5400
tttcgcaacg ggtttccgc cagaacacag gtaagtgccg tgtgtggttc ccgcgggcct    5460
ggcctcttta cgggttatgg cccttgcgtg ccttgaatta cttccacctg gctgcagtac    5520
```

```
gtgattcttg atcccgagct tcgggttgga agtgggtggg agagttcgag gccttgcgct   5580
taaggagccc cttcgcctcg tgcttgagtt gaggcctggc ctgggcgctg ggccgccgc    5640 gtgcgaatct ggtggcacct tcgcgcctgt ctcgctgctt tcgataagtc tctagccatt   5700
taaaattttt gatgacctgc tgcgacgctt tttttctggc aagatagtct tgtaaatgcg   5760
ggccaagatc tgcacactgg tatttcggtt tttggggccg cgggcggcga cggggcccgt   5820
gcgtcccagc gcacatgttc ggcgaggcgg ggcctgcgag cgcggccacc gagaatcgga   5880
cgggggtagt ctcaagctgg ccggcctgct ctggtgcctg gcctcgcgcc gccgtgtatc   5940
gccccgccct gggcggcaag gctggcccgg tcggcaccag ttgcgtgagc ggaaagatgg   6000
ccgcttcccg gccctgctgc agggagctca aaatggagga cgcggcgctc gggagagcgg   6060
gcgggtgagt cacccacaca aaggaaaagg gcctttccgt cctcagccgt cgcttcatgt   6120
gactccactg agtaccgggc gccgtccagg cacctcgatt agttctcgag cttttggagt   6180
acgtcgtctt taggttgggg ggaggggttt tatgcgatgg agtttcccca cactgagtgg   6240
gtggagactg aagttaggcc agcttggcac ttgatgtaat tctccttgga atttgccctt   6300
tttgagtttg gatcttggtt cattctcaag cctcagacag tggttcaaag ttttttttctt   6360 ccatttcagg tgtcgtgatc tagaggatcc atggccttac cagtgaccgc cttgctcctg   6420
ccgctggcct tgctgctcca cgccgccagg ccggacatcc agatgacaca gactacatcc   6480
tccctgtctg cctctctggg agacagagtc accatcagtt gcagggcaag tcaggacatt   6540
agtaaatatt taaattggta tcagcagaaa ccagatggaa ctgttaaact cctgatctac   6600
catacatcaa gattacactc aggagtccca tcaaggttca gtggcagtgg gtctggaaca   6660
gattattctc tcaccattag caacctggag caagaagata ttgccactta cttttgccaa   6720
cagggtaata cgcttccgta cacgttcgga gggggaccca agctggagat cacaggtggc   6780
ggtggctcgg gcggtggtgg gtcggtggc ggcggatctg aggtgaaact gcaggagtca   6840
ggacctggcc tggtggcgcc ctcacagagc ctgtccgtca catgcactgt ctcagggtc    6900 tcattacccg actatggtgt aagctggatt cgccagcctc cacgaaaggg tctgagtgg    6960 ctgggagtaa tatggggtag tgaaaccaca tactataatt cagctctcaa atccagactg   7020
accatcatca aggacaactc caagagccaa gttttcttaa aaatgaacag tctgcaaact   7080
gatgacacag ccatttacta ctgtgccaaa cattattact acggtggtag ctatgctatg   7140
gactactggg gccaaggaac ctcagtcacc gtctcctcaa ccacgacgcc agcgccgcga   7200
ccaccaacac cggcgcccac catcgcgtcg cagcccctgt ccctgcgccc agaggcgtgc   7260
cggccagcgg cgggggcgc agtgcacacg aggggctgg acttcgcctg tgatatctac    7320
atctgggcgc ccttggccgg gacttgtggg gtccttctcc tgtcactggt tatcaccctt   7380
tactgcaaac ggggcagaaa gaaactcctg tatatattca acaaccatt tatgagacca    7440 gtacaaacta ctcaagagga agatggctgt agctgccgat ttccagaaga agaagaagga   7500
ggatgtgaac tgagagtgaa gttcagcagg agcgcagacg cccccgcgta caagcagggc   7560
cagaaccagc tctataacga gctcaatcta ggacgaagag aggagtacga tgttttggac   7620
aagagacgtg gccgggaccc tgagatgggg ggaaagccga aaggaagaa ccctcaggaa    7680 ggcctgtaca atgaactgca gaaagataag atggcggagg cctacagtga gattgggatg   7740
aaaggcgagc gccggagggg caaggggcac gatggccttt accagggtct cagtacagcc   7800
accaaggaca cctacgacgc ccttcacatg caggcccctgc cccctcgcta agtcgacaat   7860
```

```
caacctctgg attacaaaat tgtgaaaga ttgactggta ttcttaacta tgttgctcct      7920
tttacgctat gtggatacgc tgctttaatg cctttgtatc atgctattgc ttcccgtatg      7980
gctttcattt tctcctcctt gtataaatcc tggttgctgt ctctttatga ggagttgtgg      8040
cccgttgtca ggcaacgtgg cgtggtgtgc actgtgtttg ctgacgcaac ccccactggt      8100
tggggcattg ccaccacctg tcagctcctt tccgggactt tcgctttccc cctccctatt      8160
gccacggcgg aactcatcgc cgcctgcctt gcccgctgct ggacaggggc tcggctgttg      8220
ggcactgaca attccgtggt gttgtcgggg aagctgacgt cctttccatg gctgctcgcc      8280
tgtgttgcca cctggattct gcgcgggacg tccttctgct acgtcccttc ggccctcaat      8340
ccagcggacc ttccttcccg cggcctgctg ccggctctgc ggcctcttcc gcgtcttcgc      8400
cttcgccctc agacgagtcg gatctcccct tgggccgcct cccgcctgg aattcgagct      8460 cggtaccttt aagaccaatg acttacaagg cagctgtaga tcttagccac ttttttaaaag      8520 aaaagggggg actggaaggg ctaattcact cccaacgaag acaagatctg ctttttgctt      8580
gtactgggtc tctctggtta gaccagatct gagcctggga gctctctggc taactaggga      8640
acccactgct taagcctcaa taaagcttgc cttgagtgct tcaagtagtg tgtgcccgtc      8700
tgttgtgtga ctctggtaac tagagatccc tcagaccctt ttagtcagtg tggaaaatct      8760
ctagcagtag tagttcatgt catcttatta ttcagtattt ataacttgca aagaaatgaa      8820
tatcagagag tgagaggaac ttgttttattg cagcttataa tggttacaaa taaagcaata      8880
gcatcacaaa tttcacaaat aaagcatttt tttcactgca ttctagttgt ggtttgtcca      8940
aactcatcaa tgtatcttat catgtctggc tctagctatc ccgcccctaa ctccgcccat      9000 cccgcccta actccgccca gttccgccca ttctccgccc catggctgac taattttttt      9060
tatttatgca gaggccgagg ccgcctcggc ctctgagcta ttccagaagt agtgaggagg      9120
cttttttgga ggcctaggga cgtacccaat tcgccctata gtgagtcgta ttac           9174
```

<210> SEQ ID NO 51
<211> LENGTH: 5981
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

```
ggatcccctg aggggccccc catgggctag aggatccggc ctcggcctct gcataaataa       60
aaaaaattag tcagccatga gcttggccca ttgcatacgt tgtatccata tcataatatg      120
tacatttata ttggctcatg tccaacatta ccgccatgtt gacattgatt attgactagt      180
tattaatagt aatcaattac ggggtcatta gttcatagcc catatatgga gttccgcgtt      240
acataactta cggtaaatgg cccgcctggc tgaccgccca acgacccccg cccattgacg      300
tcaataatga cgtatgttcc catagtaacg ccaatagggc ctttccattg acgtcaatgg      360
gtggagtatt tacggtaaac tgcccacttg gcagtacatc aagtgtatca tatgccaagt      420
acgcccccta ttgacgtcaa tgacggtaaa tggcccgcct ggcattatgc ccagtacatg      480
accttatggg actttcctac ttggcagtac atctacgtat tagtcatcgc tattaccatg      540
gtgatgcggt tttggcagta catcaatggg cgtggatagc ggtttgactc acggggattt      600
ccaagtctcc accccattga cgtcaatggg agtttgtttt ggcaccaaaa tcaacgggac      660
tttccaaaat gtcgtaacaa ctccgcccca ttgacgcaaa tgggcggtag gcgtgtacgg      720
```

```
tgggaggtct atataagcag agctcgttta gtgaaccgtc agatcgcctg gagacgccat    780
ccacgctgtt ttgacctcca tagaagacac cgggaccgat ccagcctccc ctcgaagctt    840
acatgtggta ccgagctcgg atcctgagaa cttcagggtg agtctatggg acccttgatg    900
ttttcttttcc ccttctttttc tatggttaag ttcatgtcat aggaagggga gaagtaacag   960
ggtacacata ttgaccaaat cagggtaatt ttgcatttgt aattttaaaa aatgctttct   1020
tcttttaata tacttttttg tttatcttat ttctaatact ttccctaatc tctttctttc   1080
agggcaataa tgatacaatg tatcatgcct ctttgcacca ttctaaagaa taacagtgat   1140
aatttctggg ttaaggcaat agcaatattt ctgcatataa atatttctgc atataaattg   1200
taactgatgt aagaggtttc atattgctaa tagcagctac aatccagcta ccattctgct   1260
tttattttat ggttgggata aggctggatt attctgagtc caagctaggc ccttttgcta   1320
atcatgttca tacctcttat cttcctccca cagctcctgg gcaacgtgct ggtctgtgtg   1380
ctggcccatc actttggcaa agcacgtgag atctgaattc aacagagatc gatctgtttc   1440
cttgacacta tgggattcac aacaaagata atcttcttat acaacctagt actggtctac   1500
gcggggtttg acgaccctcg caaagccata gaactagtac aaaagcgata tggccgacca   1560
tgcgattgca gcggaggaca gtgtccgag cctccgtcag acagggtcag tcaagtgact   1620
tgctcaggca agacagctta cttaatgccc gaccaaagat ggaaatgtaa gtcaattcca   1680
aaagacacct ccccaagcgg gccactccaa gagtgcccct gtaattctta ccagtcctca   1740
gtacacagtt cttgttatac ctcataccaa caatgcagat caggcaataa gacatattat   1800
acggctactc tgctaaaaac acaaactggg ggcaccagtg atgtacaagt attaggatcc   1860
accaacaaac ttatacaatc tccctgtaat ggcataaaag ggcagtctat atgctggagc   1920
actacagctc ctatccacgt ctctgatgga ggaggtccat tagacaccac aagaattaaa   1980
agtgttcaga gaaaactgga agaaattcat aaagccctat atcctgaact tcagtatcac   2040
cctttggcca tacctaaggt tagagataac ctcatggtcg atgcccagac tttaaacatt   2100
ctcaatgcca cttacaactt actcctaatg tccaacacga gcctagtgga cgactgttgg   2160
cttgtttaa aattaggtcc ccctactccc ctcgcaatac ctaacttcct attatcctac   2220
gtgactcgct cctcggataa tatctcttgt ttaataattc cccctcttct agttcaaccg   2280
atgcagtttt ccaattcatc ttgcctcttt tcccctcct acaacagtac agaagaaata   2340
gatctaggcc atgttgcctt cagcaactgt acctccataa ccaatgtcac cggtcccata   2400
tgcgctgtaa atggttcggt cttttctctgt ggcaataaca tggcatacac ttatctaccc   2460
acgaactgga cggggctttg cgtcctagca actctcctcc ccgacattga catcattccc   2520
ggagatgaac cggtccccat ccctgctatt gatcatttta tatatagacc taaacgggcc   2580
atacagttta ttcctttact agcagggcta gggatcaccg cagccttcac aacaggagct   2640
acaggcctag gtgtctctgt gacccaatat acaaaattat ctaatcagct aatttctgat   2700
gtacaaatct tatctagcac catacaagat ctgcaagatc aagtagactc attagccgaa   2760
gtggttctcc agaacagaag ggggctagat ctacttacag cagaacaagg aggaatctgt   2820
ttagccctgc aagaaaaatg ctgctttat gttaacaagt cagggattgt gagagacaaa   2880
ataaaaacct tacaagaaga actagaaaga cgtagaaaag atctagcttc caacccactt   2940
tggactgggc ttcaagggct cctcccttac ctcctgccct tcttggccc tctacttacc   3000
ctcctgtctct tactccaccat tgggccgtgc atttttaaca ggttggtcca gtttgttaaa   3060
gaccgcattt cagttgtgca agcgttggtg ctaacccaac agtatcaggt gctcagaacc   3120
```

```
gatgaagaag ctcaagatta actcaaatcc tgcacaacag attcttcatg tttggaccaa    3180
atcaacttgt gataccatgc tcaaagaggc ctcaattata tttgagtttt taatttttat    3240
ggaattcacc ccaccagtgc aggctgccta tcagaaagtg gtggctggtg tggctaatgc    3300
cctggcccac aagtatcact aagctcgctt tcttgctgtc caatttctat taaaggttcc    3360
tttgttccct aagtccaact actaaactgg gggatattat gaagggcctt gagcatctgg    3420
attctgccta ataaaaaaca tttatttttca ttgcaatgat gtatttaaat tatttctgaa    3480 tatttttacta aaagggaat gtgggaggtc agtgcattta aaacataaag aaatgaagag    3540
ctagttcaaa ccttgggaaa atacactata tcttaaactc catgaaagaa ggtgaggctg    3600
caaacagcta atgcacattg caacagccc ctgatgccta tgccttattc atccctcaga    3660
aaaggattca agtagaggct tgatttggag gttaaagttt tgctatgctg tattttacat    3720
tacttattgt tttagctgtc ctcatgaatg tcttttcact acccatttgc ttatcctgca    3780
tctctcagcc ttgactccac tcagttctct tgcttagaga taccacctttt ccctgaagt    3840 gttccttcca tgttttacgg cgagatggtt tctcctcgcc tggccactca gccttagttg    3900
tctctgttgt cttatagagg tctacttgaa gaggaaaaaa caggggggcat ggtttgactg    3960 tcctgtgagc ccttcttccc tgcctccccc actcacagtg acccggaatc cctcgacatg    4020
gcagtctagc actagtgcgg ccgcagatct gcttcctcgc tcactgactc gctgcgctcg    4080
gtcgttcggc tgcggcgagc ggtatcagct cactcaaagg cggtaatacg gttatccaca    4140
gaatcagggg ataacgcagg aaagaacatg tgagcaaaag gccagcaaaa ggccaggaac    4200
cgtaaaaagg ccgcgttgct ggcgttttc cataggctcc gccccctga cgagcatcac    4260 aaaaatcgac gctcaagtca gaggtggcga acccgacag gactataaag ataccaggcg    4320
tttccccctg gaagctccct cgtgcgctct cctgttccga ccctgccgct taccggatac    4380
ctgtccgcct ttctcccttc gggaagcgtg gcgctttctc atagctcacg ctgtaggtat    4440
ctcagttcgg tgtaggtcgt tcgctccaag ctgggctgtg tgcacgaacc cccgttcag    4500 cccgaccgct gcgccttatc cggtaactat cgtcttgagt ccaacccggt aagacacgac    4560
ttatcgccac tggcagcagc cactggtaac aggattagca gagcgaggta tgtaggcggt    4620
gctacagagt tcttgaagtg gtggcctaac tacggctaca ctagaagaac agtatttggt    4680
atctgcgctc tgctgaagcc agttaccttc ggaaaaagag ttggtagctc ttgatccggc    4740
aaacaaacca ccgctggtag cggtggtttt tttgtttgca agcagcagat tacgcgcaga    4800
aaaaaaggat ctcaagaaga tcctttgatc ttttctacgg ggtctgacgc tcagtggaac    4860
gaaaactcac gttaagggat tttggtcatg agattatcaa aaaggatctt cacctagatc    4920
cttttaaatt aaaaatgaag ttttaaatca atctaaagta tatatgagta aacttggtct    4980
gacagttacc aatgcttaat cagtgaggca cctatctcag cgatctgtct atttcgttca    5040
tccatagttg cctgactccc cgtcgtgtag ataactacga tacggagggg cttaccatct    5100
ggccccagtg ctgcaatgat accgcgagac ccacgctcac cggctccaga tttatcagca    5160
ataaccagcc agccggaag ggccgagcgc agaagtggtc ctgcaacttt atccgcctcc    5220
atccagtcta ttaattgttg ccgggaagct agagtaagta gttcgccagt taatagtttg    5280
cgcaacgttg ttgccattgc tacaggcatc gtggtgtcac gctcgtcgtt tggtatggct    5340
tcattcagct ccggttccca acgatcaagg cgagttacat gatcccccat gttgtgcaaa    5400
aaagcggtta gctccttcgg tcctccgatc gttgtcagaa gtaagttggc cgcagtgtta    5460
```

```
                                                               -continued
tcactcatgg ttatggcagc actgcataat tctcttactg tcatgccatc cgtaagatgc    5520
ttttctgtga ctggtgagta ctcaaccaag tcattctgag aatagtgtat gcggcgaccg    5580
agttgctctt gcccggcgtc aatacgggat aataccgcgc cacatagcag aactttaaaa    5640
gtgctcatca ttggaaaacg ttcttcgggg cgaaaactct caaggatctt accgctgttg    5700
agatccagtt cgatgtaacc cactcgtgca cccaactgat cttcagcatc ttttactttc    5760
accagcgttt ctgggtgagc aaaaacagga aggcaaaatg ccgcaaaaaa gggaataagg    5820
gcgacacgga aatgttgaat actcatactc ttcctttttc aatattattg aagcatttat    5880
cagggttatt gtctcatgag cggatacata tttgaatgta tttagaaaaa taaacaaata    5940
ggggttccgc gcacatttcc ccgaaaagtg ccacctgacg t                        5981
```